US010800760B2

(12) United States Patent
Tao et al.

(10) Patent No.: US 10,800,760 B2
(45) Date of Patent: Oct. 13, 2020

(54) TRK INHIBITION

(71) Applicant: NantBio, Inc., Culver City, CA (US)

(72) Inventors: Chunlin Tao, Newport Coast, CA (US); Qinwei Wang, Alhambra, CA (US); Sharif Asad, Lake Forest, CA (US); Paul Weingarten, Anaheim, CA (US); Sherry Ci, San Marino, CA (US)

(73) Assignee: NANTBIO, INC., Culver City, CA (US)

( * ) Notice: Subject to any disclaimer, the term of this patent is extended or adjusted under 35 U.S.C. 154(b) by 0 days.

(21) Appl. No.: 15/993,214

(22) Filed: May 30, 2018

(65) Prior Publication Data

US 2018/0346450 A1 Dec. 6, 2018

Related U.S. Application Data

(60) Provisional application No. 62/513,095, filed on May 31, 2017.

(51) Int. Cl.
C07D 401/14 (2006.01)
C07D 403/12 (2006.01)
C07D 405/14 (2006.01)
C07D 409/14 (2006.01)

(52) U.S. Cl.
CPC ......... *C07D 403/12* (2013.01); *C07D 401/14* (2013.01); *C07D 405/14* (2013.01); *C07D 409/14* (2013.01)

(58) Field of Classification Search
CPC .................................................. C07D 401/14
See application file for complete search history.

(56) References Cited

U.S. PATENT DOCUMENTS

| 5,916,596 | A | 6/1999 | Desai et al. |
|---|---|---|---|
| 6,506,405 | B1 | 1/2003 | Desai et al. |
| 6,537,579 | B1 | 3/2003 | Desai et al. |
| 9,458,137 | B2 | 10/2016 | Tao et al. |
| 9,670,207 | B2 | 6/2017 | Sasmal et al. |
| 9,688,672 | B2 | 6/2017 | Caferro et al. |
| 9,790,204 | B2 | 10/2017 | Leleti et al. |
| 2012/0172361 | A1 | 7/2012 | Tao et al. |
| 2012/0238576 | A1 | 9/2012 | Tao et al. |
| 2013/0023497 | A1 | 1/2013 | Tao et al. |
| 2016/0168156 | A1 | 6/2016 | Kim et al. |

FOREIGN PATENT DOCUMENTS

WO WO-2013026021 A2 * 2/2013 ............ C07K 14/71

OTHER PUBLICATIONS

Allwein, Shawn P., et al., "Efficient synthesis of chiral phenethylamines: preparation, asymmetric hydrogenation, and mild deprotection of ene-trifluoroacetamides." Tetrahedron letters 47.36 (2006): 6409-6412.
Bishop, Justin A., et al., "Most non-parotid "acinic cell carcinomas" represent mammary analogue secretory carcinomas." The American journal of surgical pathology 37.7 (2013): 1053.
Brenca, Monica, et al., "Transcriptome sequencing identifies ETV6-NTRK3 as a gene fusion involved in GIST." The Journal of Pathology 238.4 (2016): 543-549.
Delafoy, Laure, et al., "Role of nerve growth factor in the trinitrobenzene sulfonic acid-induced colonic hypersensitivity." Pain 105.3 (2003): 489-497.
Di Mola, F. F., et al., "Nerve growth factor and Trk high affinity receptor (TrkA) gene expression in inflammatory bowel disease." Gut 46.5 (2000): 670-678.
Doebele, R. C., et al., An oncogenic NTRK Fusion in a patient with soft-tissue sarcoma with response to the tropomyosin-related kinase inhibitor LOXO-101. Cancer Discov. 2015; 5: 1049-1057.
Dou, Ying-Chun, et al., "Increased nerve growth factor and its receptors in atopic dermatitis: an immunohistochemical study." Archives of dermatological research 298.1 (2006): 31-37.
Freund-Michei, V., and N. Frossard. "The nerve growth factor and its receptors in airway inflammatory diseases." Pharmacology & Therapeutics 117.1 (2008): 52-76.
Hu, Vivian Y., et al., "Decrease in bladder overactivity with REN1820 in rats with cyclophosphamide induced cystitis." The Journal of Urology 173.3 (2005): 1016-1021.
Huang, Eric J., and Louis F. Reichardt. "Trk receptors: roles in neuronal signal transduction." Annual review of biochemistry 72.1 (2003): 609-642.
Jaggar, S. I., et al., "Inflammation of the rat urinary bladder is associated with a referred thermal hyperalgesia which is nerve growth factor dependent." British journal of anaesthesia 83.3 (1999): 442-448.
Lamb, K., et al., "Nerve growth factor and gastric hyperalgesia in the rat." Neurogastroenterology & Motility 15.4 (2003): 355-361.
Ma, Qing-Ping, and Clifford J. Woolf, "The progressive tactile hyperalgesia induced by peripheral inflammation is nerve growth factor dependent." Neuroreport 8.4 (1997): 807-810.
Maryanoff, Bruce E., et al., "Pyrroloisoquinoline antidepressants. 2. In-depth exploration of structure-activity relationships." Journal of medicinal chemistry 30.8 (1987): 1433-1454.
Maryanoff, Bruce E., et al., "Pyrroloisoquinoline antidepressants. 3. A focus on serotonin." Journal of medicinal chemistry 33.10 (1990): 2793-2797.
Mcmahon, Stephen B., et al., "The biological effects of endogenous nerve growth factor on adult sensory neurons revealed by a trkA-IgG fusion molecule." Nature medicine 1.8 (1995): 774.

(Continued)

*Primary Examiner* — Marcos L Sznaidman
*Assistant Examiner* — Rayna Rodriguez
(74) *Attorney, Agent, or Firm* — Mintz, Levin, Cohn, Ferris, Glovsky and Popeo, P.C.

(57) ABSTRACT

The present invention relates to the use of substituted pyrazole derivatives to modulate tropomyosin-related kinase (Trk) family protein kinase, and the use of the substituted pyrazole derivatives for the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

2 Claims, No Drawings

(56) References Cited

OTHER PUBLICATIONS

Patapoutian, Ardem, and Louis F. Reichardt. "Trk receptors: mediators of neurotrophin action." Current opinion in neurobiology 11.3 (2001): 272-280.
Prasad, Manju L., et al., "NTRK fusion oncogenes in pediatric papillary thyroid carcinoma in northeast United States." Cancer 122.7 (2016): 1097-1107.
Raychaudhuri, Siba P., et al, "K252a, a high-affinity nerve growth factor receptor blocker, improves psoriasis: an in vivo study using the severe combined immunodeficient mouse-human skin model." Journal of investigative dermatology 122.3 (2004): 812-819.
Shelton, David L., et al., "Nerve growth factor mediates hyperalgesia and cachexia in auto-immune arthritis." Pain 116.1-2 (2005): 8-16.
Sohrabji, Farida, and Danielle K. Lewis. "Estrogen-BDNF interactions: implications for neurodegenerative diseases." Frontiers in neuroendocrinology 27.4 (2006): 404-414.
Vaishnavi, Aria, et al., "TRKing down an old oncogene in a new era of targeted therapy." Cancer discovery 5.1 (2015): 25-34.
Whitesell, Luke, et al., "The stress response: implications for the clinical development of hsp90 inhibitors." Current cancer drug targets 3.5 (2003): 349-358.
Woolf, Clifford J., et al., "Nerve growth factor contributes to the generation of inflammatory sensory hypersensitivity." Neuroscience 62.2 (1994): 327-331.
Zahn, Peter K., et al., "Effect of blockade of nerve growth factor and tumor necrosis factor on pain behaviors after plantar incision." The Journal of Pain 5.3 (2004): 157-163.

* cited by examiner

TRK INHIBITION

CROSS REFERENCE TO RELATED APPLICATION

This application claims the benefit of U.S. Provisional Patent Application No. 62/513,095, filed on May 31, 2017, the disclosure of which is incorporated by reference in its entirety.

FIELD OF THE INVENTION

The present invention relates to the use of substituted pyrazole derivatives to modulate tropomyosin-related kinase (Trk) family protein kinase, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

BACKGROUND OF THE INVENTION

The tropomyosin receptor kinase (Trk) receptors are a family of tyrosine kinases that regulates synaptic strength and plasticity in the mammalian nervous system (Huang E J, Reichardt L F (2003). Annu. Rev. Biochem. 72: 609-642) (incorporated herein by reference). The Trk receptor family comprises 3 transmembrane proteins referred to as TrkA, TrkB and TrkC receptors that are encoded by the NTRK1, NTRK2 and NTRK3 genes, respectively. These receptor tyrosine kinases are expressed in human neuronal tissue and play an essential role in the physiology of development and function of the nervous system through activation by neurotrophins (Patapoutian, A. et al. (2001) *Current Opinion in Neurobiology* 11: 272-280) (incorporated herein by reference).

Trk kinase fusions have been described in multiple cancers including colorectal cancer, lung adenocarcinoma, salivary gland cancer, head and neck squamous cell cancer, glioblastoma multiforme, and thyroid cancer (Vaishnavi A, Le A T, Doebele R C (2015). Cancer Discov. 5 (1): 25-34; Bishop J A et al. J Surg Pathol. 2013 37(7):1053-7; Prasad M L et al. Cancer, 2016 Jan. 19; brenca M. et al. J Pathol 2016, 238(4): 543-9) (each of which is incorporated herein by reference). Trk kinase fusions have further fueled the development of pan-Trk inhibitor drugs for use in oncology. In accordance with the potential for Trk fusions to be used as molecular targets in cancer, Trk inhibition has been shown in vitro to inhibit the proliferation of cell lines expressing Trk fusions. Recent clinical study details strong clinical response to a Trk inhibitor by a sarcoma patient, and thus the patient could be rationally treated with a pan-Trk inhibitor drug (Robert C. Doebert et al. (2015) Cancer Discov. 5(10): 1049-1057) (Incorporated herein by reference).

Inhibitors of the Trk/neutrophin pathway have been demonstrated to be highly effective in numerous pre-clinical animal models of pain. AntagonisticNGF and TrkA antibodies have been shown to be efficacious in inflammatory and neuropathic pain animal models and in human clinical trials (Woolf, C. J. et al. (1994) *Neuroscience* 62, 327-331; Zahn, P. K. et al. (2004) *J Pain* 5, 157-163; McMahon5 S. B. et al., (1995) *Nat. Med.* 1, 774-780; Ma, Q. P. and Woolf, C. J. (1997) *Neuroreport* 8, 807-810; Shelton, D. L. et al. (2005) *Pain* 116, 8-16; Delafoy, L. et al. (2003) *Pain* 105,489-497; Lamb, K. e t a 1(2003) *Neurogastroenterol Motil* 15, 355-361; and Jaggar, S. I. et al. (199) *Br. J. Anaesth.* 83,442-448) (each of which is incorporated herein by reference). Also promising is the utility of Trk inhibitors in the treatment of inflammatory lung diseases such as asthma (Freund-Michel, V; et al, *Pharmacology & Therapeutics* (2008), 117(1), 52-76) (incorporated herein by reference), interstitial cystitis (Hu Vivian Y; et. al., *J of Urology* (2005), 173(3), 1016-21) (incorporated herein by reference), inflammatory bowel disease including ulcerative colitis and Crohn's disease (Di Mola, F. F., et al., *Gut* (2000), 46(5), 670-678) (incorporated herein by reference) and inflammatory skin diseases such as atopic dermatitis (Dou, Y. C., et. Al., *Archives of Dermatological Research* (2006), 298(1), 31-37) (incorporated herein by reference), eczema and psoriasis (Raychaudhuri, S. P. et. al., *J of Investigative Dermatology* (2004), 122(3), 812-819). Modulation of the neutrophin/Trk pathway also has been shown to have an effect in the etiology of neurodegenerative diseases including multiple sclerosis, Parkinson's disease and Alzheimer's disease (Sohrabji, et. a 1, Neuroendocrinology (2006), 27(4), 404-414) (incorporated herein by reference).

Despite this promising research, a need exists for compounds acting as Trk kinase mediators or inhibitors.

SUMMARY OF THE INVENTION

The present invention provides an agent comprising substituted pyrazole derivatives as described in formula (I), pharmaceutically-acceptable formulations thereof, methods for making novel compounds and compositions for using the compounds. The compounds and compositions comprising the compounds in formula (I) are useful as a Trk kinase mediator of NGF driven biological responses, an inhibitor of TrkA and other Trk kinases. The invention involves use of the compounds as Trk kinase inhibitors for the treatment of a variety of diseases associated with Trk kinases, including multiple types of cancers, acute and chronic pain, inflammation, neurodegenerative diseases, certain infectious diseases, respiratory distress, and others.

DETAILED DESCRIPTION OF THE INVENTION

The present invention is related to compounds having general Formula (I)

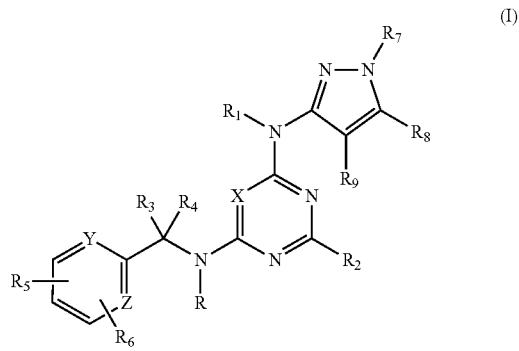

(I)

or a pharmaceutically acceptable salt thereof, wherein:
$R_1$ and R respectively represent hydrogen, $C_1$-$C_4$ alkyl.
$R_2$ represents hydrogen, $NH_2$ and $C_1$-$C_4$ alkyl.
$R_3$ and $R_4$ respectively represent hydrogen, CN, $C_1$-$C_4$ alkyl, cycloalkyl, hydroxy, a 4- to 7-membered heterocycle, $C_1$-$C_6$ alkoxy, and $C_1$-$C_6$ alkoxycarbonyl, each of which is substituted with from 0 to 4 substituents independently chosen from halogen, hydroxy, cyano, amino, —COOH and oxo, wherein, optionally, $R_3$ and $R_4$ together form a cycloalkyl or heterocycle ring.

$R_5$ and $R_6$ respectively represent hydrogen, F, Cl, Br, I, CN, $CF_3$, $CF_2H$, $CFH_2$, $C_1$-$C_4$ alkyl, $C_1$-$C_6$ alkoxy, $C_2$-$C_6$ alkenyl, $C_2$-$C_6$ alkynyl, $N(R_{10})R_{11}$ and $CON(R_{10})R_{11}$.

R7 is selected from the group consisting of hydrogen, $C_1$-$C_4$ alkyl, (4- to 7-membered heterocycle)$C_0$-$C_4$ alkyl, $C_3$-$C_{10}$ aryl or heteroaryl and $C_2$-$C_6$ alkenyl, each of which is substituted with from 0 to 4 substituents independently selected from the group consisting of halogen, hydroxy, $C_1$-$C_4$ alkyl, $C_1$-$C_6$ alkoxy, cyano, amino, —COOH, and oxo.

$R_8$ represents hydrogen, CN, $CF_3$, $CF_2H$, $CFH_2$, $N(R_{10})R_{11}$, $CON(R_{10})R_{11}$, $C_1$-$C_4$ alkyl, $C_1$-$C_6$ alkoxy, $C_2$-$C_6$ alkenyl, $C_2$-$C_6$ alkynyl, $C_3$-$C_{10}$ aryl or heteroaryl, $C_3$-$C_7$ cycloalkyl, ($C_3$-$C_7$cycloalkyl)$C_1$-$C_4$ alkyl, $C_1$-$C_6$ haloalkyl, $C_1$-$C_6$ alkylthio, $C_2$-$C_6$ alkanoyl, $C_1$-$C_6$ alkoxycarbonyl, $C_2$-$C_6$ alkanoyloxy, mono- and di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- and di-($C_1$-$C_6$ alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH and oxo.

$R_9$ represents hydrogen, halogen, CN, $C_1$-$C_4$ alkyl, $C_1$-$C_6$ alkoxy, $C_2$-$C_6$ alkenyl, $C_2$-$C_6$ alkynyl, $N(R_{10})R_{11}$ and $CON(R_{10})R_{11}$.

$R_{10}$ and $R_{11}$ are independently selected from hydrogen, $C_1$-$C_4$ alkyl, $C_2$-$C_6$ alkenyl, $C_2$-$C_6$ alkynyl, each of which is substituted with from 0 to 4 substituents independently chosen from halogen, hydroxy, cyano, amino, —COOH and oxo.

X represents N and $CR_{12}$.

$R_{12}$ represents hydrogen, F, Cl, Br, I, CN, $NO_2$, $C_1$-$C_4$ alkyl, $C_1$-$C_6$ alkoxy, $C_2$-$C_6$ alkenyl, $CF_3$, $CF_2H$, $CFH_2$, $C_2$-$C_6$ alkynyl, $N(R_{10})R_{11}$ and $CON(R_{10})R_{11}$.

Y represents $CR_5$ and N.

Z represents $CR_6$ and N.

The term "halo" or "halogen" refers to fluorine, chlorine, bromine or iodine.

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some embodiments of the present invention, alkyl groups are substituted with, for example, amino, heterocycloalkyl, such as morpholine, piperazine, piperidine, azetidine, hydroxyl, methoxy, or heteroaryl groups such as pyrrolidine, The term 'cycloalkyl' herein alone or as part of another group refers to fully saturated and partially unsaturated hydrocarbon rings of 3 to 9 carbon atoms. The examples include cyclopropyl, cyclobutyl, cyclopentyl and cyclohexyl, and like. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" are independently selected from hydrogen, alkyl, substituted alkyl, and cycloalkyl, or R' and R" together form a heterocyclo or heteroaryl ring.

The term 'alkenyl" herein alone or as part of another group refers to a hydrocarbon radical straight, branched or cyclic containing from 2 to 12 carbon atoms and at least one carbon to carbon double bond. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, and like. Alkenyl groups may also be substituted at any available point of attachment. Exemplary substituents for alkenyl groups include those listed above for alkyl groups, and especially include $C_3$ to $C_7$ cycloalkyl groups such as cyclopropyl, cyclopentyl and cyclohexyl, which may be further substituted with, for example, amino, oxo, hydroxyl, etc.

The term "alkynyl" refers to straight or branched chain alkyne groups, which have one or more unsaturated carbon-carbon bonds, at least one of which is a triple bond. Alkynyl groups include $C_2$-$C_8$ alkynyl, $C_2$-$C_6$ alkynyl and $C_2$-$C_4$ alkynyl groups, which have from 2 to 8, 2 to 6 or 2 to 4 carbon atoms, respectively. Illustrative of the alkynyl group include ethenyl, propenyl, isopropenyl, butenyl, isobutenyl, pentenyl, and hexenyl. Alkynyl groups may also be substituted at any available point of attachment. Exemplary substituents for alkynyl groups include those listed above for alkyl groups such as amino, alkylamino, etc. The numbers in the subscript after the symbol "C" define the number of carbon atoms a particular group can contain.

The term "alkoxy" alone or as part of another group denotes an alkyl group as described above bonded through an oxygen linkage (—O—). Alkoxy groups may have from 1 to 8 carbon atoms. Examples of such groups include the methoxy, ethoxy, n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "alkylthio" refers to an alkyl group as described above attached via a sulfur bridge. Alkoxy and alkylthio groups may be those in which an alkyl group is attached via the heteroatom bridge. Alkylthio groups for use in the present invention may have from 1 to 8 carbon atoms. Examples of such groups include the methylthio, ethylthio, n-propylthio, n-butylthio, and like.

The term "oxo," as used herein, refers to a keto (C=O) group. An oxo group that is a substituent of a nonaromatic carbon atom results in a conversion of —$CH_2$— to —C(=O)—.

The term "alkoxycarbonyl" herein alone or as part of another group denotes an alkoxy group bonded through a carbonyl group. An alkoxycarbonyl radical is represented by the formula: —C(O)OR, where the R group is a straight or branched $C_1$-$C_6$ alkyl group, cycloalkyl, aryl, or heteroaryl.

The term "arylalkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 20 atoms therein, with alternating (resonating) double bonds between adjacent carbon atoms or suitable heteroatoms. Aryl groups may optionally be substituted with one or more groups including, but not limited to halogen such as I, Br, F, or Cl; alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl S(O)m (m=O, 1, 2), or thiol.

The term "aromatic" refers to a cyclically conjugated molecular entity with a stability, due to delocalization, significantly greater than that of a hypothetical localized structure, such as the Kekule structure.

The term "amino" herein alone or as part of another group refers to —NH2. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "alkylsulfonyl" refers to groups of the formula $(SO_2)$-alkyl, in which the sulfur atom is the point of attachment. Alkylsulfonyl groups for use in the present invention may include C1-C6 alkylsulfonyl groups, which have from 1 to 6 carbon atoms. Methylsulfonyl is one representative alkylsulfonyl group.

The term "heteroatom" refers to any atom other than carbon, for example, N, O, or S.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (0, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom.

The term "heterocycle" or "heterocycloalkyl" herein alone or as part of another group refers to a cycloalkyl group (nonaromatic) in which one of the carbon atoms in the ring is replaced by a heteroatom selected from O, S or N. The "heterocycle" has from 1 to 3 fused, pendant or spiro rings, at least one of which is a heterocyclic ring (i.e., one or more ring atoms is a heteroatom, with the remaining ring atoms being carbon). The heterocyclic ring may be optionally substituted, which means that the heterocyclic ring may be substituted at one or more substitutable ring positions by one or more groups independently selected from alkyl (for examplelower alkyl), heterocycloalkyl, heteroaryl, alkoxy (for example lower alkoxy), nitro, monoalkylamino for example a lower alkylamino), dialkylamino (for example an alkylamino), cyano, halo, haloalkyl (for example trifluoromethyl), alkanoyl, aminocarbonyl, monoalkylaminocarbonyl, dialkylaminocarbonyl, alkyl amido (for example lower alkyl amido), alkoxyalkyl (for example a lower alkoxy; lower alkyl), alkoxycarbonyl (for example a lower alkoxycarbonyl), alkylcarbonyloxy (for example a lower alkylcarbonyloxy) and aryl (for example phenyl), said aryl being optionally substituted by halo, lower alkyl and lower alkoxy groups. A heterocyclic group may generally be linked via any ring or substituent atom, provided that a stable compound results. N-linked heterocyclic groups are linked via a component nitrogen atom.

Typically, a heterocyclic ring comprises 1-4 heteroatoms; within certain embodiments each heterocyclic ring has 1 or 2 heteroatoms per ring. Each heterocyclic ring generally contains from 3 to 8 ring members (rings having from to 7 ring members are recited in certain embodiments), and heterocycles comprising fused, pendant or spiro rings typically contain from 9 to 14 ring members which consists of carbon atoms and contains one, two, or three heteroatoms selected from nitrogen, oxygen and/or sulfur.

Examples of "heterocycle" or "heterocycloalkyl" groups include piperazine, piperidine, morpholine, thiomorpholine, pyrrolidine, imidazolidine and thiazolide.

The term "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (such as a carbon or nitrogen atom) that is a ring member.

The term "optionally substituted" indicates that the referenced aryl or heterocyclyl or other group may be substituted at one or more substitutable positions by one or more groups independently selected from alkyl (for example lower alkyl), alkoxy (preferably lower alkoxy), nitro, monoalkylamino (for example with one to six carbons), dialkylamino (for example with one to six carbons), cyano, halo, haloalkyl (preferably trifluoromethyl), alkanoyl, aminocarbonyl, monoalkylaminocarbonyl, dialkylaminocarbonyl, alkyl amido (for example lower alkyl amido), alkoxyalkyl (for example a lower alkoxy and lower alkyl), alkoxycarbonyl (for example a lower alkoxycarbonyl), alkylcarbonyloxy (for example a lower alkylcarbonyloxy) and aryl (for example phenyl), said aryl being optionally substituted by halo, lower alkyl and lower alkoxy groups. Optional substitution is also indicated by the phrase "substituted with from 0 to X substituents," where X is the maximum number of possible substituents. Certain optionally substituted groups are substituted with from 0 to 2, 3 or 4 independently selected substituents.

A dash ("-") that is not between two letters or symbols is used to indicate a point of attachment for a substituent. For example, —CONH2 is attached through the carbon atom.

A dashed cycle located inside of a heterocyle ring is used to indicate a conjugated system. The bonds between two atoms may be single bond or double bond.

The term "kinase" refers to any enzyme that catalyzes the addition of phosphate groups to a protein residue; for example, serine and threonine kineses catalyze the addition of phosphate groups to serine and threonine residues.

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

The term "pharmaceutically acceptable" refers to the fact that the carrier, diluent or excipient must be compatible with the other ingredients of the formulation and not deleterious to the recipient thereof.

The terms "administration of a compound" or "administering a compound" refer to the act of providing a compound of the invention or pharmaceutical composition comprising a compound of the invention to the subject in need of treatment.

The term "protected" refers that the group is in modified form to preclude undesired side reactions at the protected site. Suitable protecting groups for the compounds of the present invention will be recognized by those skilled in the art in view of the present application, and with reference to standard textbooks, such as Greene, T. W. et al., Protective Groups in Organic Synthesis, John Wiley & Sons, New York (1999).

The term "pharmaceutically acceptable salt" of a compound recited herein is an acid or base salt that is suitable for use in contact with the tissues of human beings or animals without excessive toxicity or carcinogenicity, and, for example, without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$-COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is suitable. It will be apparent that each compound of Formula I may, but need not, be formulated as a hydrate, solvate or non-covalent complex. In addition, the various crystal forms and polymorphs are within the scope of the present invention.

In one embodiment, Formula (I) is in the form of (Ia) as below:

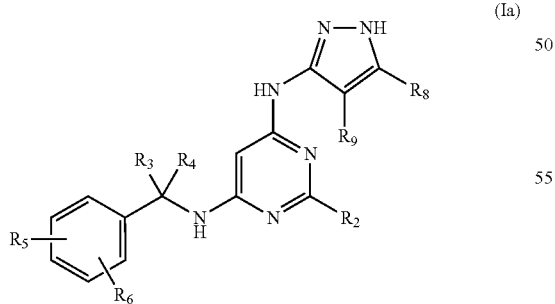

(Ia)

or a pharmaceutically acceptable salt thereof, wherein:
$R_2$ represents hydrogen, $NH_2$ and $C_1$-$C_4$ alkyl.
$R_3$ and $R_4$ respectively represent hydrogen, CN, $C_1$-$C_4$ alkyl, cycloalkyl, hydroxy, a 4- to 7-membered heterocycle, $C_1$-$C_6$ alkoxy, and $C_1$-$C_6$ alkoxycarbonyl, each of which is substituted with from 0 to 4 substituents independently chosen from halogen, hydroxy, cyano, amino, —COOH and oxo, wherein, optionally, $R_3$ and $R_4$ together form a cycloalkyl or heterocycle ring.

$R_5$ and $R_6$ respectively represent hydrogen, F, Cl, Br, I, CN, $CF_3$, $CF_2H$, $CFH_2$, $C_1$-$C_4$ alkyl, $C_1$-$C_6$ alkoxy, $C_2$-$C_6$ alkenyl, $C_2$-$C_6$ alkynyl, $N(R_{10})R_{11}$ and $CON(R_{10})R_{11}$.

$R_8$ represents hydrogen, CN, $CF_3$, $CF_2H$, $CFH_2$, $N(R_{10})R_{11}$, $CON(R_{10})R_{11}$, $C_1$-$C_4$ alkyl, $C_1$-$C_6$ alkoxy, $C_2$-$C_6$ alkenyl, $C_2$-$C_6$ alkynyl, $C_3$-$C_{10}$ aryl or heteroaryl, $C_3$-$C_7$ cycloalkyl, $(C_3$-$C_7$cycloalkyl)$C_1$-$C_4$ alkyl, $C_1$-$C_6$ haloalkyl, $C_1$-$C_6$ alkylthio, $C_2$-$C_6$ alkanoyl, $C_1$-$C_6$ alkoxycarbonyl, $C_2$-$C_6$ alkanoyloxy, mono- and di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- and di-($C_1$-$C_6$ alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH and oxo.

$R_9$ represents hydrogen, halogen, CN, $C_1$-$C_4$ alkyl, $C_1$-$C_6$ alkoxy, $C_2$-$C_6$ alkenyl, $C_2$-$C_6$ alkynyl, $N(R_{10})R_{11}$ and $CON(R_{10})R_{11}$.

$R_{10}$ and $R_{11}$ are independently selected from hydrogen, $C_1$-$C_4$ alkyl, $C_2$-$C_6$ alkenyl, $C_2$-$C_6$ alkynyl, each of which is substituted with from 0 to 4 substituents independently chosen from halogen, hydroxy, cyano, amino, —COOH and oxo.

In another embodiment, Formula (I) is in the form of (Ib) as below:

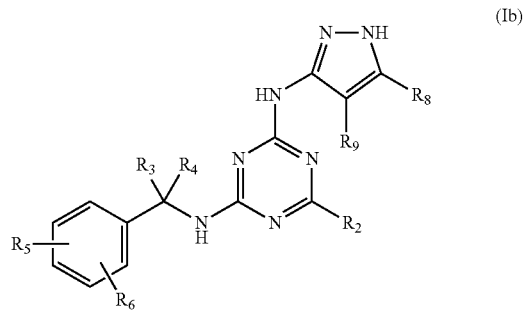

(Ib)

or a pharmaceutically acceptable salt thereof, wherein:
$R_2$ represents hydrogen, $NH_2$ and $C_1$-$C_4$ alkyl.
$R_3$ and $R_4$ respectively represent hydrogen, CN, $C_1$-$C_4$ alkyl, cycloalkyl, hydroxy, a 4- to 7-membered heterocycle, $C_1$-$C_6$ alkoxy, and $C_1$-$C_6$ alkoxycarbonyl, each of which is substituted with from 0 to 4 substituents independently chosen from halogen, hydroxy, cyano, amino, —COOH and oxo, wherein, optionally, $R_3$ and $R_4$ together form a cycloalkyl or heterocycle ring.

$R_5$ and $R_6$ respectively represent hydrogen, F, Cl, Br, I, CN, $CF_3$, $CF_2H$, $CFH_2$, $C_1$-$C_4$ alkyl, $C_1$-$C_6$ alkoxy, $C_2$-$C_6$ alkenyl, $C_2$-$C_6$ alkynyl, $N(R_{10})R_{11}$ and $CON(R_{10})R_{11}$.

$R_8$ represents hydrogen, CN, $CF_3$, $CF_2H$, $CFH_2$, $N(R_{10})R_{11}$, $CON(R_{10})R_{11}$, $C_1$-$C_4$ alkyl, $C_1$-$C_6$ alkoxy, $C_2$-$C_6$ alkenyl, $C_2$-$C_6$ alkynyl, $C_3$-$C_{10}$ aryl or heteroaryl, $C_3$-$C_7$ cycloalkyl, ($C_3$-$C_7$cycloalkyl)$C_1$-$C_4$ alkyl, $C_1$-$C_6$ haloalkyl, $C_1$-$C_6$ alkylthio, $C_2$-$C_6$ alkanoyl, $C_1$-$C_6$ alkoxycarbonyl, $C_2$-$C_6$ alkanoyloxy, mono- and di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- and di-($C_1$-$C_6$ alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH and oxo.

$R_9$ represents hydrogen, halogen, CN, $C_1$-$C_4$ alkyl, $C_1$-$C_6$ alkoxy, $C_2$-$C_6$ alkenyl, $C_2$-$C_6$ alkynyl, N($R_{10}$)$R_{11}$ and CON($R_{10}$)$R_{11}$.

$R_{10}$ and $R_{11}$ are independently selected from hydrogen, $C_1$-$C_4$ alkyl, $C_2$-$C_6$ alkenyl, $C_2$-$C_6$ alkynyl, each of which is substituted with from 0 to 4 substituents independently chosen from halogen, hydroxy, cyano, amino, —COOH and oxo.

Examples of X of formula (I) are: F, Cl, Br, CN, $CF_3$, $CF_2H$, $CFH_2$, $CH_3$, $OCH_3$, $NH_2$ Examples of the pyrazole fragment of formula (I) are listed below:

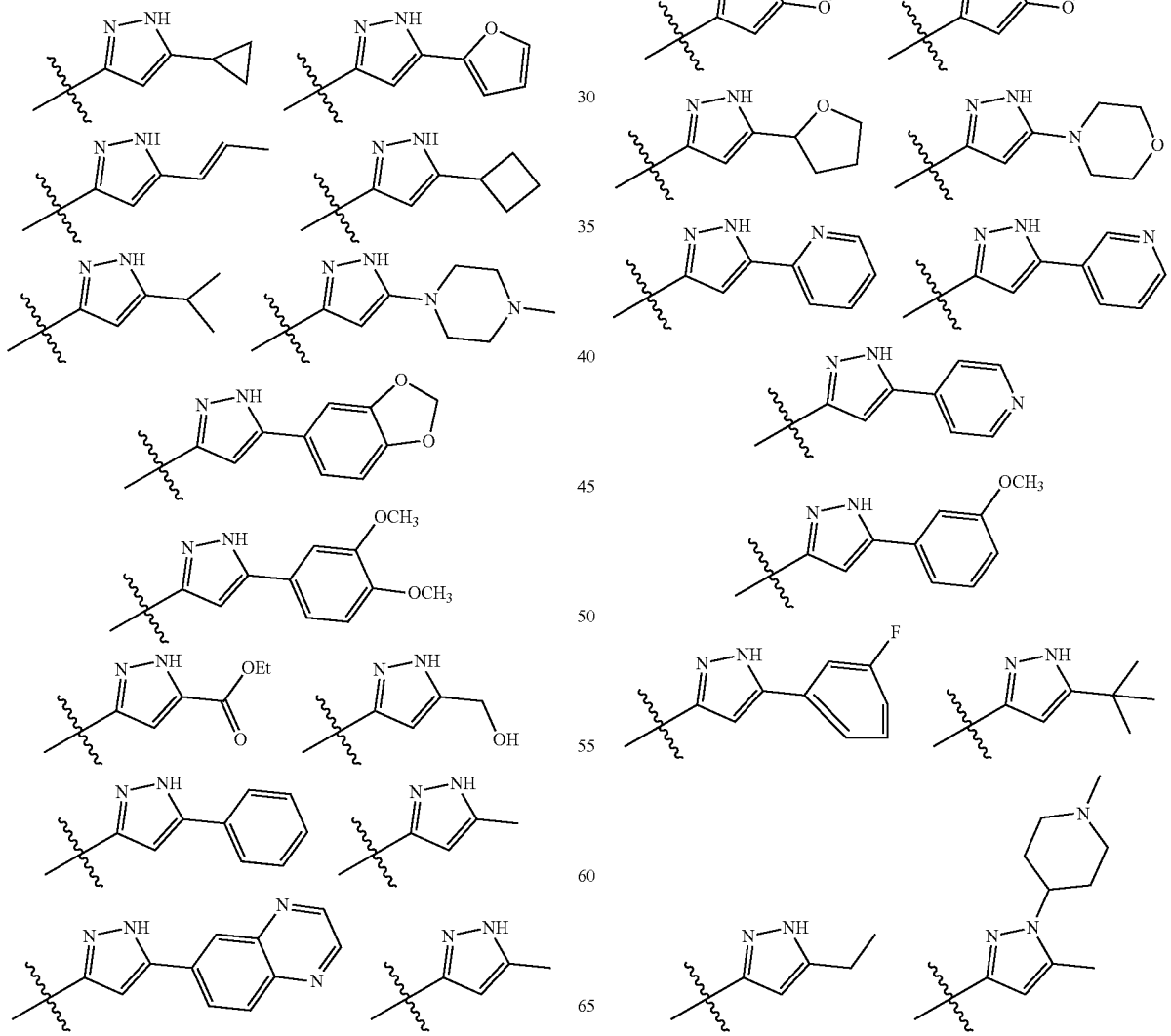

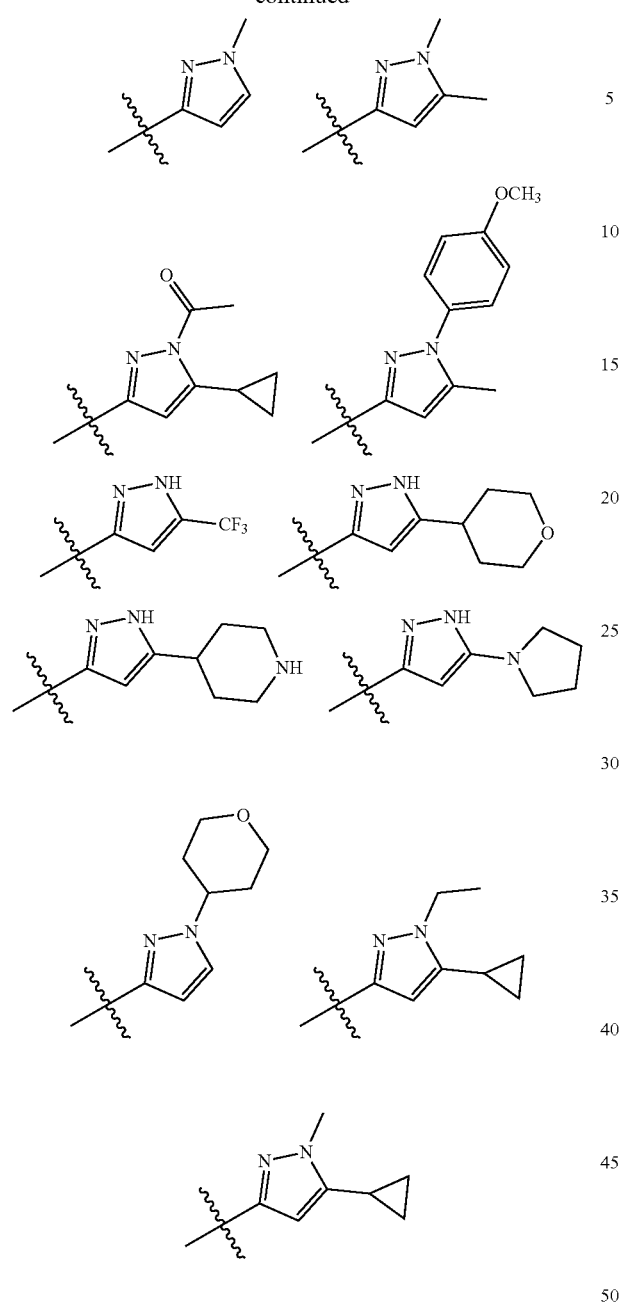
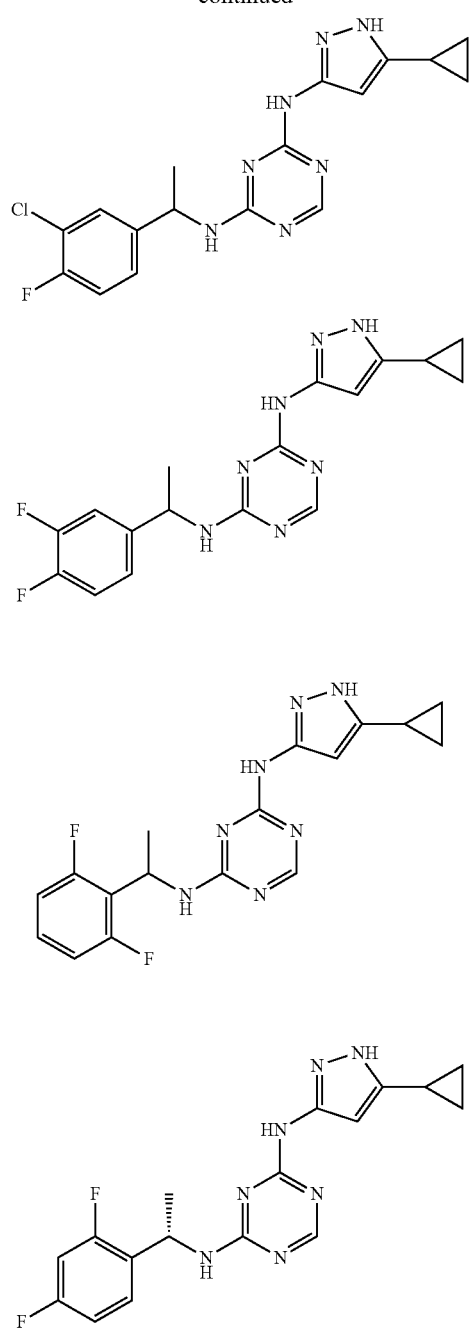
Examples of specific compounds of the present invention are those compounds defined in the following:
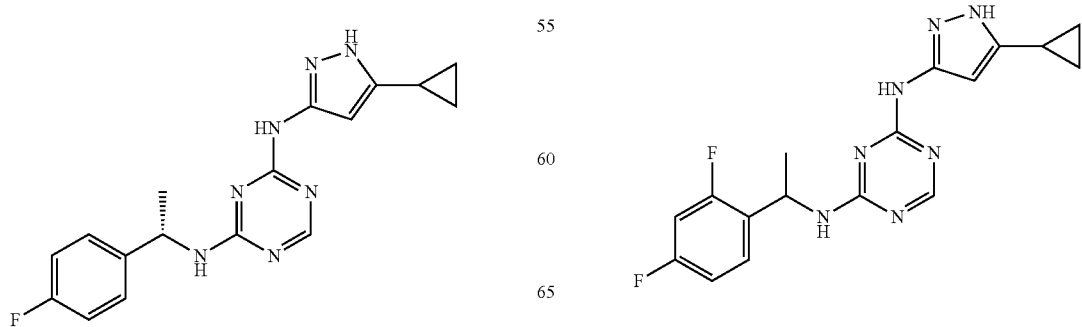

-continued
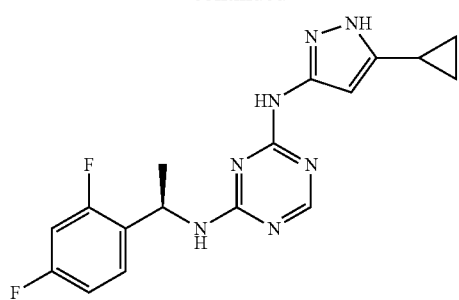 [SMILES: C[C@@H](Nc1ncnc(Nc2cc(C3CC3)[nH]n2)n1)c1ccc(F)cc1F]
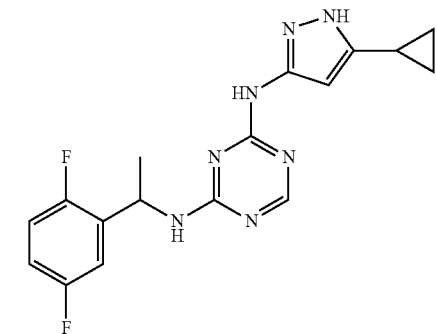
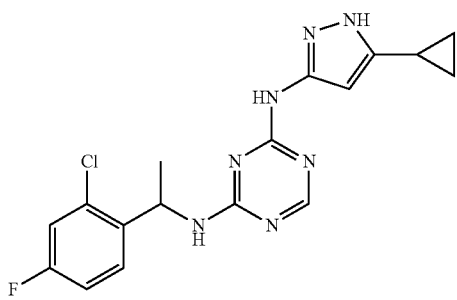
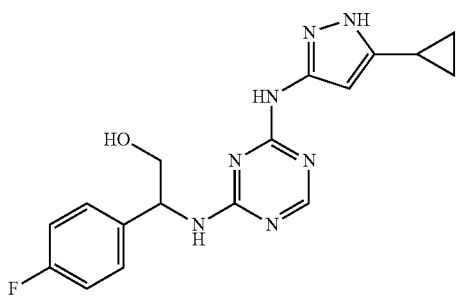
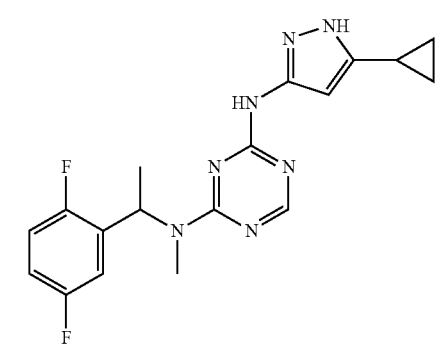
-continued
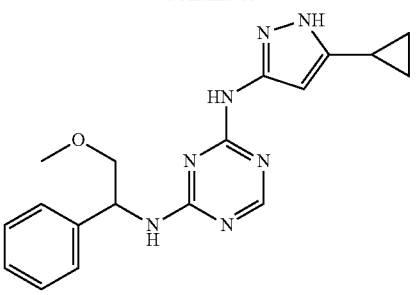
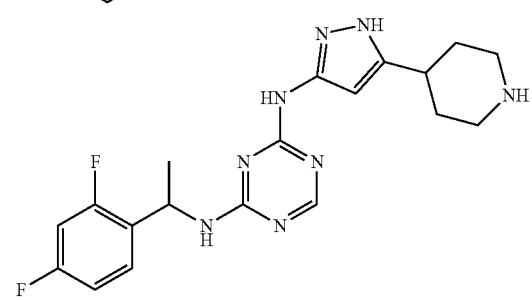
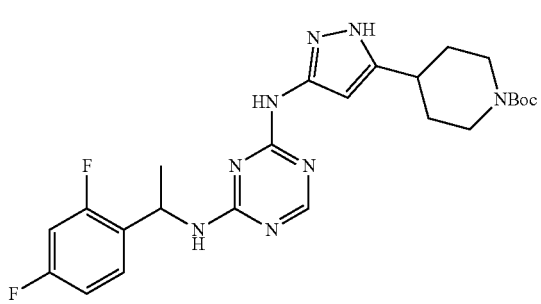
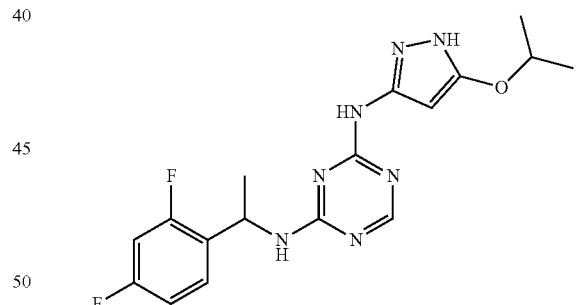
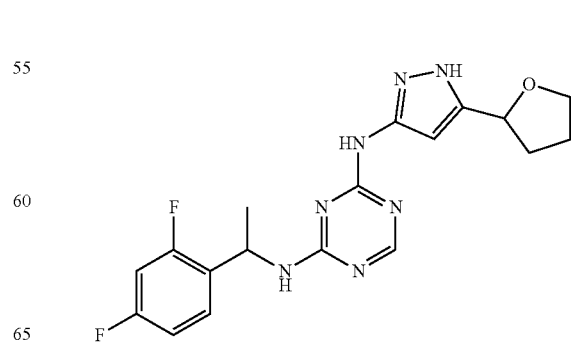

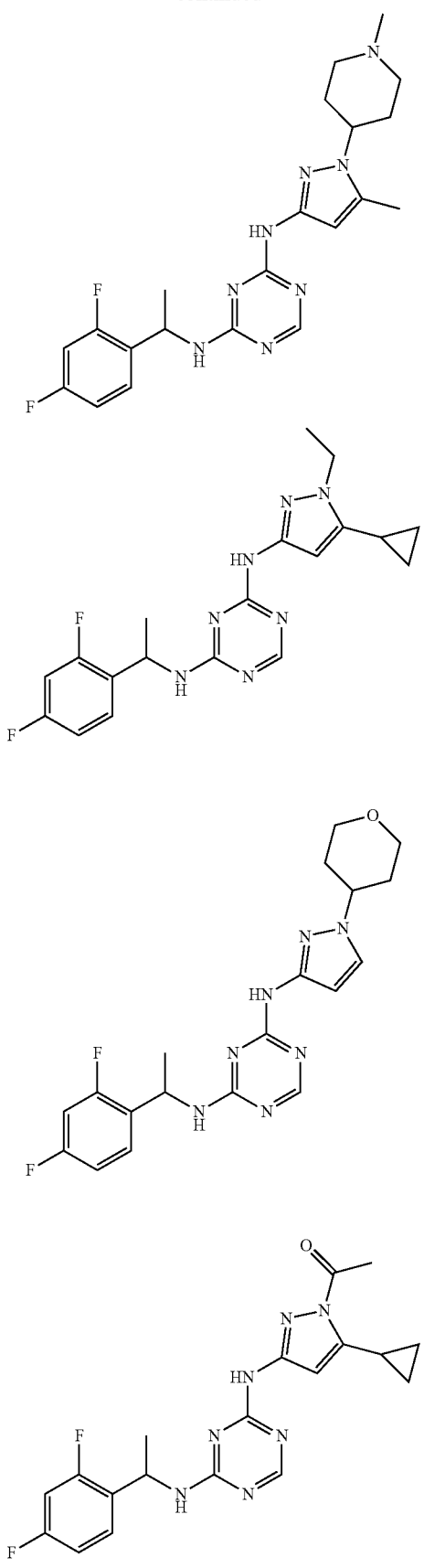
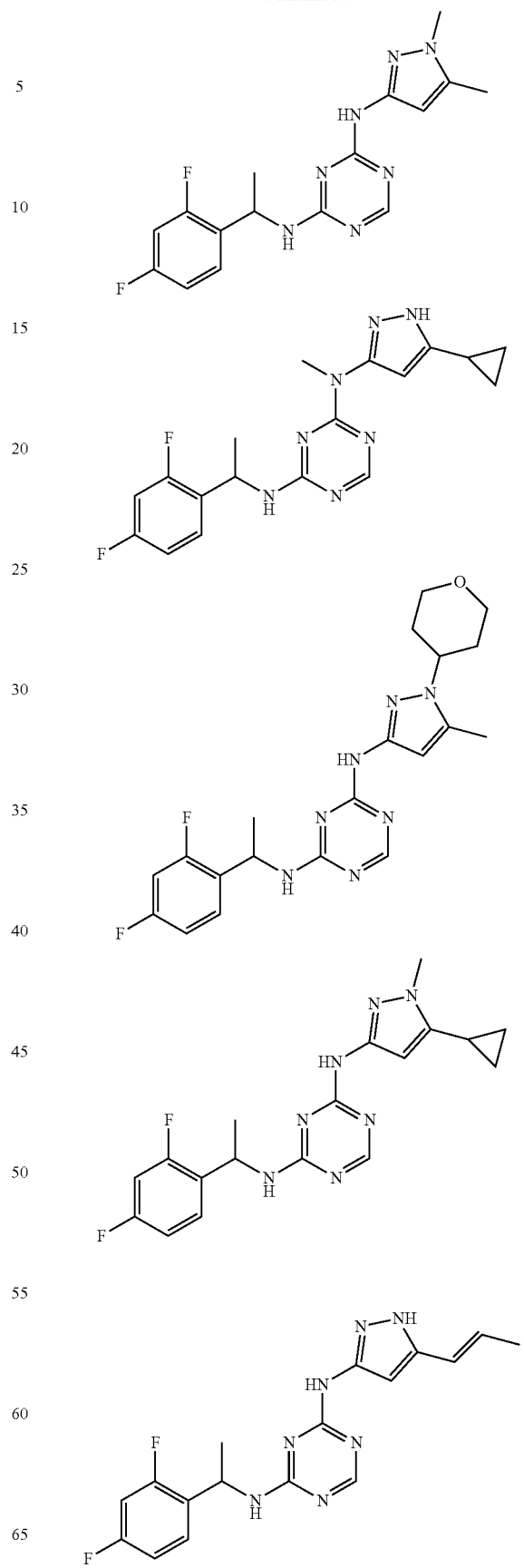

-continued
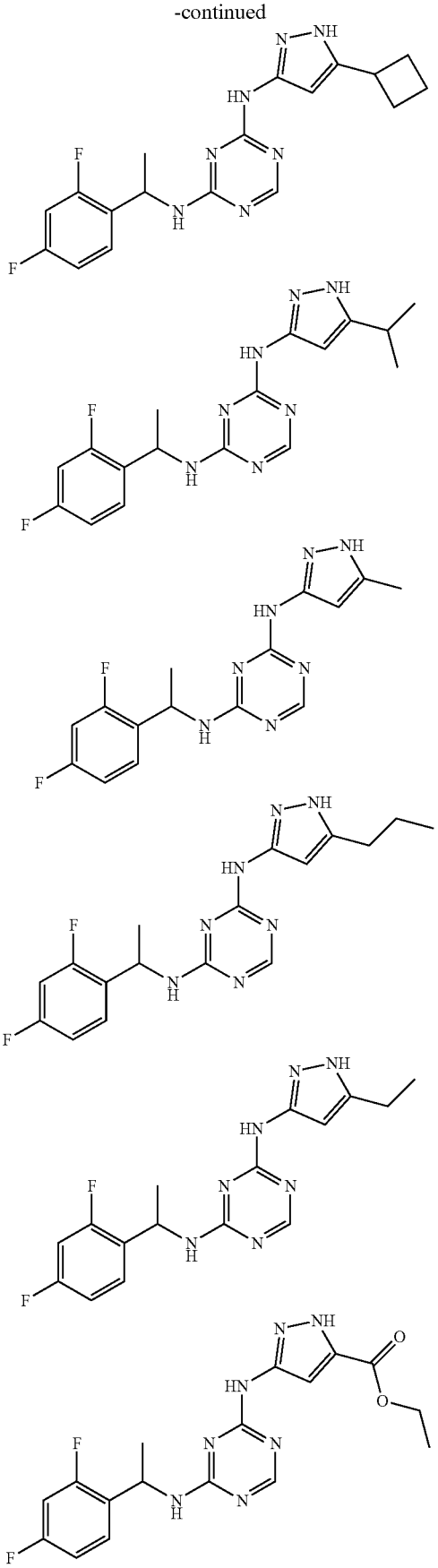
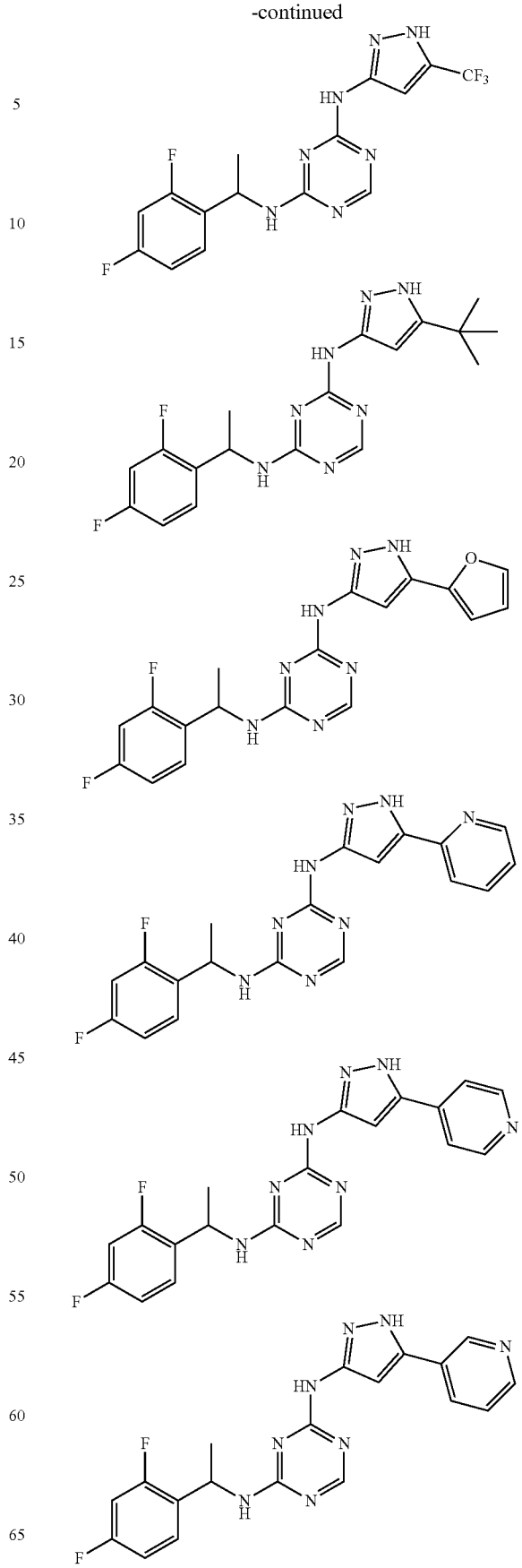

19
-continued
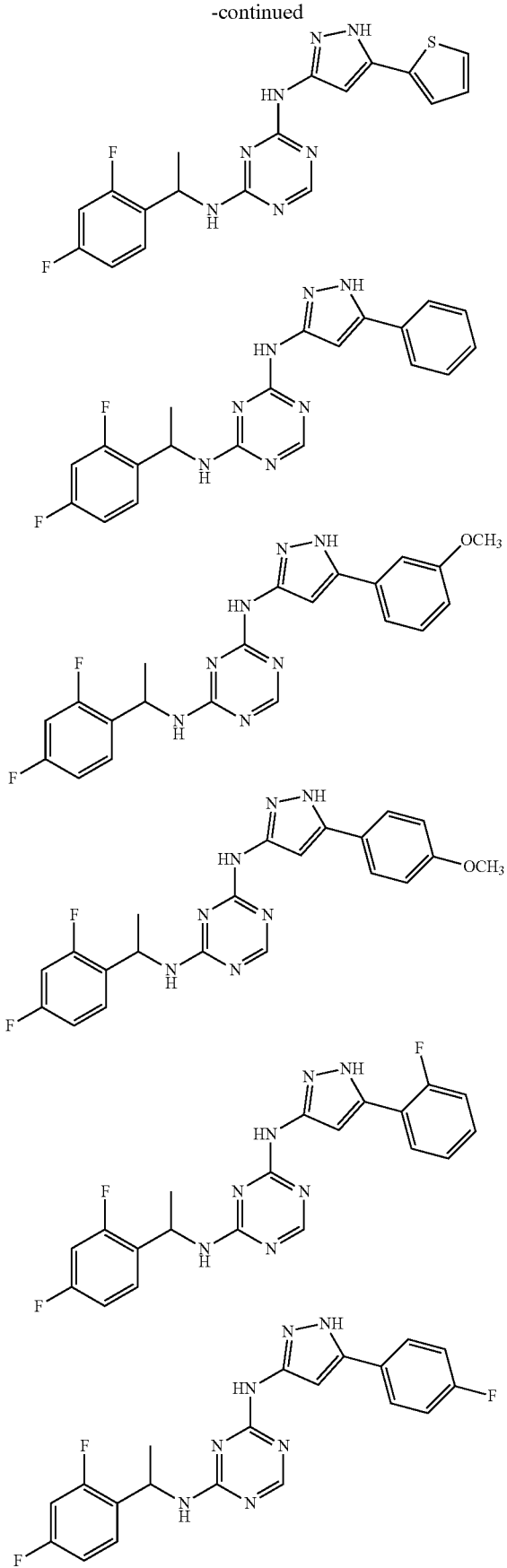
20
-continued
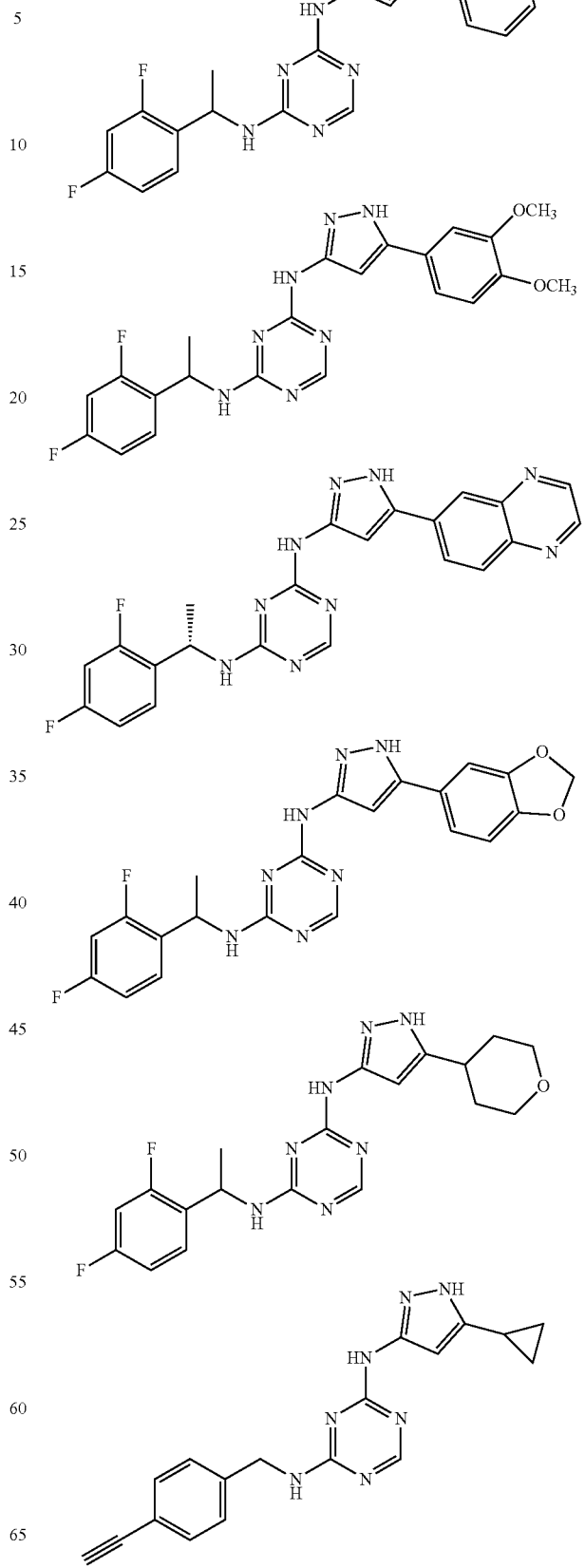

-continued
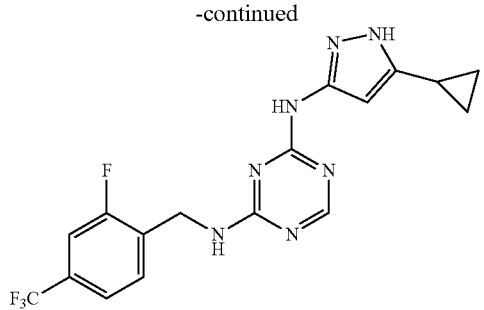
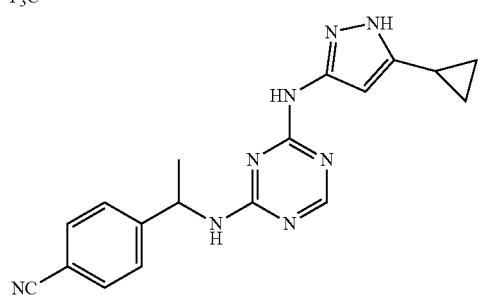
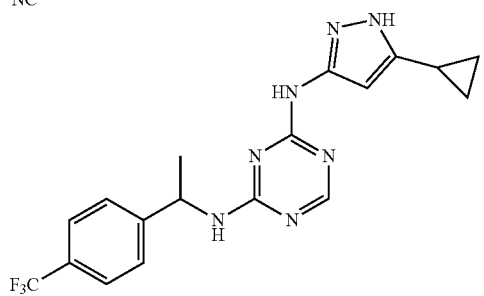
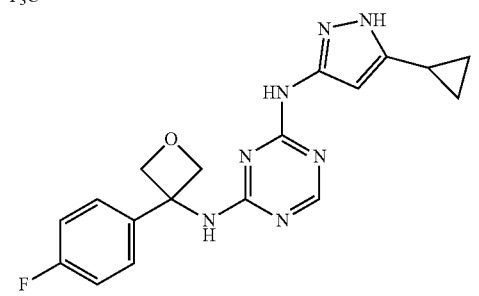
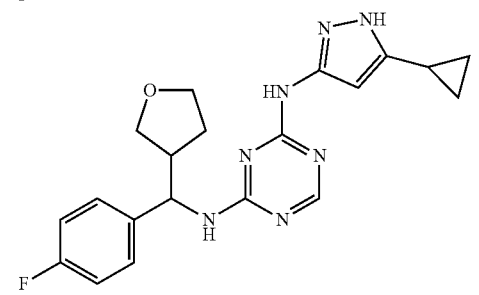
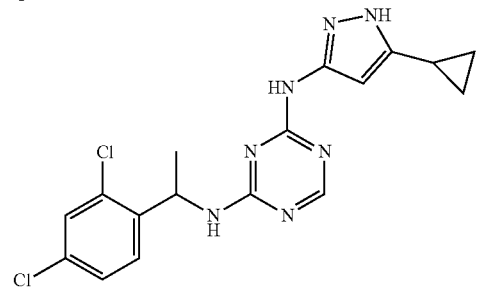
-continued
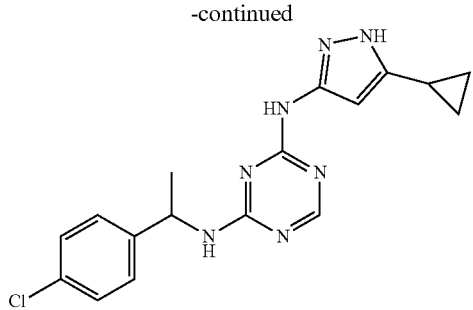
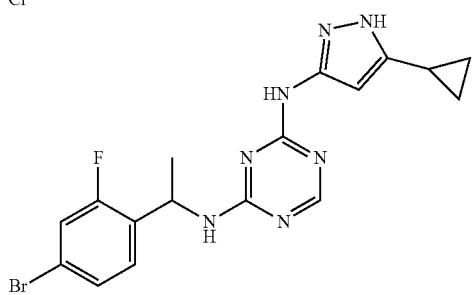
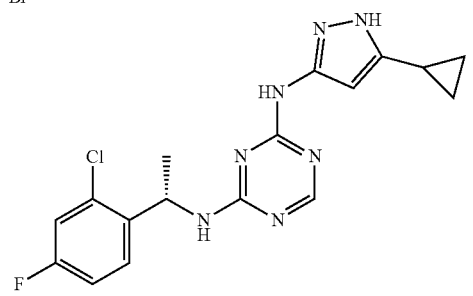
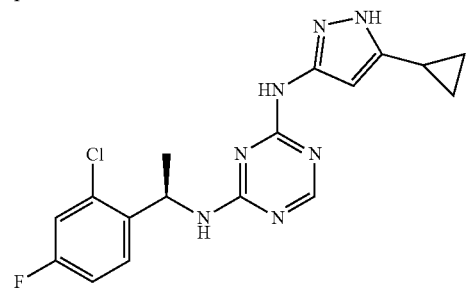
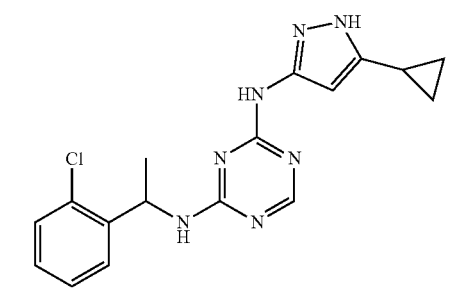
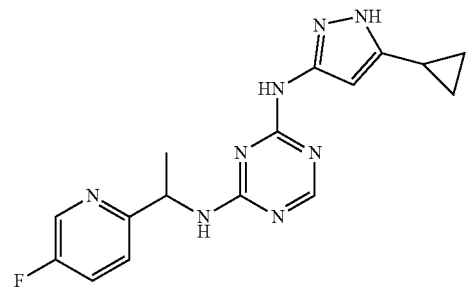

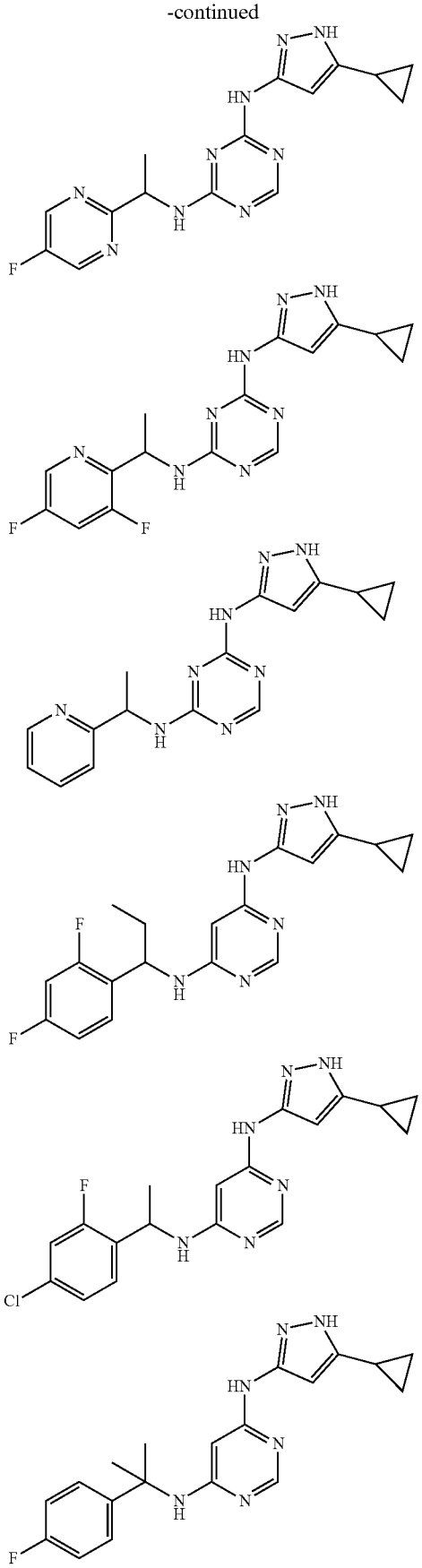
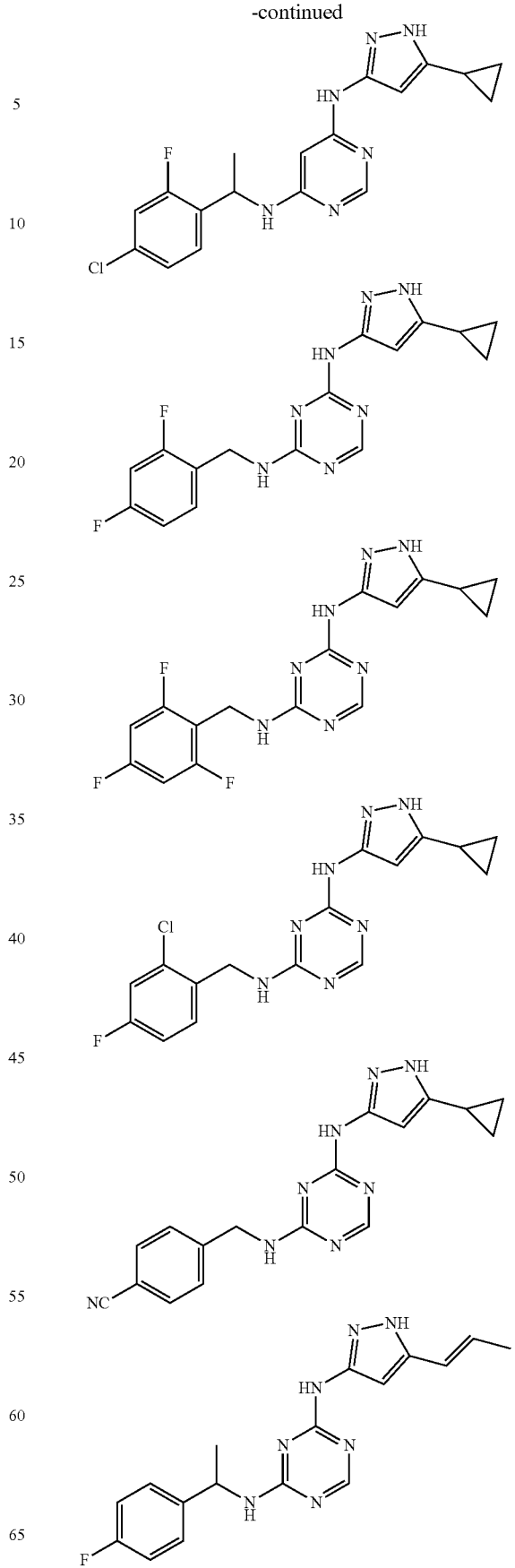

-continued
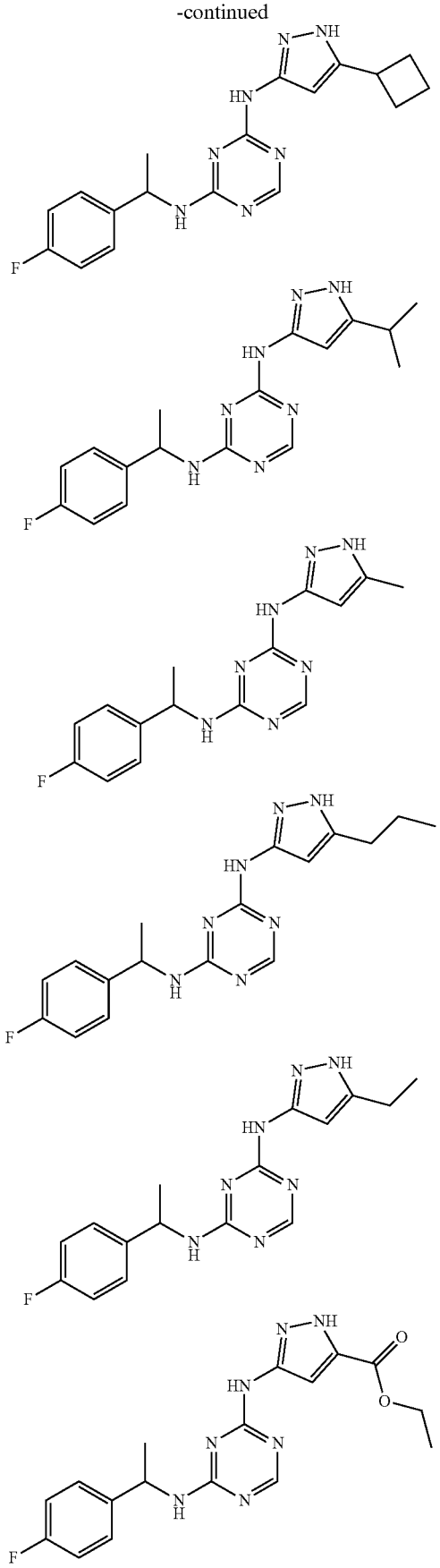
-continued
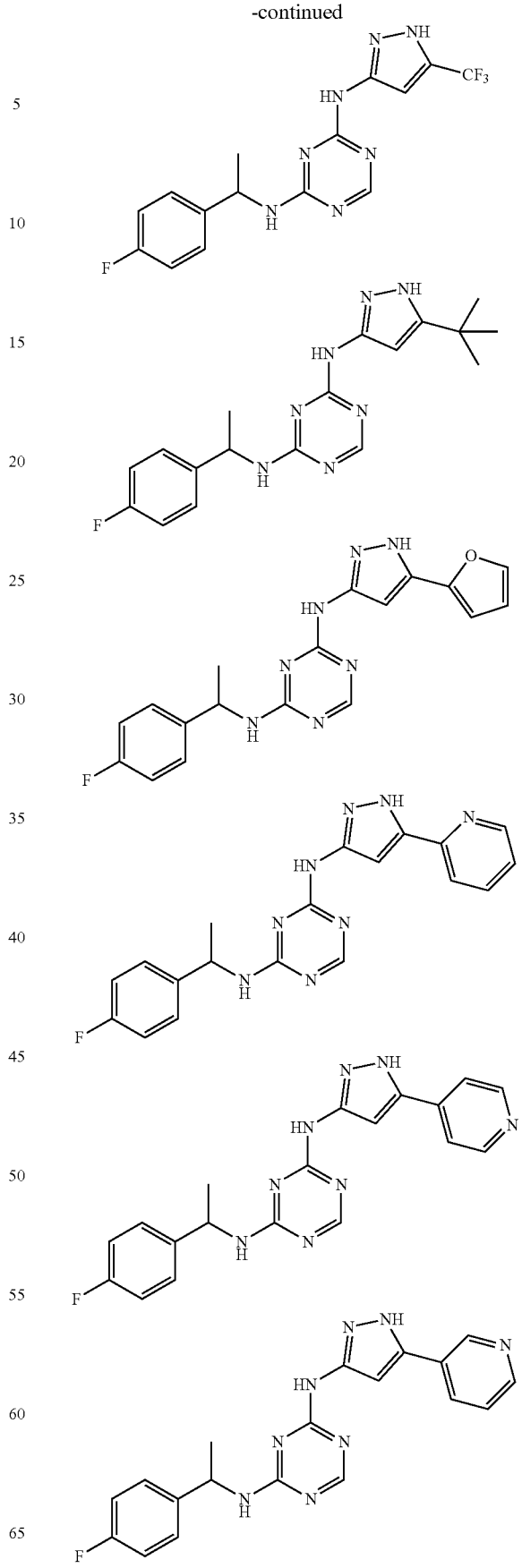

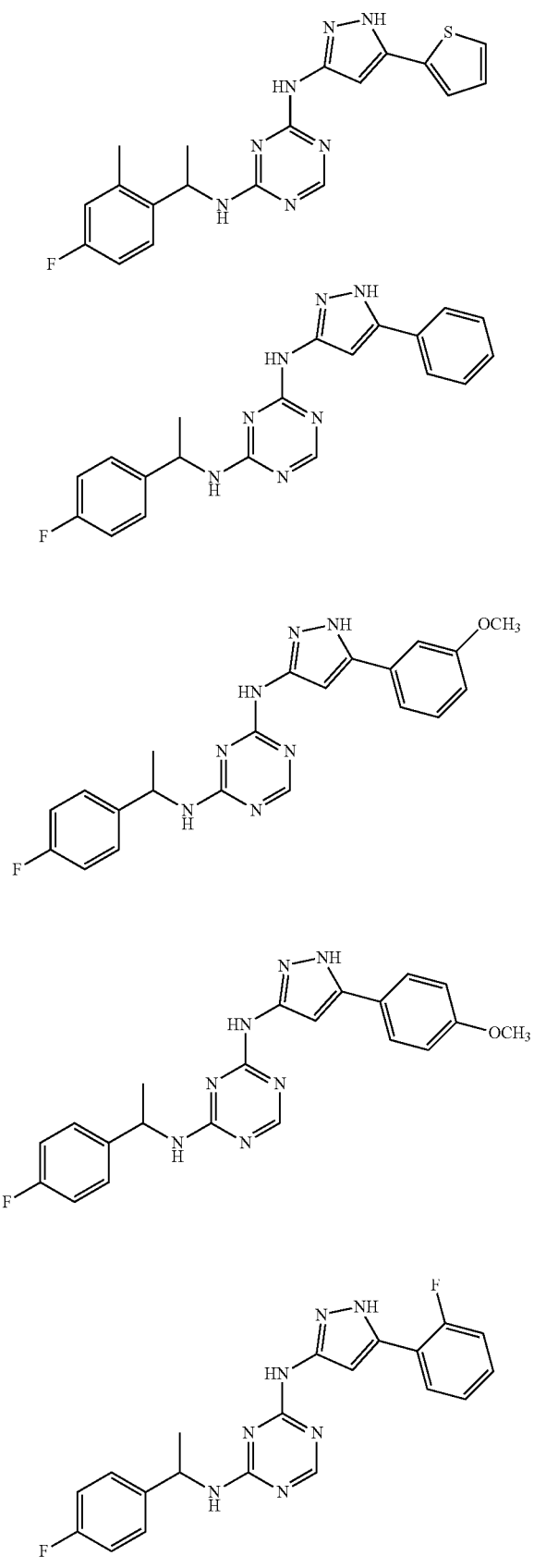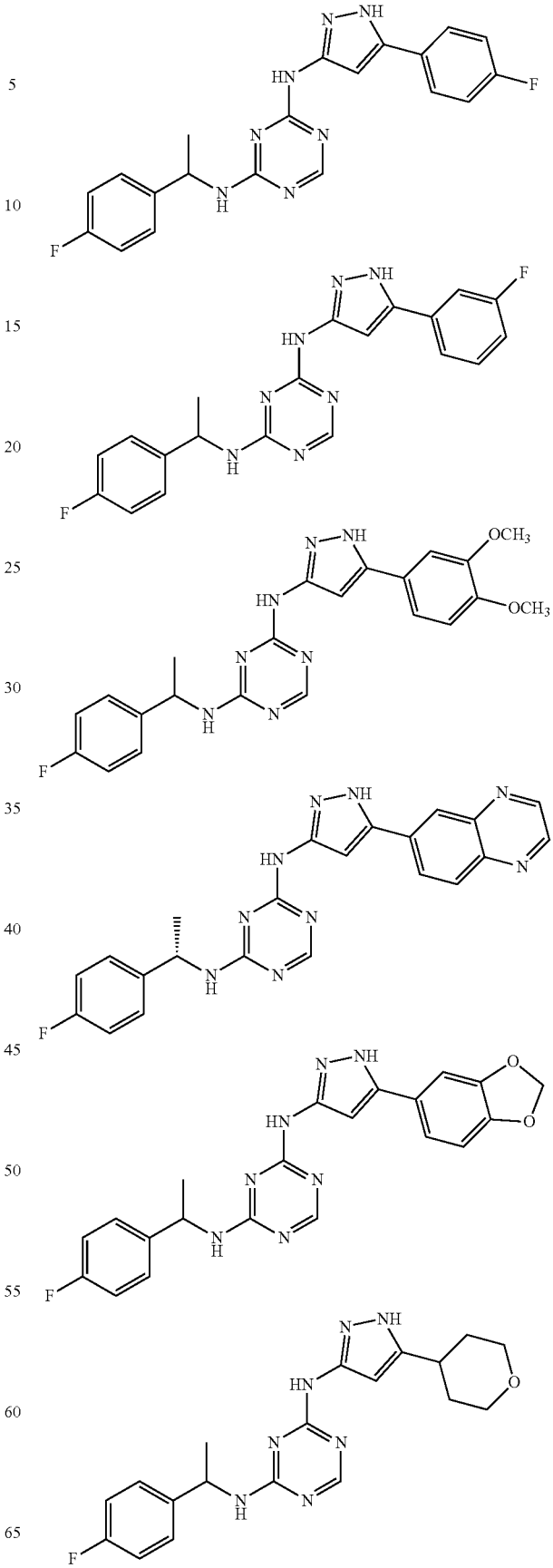

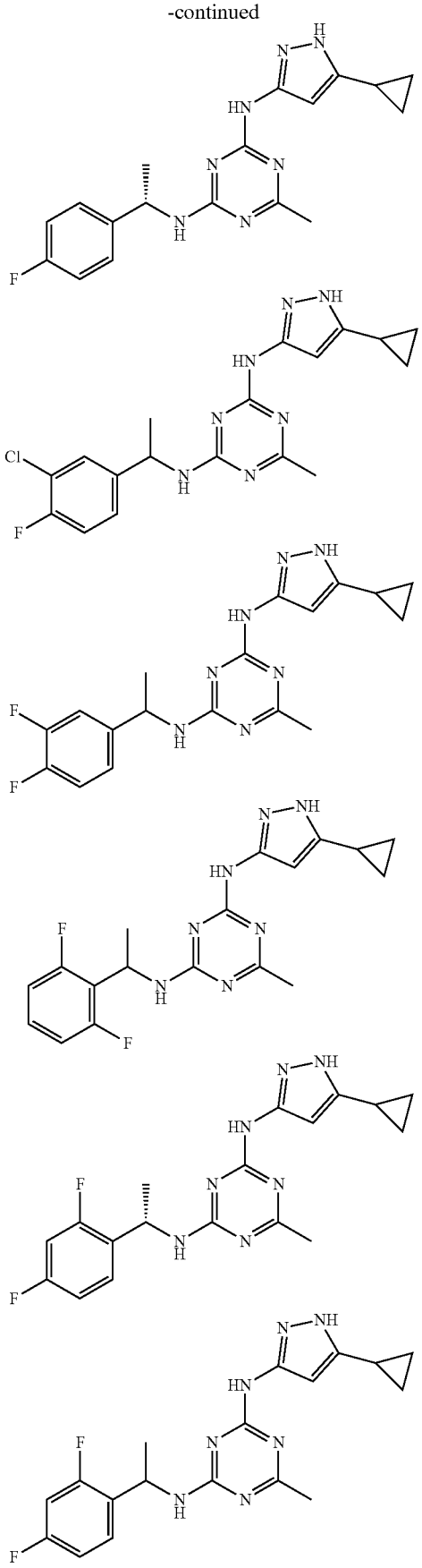
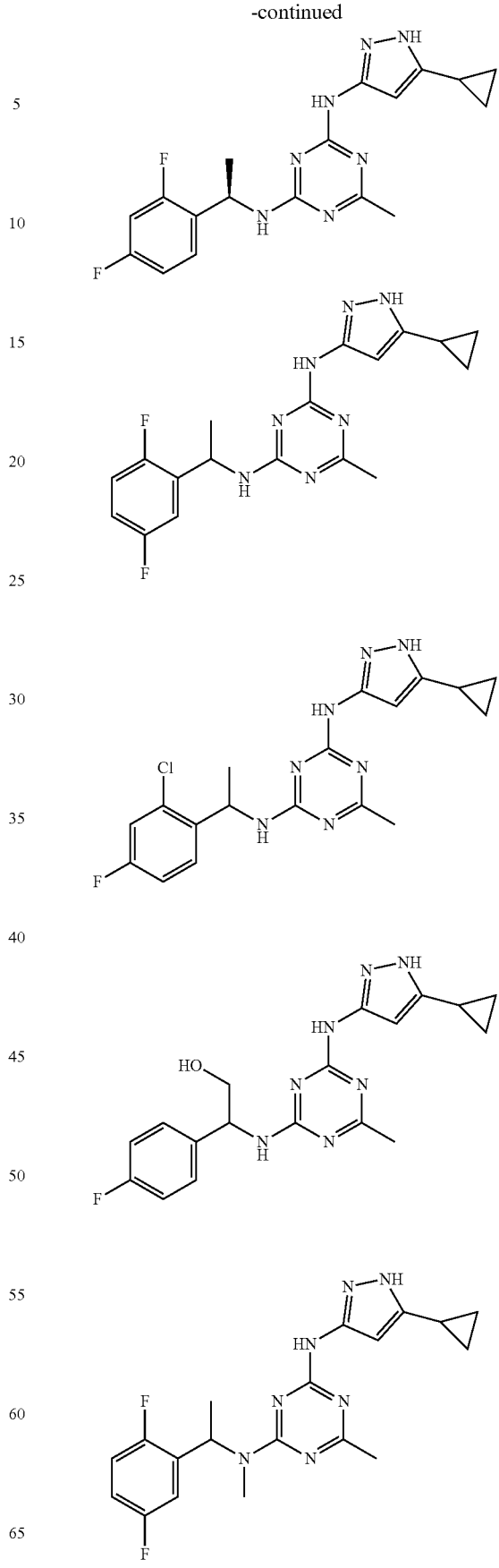

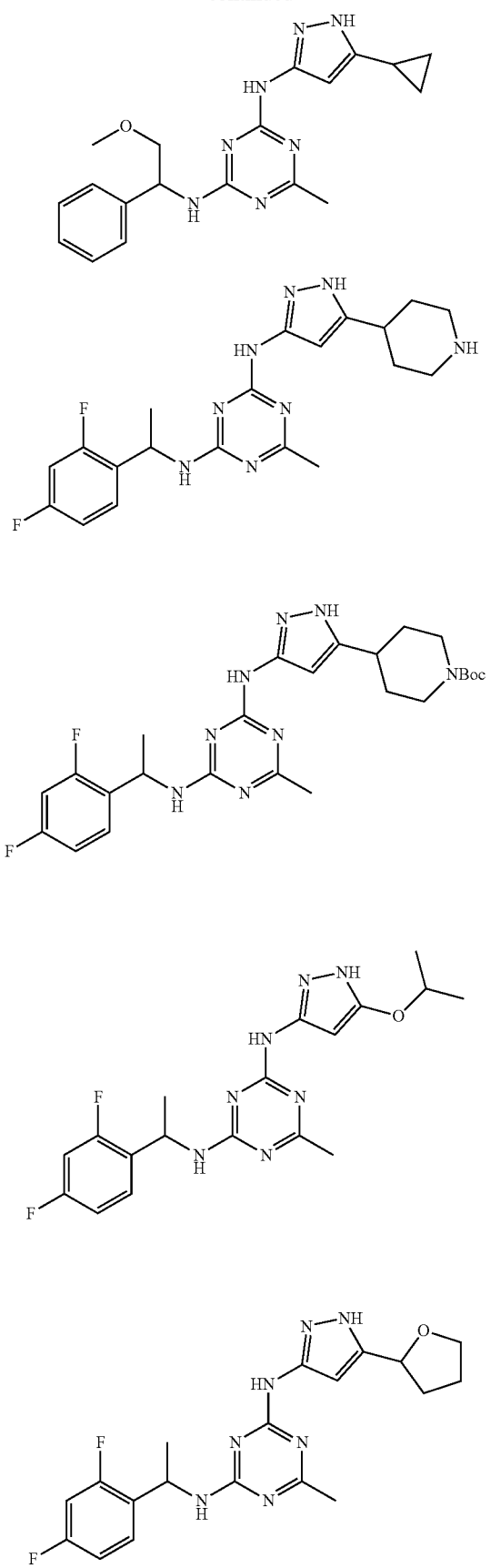
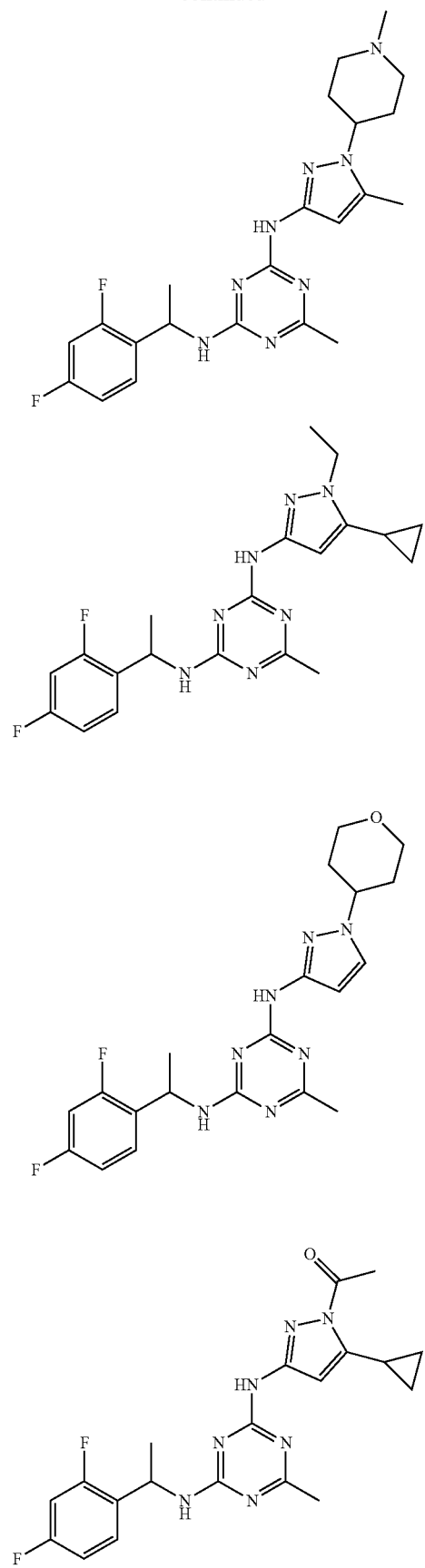

-continued
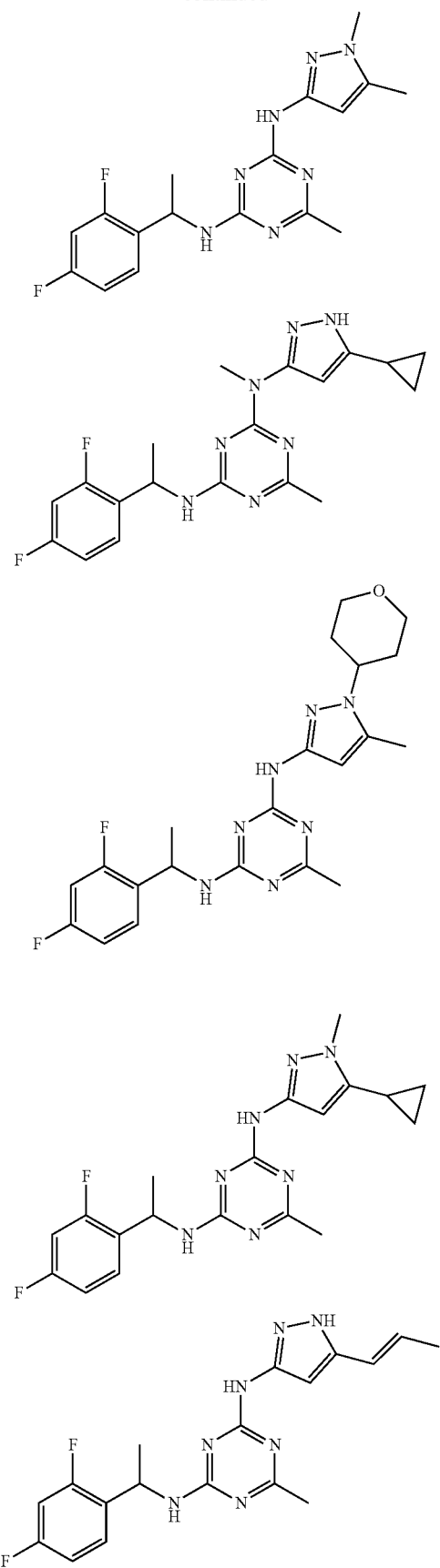
-continued
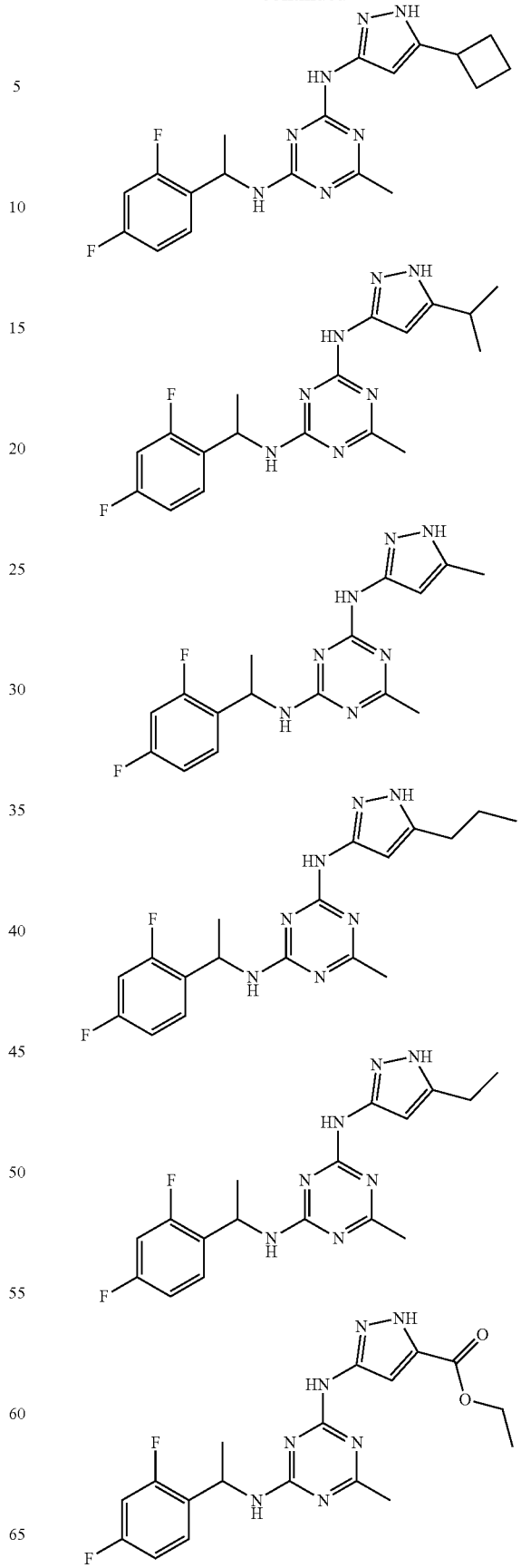

-continued
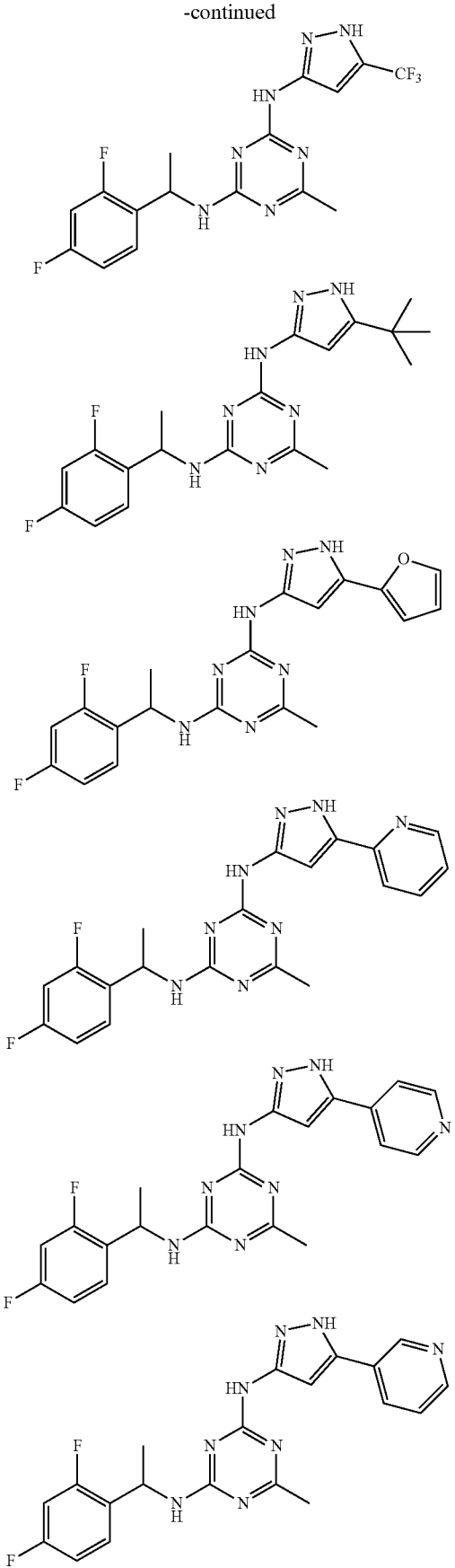
-continued
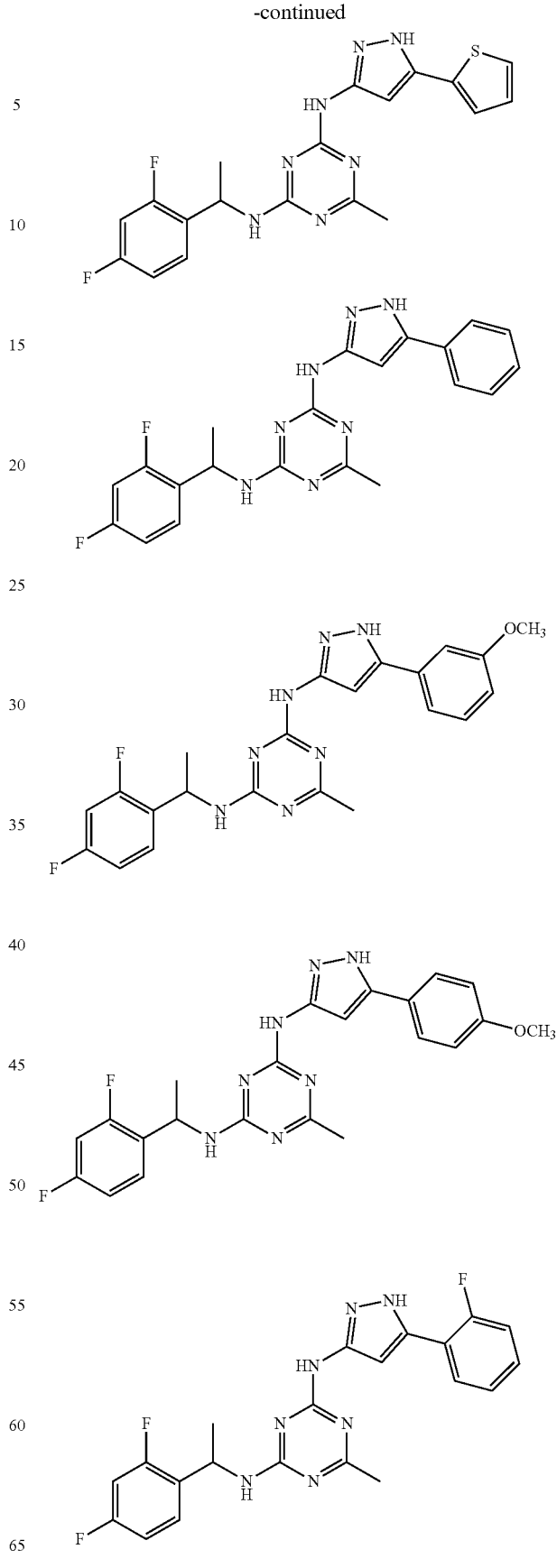

37
-continued
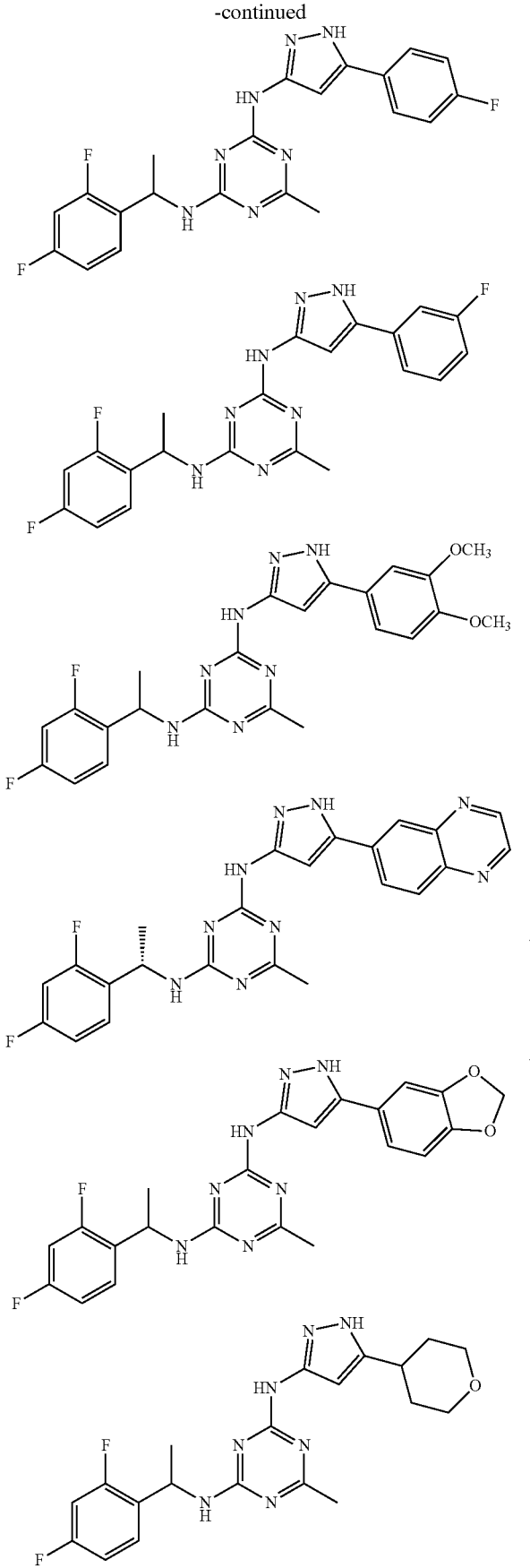
38
-continued
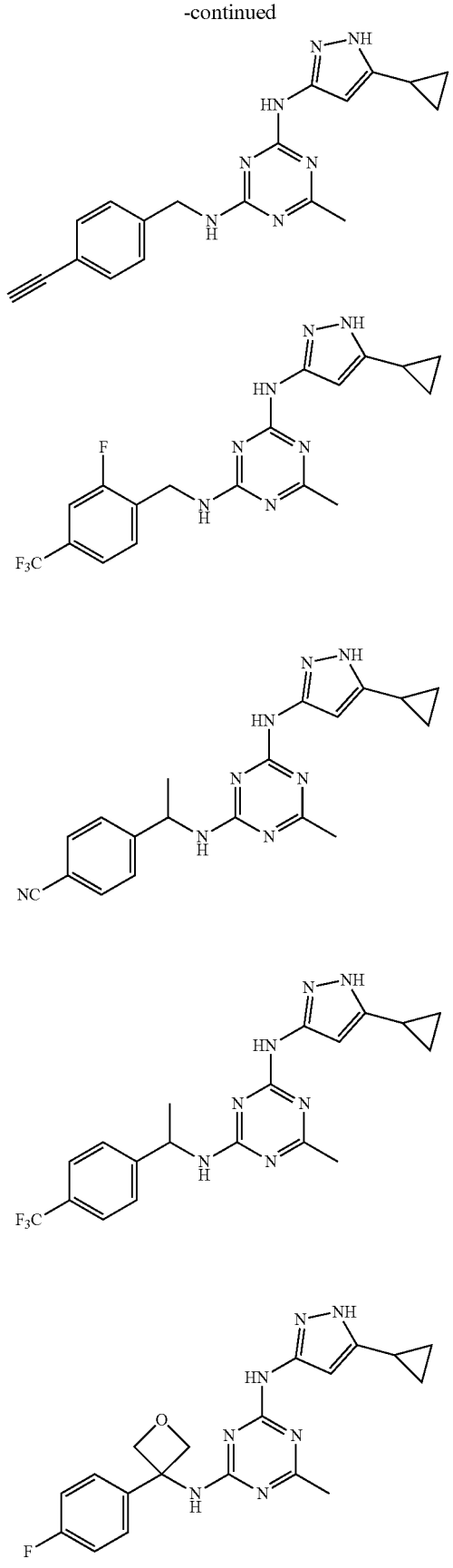

-continued
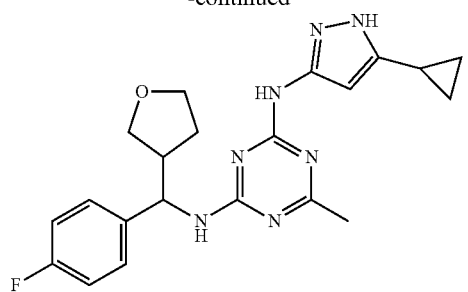
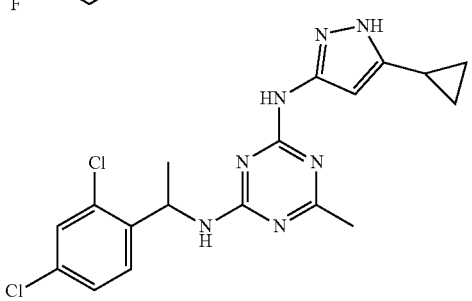
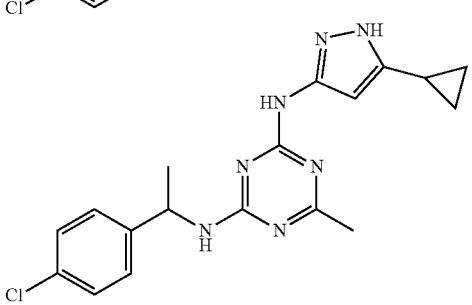
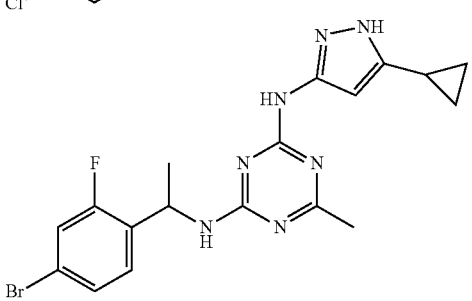
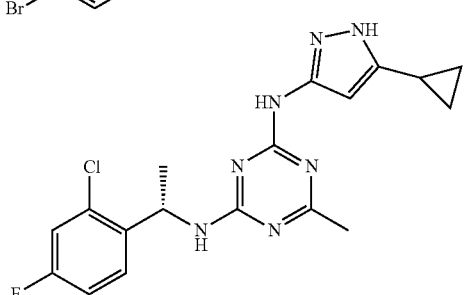
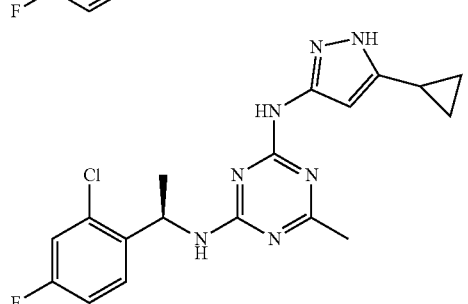
-continued
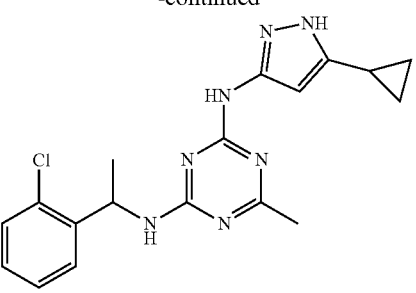
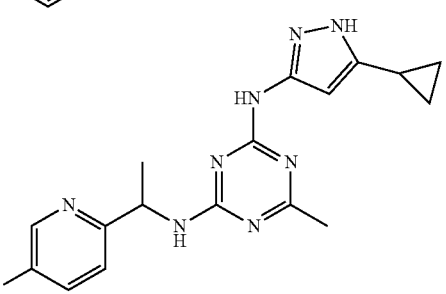
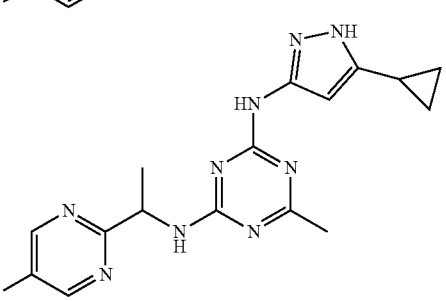
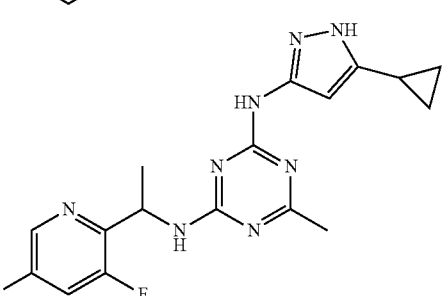
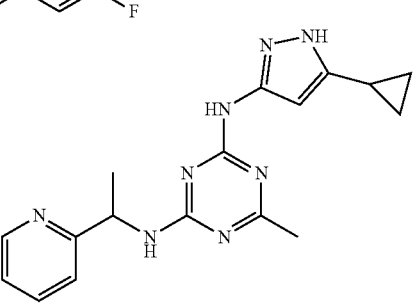
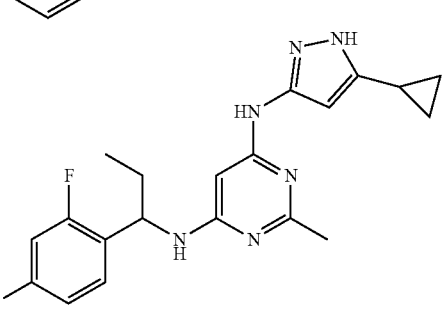

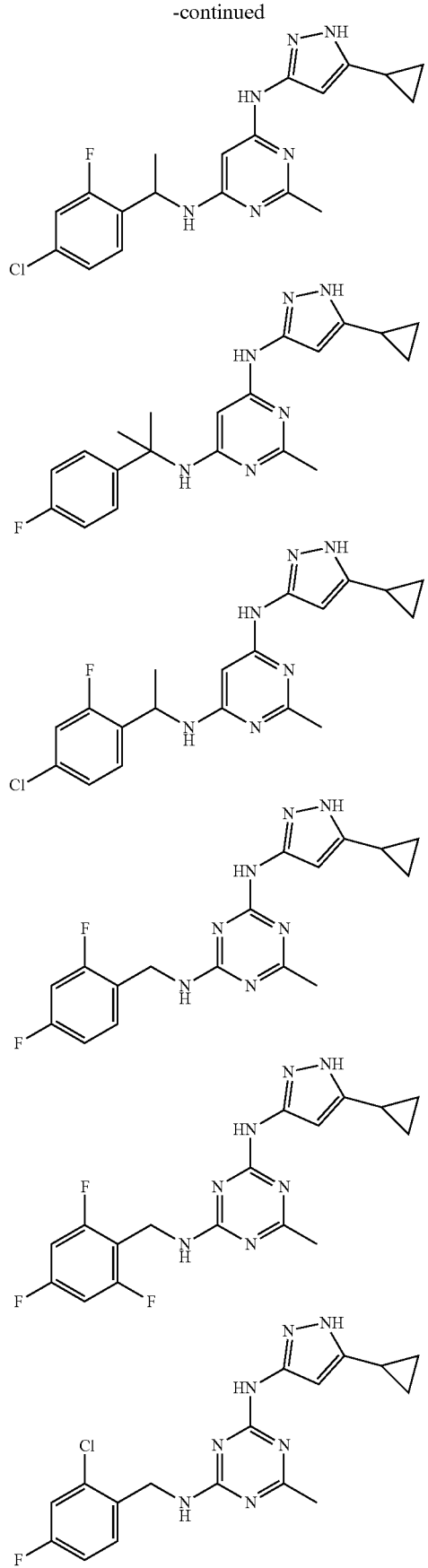
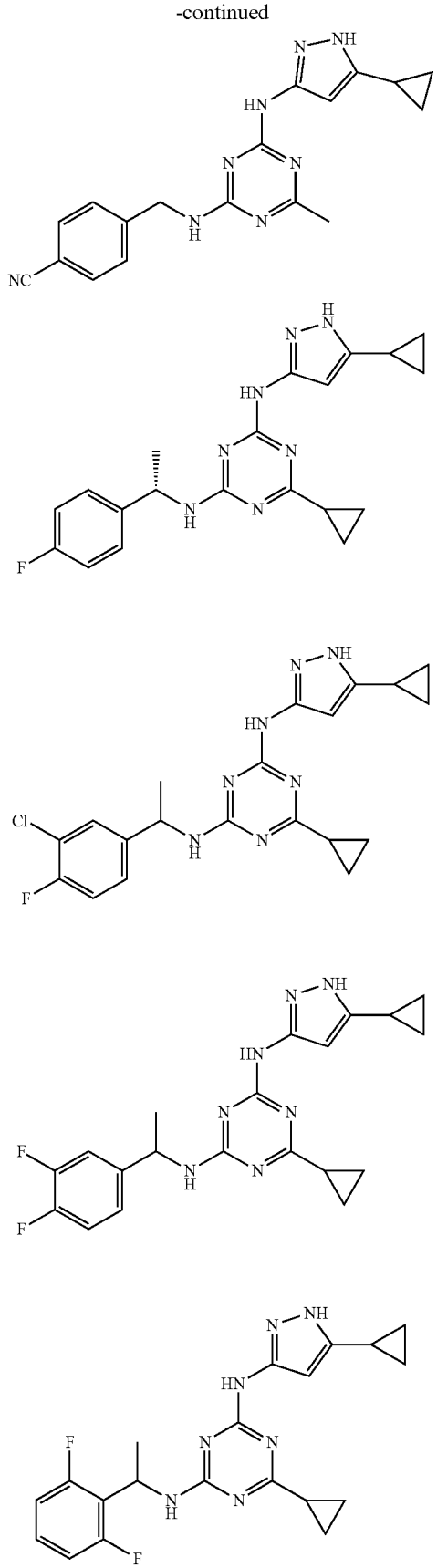

-continued
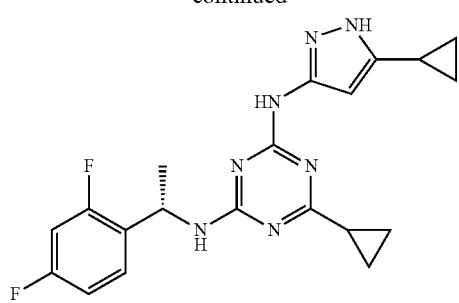
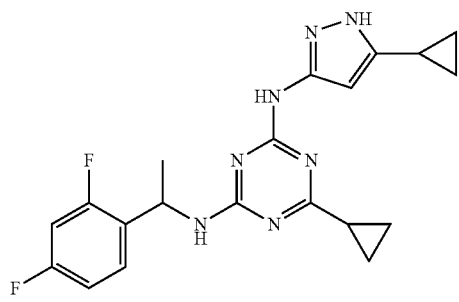
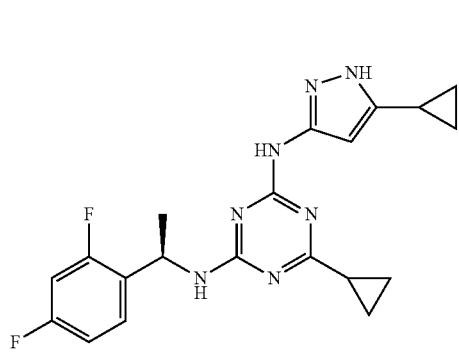
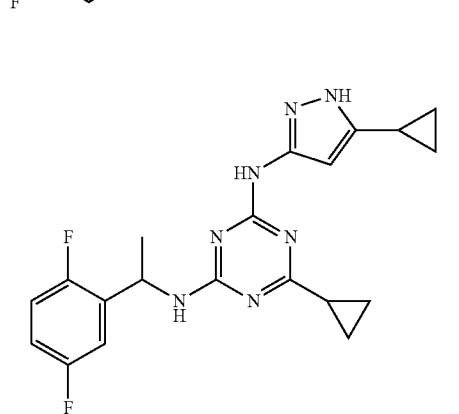
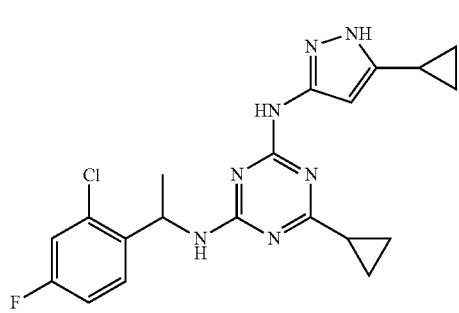 [SMILES: C[C@H](Nc1nc(Nc2cc(C3CC3)[nH]n2)nc(C2CC2)n1)c1ccc(F)cc1F]
-continued
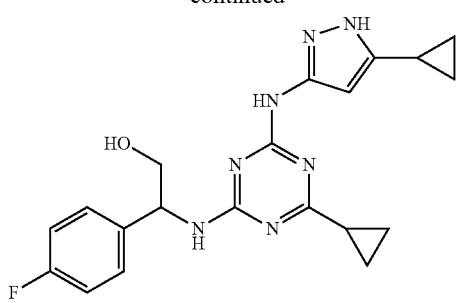
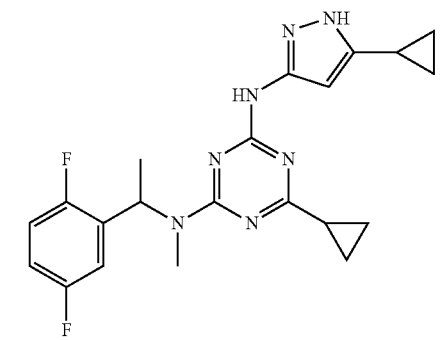
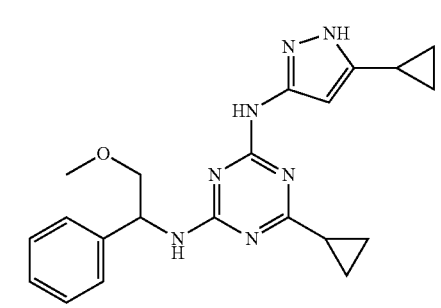
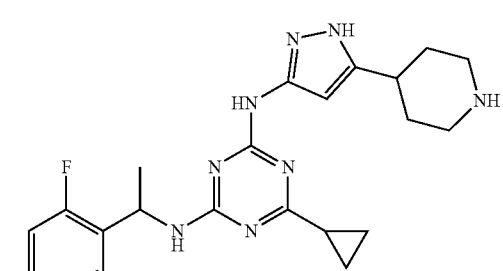
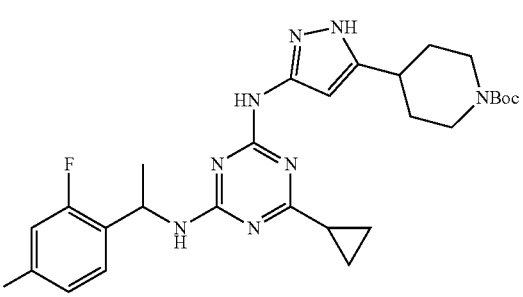

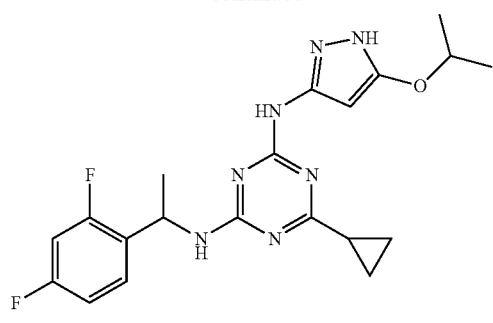
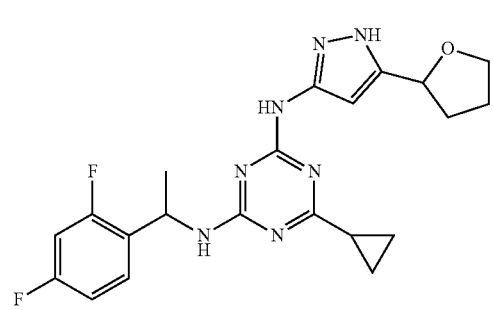
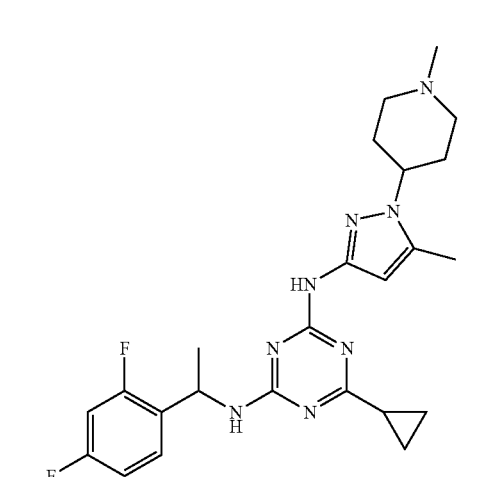
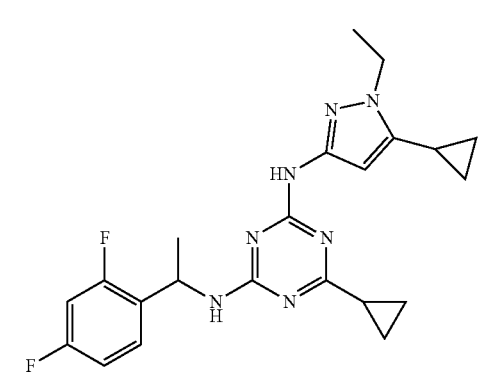
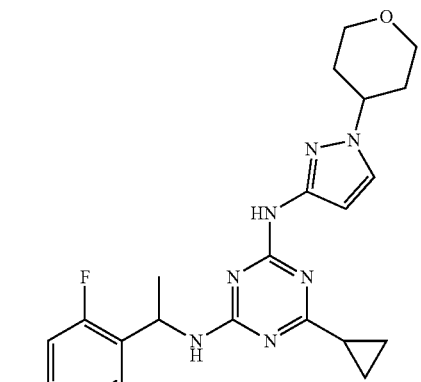

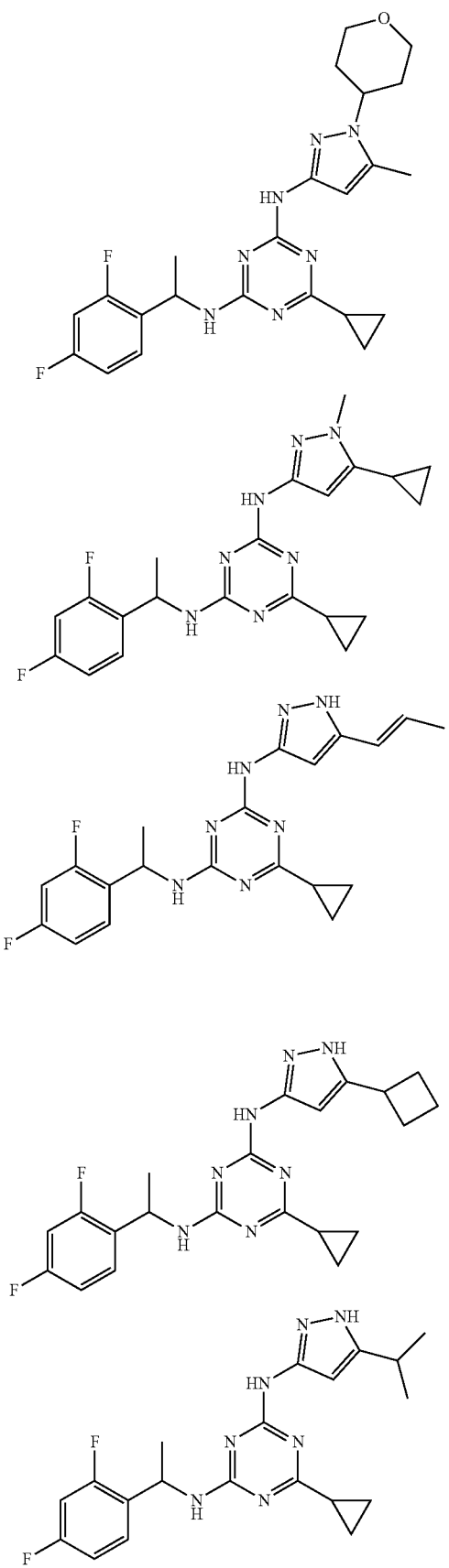
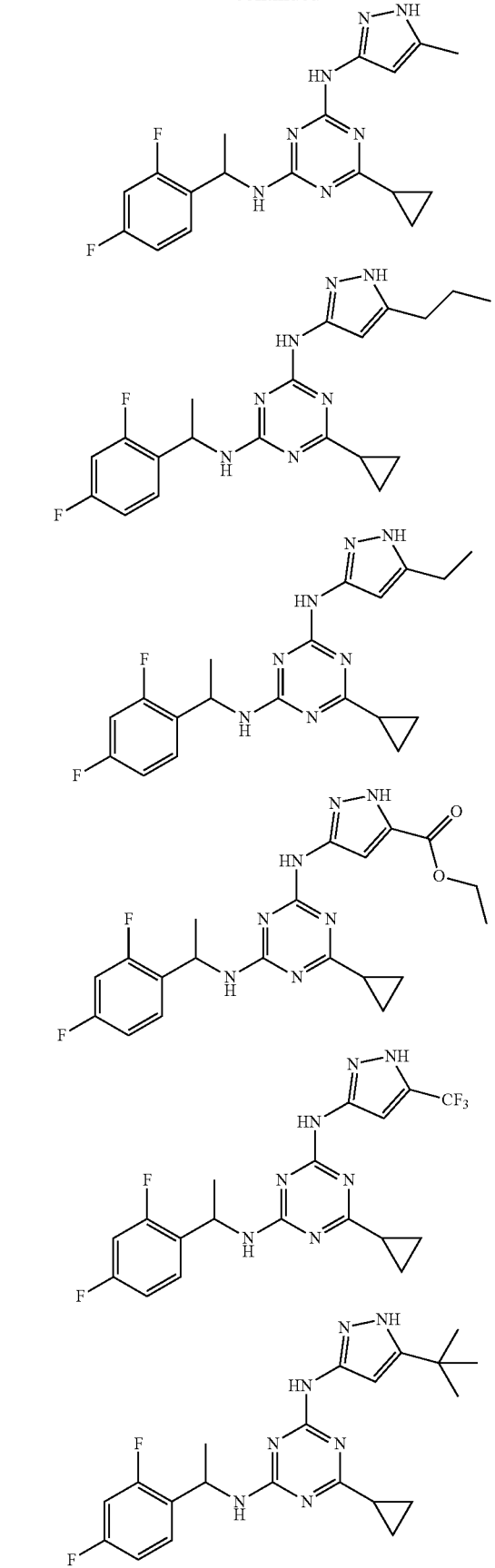

-continued
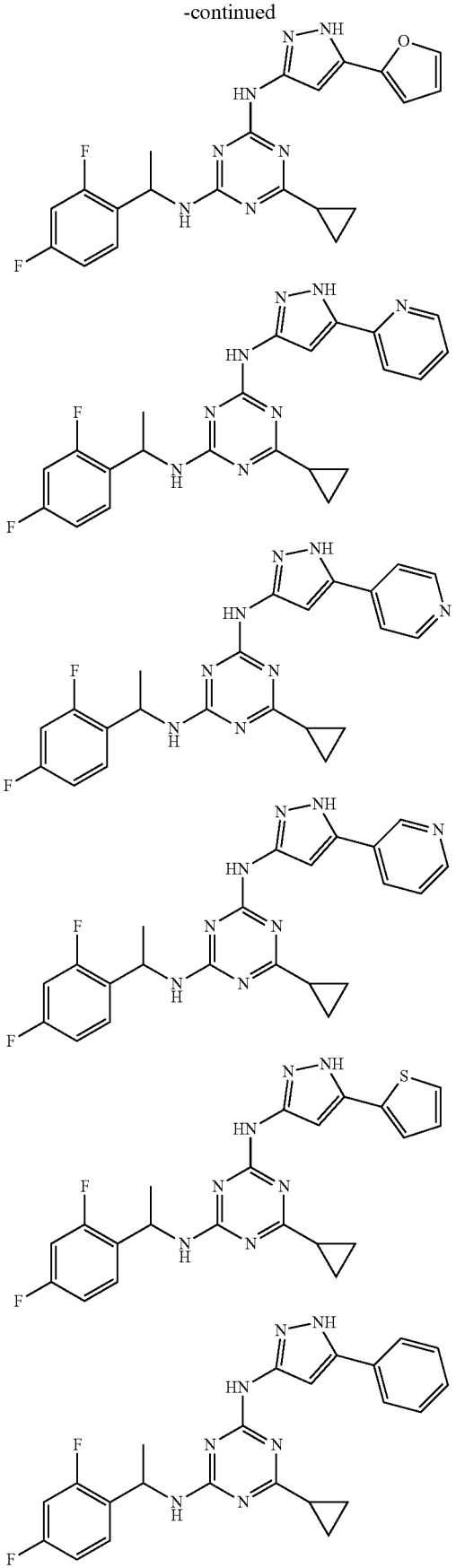
-continued
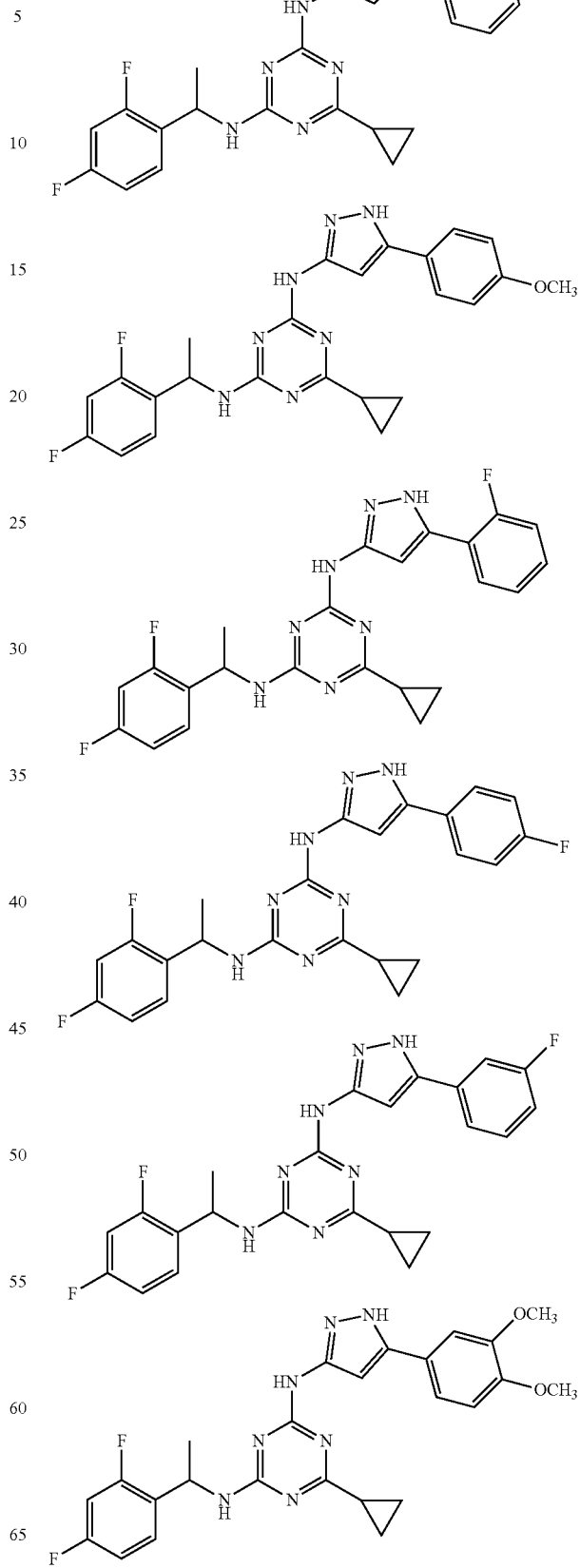

51
-continued
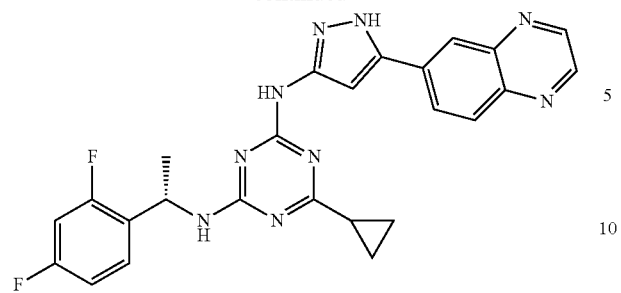
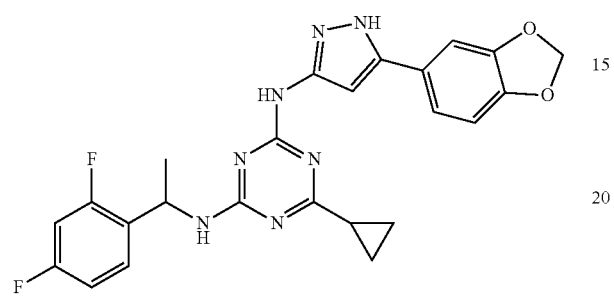
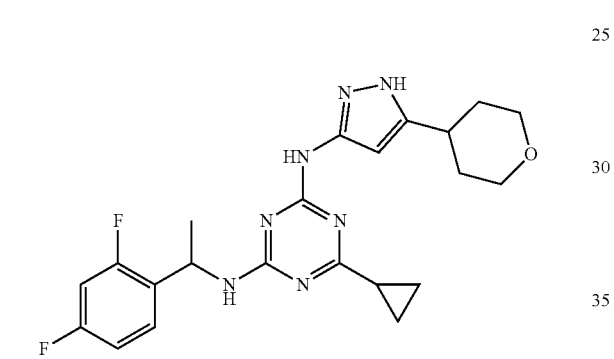
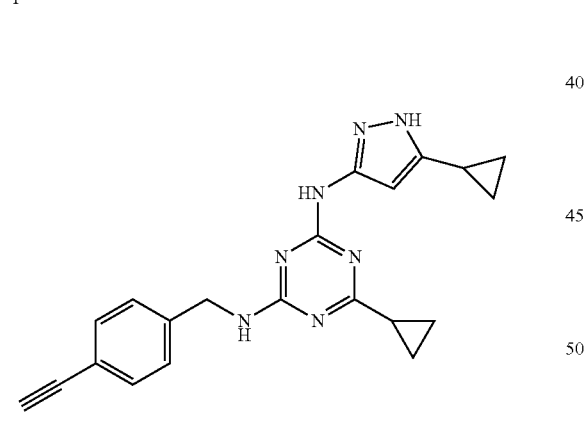
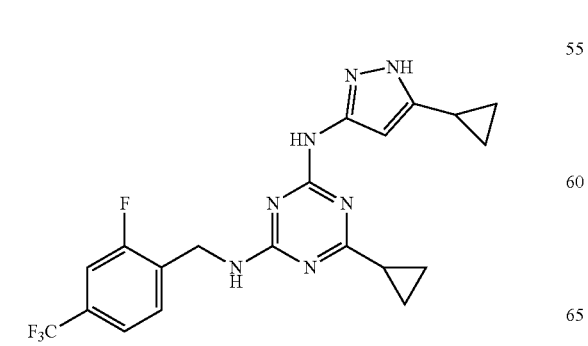
52
-continued
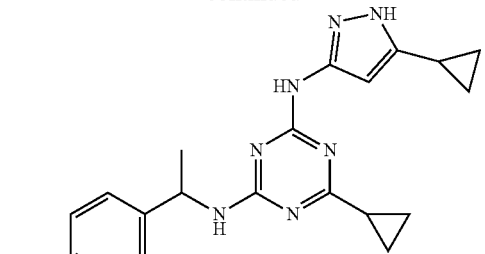
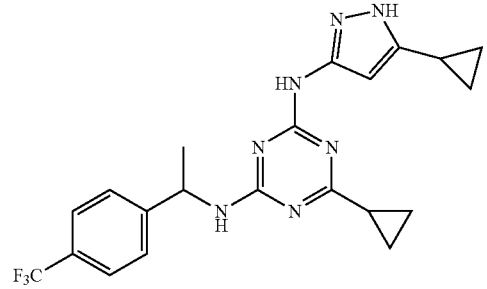
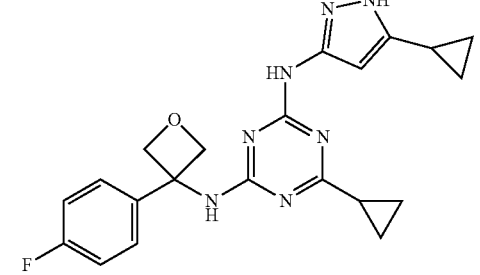
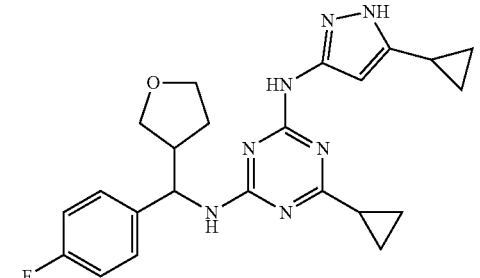
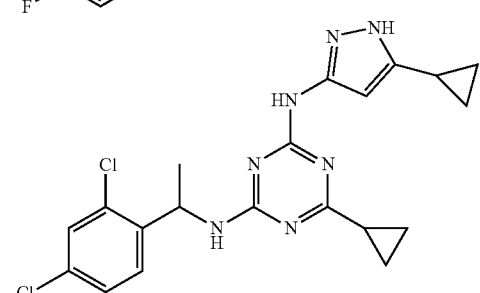
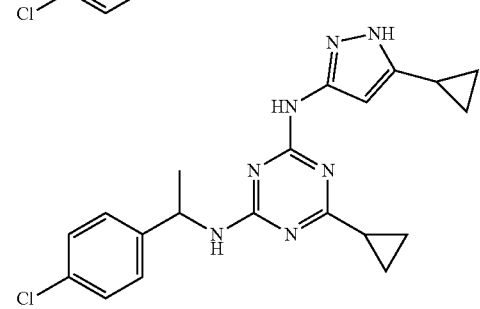

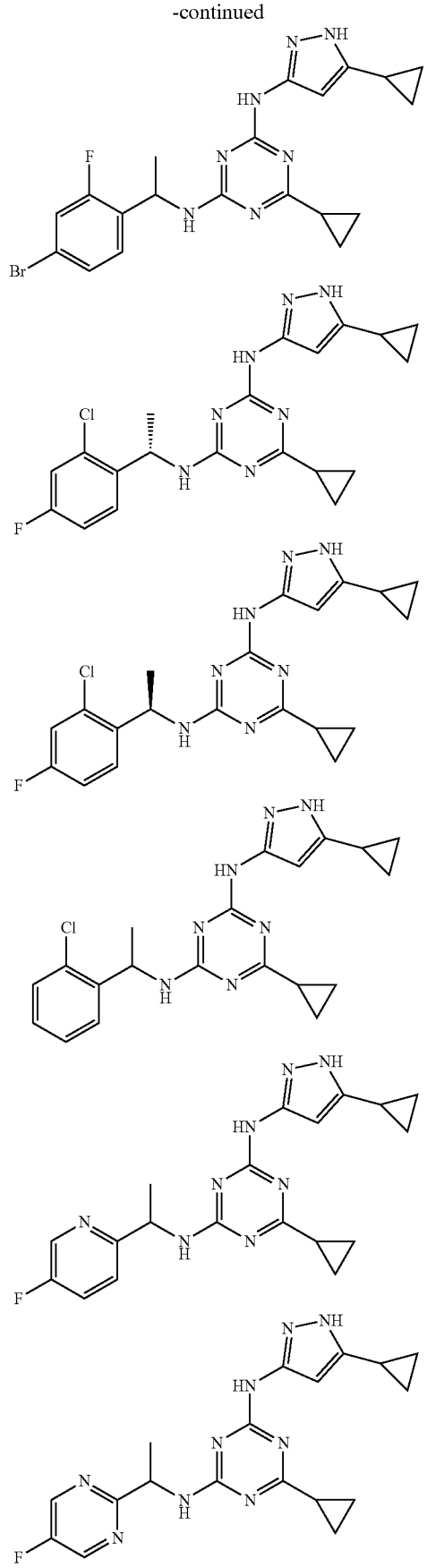
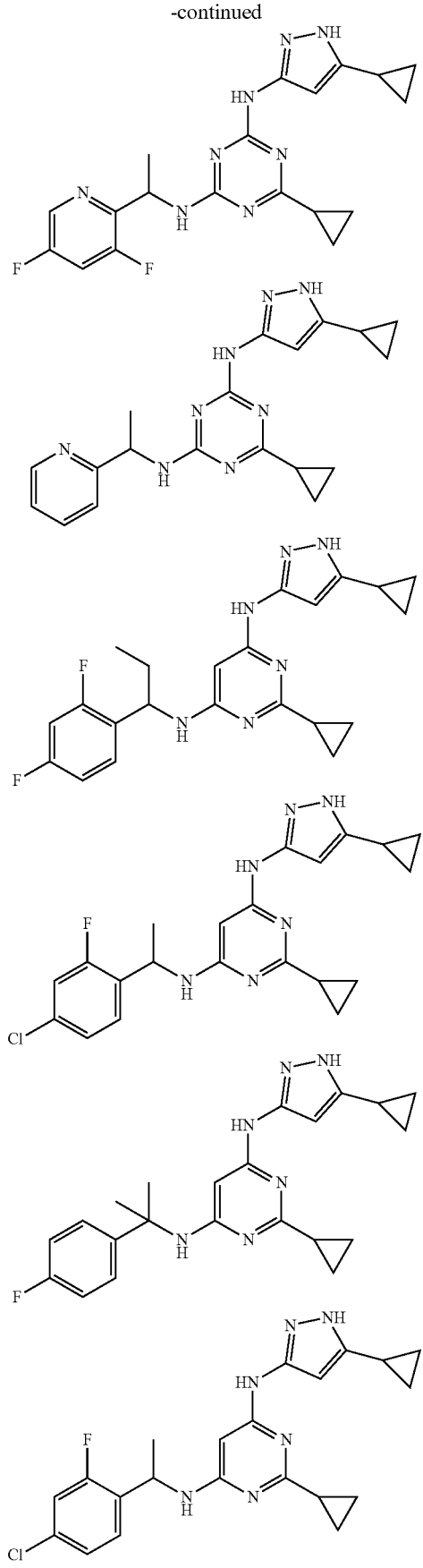

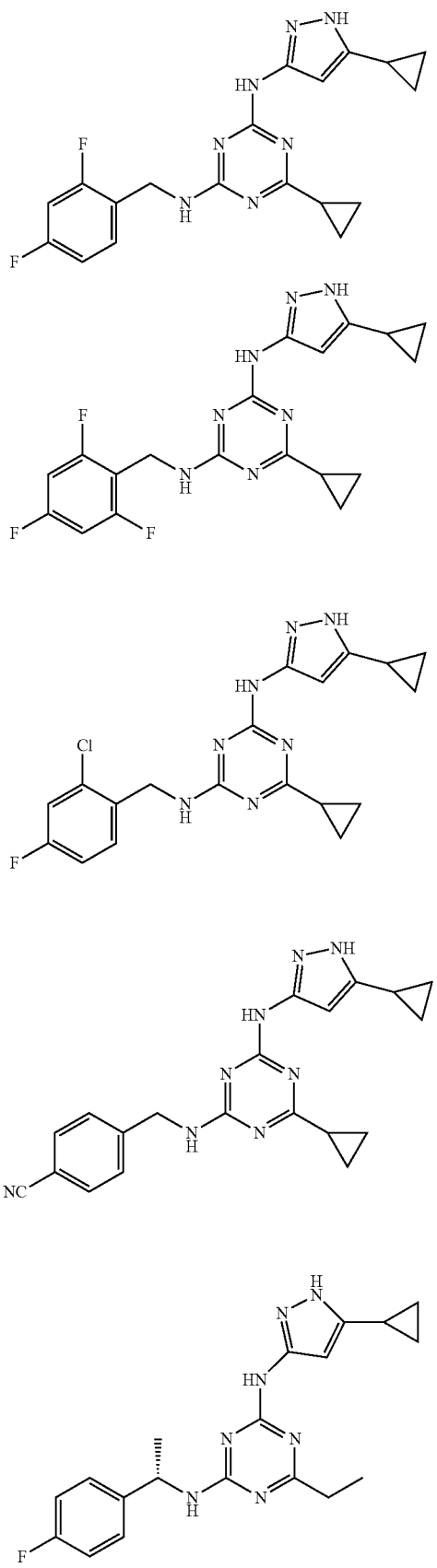
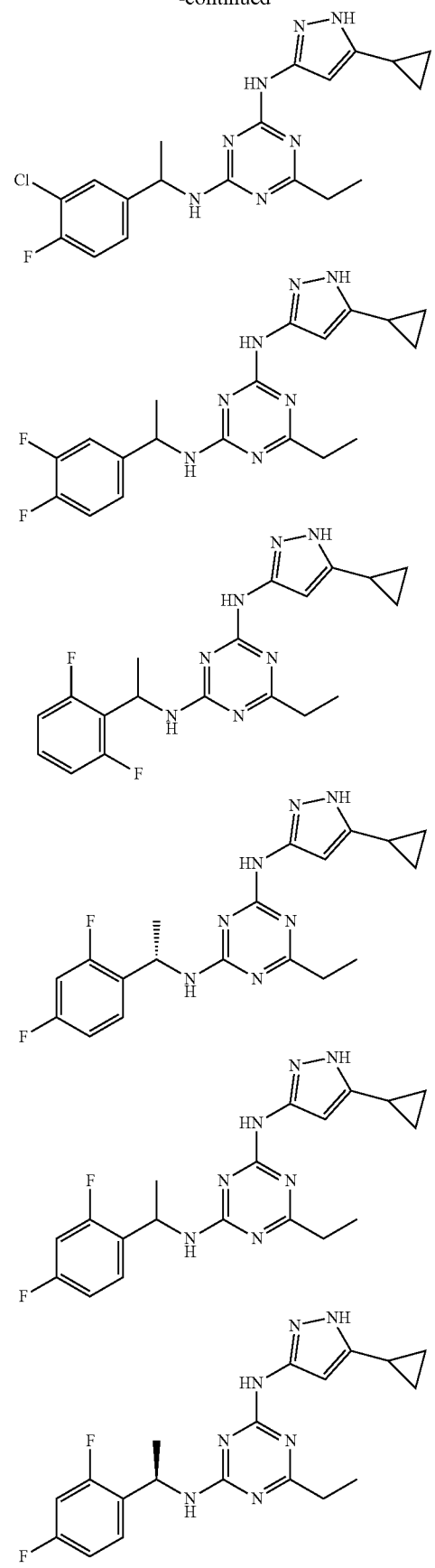

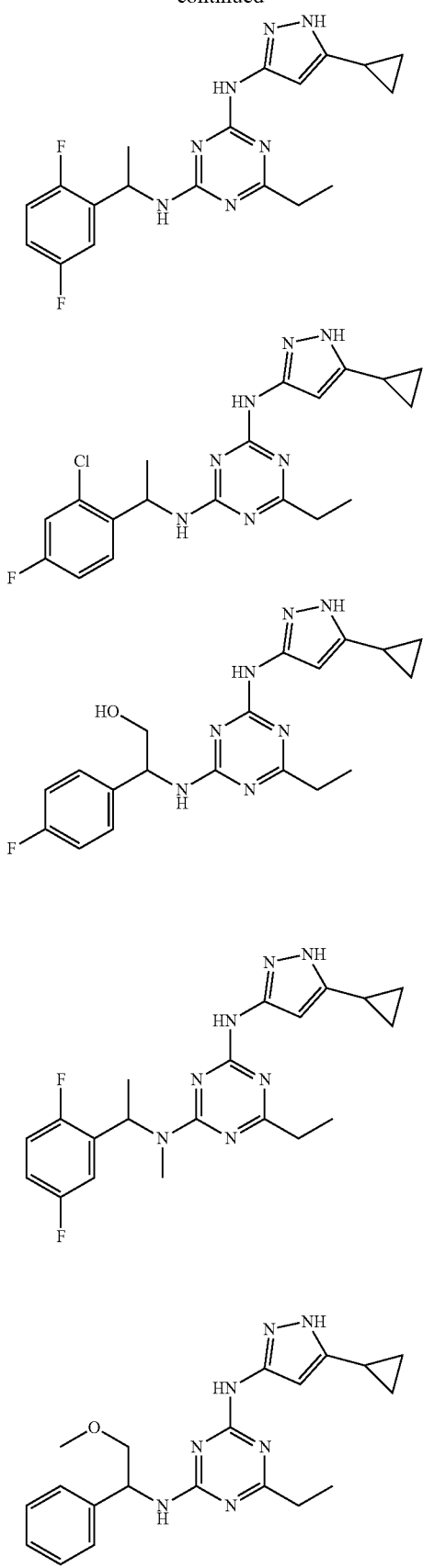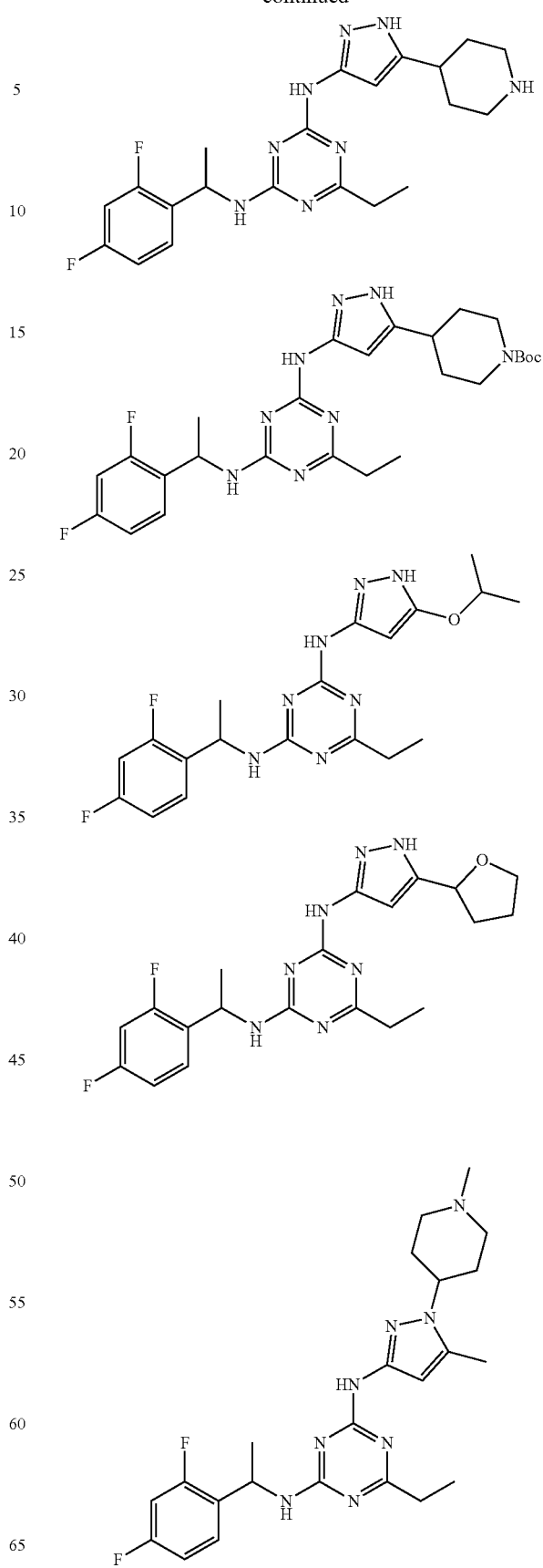

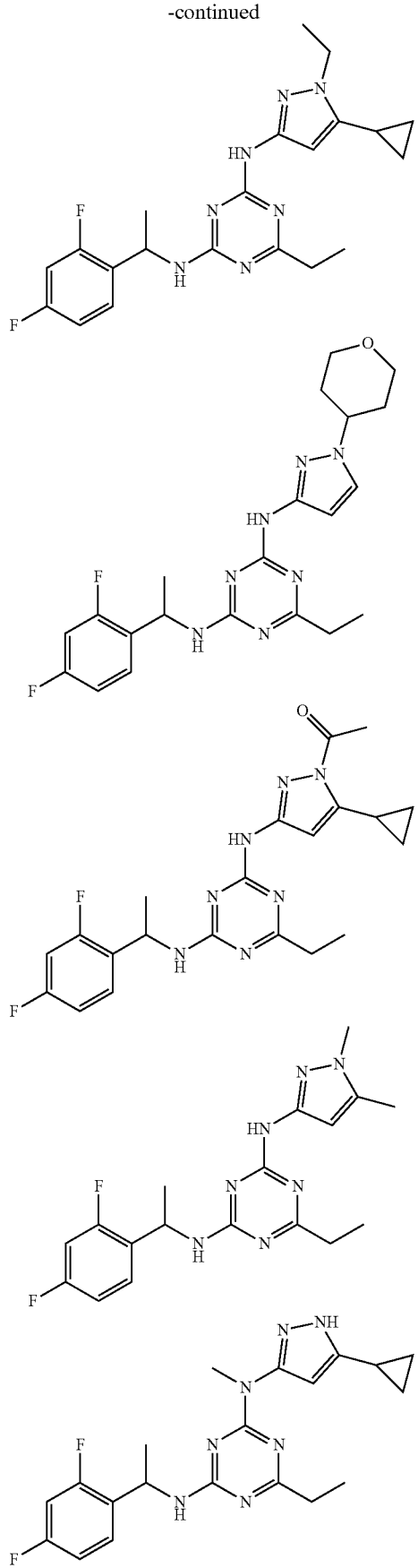
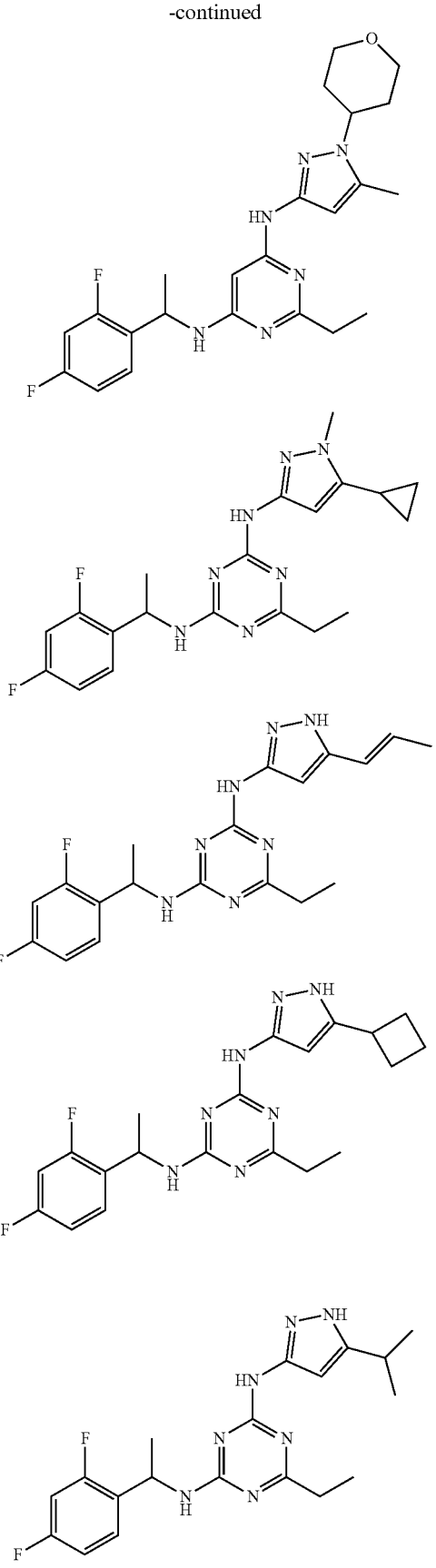

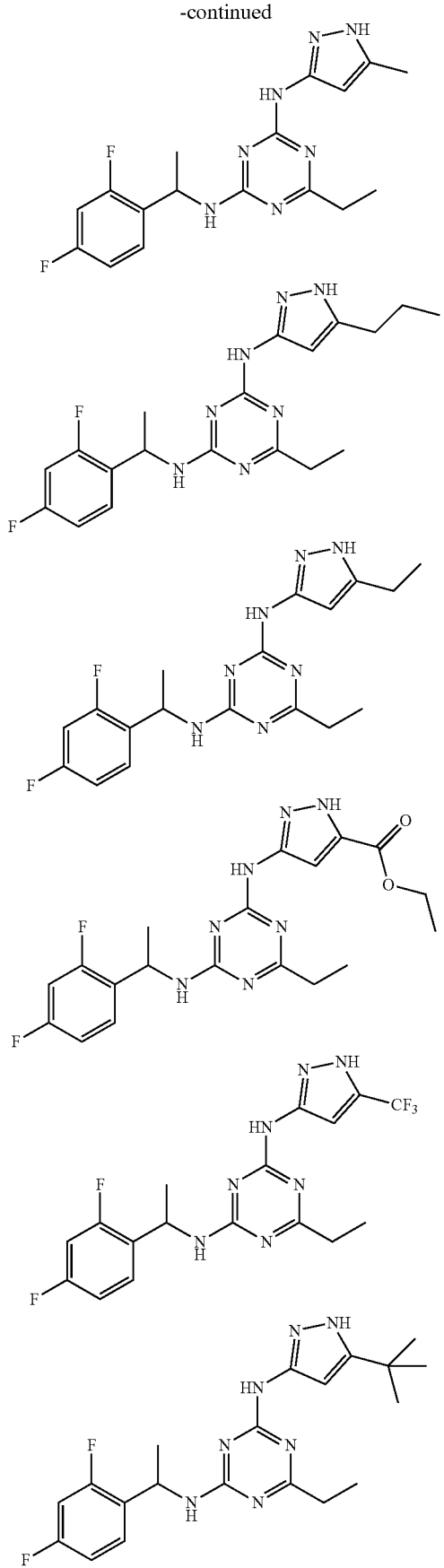
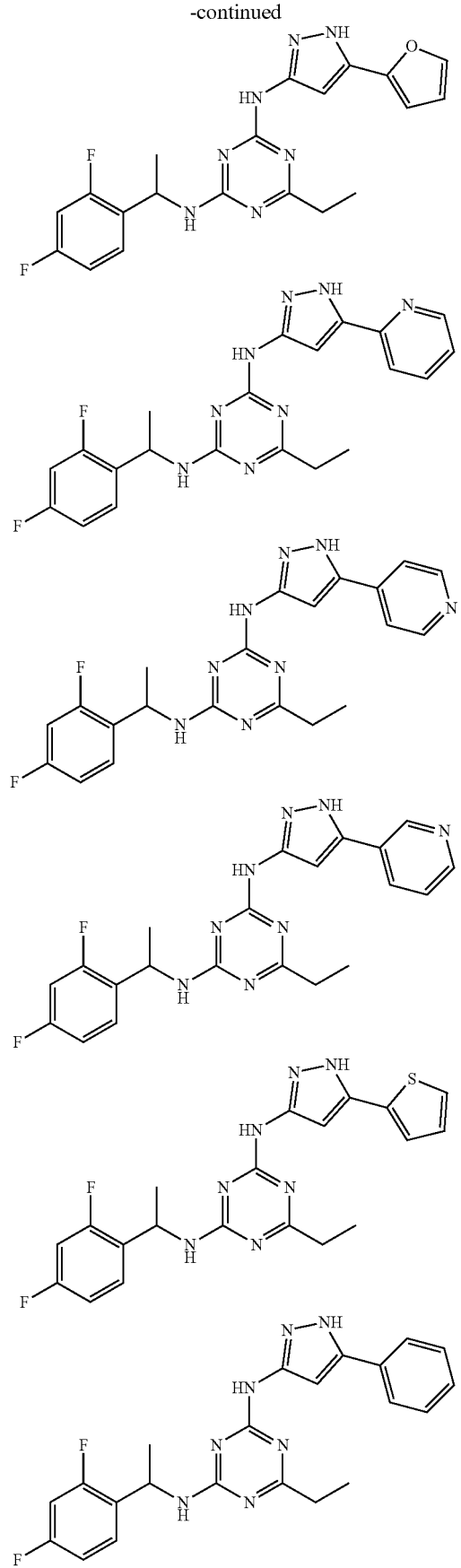

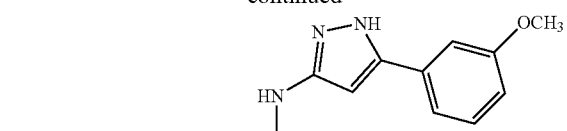
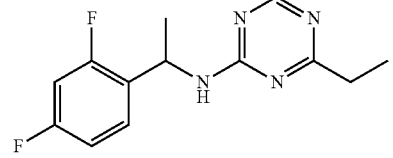
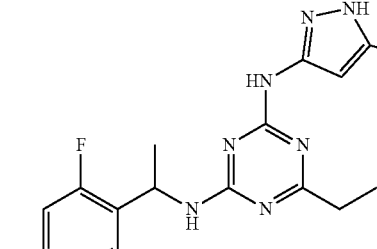
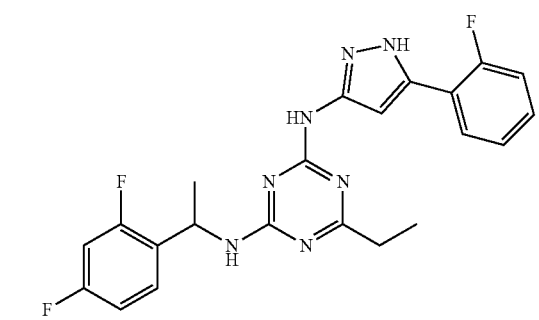
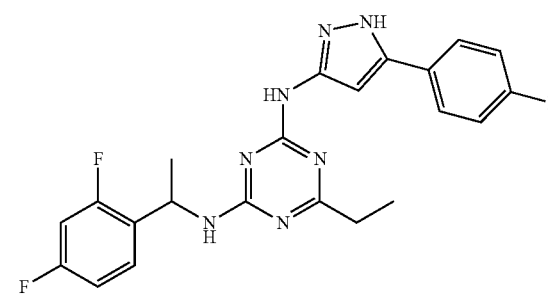
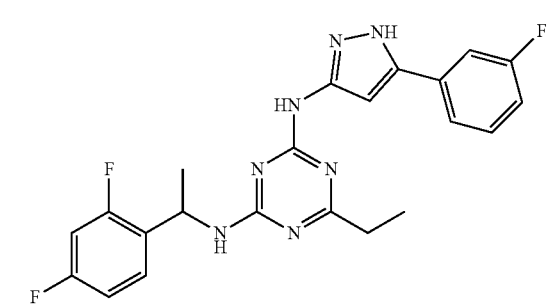
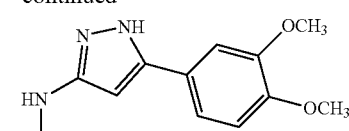
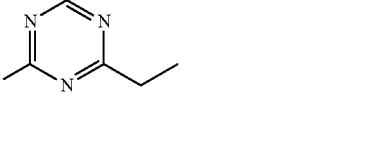
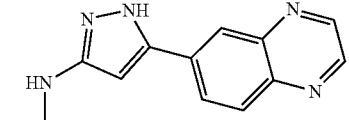
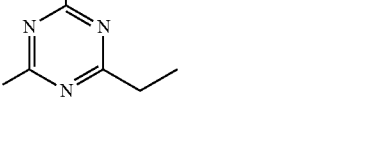
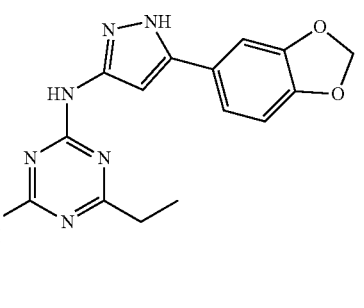
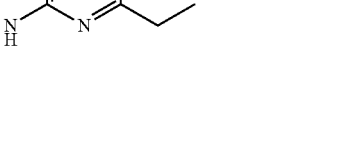
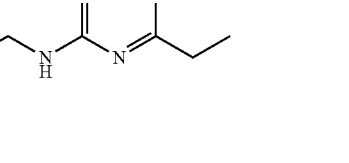

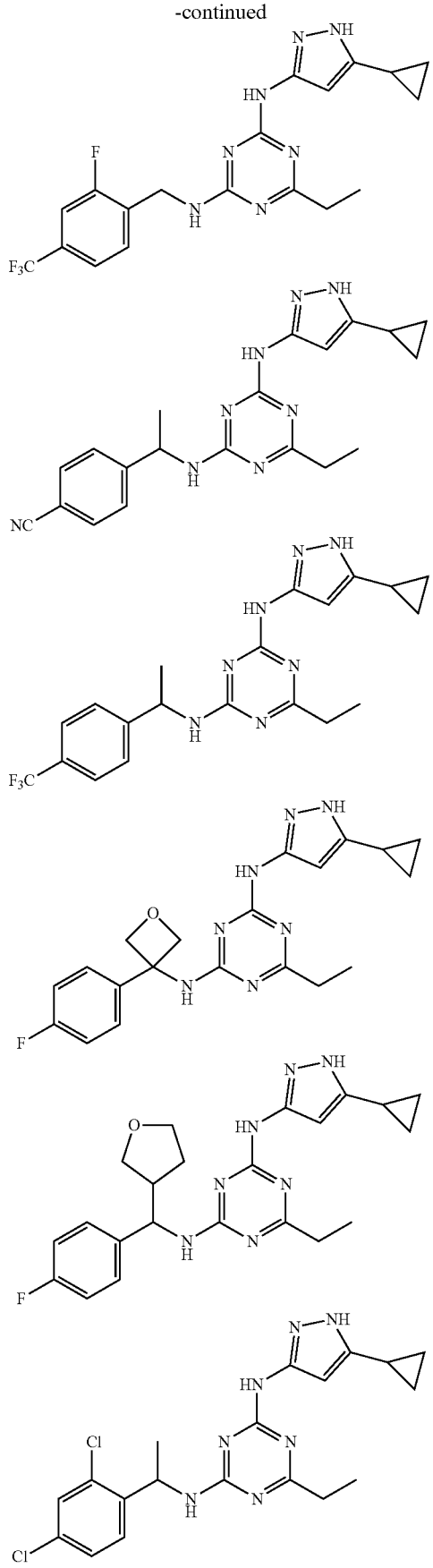
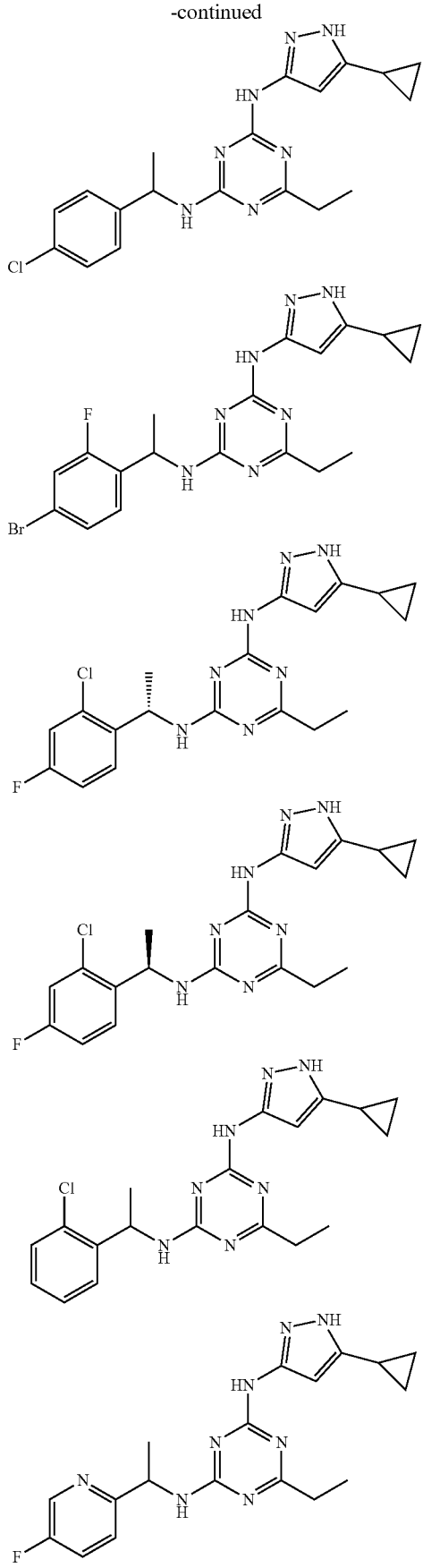

-continued
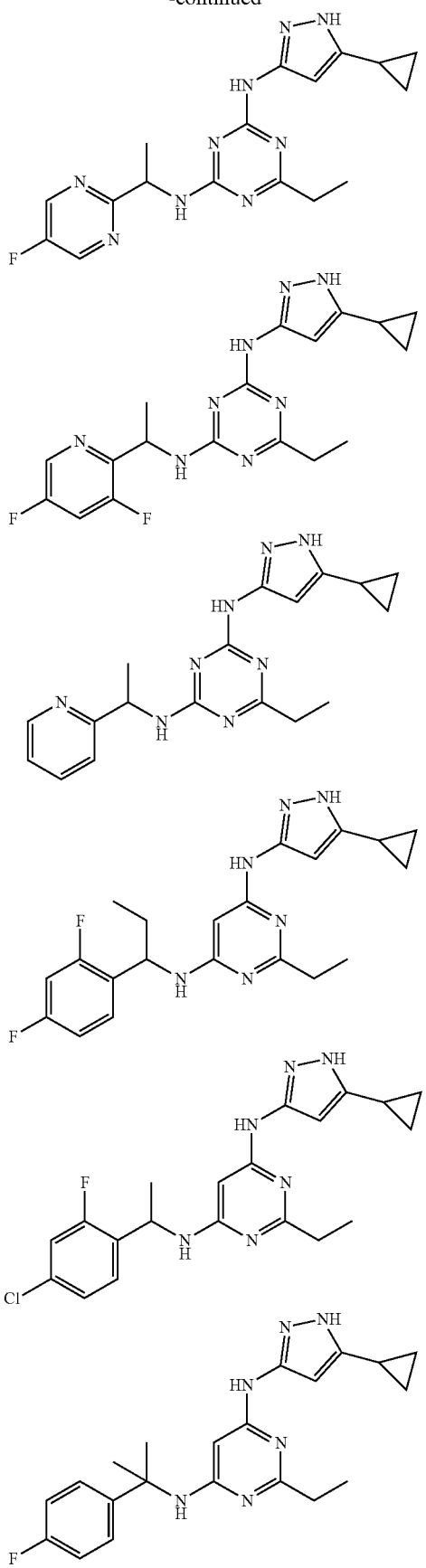
-continued
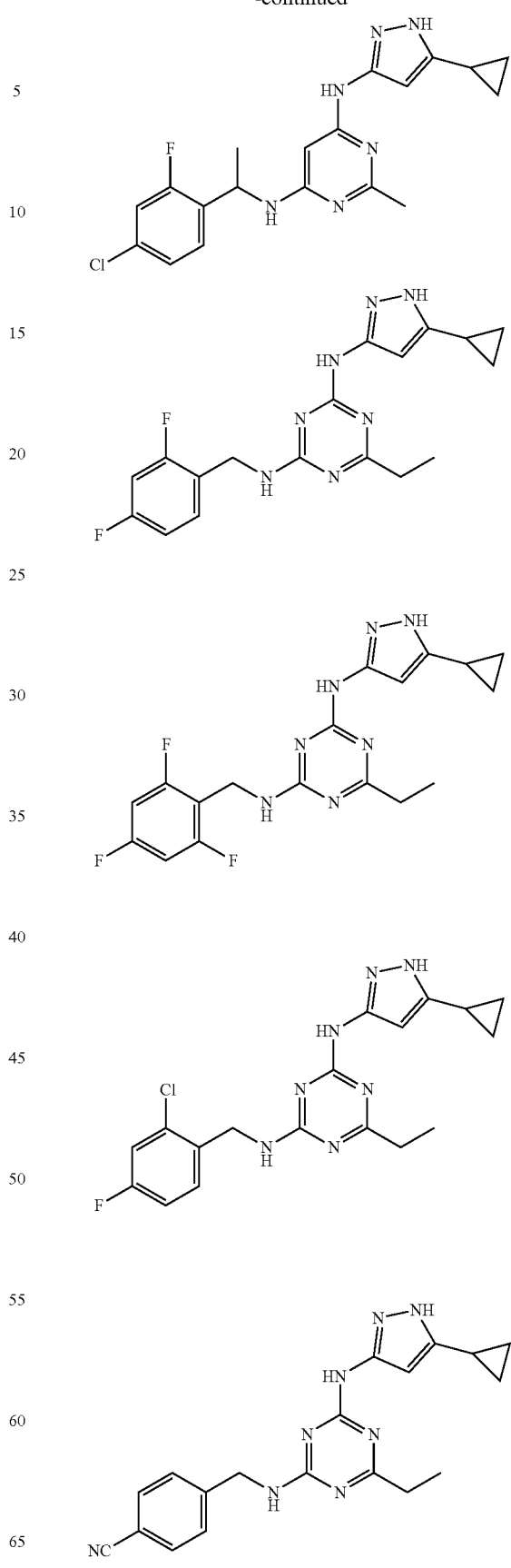

69
-continued
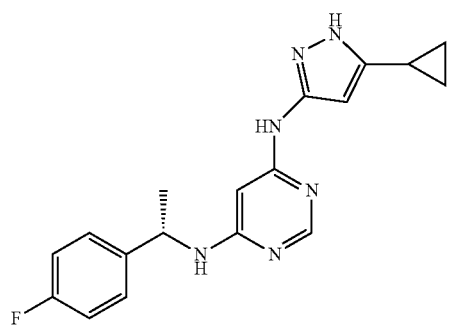
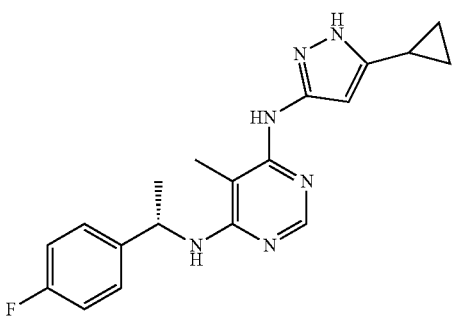
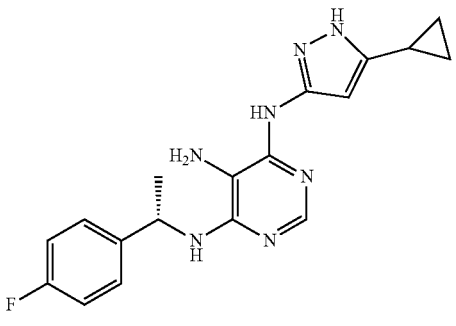
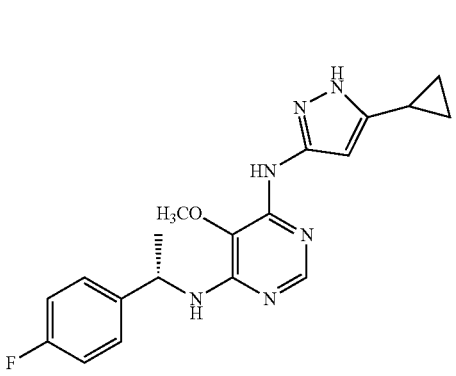
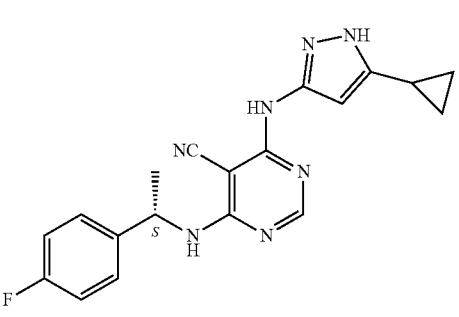
70
-continued
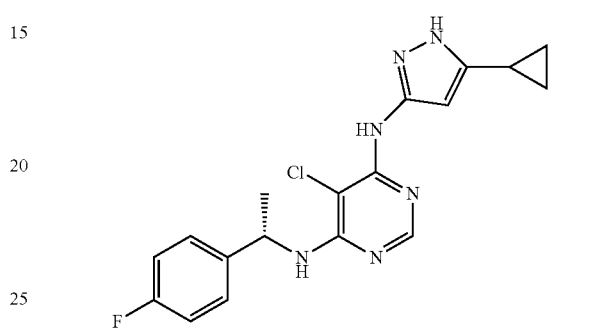
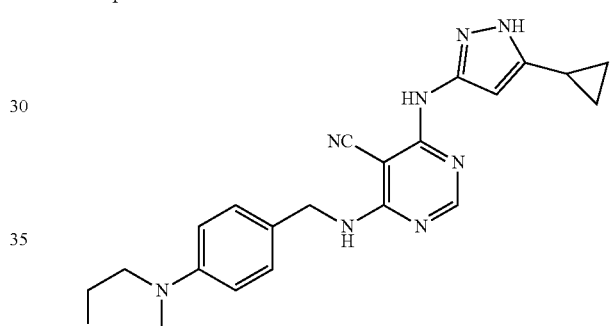
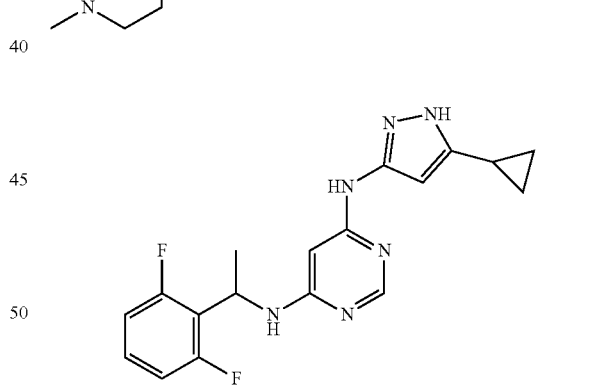
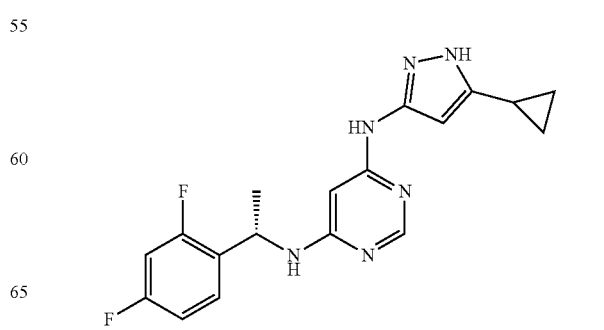

-continued
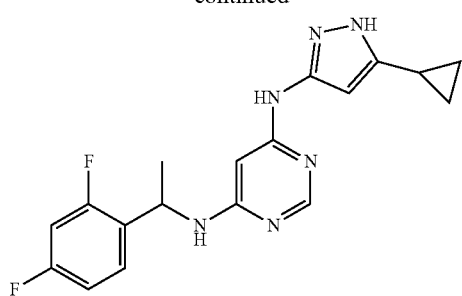
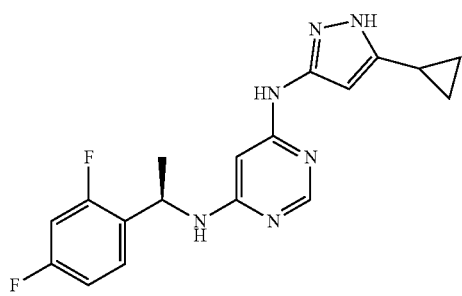
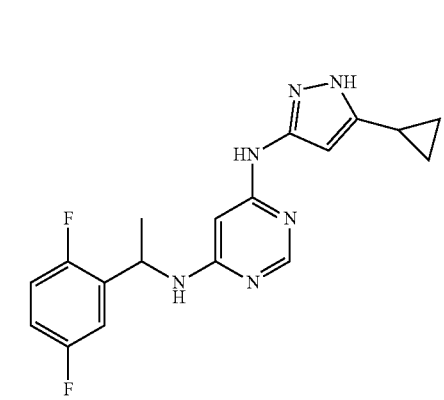
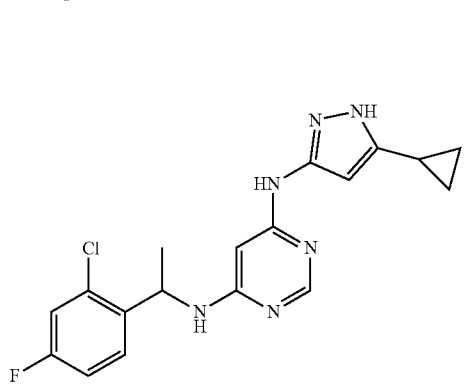
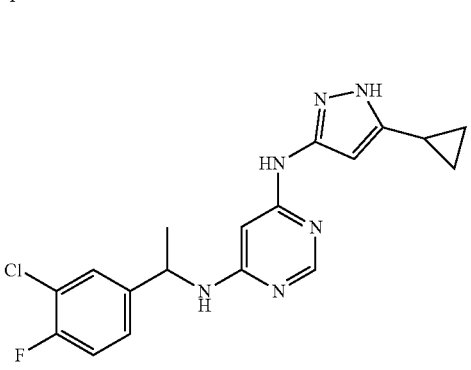
-continued
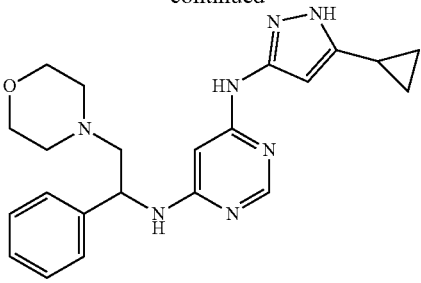
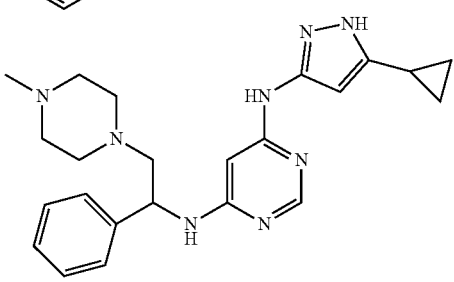
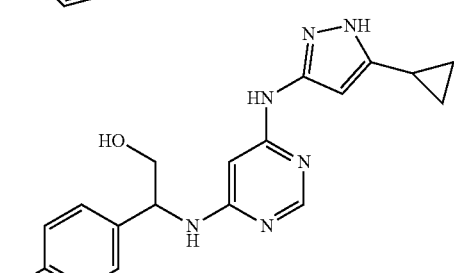
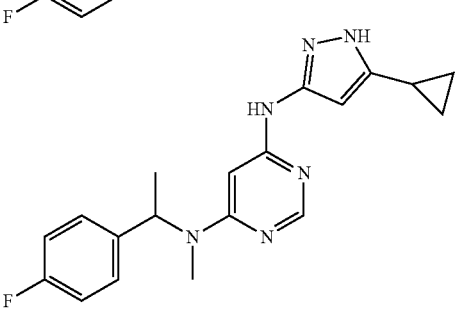
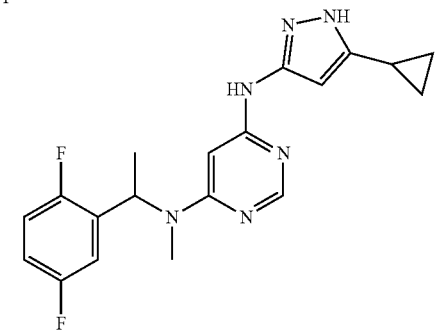
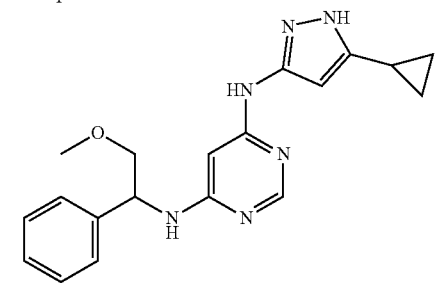

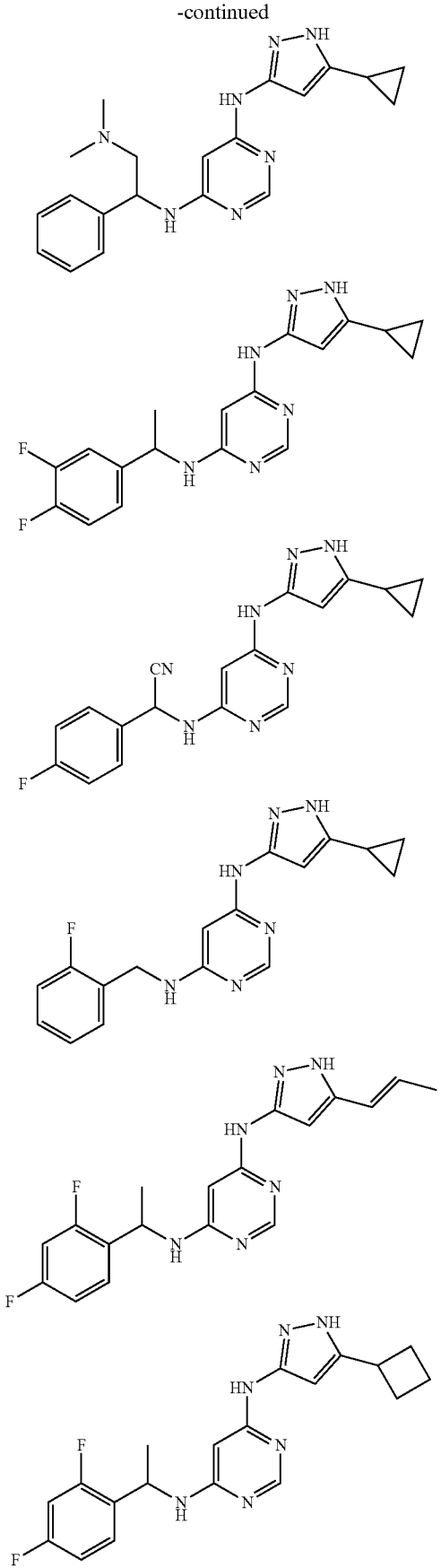
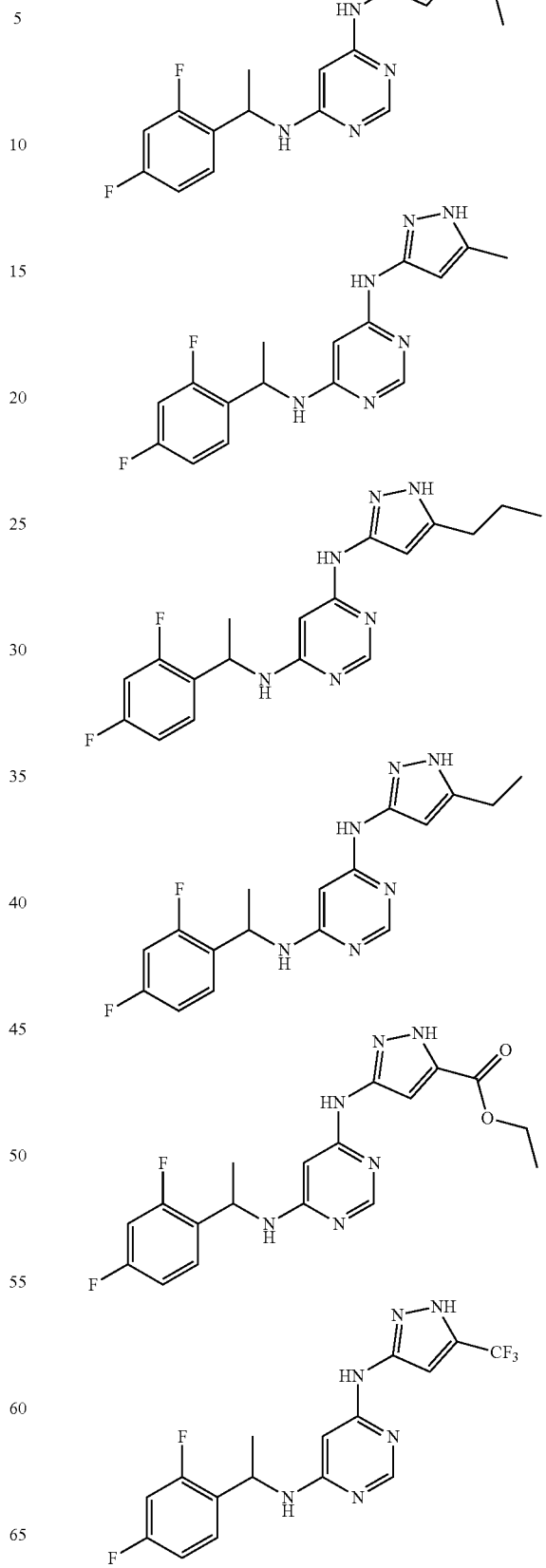

75
-continued
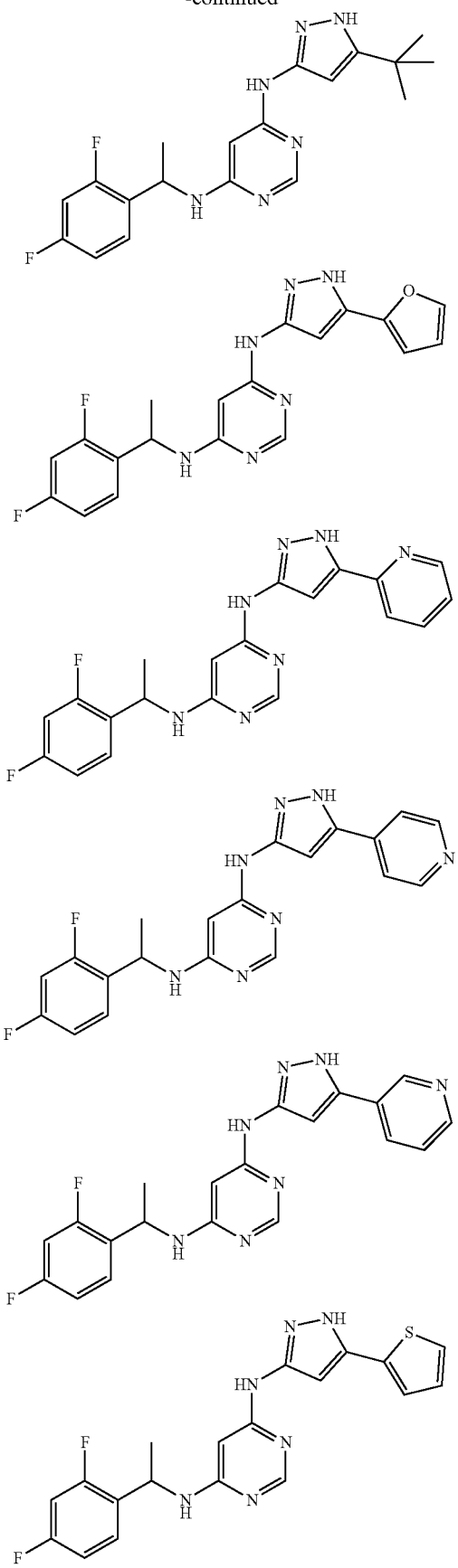
76
-continued
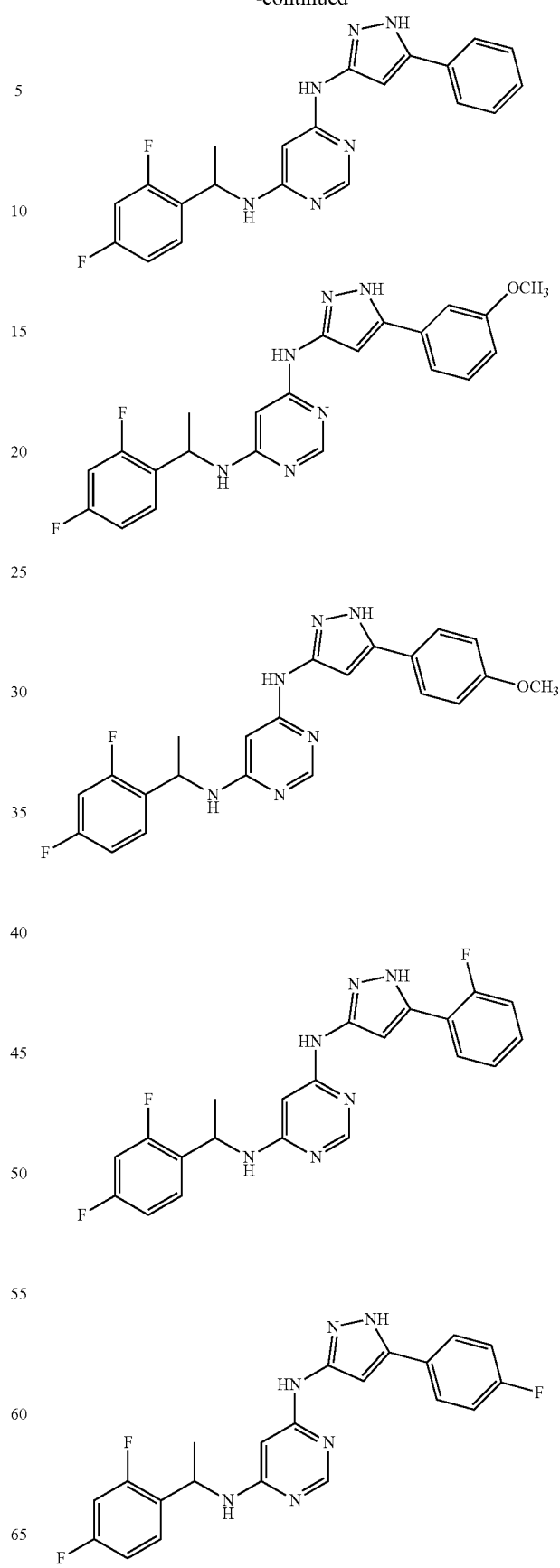

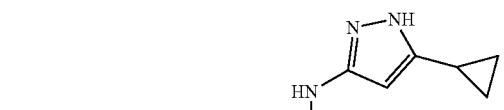
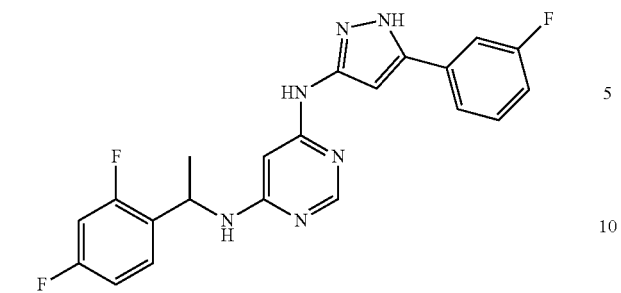
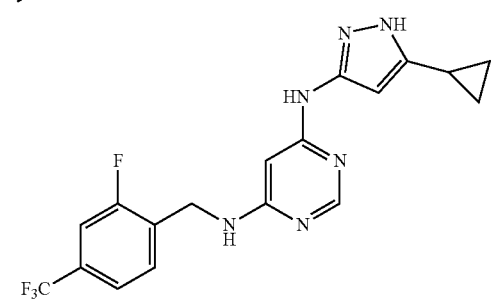
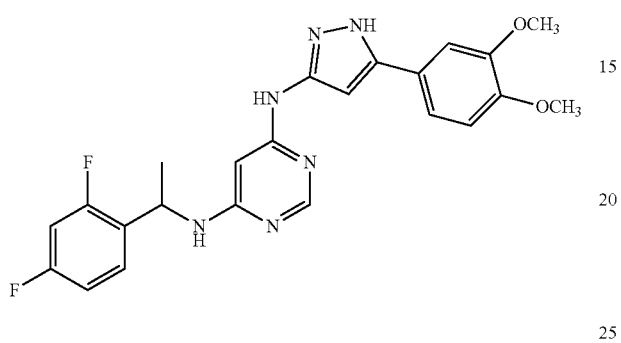
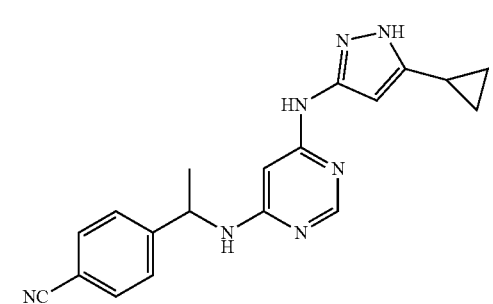
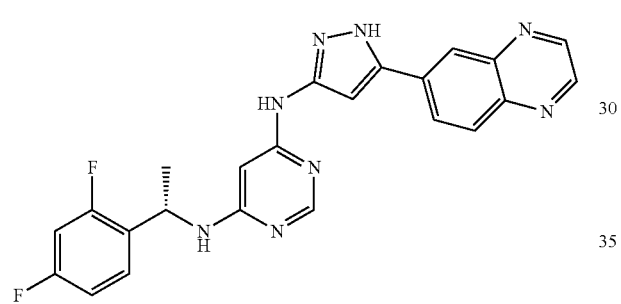
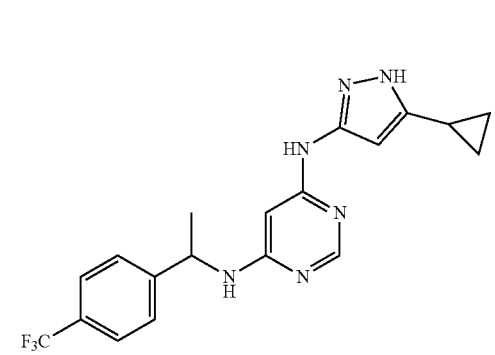
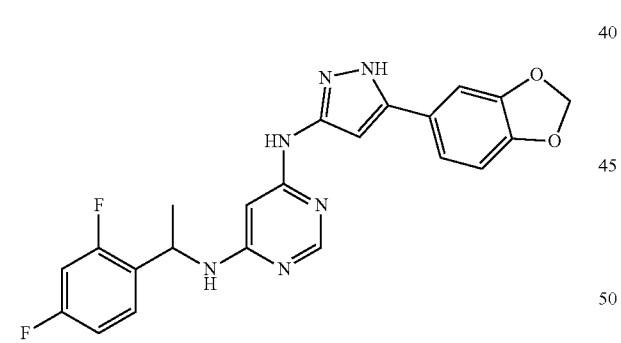
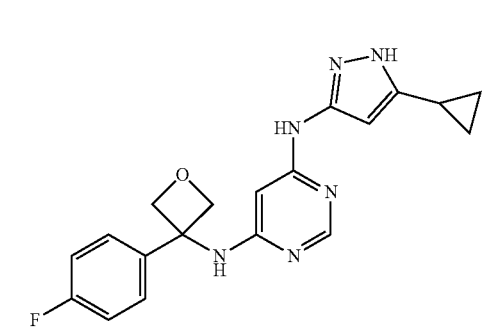
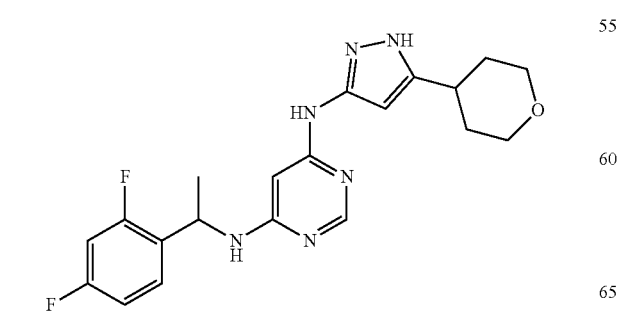

-continued
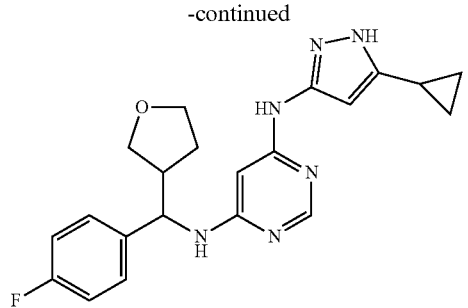
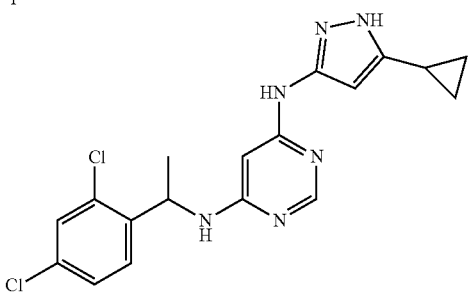
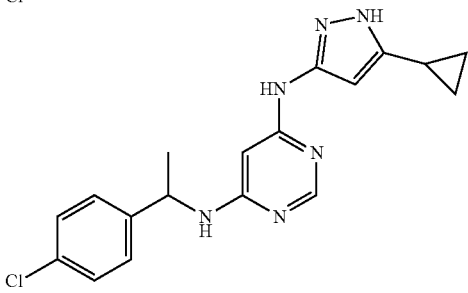
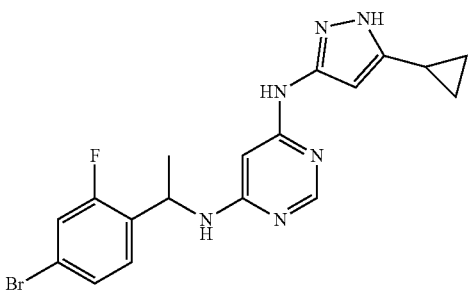
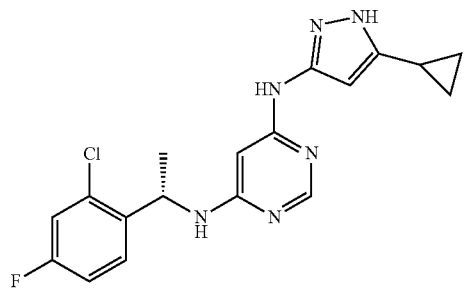
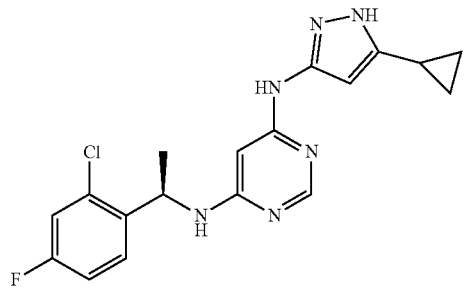
-continued
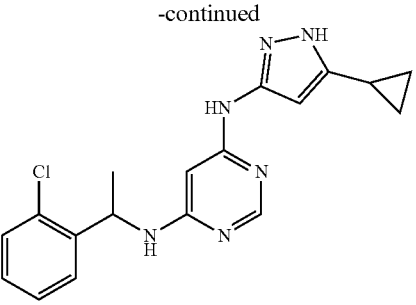
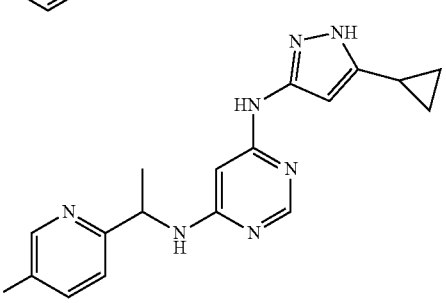
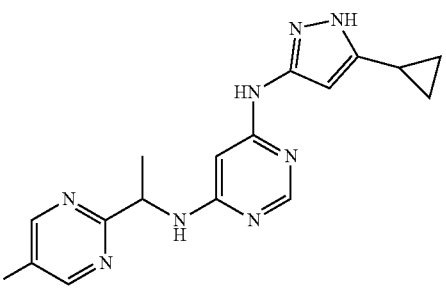
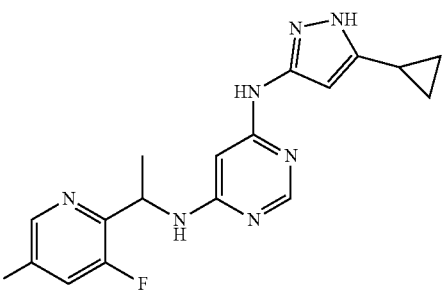
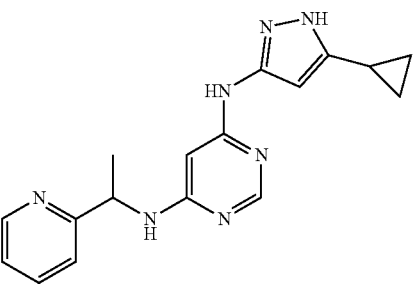
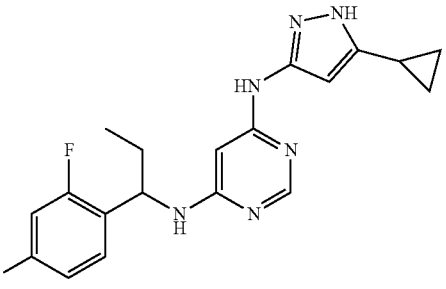

-continued
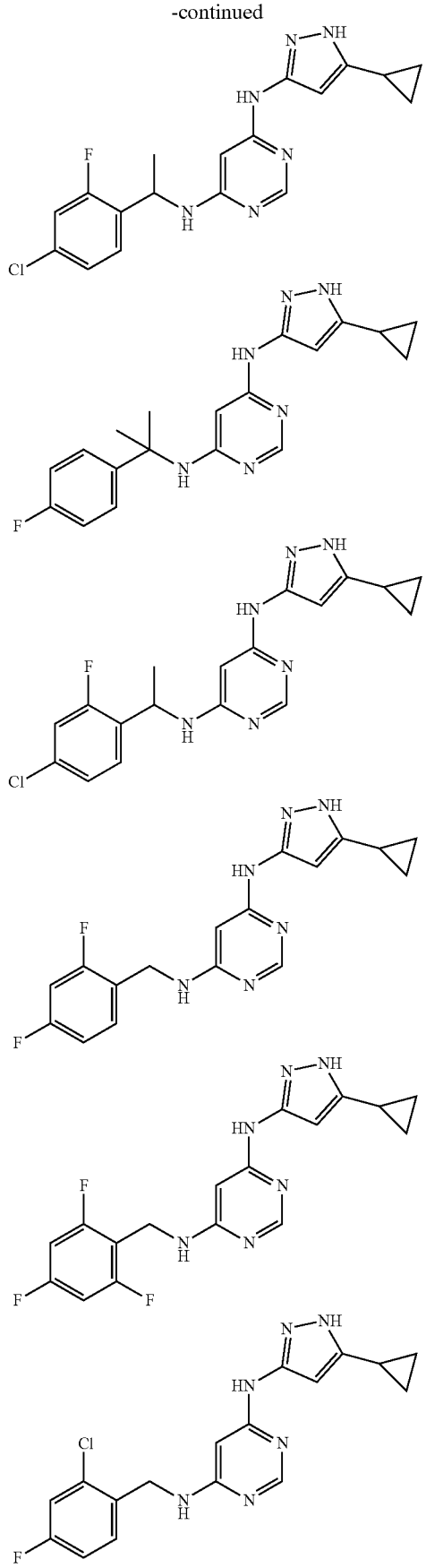
-continued
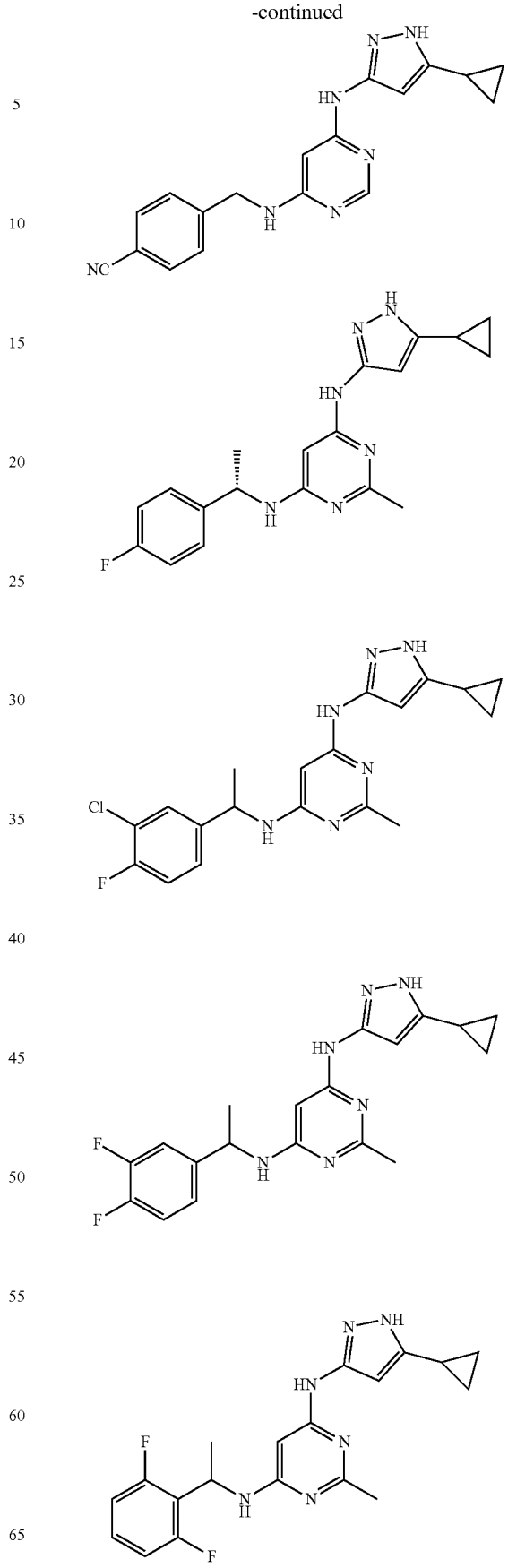

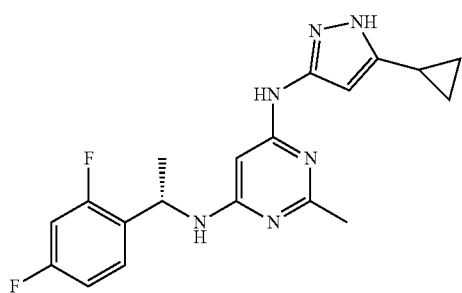
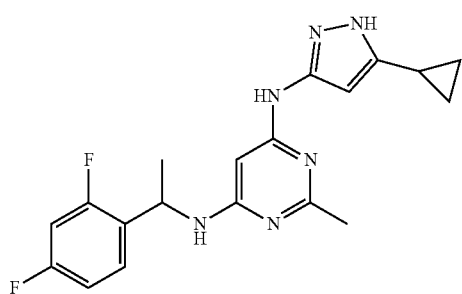
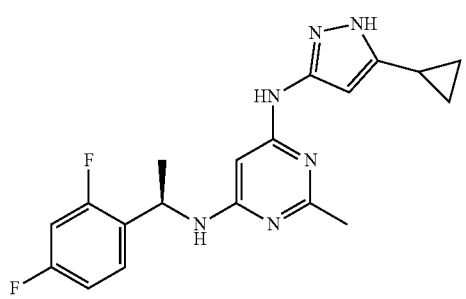
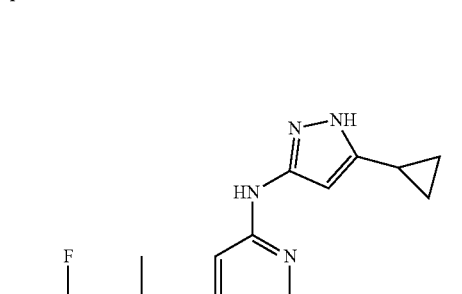
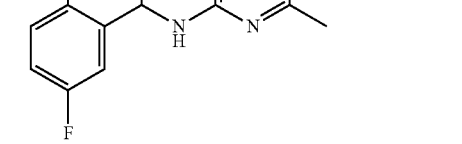
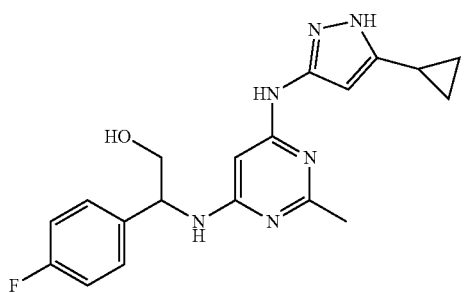
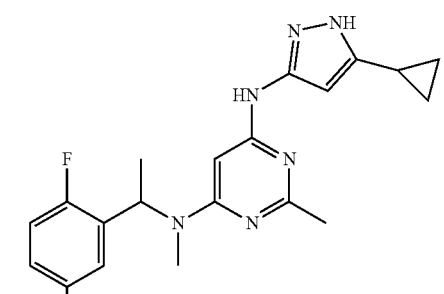
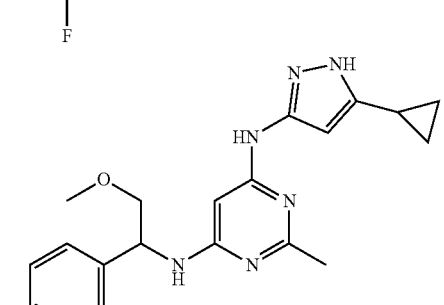
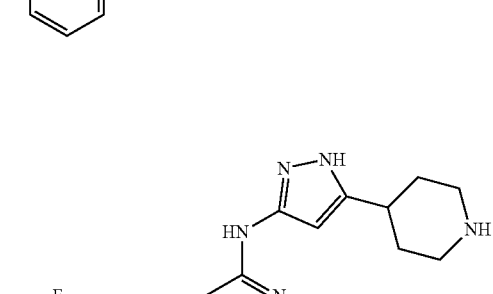
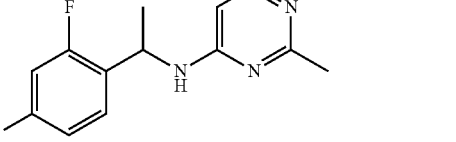
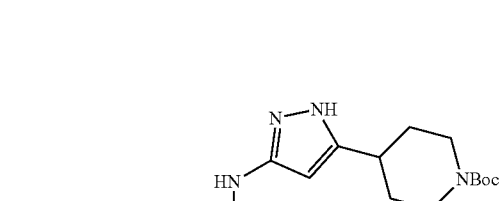
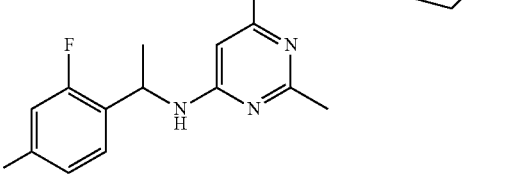

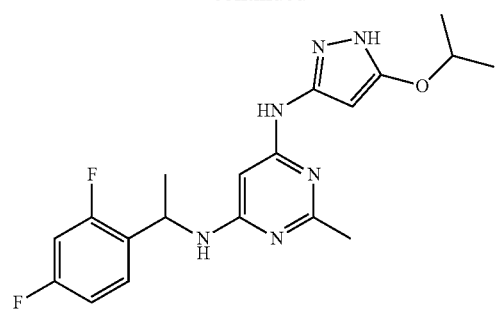
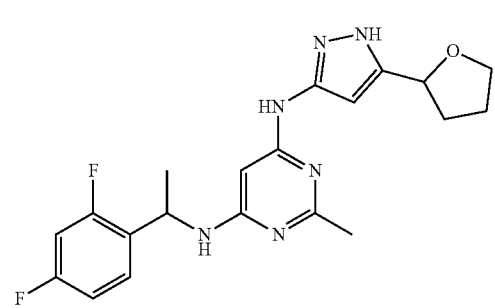
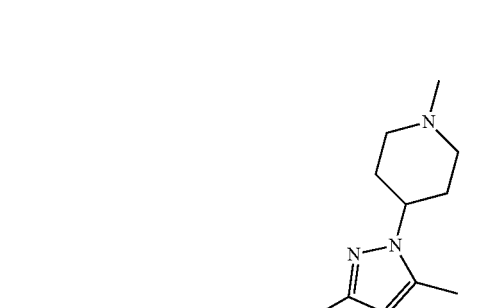
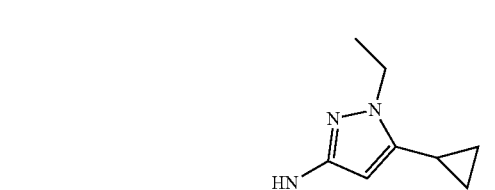
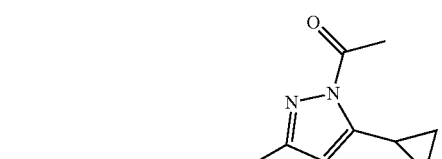
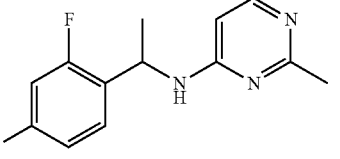
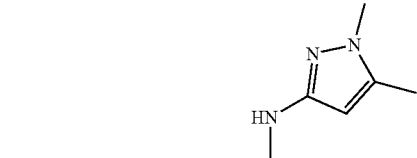
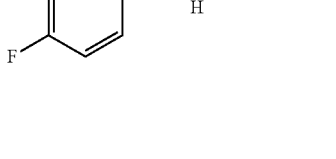

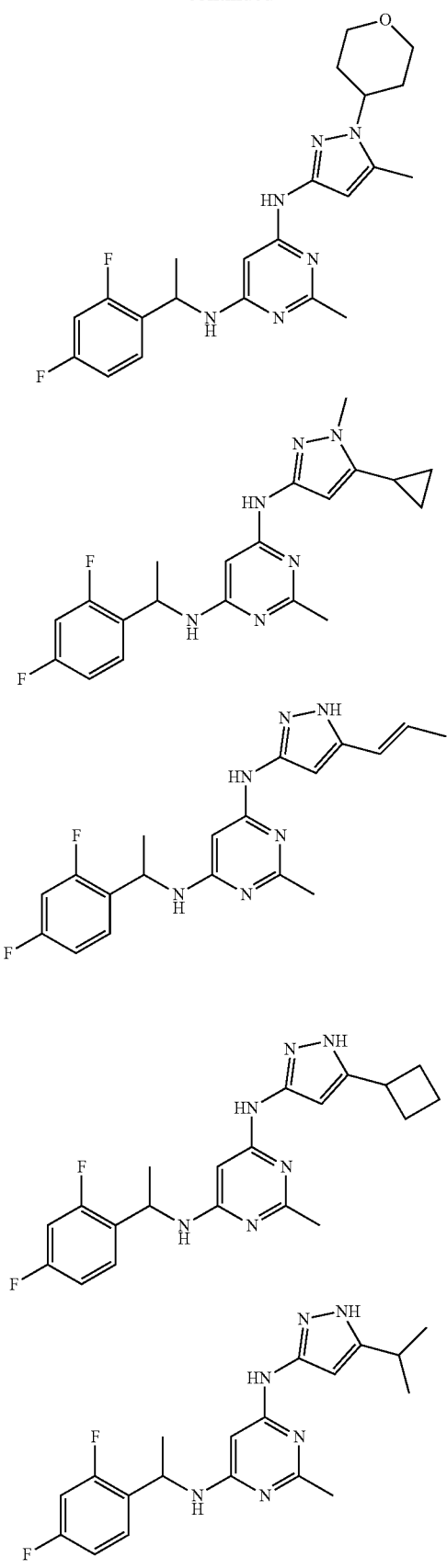
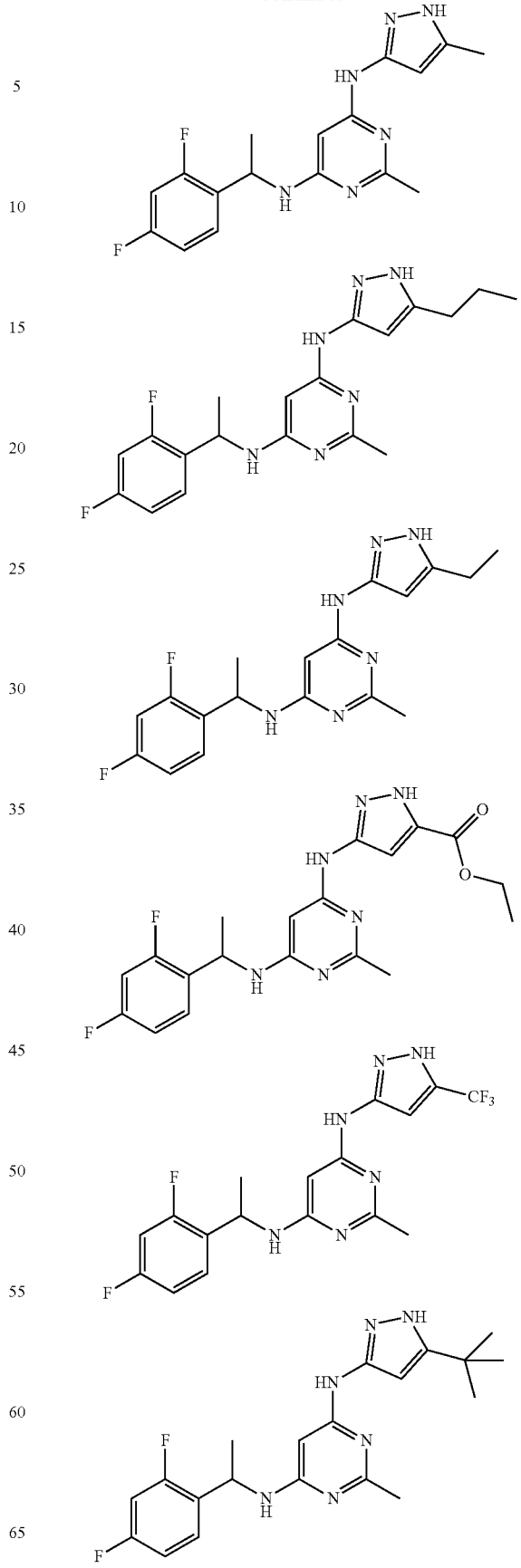

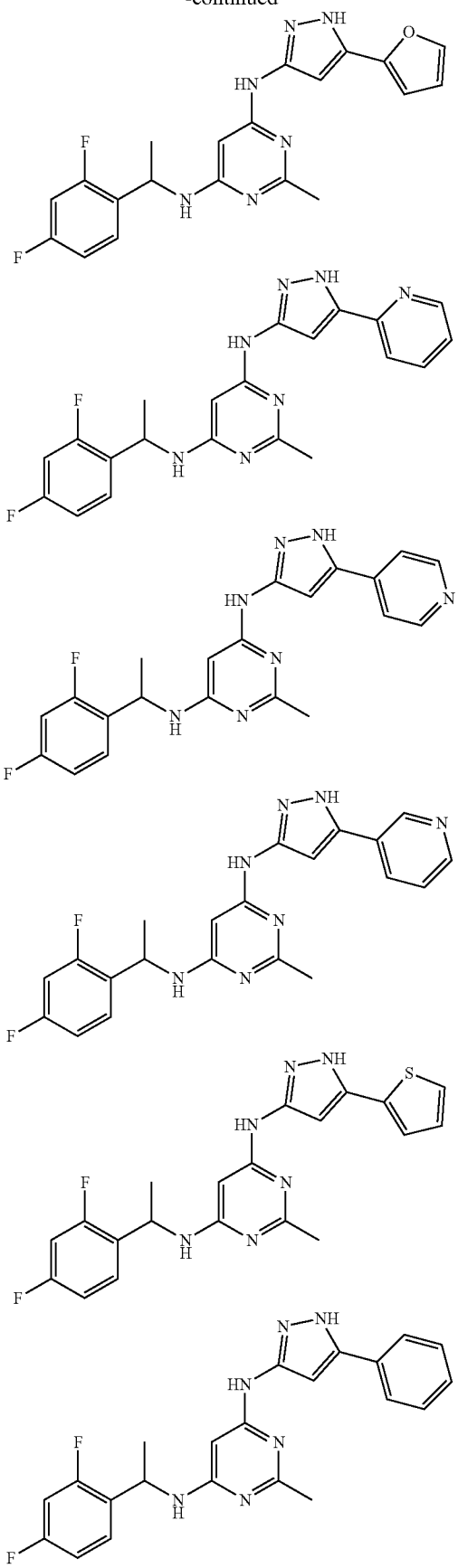
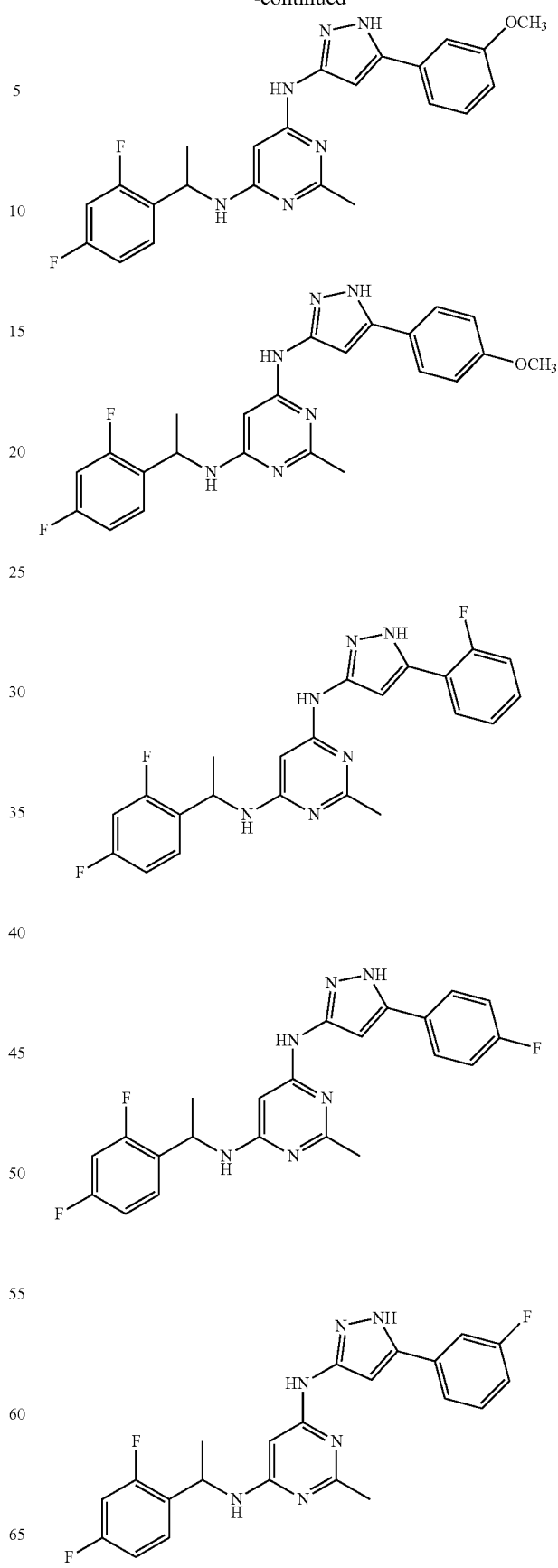

-continued
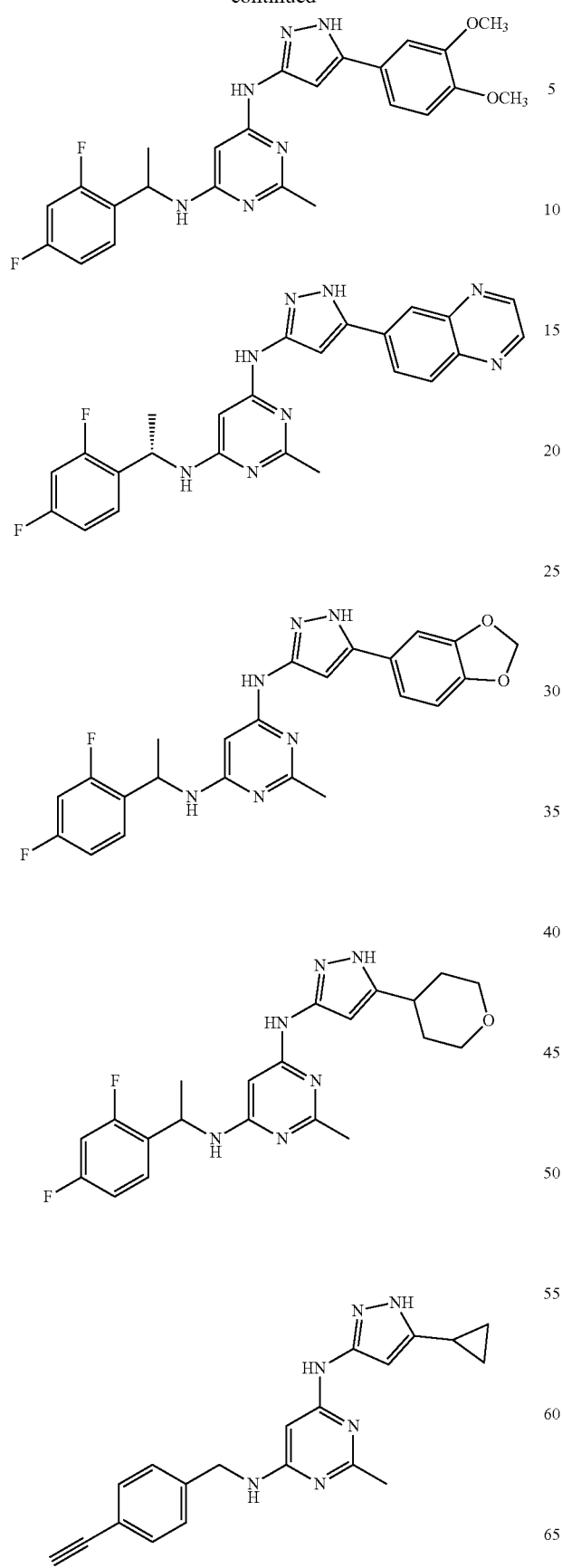
-continued
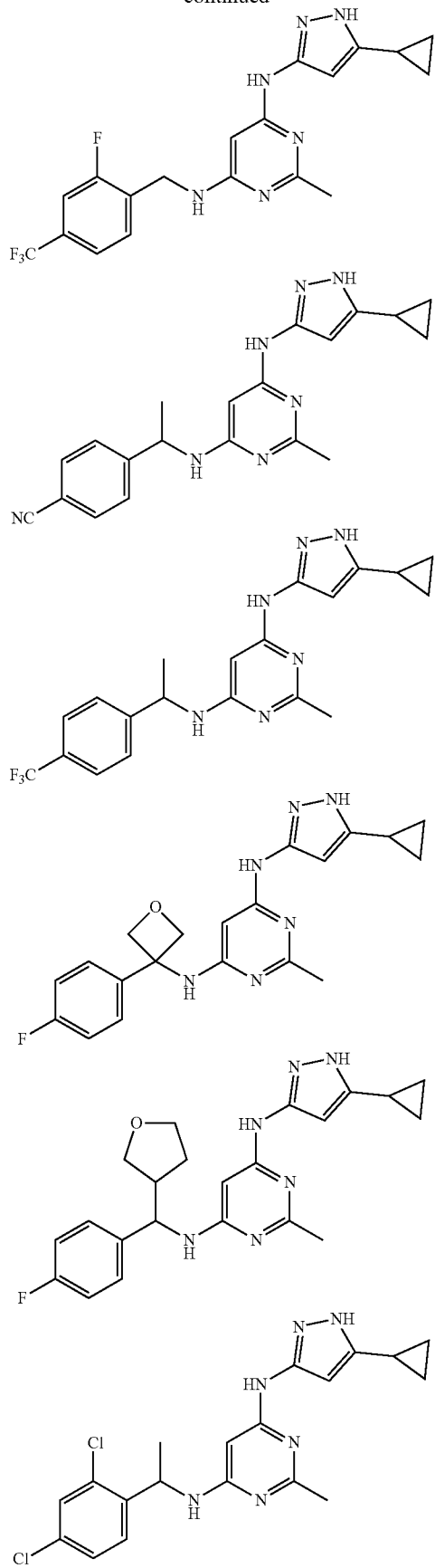

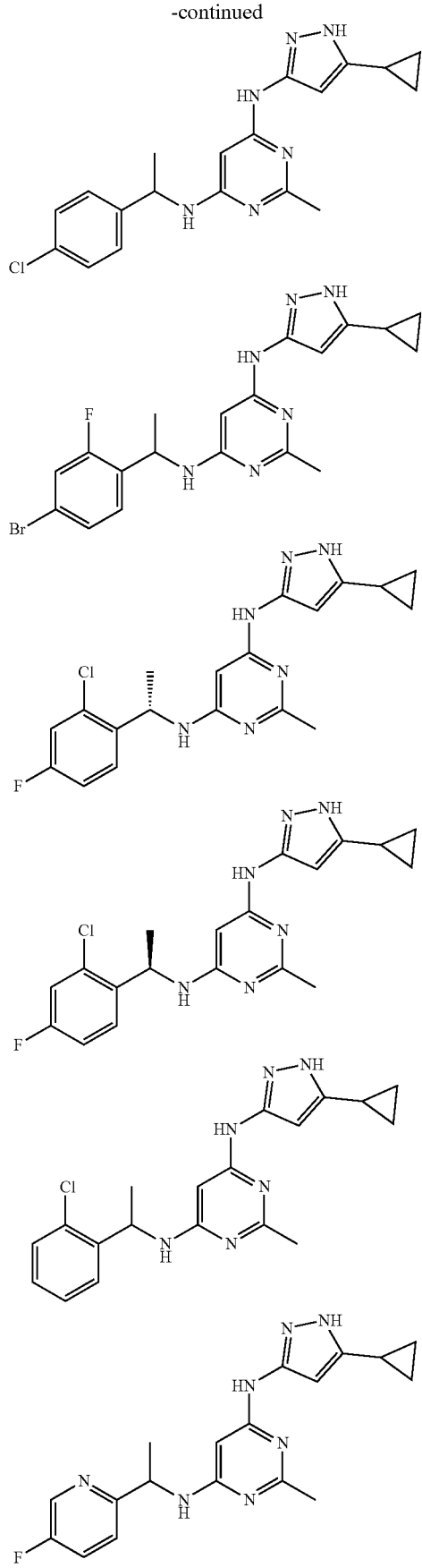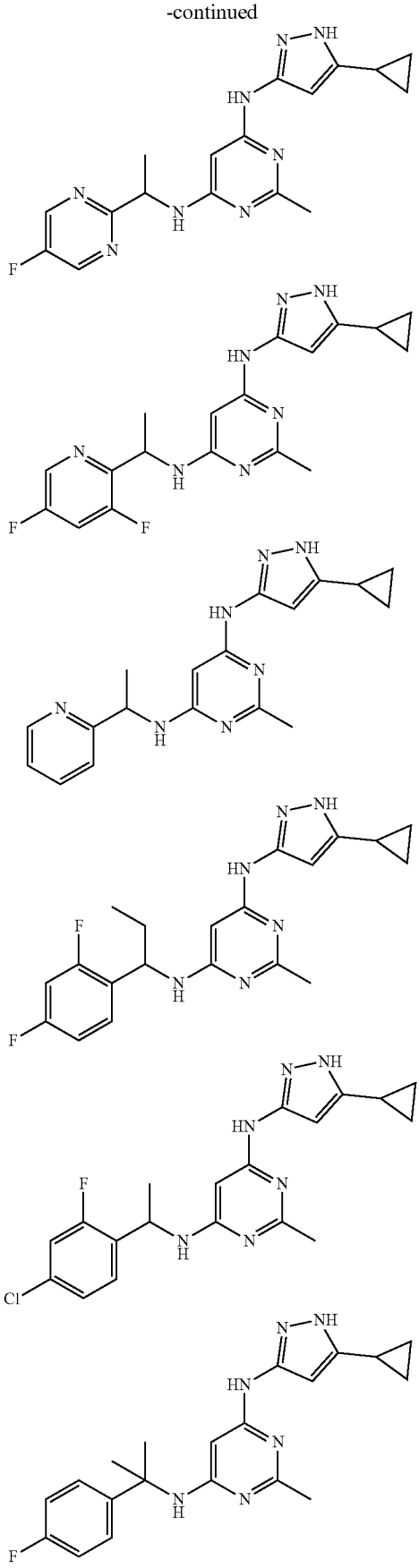

-continued
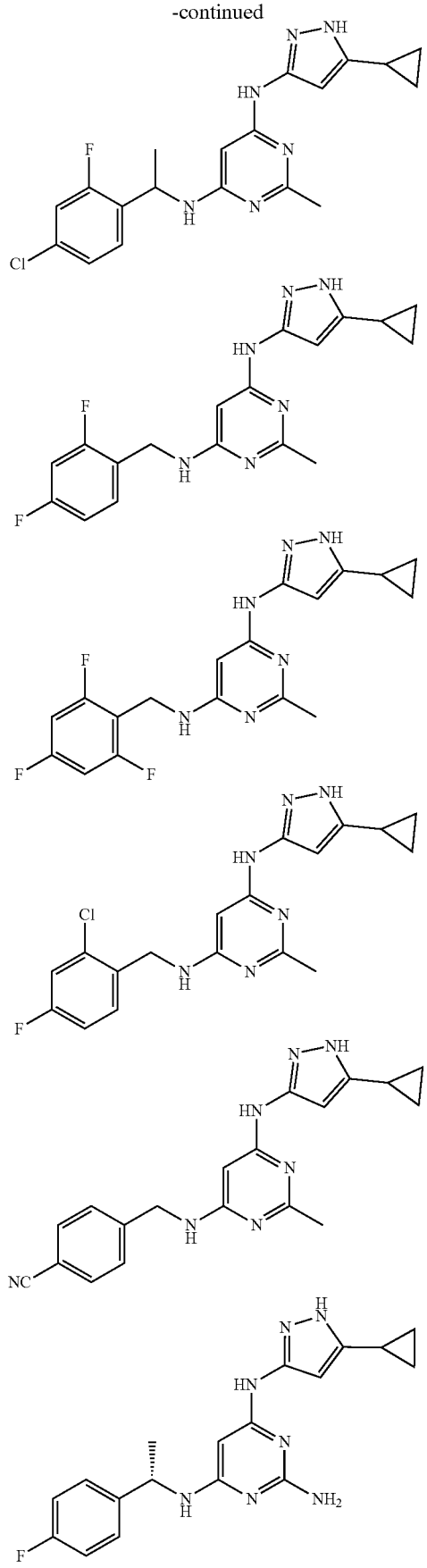
-continued
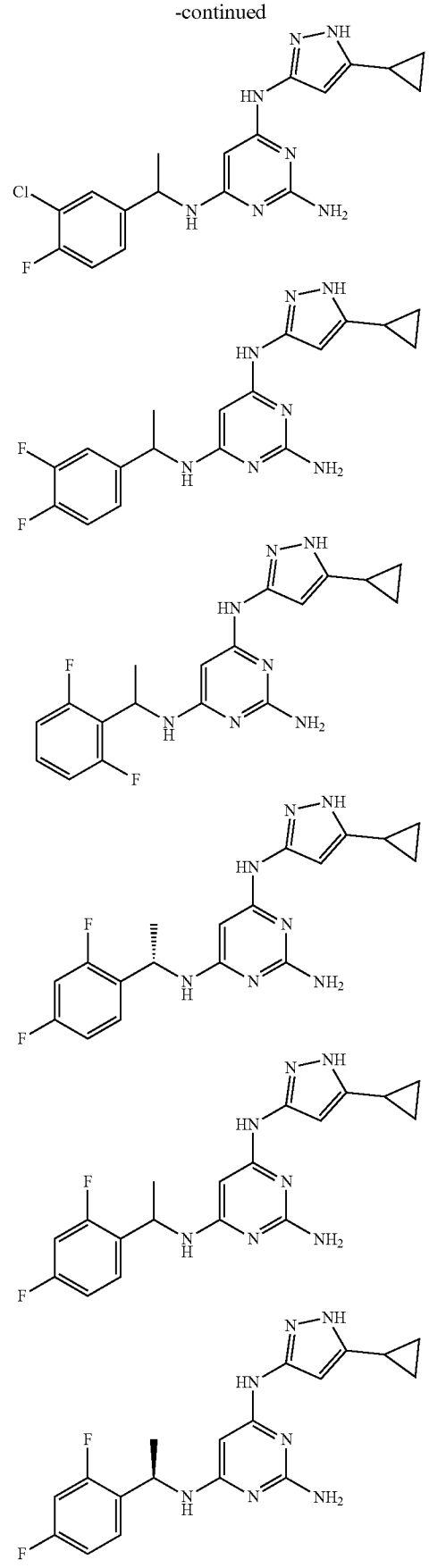

-continued
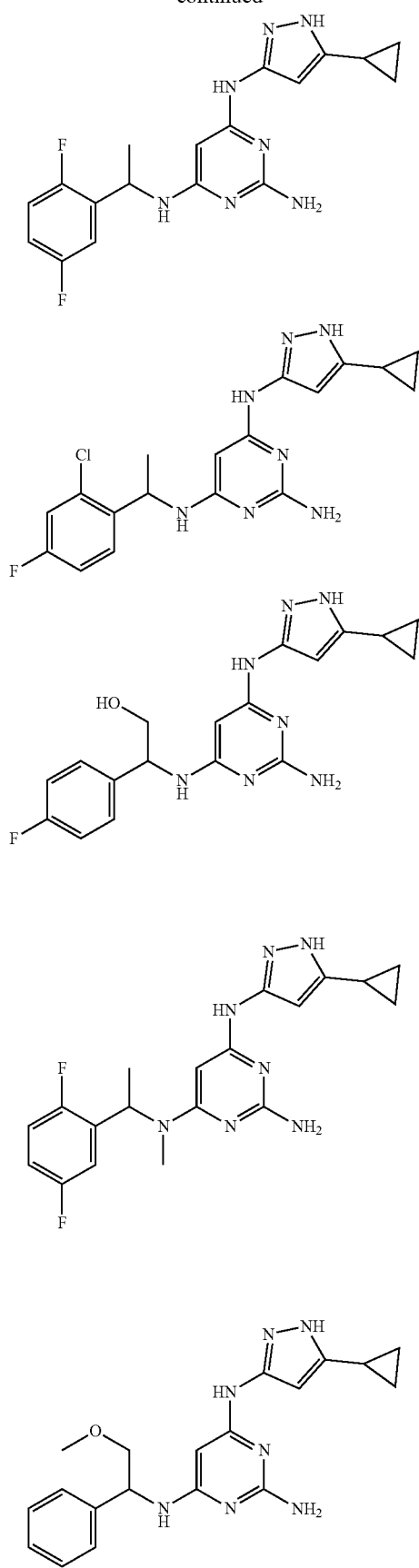
-continued
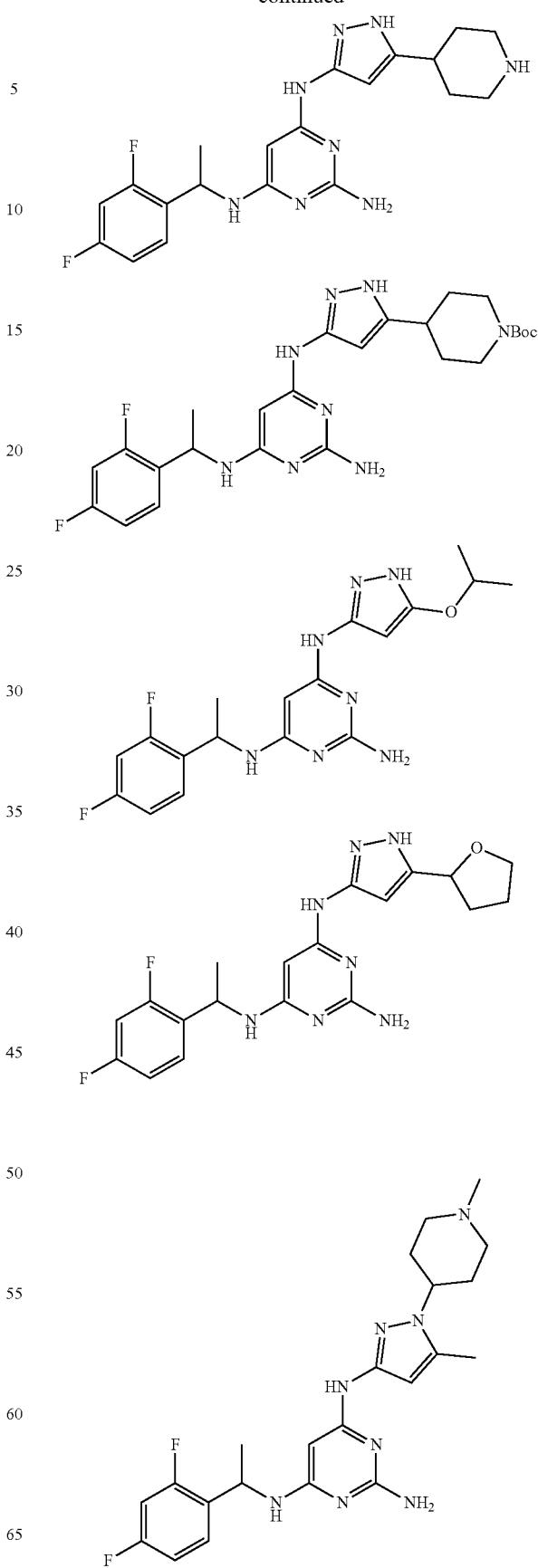

-continued
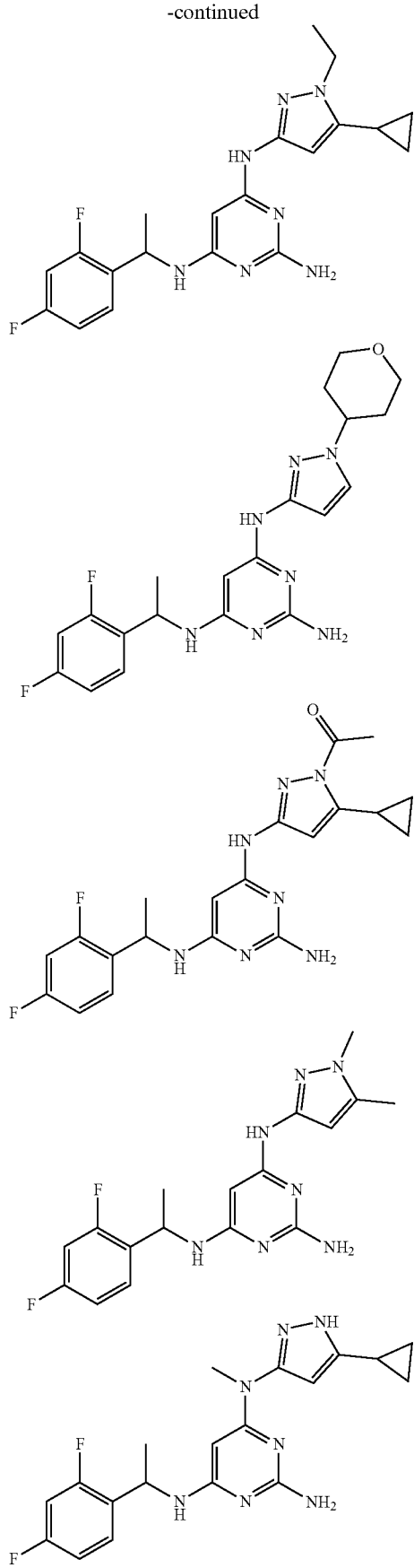
-continued
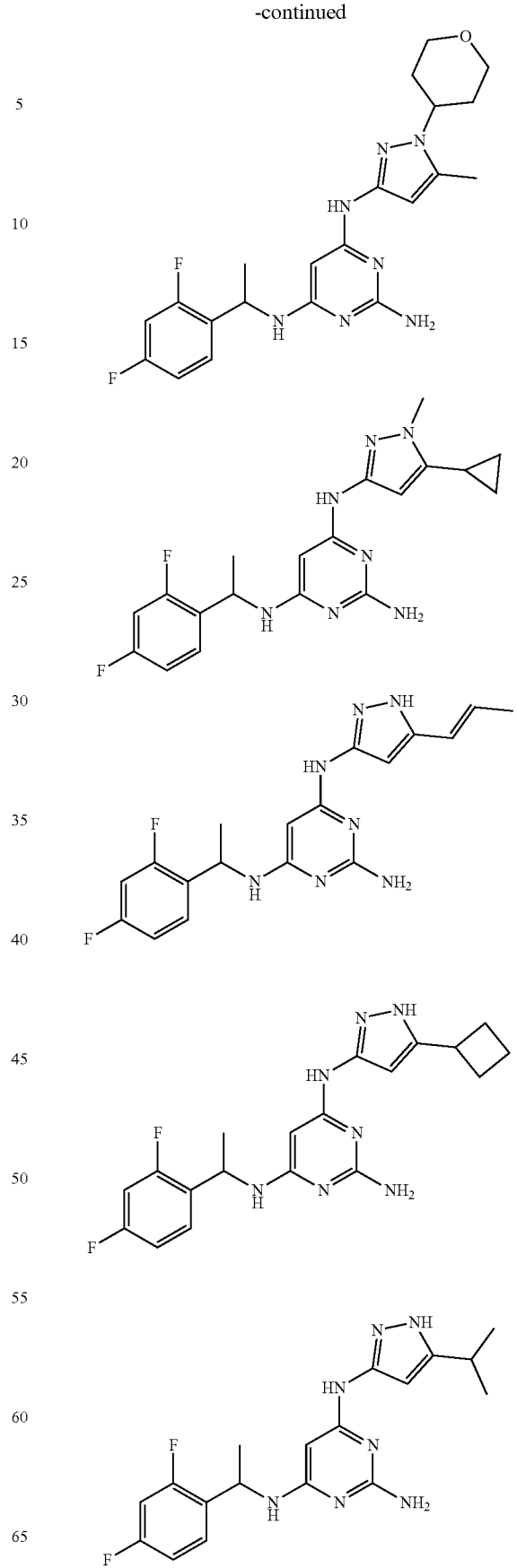

101
-continued
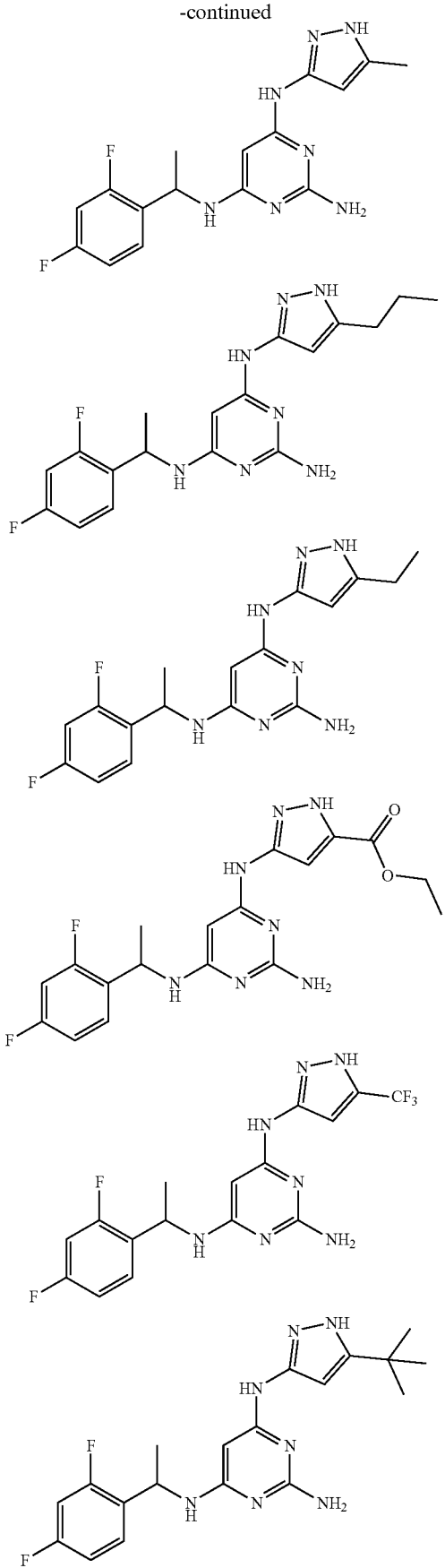
102
-continued
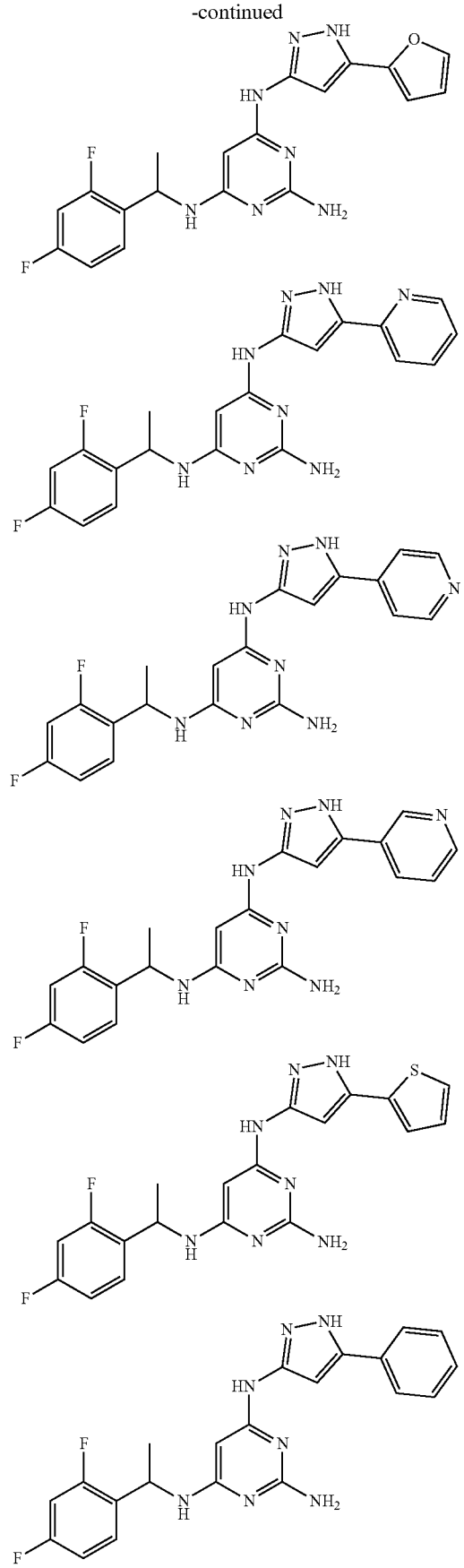

-continued
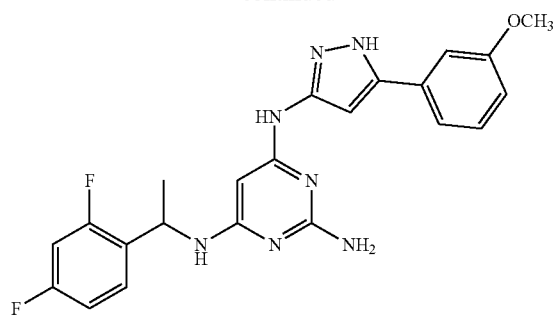
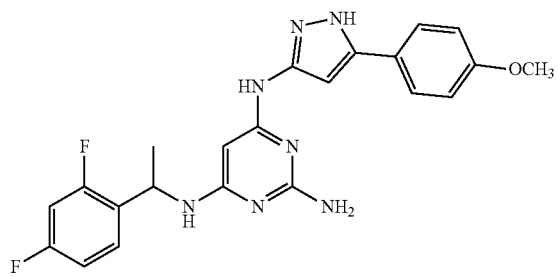
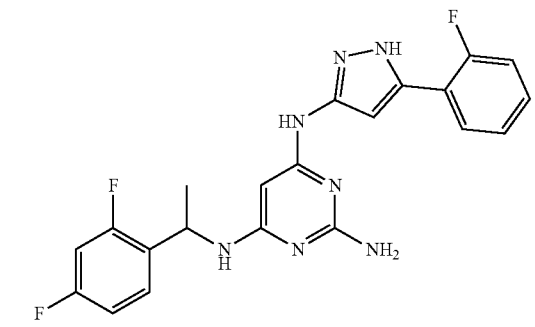
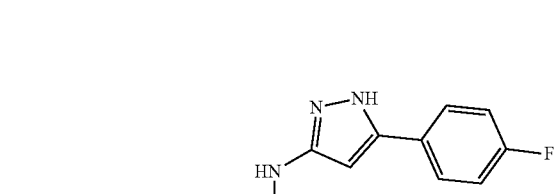
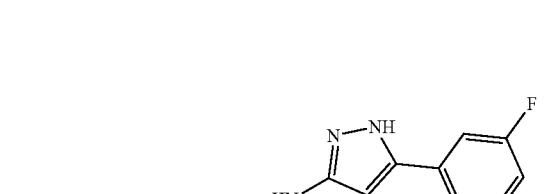
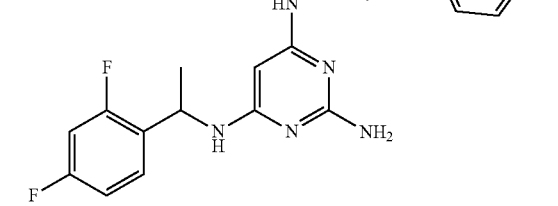
-continued
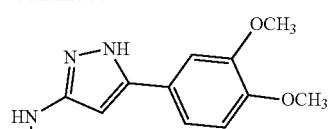
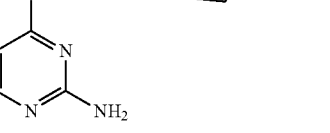
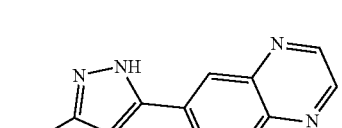
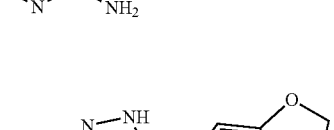
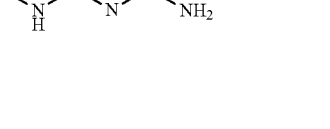

-continued
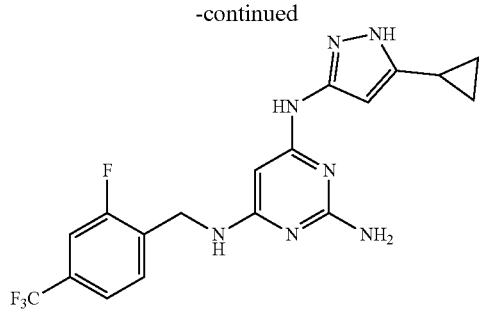
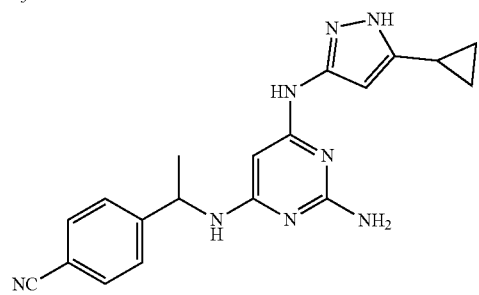
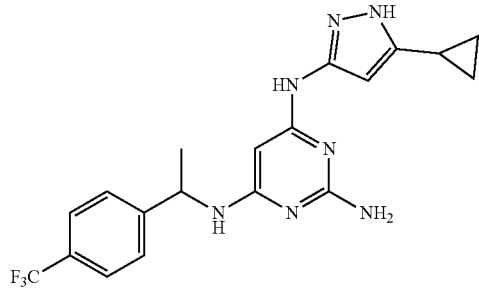
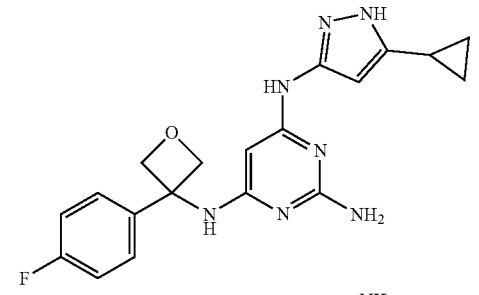
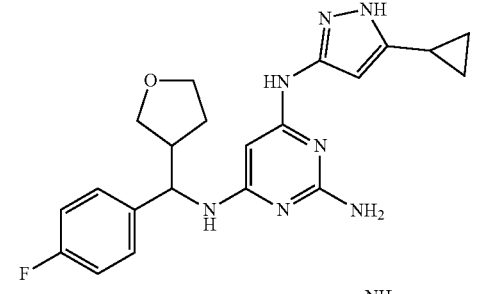
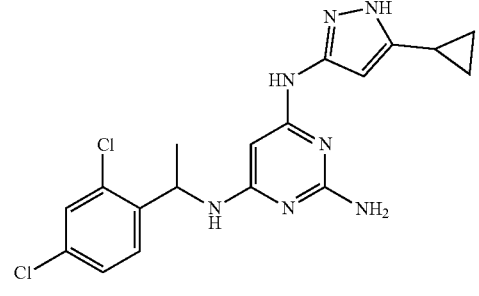
-continued
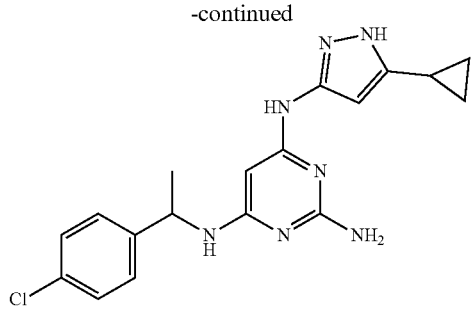
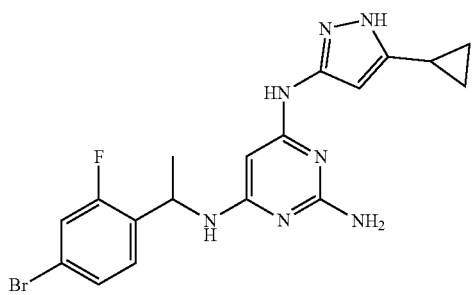
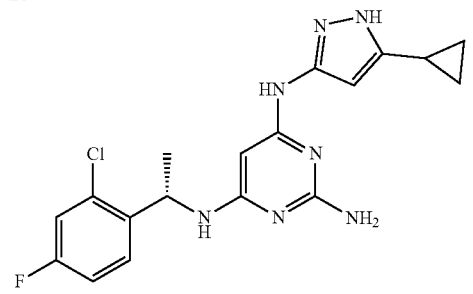
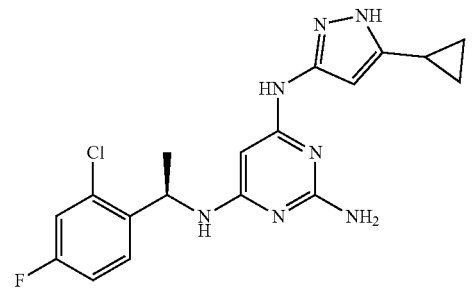
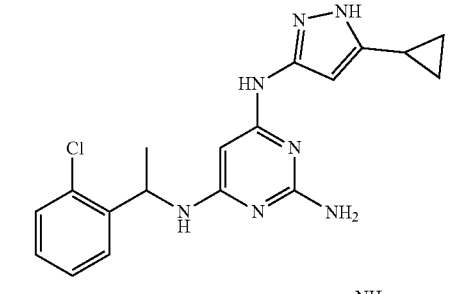
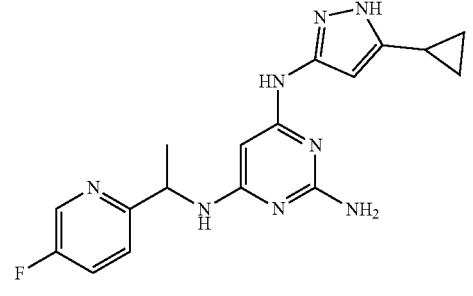

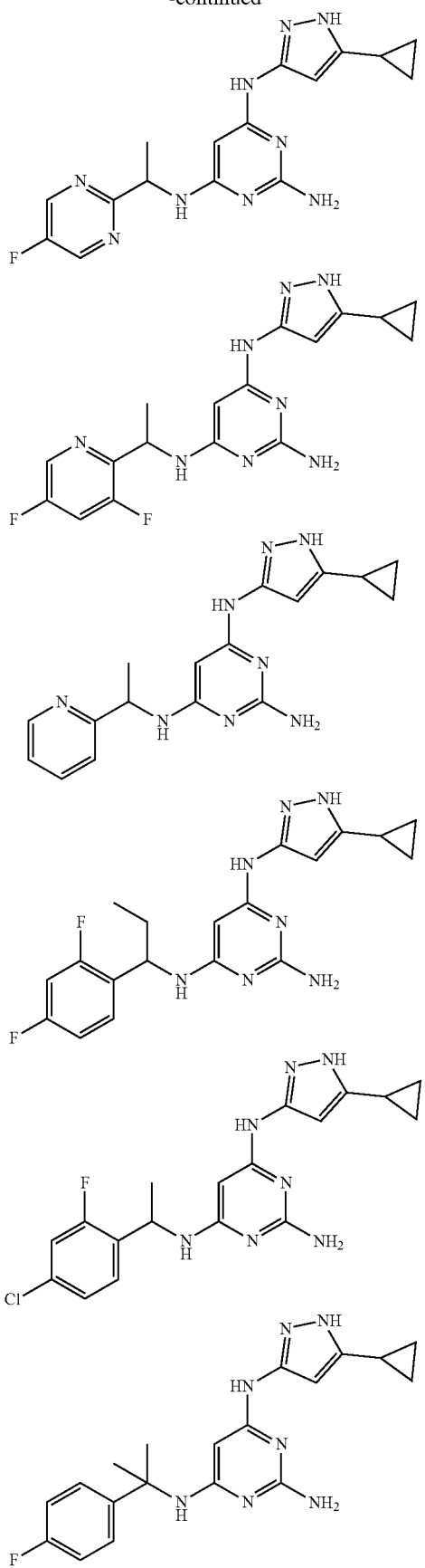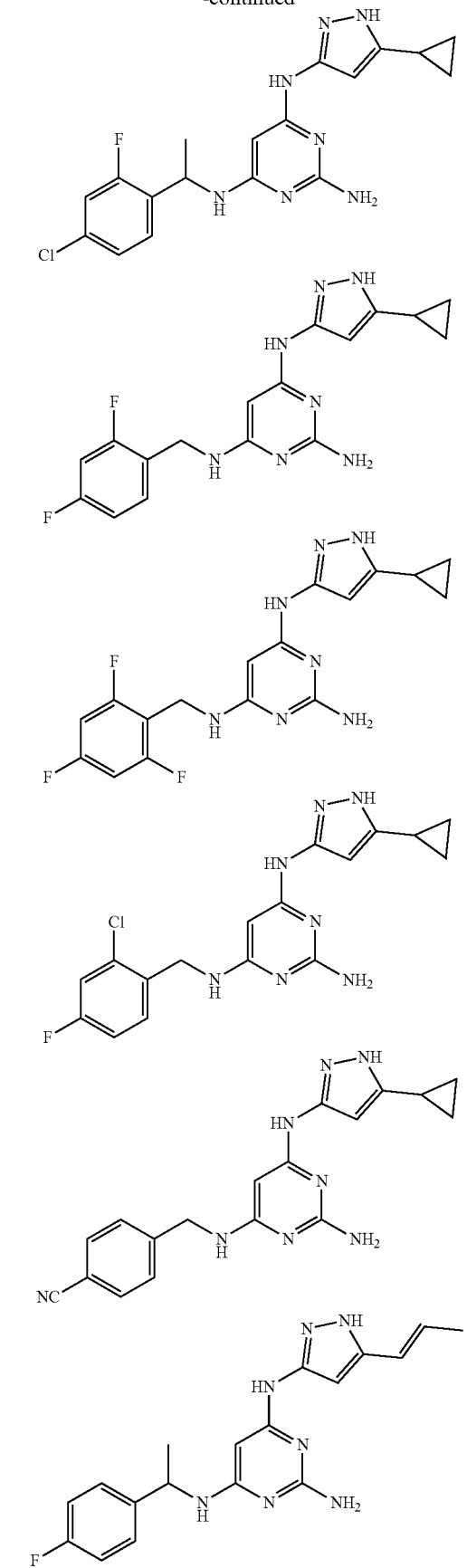

-continued
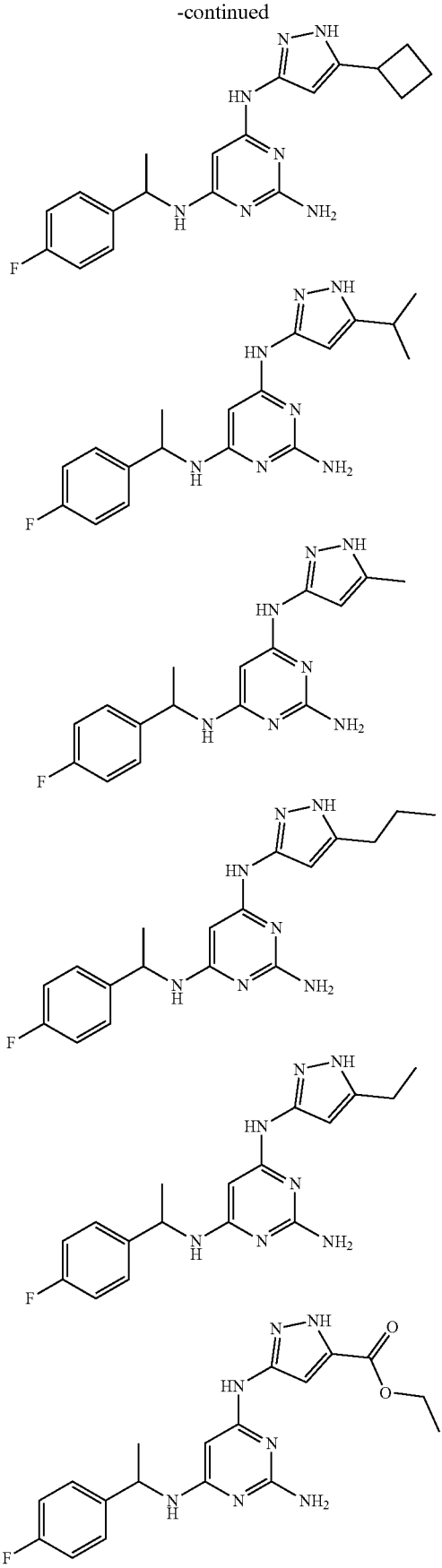
-continued
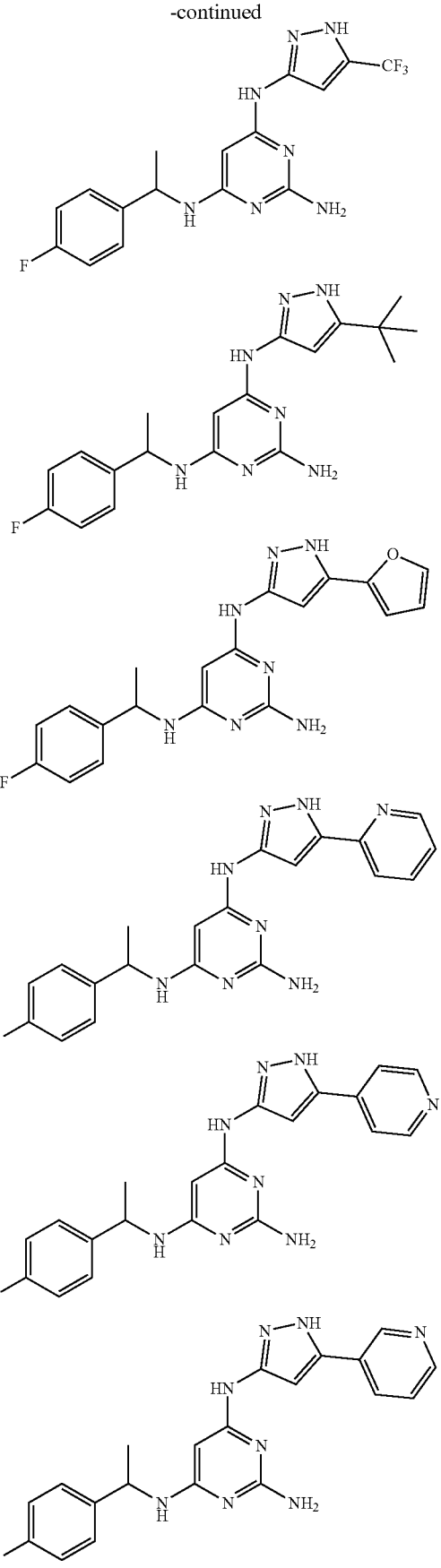

111
-continued
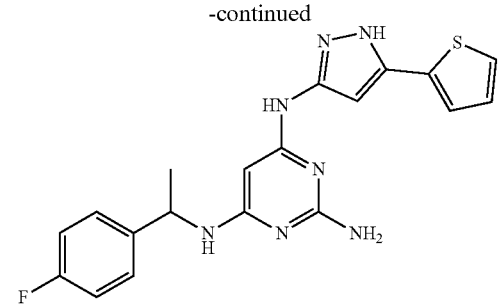
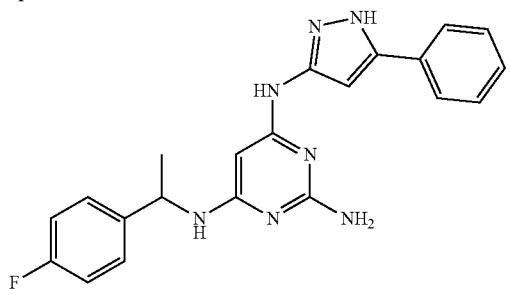
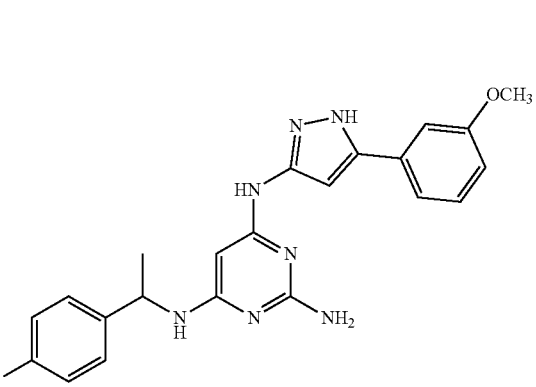
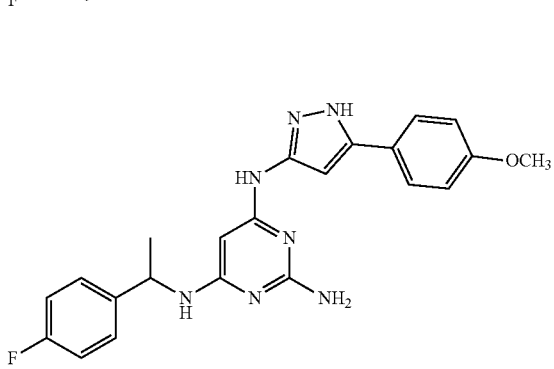
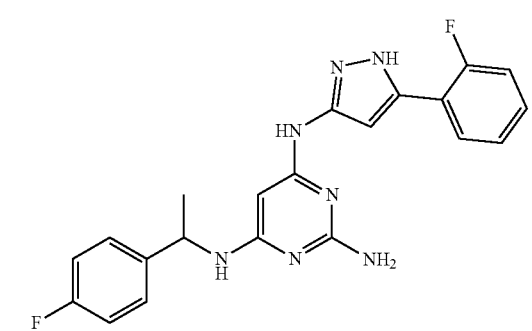
112
-continued
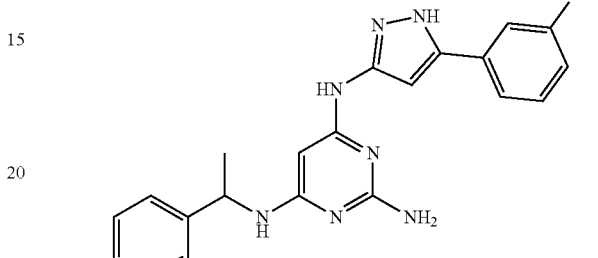
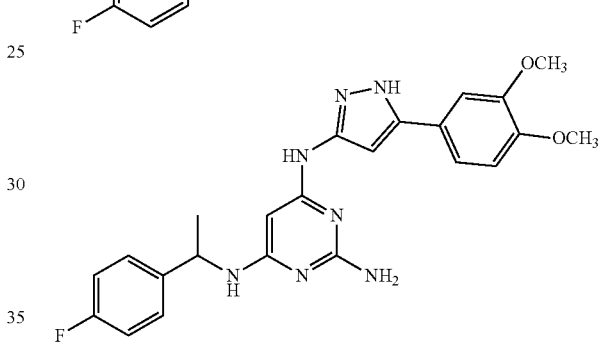
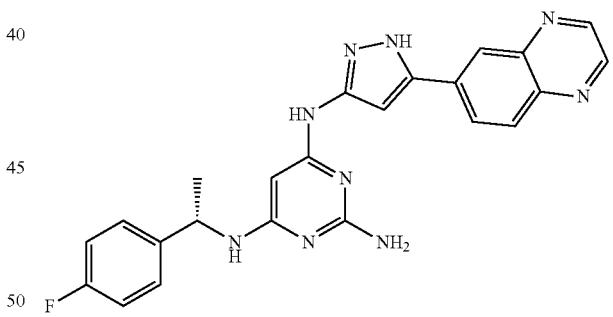
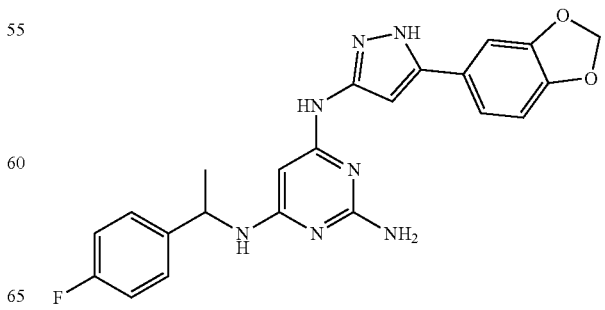

-continued
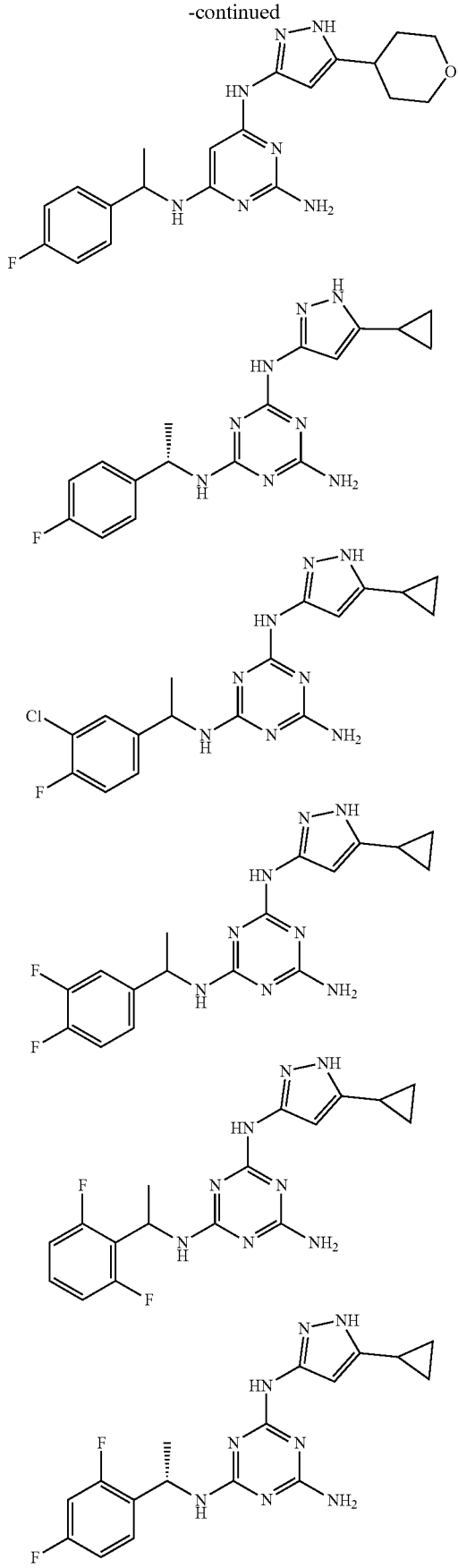
-continued
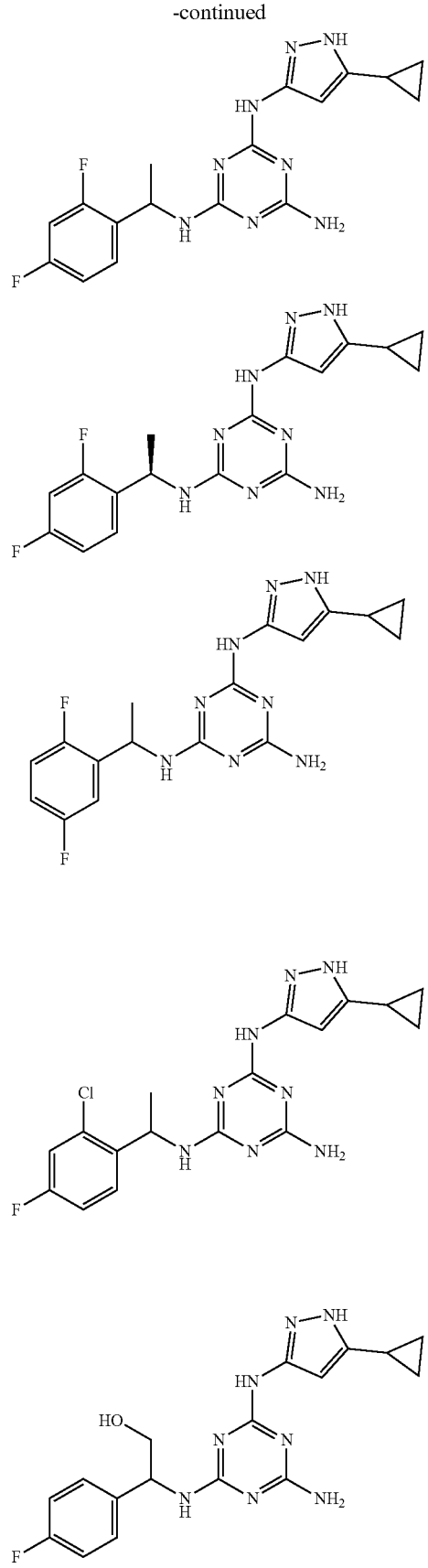

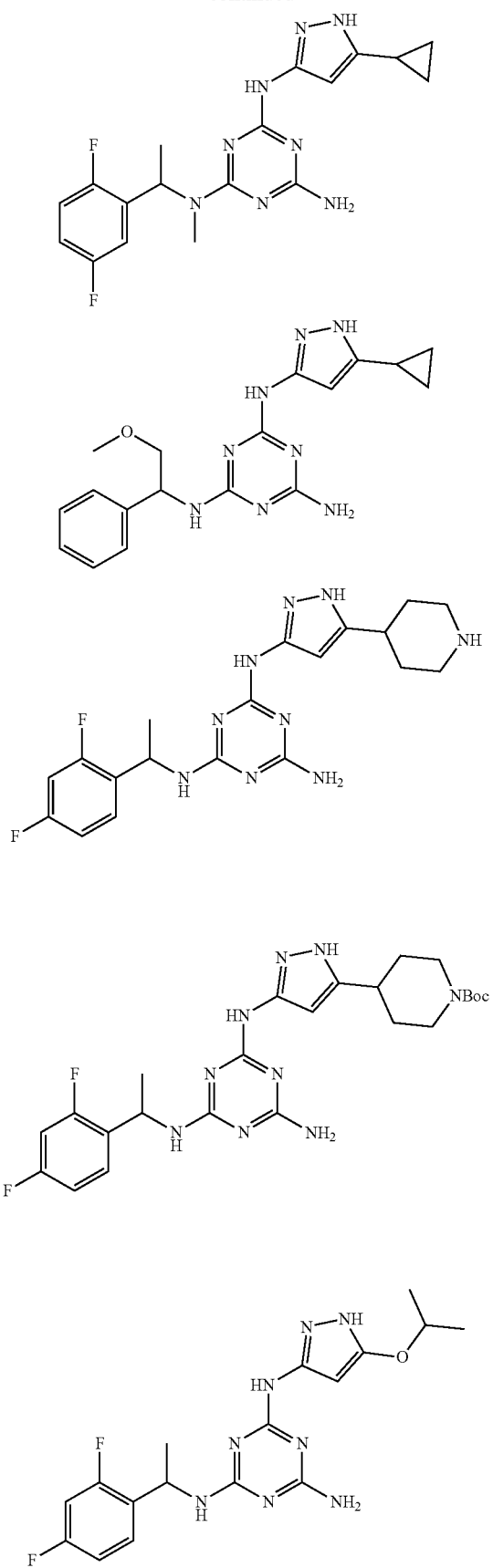
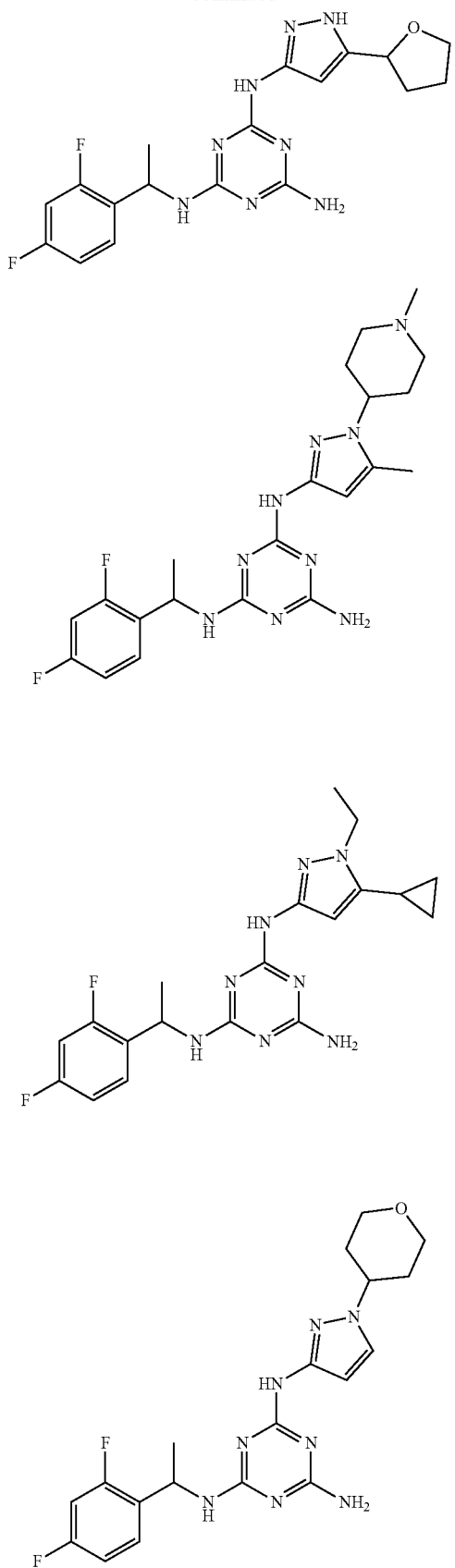

117
-continued
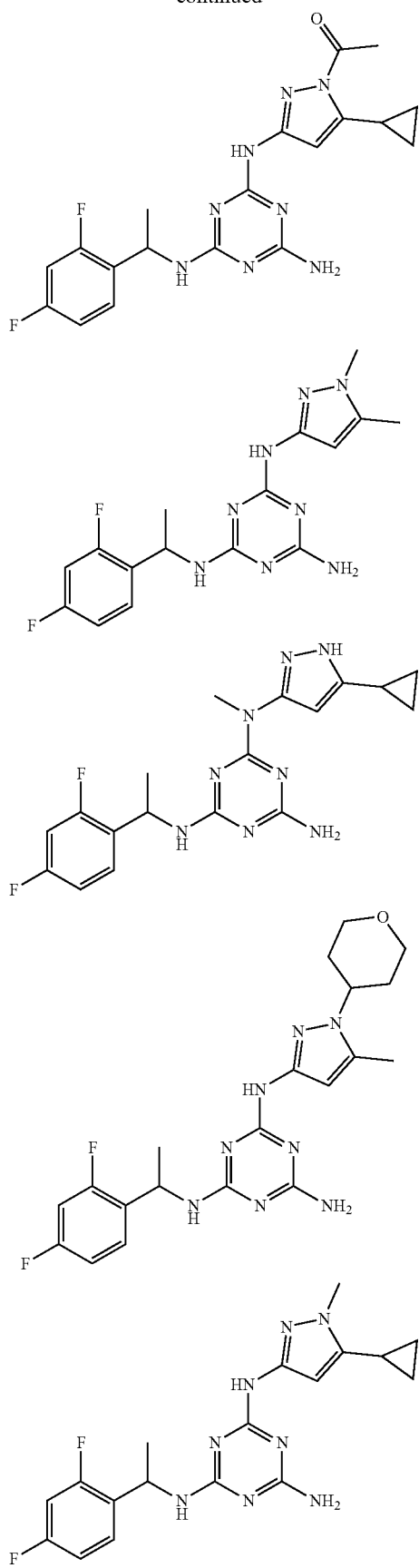
118
-continued
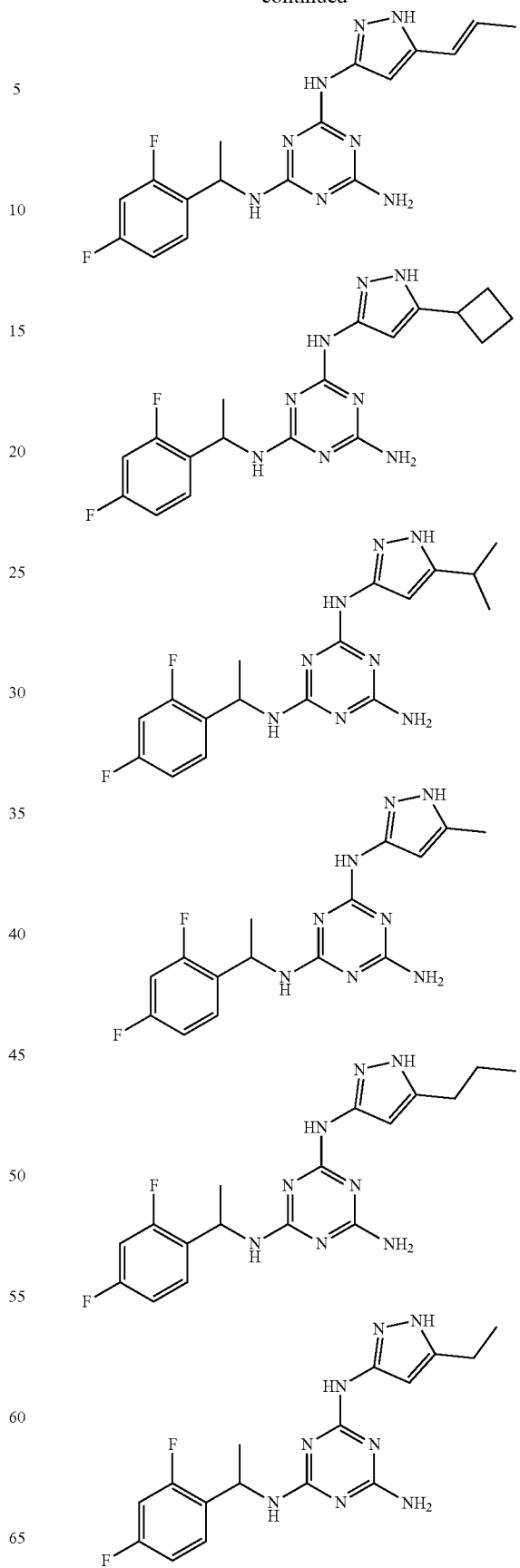

119
-continued
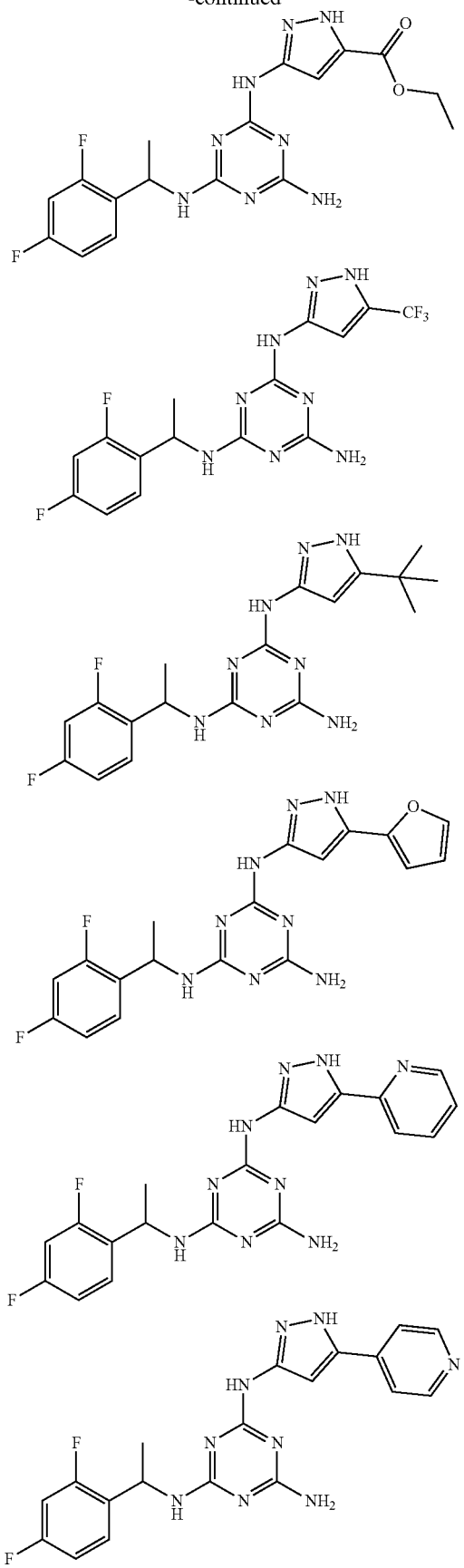
120
-continued
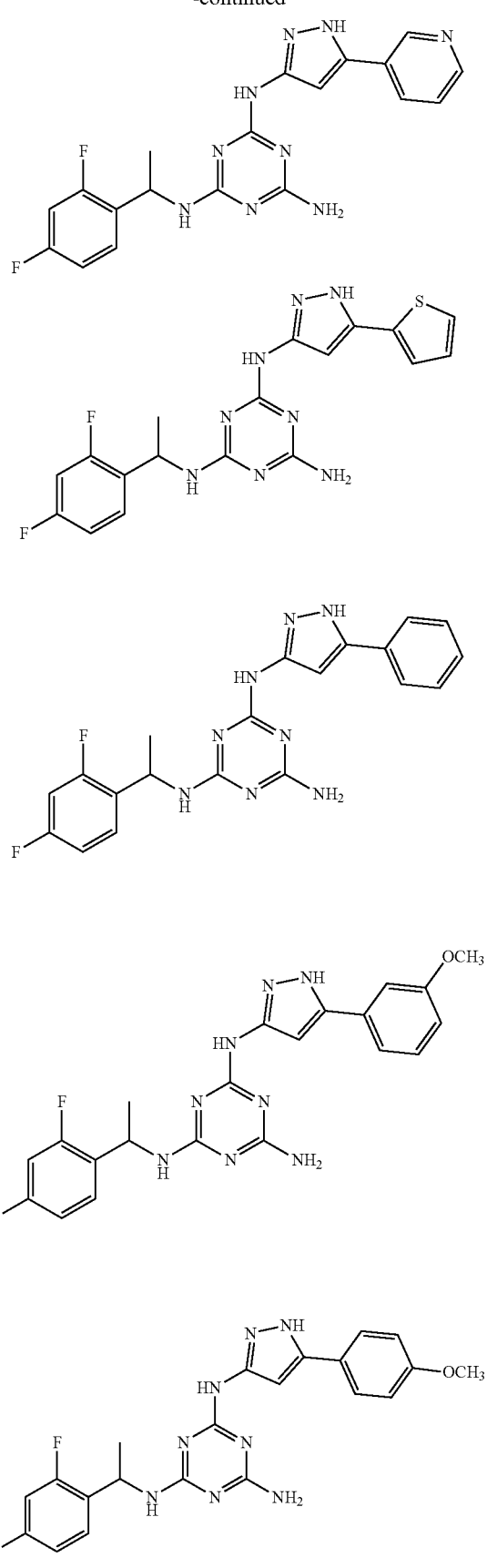

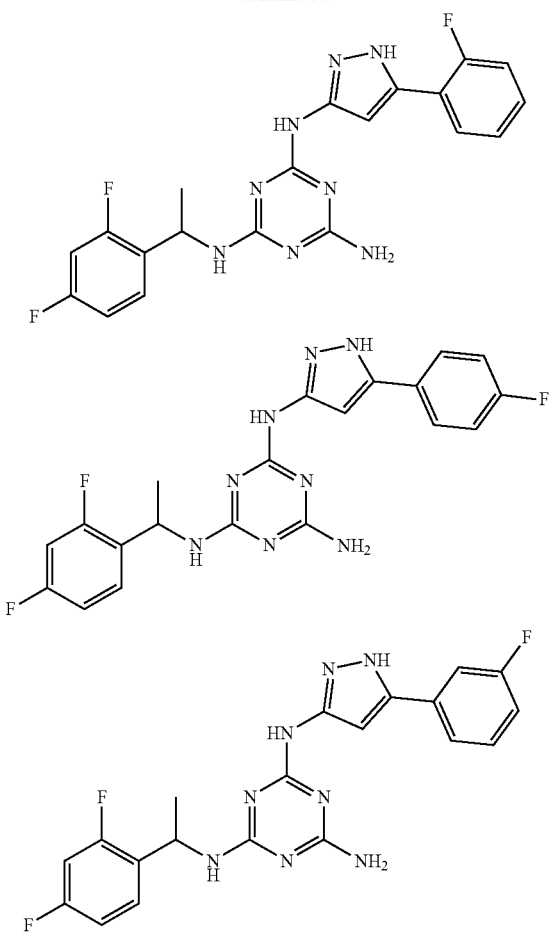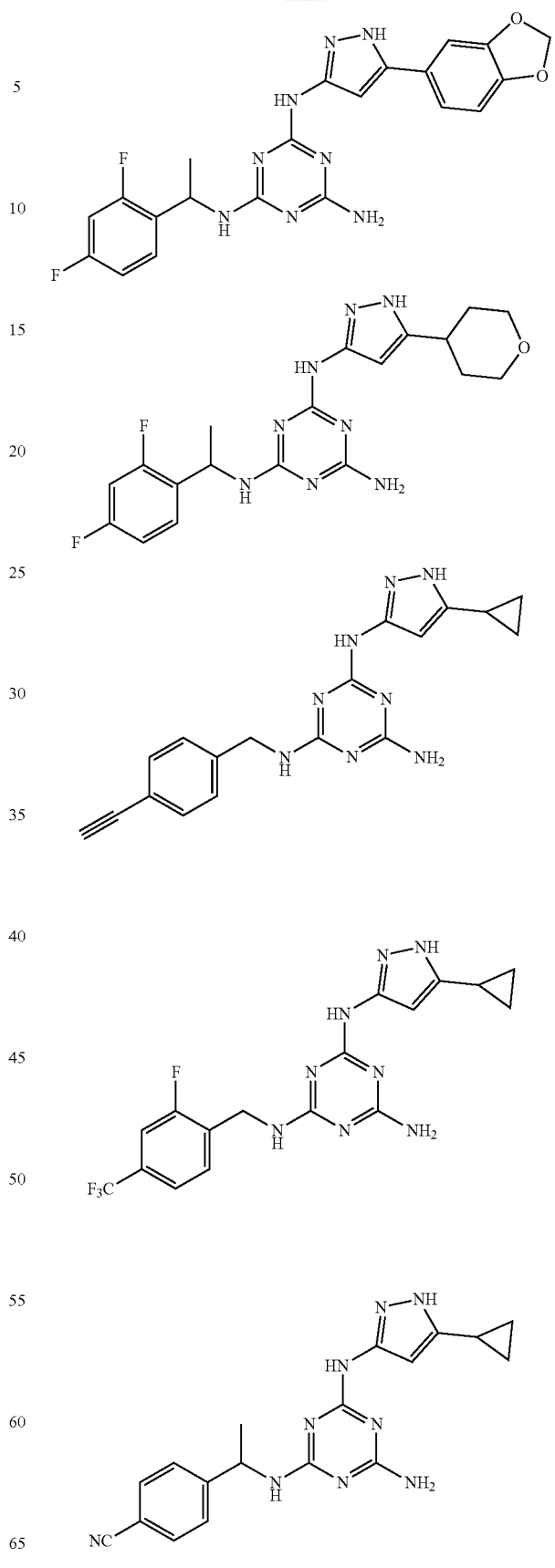

-continued
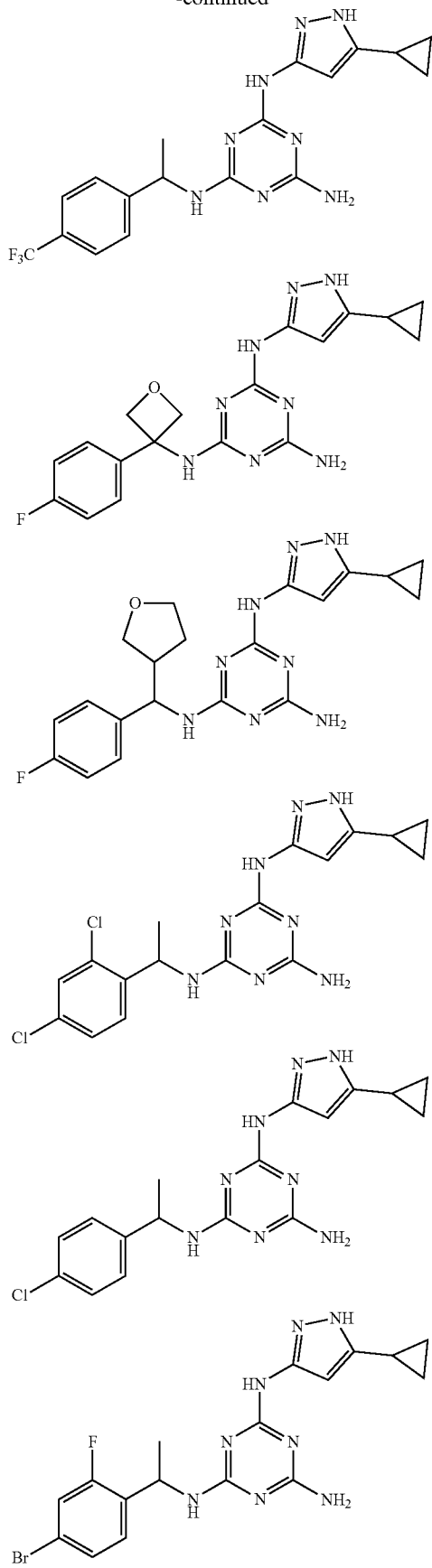
-continued
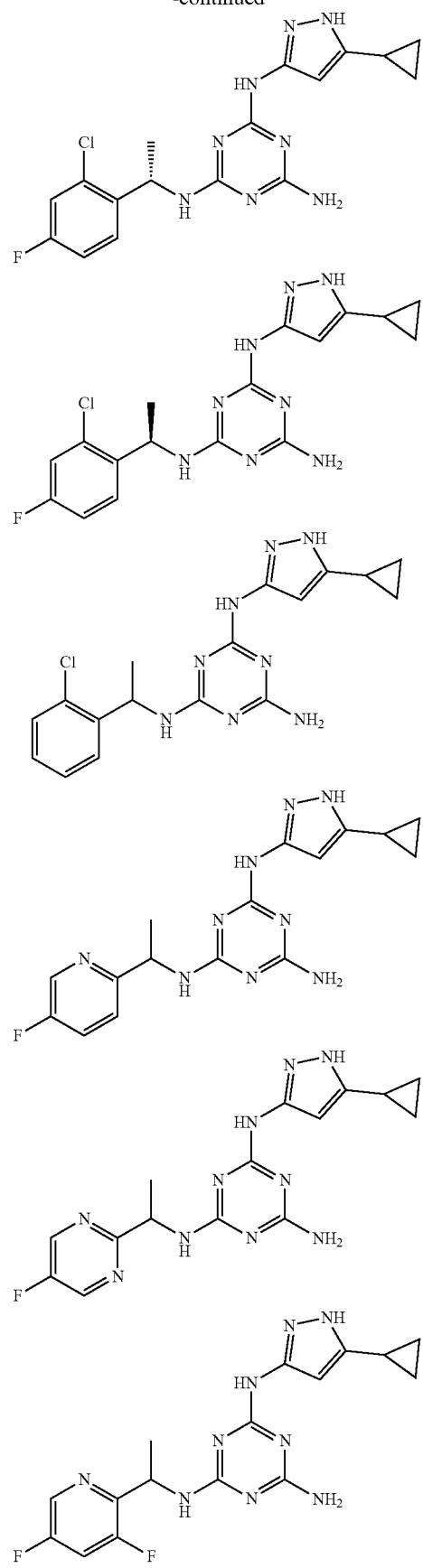

-continued
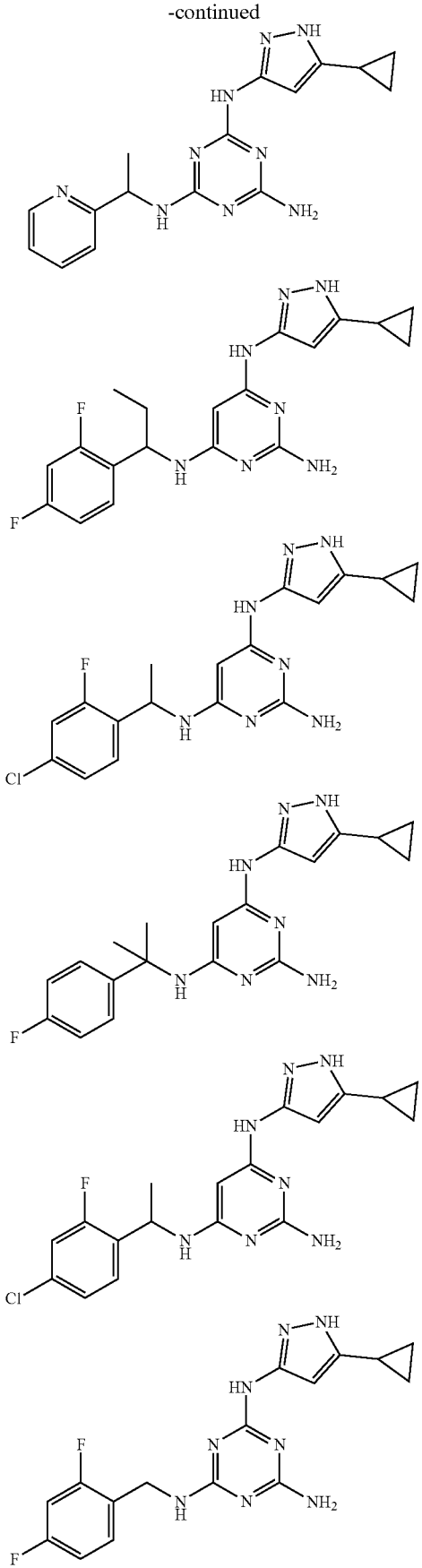
-continued
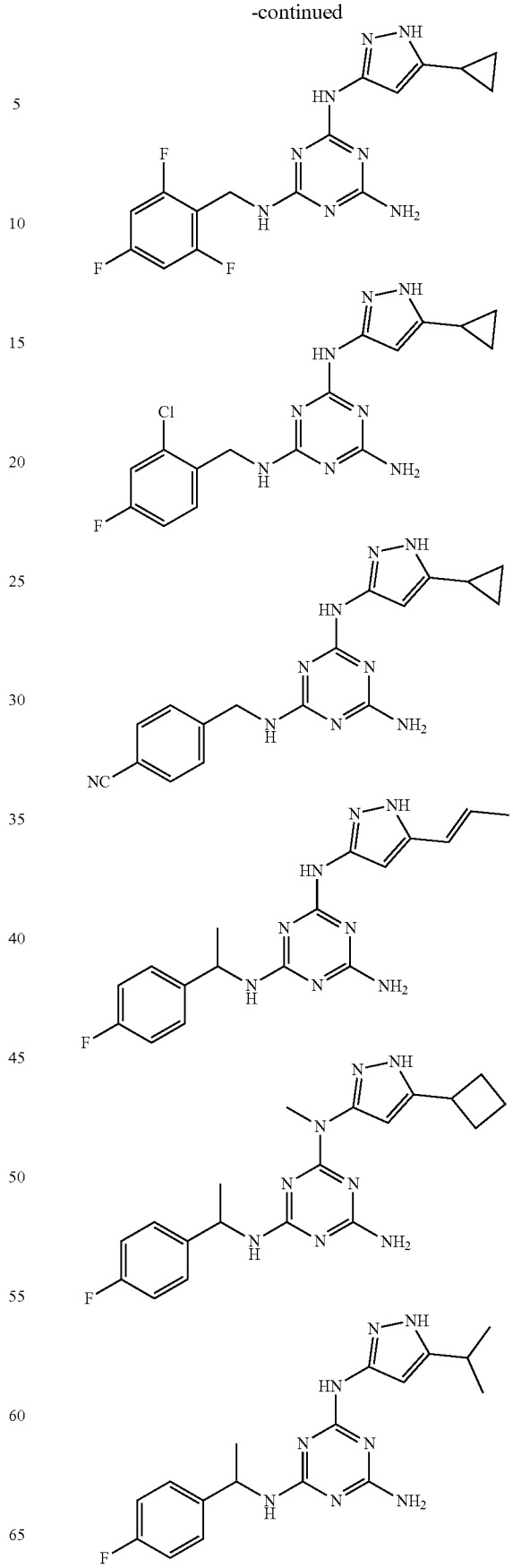

127
-continued
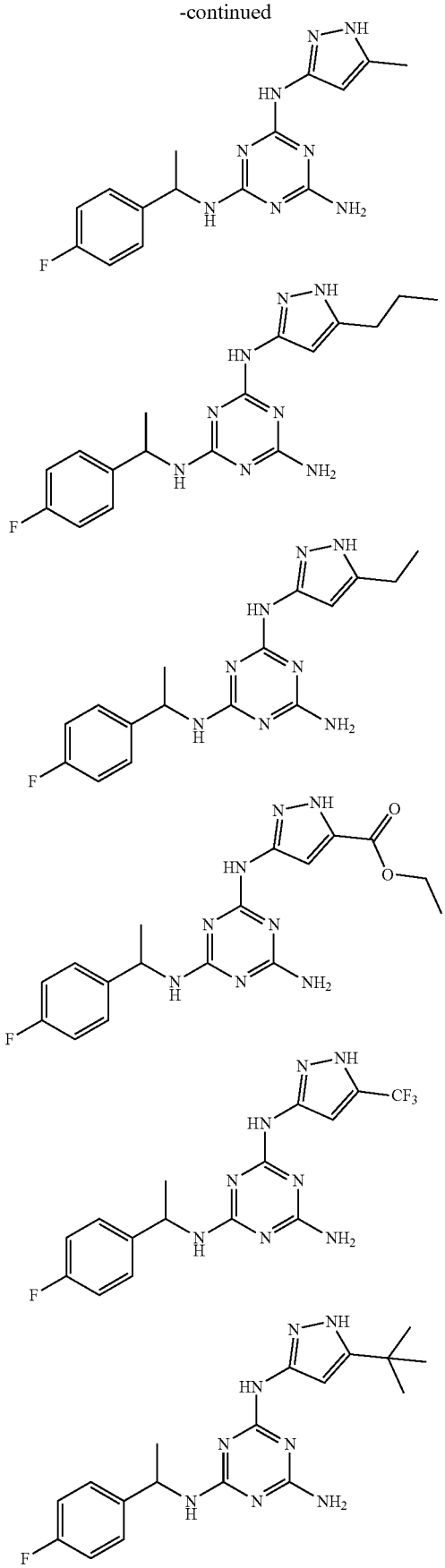
128
-continued
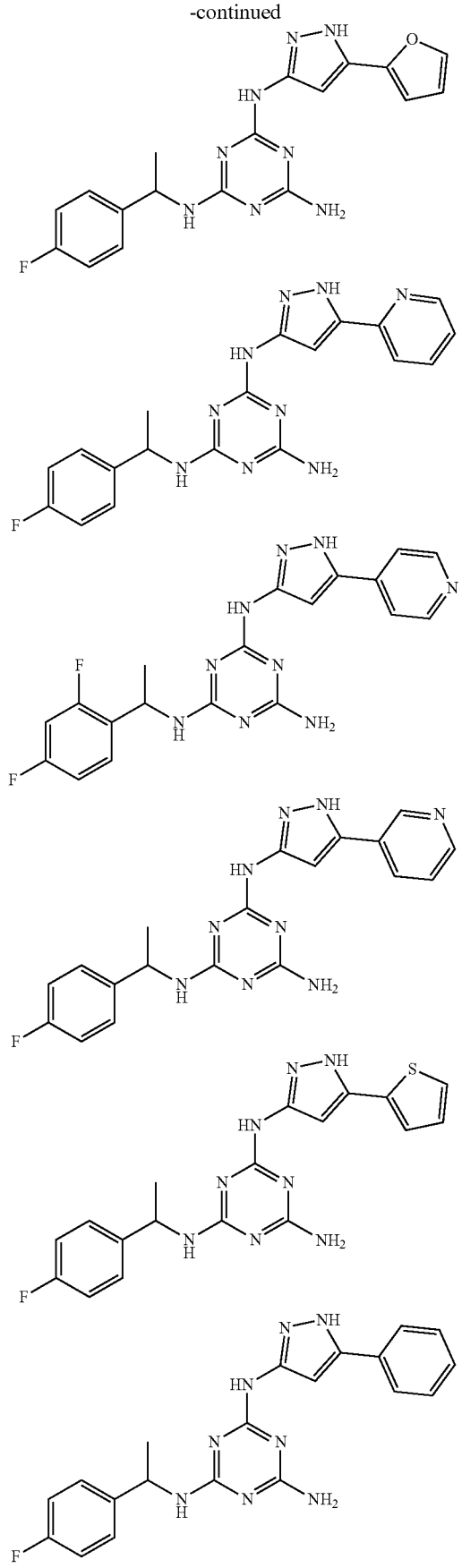

129
-continued
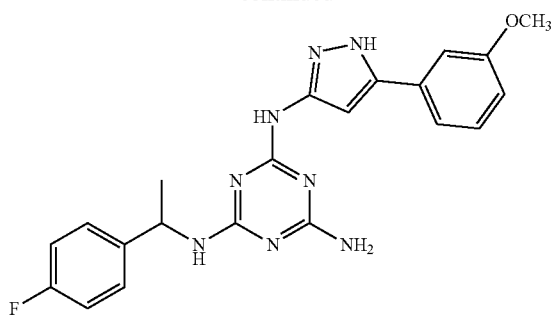
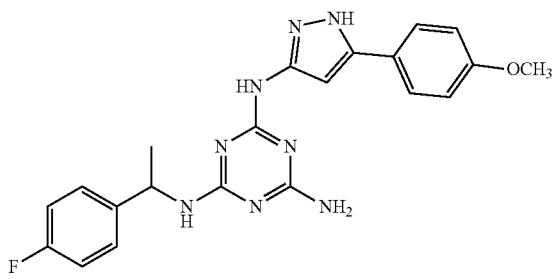
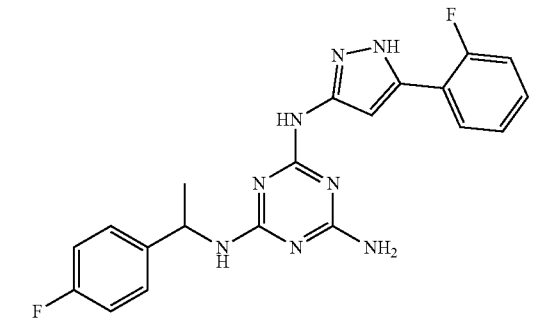
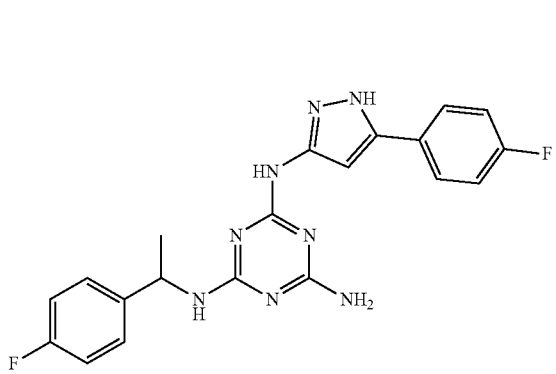
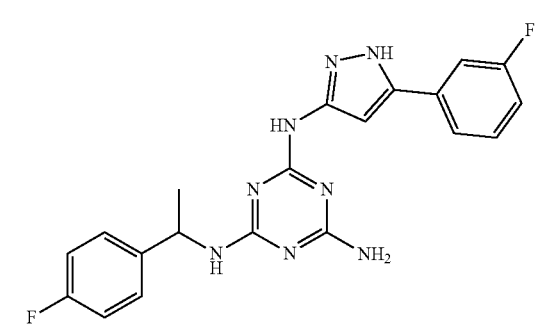
130
-continued
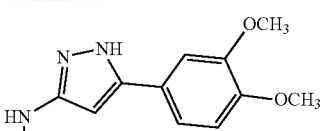
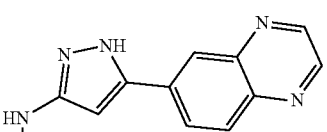
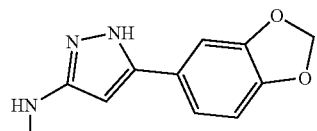
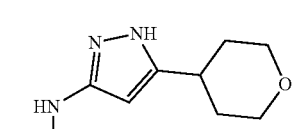
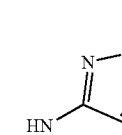

131
-continued

132
-continued

-continued

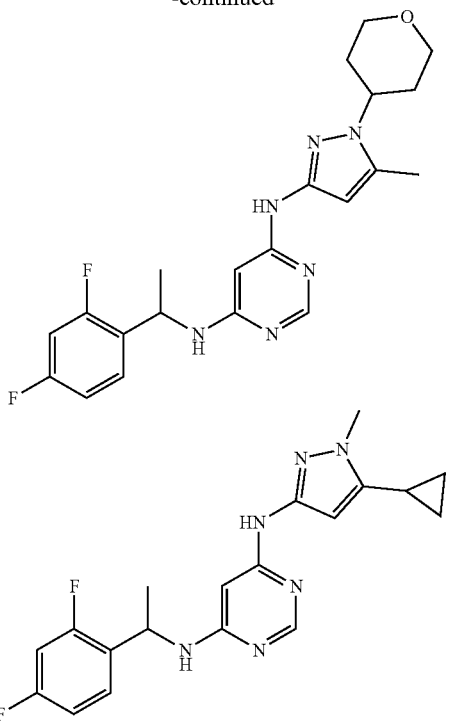

In another embodiment, a method of preparing the inventive compounds is provided. The compounds of the present invention can be generally prepared using 4, 6-dichloro-pyrimidine, or 2-Amino-4,6-dichloropyrimidine, with various substituents on position "5". Compound (I) may contain various stereoisomers, geometric isomers, tautomeric isomers, and the like. All of possible isomers and their mixtures are included in the present invention, and the mixing ratio is not particularly limited.

By way of example, a synthetic route similar to that shown in any of the following Schemes may be used, together with synthetic methods known in the art of synthetic organic chemistry, or variations thereon as appreciated by those skilled in the art. Each variable in the following schemes refers to any group consistent with the description of the compounds provided herein.

The compounds of Formula (I) may be prepared by use of known chemical reactions and procedures. The following general preparative methods are presented to aid one of skill in the art in synthesizing the inhibitors, with more detailed examples being presented in the experimental section describing the working examples.

Propenyl-pyrazol amine as defined in formula (II) is not commercially available. It can be prepared by several methods as described earlier (WO 2014071378).

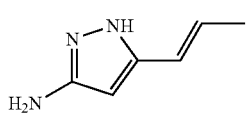
(II)

Precursors of substituted amines as defined in formula (III) can be purchased from suppliers, or synthesized from commercially available precursors using established protocols. (PCT Int. Appl., 2014141104, 18 Sep. 2014; Tetrahedron Letters, 47(36), 6409-6412; 2006; PCT Int. Appl., 2013082429, 6 Jun. 2013) (each of which is incorporated herein by reference).

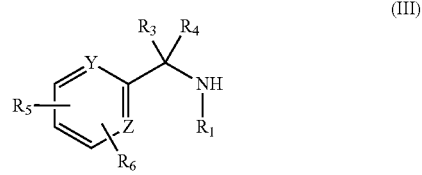
(III)

Precursors of 4, 6-dichloro-pyrimidines as defined in formula (IVa) and 4, 6-dichloro-1,3,5-triazine as defined in formula (IVb) can be purchased from suppliers, or prepared according to using established protocols (PCT Int. Appl., 2010144345, 16 Dec. 2010; PCT Int. Appl., 2010144338, 16 Dec. 2010; F PCT Int. Appl., 2010144359, 16 Dec. 2010) (each of which is incorporated herein by reference))

(IVa)

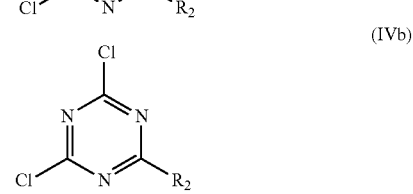
(IVb)

Generally, precursors of hetero-amine (Het-NHR$_1$) can be purchased from suppliers. Precursors of substituted pyrazol-amine as defined in formula (V) can be purchased from suppliers.

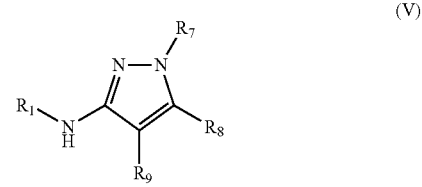
(V)

The preparation of the compounds of formula (I) in this invention can be carried out by methods listed in scheme 1.

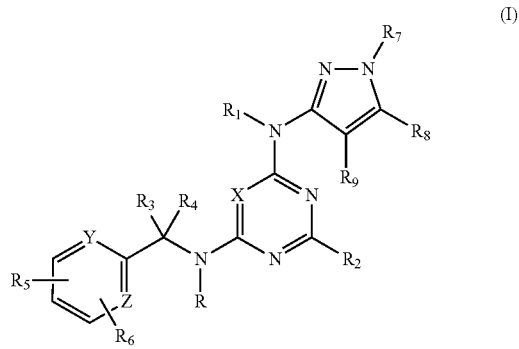
(I)

As shown in scheme 1, the pyrimidine derivative (I) can be synthesized by the reaction of substituted 4,6-dichloropyrimidine (IVa), or 4,6-dichloro-1,3,5-triazine (IVb) with a sequence of substituted amine to give monochlororopyrimidine intermediate of compound b, which can react with amino-pyrazole (V)) to produce the final compound (I). The reaction can be stepwise or in one pot. Alternative sequence can also be used to make pyrimidine derivatives.

The reaction may be conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halo-

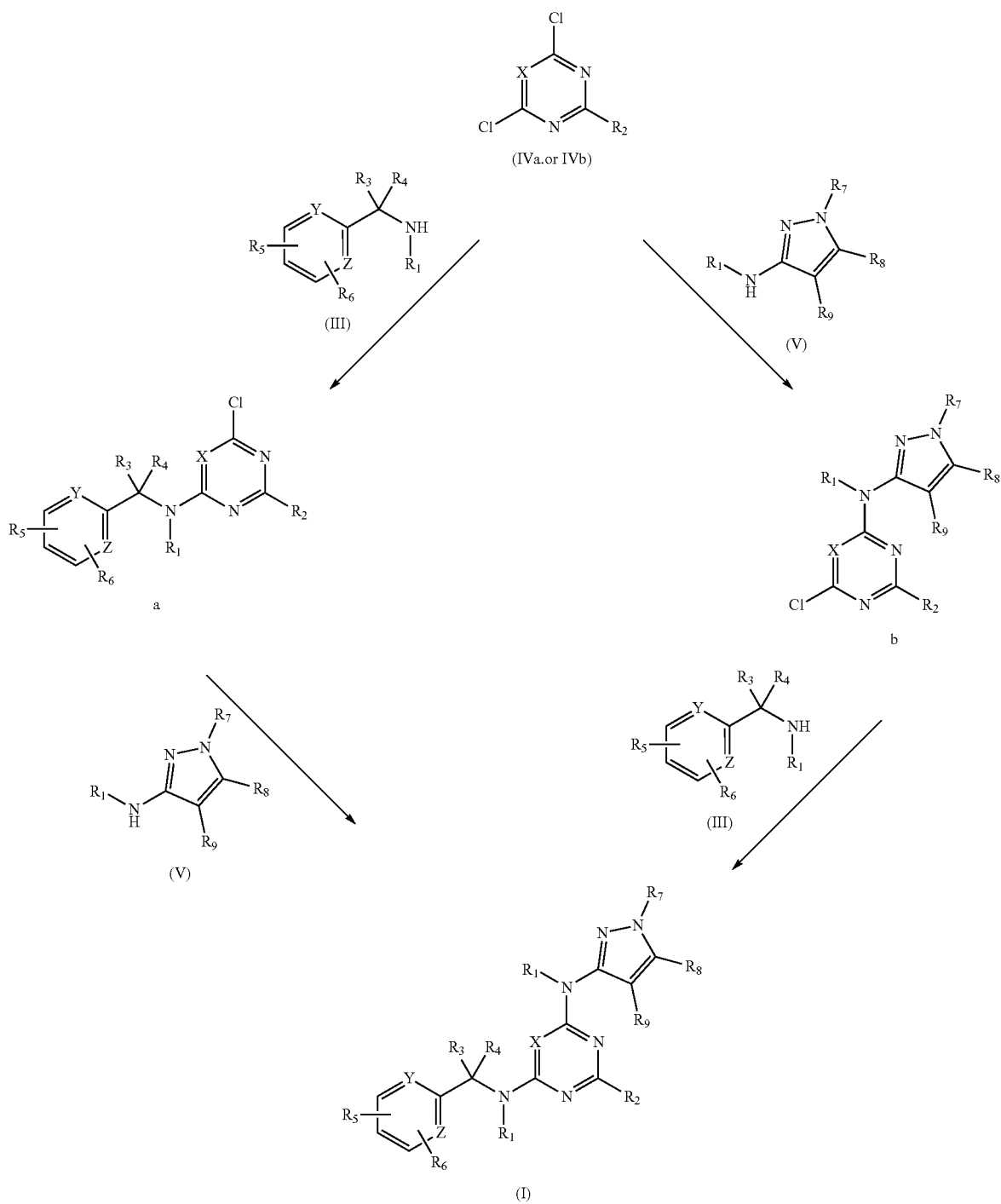

genated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane. dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. For example, the reaction may be carried out at a temperature of from −50° C. to 200° C.

The present invention provides compositions of matter that are formulations of one or more active drugs and a pharmaceutically-acceptable carrier. In this regard, the invention provides a composition for administration to a mammalian subject (preferably, though not limited to, human subjects or patients), which may include a compound of formula I, or its pharmaceutically acceptable salts.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+($C_{1-4}$ alkyl)$_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In certain embodiments, the compositions are administered orally, intraperitoneally or intravenously.

The pharmaceutically acceptable compositions of this invention may be orally administered in any orally acceptable dosage form including, but not limited to, capsules, tablets, troches, elixirs, suspensions, syrups, wafers, chewing gums, aqueous suspensions or solutions.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, suitable methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

In accordance with the invention, there are provided compositions containing pyrazole derivatives and methods useful for the in vivo delivery of pyrazole derivatives in the form of nanoparticles, which are suitable for any of the aforesaid routes of administration.

U.S. Pat. Nos. 5,916,596, 6,506,405 and 6,537,579 (each of which is incorporated herein by reference) teach the preparation of nanoparticles from the biocompatible polymers, such as albumin. Thus, in accordance with the present invention, there are provided methods for the formation of nanoparticles of the present invention by a solvent evaporation technique from an oil-in-water emulsion prepared under conditions of high shear forces (e.g., sonication, high pressure homogenization, or the like).

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, for example as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the pharmaceutically acceptable compositions of this invention are formulated for oral administration.

In accordance with the invention, the compounds of the invention may be used to treat diseases associated with cellular proliferation or hyperproliferation, such as cancers which include but are not limited to tumors of the nasal cavity, paranasal sinuses, nasopharynx, oral cavity, oropharynx, larynx, hypopharynx, salivary glands, and paragangliomas. The compounds of the invention may also be used to treat cancers of the liver and biliary tree (particularly hepatocellular carcinoma), intestinal cancers, particularly colorectal cancer, ovarian cancer, small cell and non-small cell lung cancer, breast cancer, sarcomas (including fibrosarcoma, malignant fibrous histiocytoma, embryonal rhabdomysocarcoma, leiomysosarcoma, neuro-fibrosarcoma, osteosarcoma, synovial sarcoma, liposarcoma, and alveolar soft part sarcoma), neoplasms of the central nervous systems (particularly brain cancer), and lymphomas (including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma).

The compounds and methods of the present invention, either when administered alone or in combination with other agents (e.g., chemotherapeutic agents or protein therapeutic agents described below) are also useful in treating a variety of disorders, including but not limited to, for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), pleural effusions, rheumatoid arthritis, diabetic retinopathy, retinitis pigmentosa, and retinopathies, including diabetic retinopathy and retinopathy of prematurity, inflammatory diseases, restenosis, asthma, acute or adult respiratory distress syndrome (ARDS), lupus, vascular leakage, protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kineses such as Src-family kineses are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemialreperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener s granulomatosis, and Behcet's disease; scleroderma; preeclampsia; thalassemia; Kaposi's sarcoma; von Hippel Lindau disease; and the like.

In accordance with the invention, the compounds of the invention may be used to treat diseases associated with undesired cellular proliferation or hyperproliferation, wherein the disease or condition is associated with a kinase, comprising identifying the mammal afflicted with said disease or condition and administering to said afflicted mammal a composition comprising the compound of formula 1.

The invention also provides methods of treating a mammal (preferably a human patient or subject, but not limited to humans) afflicted with the above diseases and conditions. The amount of the compounds of the present invention that may be combined with the carrier materials to produce a composition in a single dosage form will vary depending upon the host treated, the particular mode of administration. The compositions may be formulated so that a dosage of between, for example, 0.01-100 mg/kg body weight/day of the inhibitor can be administered to a patient receiving these compositions.

In one embodiment, the invention compounds are administered in combination with another active agent such as, for example, a chemotherapeutic agent, an anti-inflammatory agent, antihistamines, chemotherapeutic agent, immunomodulator, therapeutic antibody or a protein kinase inhibitor, e.g., a tyrosine kinase inhibitor, to a subject in need of such treatment.

The method includes administering one or more of the inventive compounds to the afflicted mammal. The method may further include the administration of a second active agent, such as a cytotoxic agent, including alkylating agents, tumor necrosis factors, intercalators, microtubulin inhibitors, and topoisomerase inhibitors. The second active agent may be co-administered in the same composition or in a second composition. Examples of suitable second active agents include, but are not limited to, a cytotoxic drug such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

In accordance with the invention, the compounds and compositions may be used at sub-cytotoxic levels in combination with other agents in order to achieve highly selective activity in the treatment of non-neoplastic disorders, such as heart disease, stroke and neurodegenerative diseases (Whitesell et al., Curr Cancer Drug Targets (2003), 3(5), 349-58) (incorporated herein by reference).

The exemplary therapeutic agents that may be administered in combination with invention compounds include EGFR inhibitors, such as gefitinib, erlotinib, and cetuximab. Her2 inhibitors include canertinib, EKB-569, and GW-572016. Also included are Src inhibitors, dasatinib, as well as Casodex (bicalutamide), Tamoxifen, MEK-1 kinase inhibitors, MARK kinase inhibitors, PI3 inhibitors, and PDGF inhibitors, such as imatinib, Hsp90 inhibitors, such as 17-AAG and 17-DMAG. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kineses, and inhibitors of integrin.

The pharmaceutical composition and method of the present invention may further combine other protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay. The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

Other therapeutic agents for the combinatory therapy include cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and for gpn39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HM:G CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one having ordinary skill in the art.

EXAMPLES

The following examples are provided to further illustrate the present invention but, of course, should not be construed as in any way limiting its scope.

All experiments were performed under anhydrous conditions (i.e. dry solvents) in an atmosphere of argon, except where stated, using oven-dried apparatus and employing standard techniques in handling air-sensitive materials. Aqueous solutions of sodium bicarbonate (NaHCO$_3$) and sodium chloride (brine) were saturated.

Analytical thin layer chromatography (TLC) was carried out on Merck Kiesel gel 60 F254 plates with visualization by ultraviolet and/or anisaldehyde, potassium permanganate or phosphomolybdic acid dips.

NMR spectra: 1H Nuclear magnetic resonance spectra were recorded at 400 MHz. Data are presented as follows: chemical shift, multiplicity (s=singlet, d=doublet, t=triplet, q=quartet, qn=quintet, dd=doublet of doublets, m=multiplet, bs=broad singlet), coupling constant (J/Hz) and integration. Coupling constants were taken and calculated directly from the spectra and are uncorrected.

Low resolution mass spectra: Electrospray (ES+) ionization was used. The protonated parent ion (M+H) or parent sodium ion (M+Na) or fragment of highest mass is quoted. Analytical gradient consisted of 10% ACN in water ramping up to 100% ACN over 5 minutes unless otherwise stated.

High performance liquid chromatography (HPLC) was use to anaylize the purity of triazine derivatives. HPLC was performed on a Phenomenex Synergi Polar-RP, 4u, 80A, 150×4.6 mm column using a vShimadzusystem equipted with SPD-M10A Phosphodiode Array Detector. Mobile phase A was water and mobile phase B was acetonitrile with a gradient from 20% to 80% B over 60 minutes and re-equilibrate at A/B (80:20) for 10 minutes. UV detection was at 220 and 54 nm.

Example 1

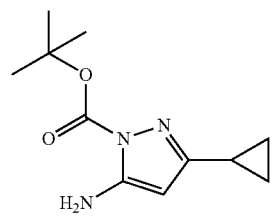

1

A solution of 3-cyclopropyl-1-H-pyrazole-5-amine (3.05 g, 24.77 mmol) in THF (20 ml) was added to a cold suspension of sodium hydride (60% in mineral oil, 1.09 g, 27.24 mmol) in THF (20 ml) at 0° C. slowly. After stirring at 0° C. for 30 minute, di-tert-butyldicarboxate (5.95 g, 27.24 mmol) was added. (THF was used to help the addition of di-tert-butyldicarboxate, total 125 mL was in the bottle). The mixture was stirred at 0° C. for 30 minute. TLC was checked and the starting material was consumed. The reaction mixture was quenched with ice-water, extracted with ethyl acetate (3×50 ml). The combined organic was washed by brine, dried over sodium sulfate and concentrated to minimum amount solvents. Hexanes were added (~100 ml), and the mixture was sonicated to make a homogenous suspension. The yellow solids were collected by filtration, washed by hexanes to give compound 1 as a mixture of 2 isomers (about 1:3) of protection group on the ring (3.73 g, 69% yield). $^1$H NMR (400 MHz, DMSO-d$_6$) δ: for the major isomer: 6.16 (br, 2H), 4.92 (s, 1H), 1.68 (m, 1H), 1.49 (s, 9H), 0.86 (m, 2H), 0.78 (m, 2H); for the minor isomer: 5.35 (s, 1H), 5.20 (br, 2H), 2.05 (m, 1H), 1.49 (s, 9H), 0.88 (m, 2H), 0.78 (m, 2H).

Example 2

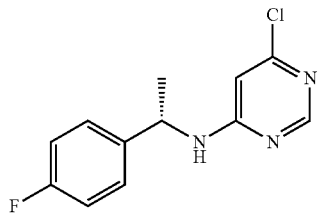

2

A solution of 4,6-dichloropyrimidine (500 mg, 3.36 mmol) and (S)-1-(4-fluorophenyl)ethan-1-amine (467 mg, 3.36 mmol) in isopropanol (10 mL) was added DIPEA (1.75 mL, 10.07 mmol). The solution was stirred for 5 h at 50° C. H$_2$O (50 mL) was added to the cooled solution and extracted with 10% IPA/DCM (3×50 mL). The combined organic extracts were dried over anhydrous Na$_2$SO$_4$ and concentrated in vacuo to afford (S)-6-chloro-N-(1-(4-fluorophenyl)ethyl)pyrimidin-4-amine compound 2 (865 mg, ~100%) as thick orange liquid. The compound was used for the next step without further purification. MS (ESI): Calcd. for C$_{12}$H$_{11}$ClFN$_3$: 251, found 252 (MH$^+$).

Example 3

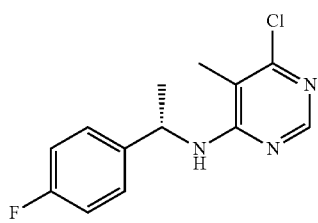

3

A solution of 4,6-dichloro-5-methylpyrimidine (500 mg, 3.07 mmol) and (S)-1-(4-fluorophenyl)ethan-1-amine (427 mg, 3.07 mmol) in THF (5 mL) was added DIPEA (1.60 mL, 9.20 mmol). The solution was stirred for 24 h at 50° C. H$_2$O (50 mL) was added to the cooled solution and extracted with 10% IPA/DCM (3×50 mL). The combined organic extracts were dried over anhydrous Na$_2$SO$_4$ and concentrated in vacuo to afford (S)-6-chloro-N-(1-(4-fluorophenyl)ethyl)-5-methylpyrimidin-4-amine compound 3 (482 mg, 59%) as light brown solid. The compound was used for the next step without further purification. MS (ESI): Calcd. for C$_{13}$H$_{13}$ClFN$_3$: 265, found 266 (MH$^+$).

Example 4

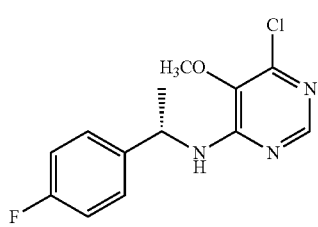

4

A solution of 4,6-dichloro-5-methoxypyrimidine (500 mg, 2.79 mmol) and (S)-1-(4-fluorophenyl)ethan-1-amine (389 mg, 2.79 mmol) in THF (5 mL) was added DIPEA (1.46 mL, 8.38 mmol). The solution was stirred for 24 h at 50° C. H$_2$O (50 mL) was added to the cooled solution and extracted with 10% IPA/DCM (3×50 mL). The combined organic extracts were dried over anhydrous Na$_2$SO$_4$ and concentrated in vacuo to afford (S)-6-chloro-N-(1-(4-fluorophenyl)ethyl)-5-methoxypyrimidin-4-amine compound 4 (770 mg, 98%) as thick orange liquid. The compound was used for the next step without further purification. MS (ESI): Calcd. for C$_{13}$H$_{13}$ClFN$_3$O: 281, found 282 (MH$^+$).

Example 5

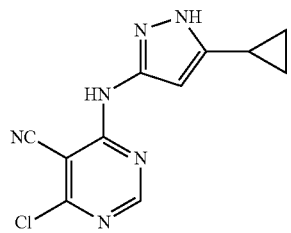

5

To a cold solution of 4,6-dichloropyrimidine-5-carbonitrile (500 mg, 2.87 mmol) in THF (10 mL) was added N,N-diisopropylethylamine (1.00 ml g, 5.75 mmol), followed by a solution of 3-cylopropyl-1-H-pyrazole amine (354 mg, 2.87 mmol) at 0° C. The resulting mixture was stirred at 0° C. for 2 hours. TLC was checked and the reaction was completed. After cooled to room temperature, half-saturated ammonium chloride in water (80 mL) was added and the mixture was stirred at room temperature for 15 min. The resulting solids were collected by filtration, washed by water to afford compound 5 as yellow solids. (644 mg, 86% yield). $^1$H NMR (400 MHz, DMSO-d$_6$) δ 12.42 (br, 1H), 10.35 (br, 1H), 8.55 (s, 1H), 6.12 (s, 1H), 1.89 (m, 1H), 0.92 (m, 2H), 0.67 (m, 2H); ESI-MS: calcd for (C$_{11}$H$_9$ClN$_6$) 260, found 281 (MH$^+$).

Example 6

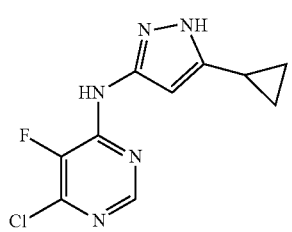

6

The solution of 4,6-dichloro-5-fluoropyrimidine (873 mg, 2.87 mmol), 3-cylopropyl-1-H-pyrazole amine (644 mg, 5.23 mmol) and N,N-diisopropylethylamine (2.28 m, 13.07 mmol) in THF (5 mL) was stirred at room temperature for overnight. TLC was checked and the reaction was completed. After removal of the solvents, the residue was triturated by half-saturated ammonium chloride in water (15 mL) and stirred at room temperature for 15 min. The resulting solids were collected by filtration, washed by water to afford compound 6 as beige solids. (1.15 g, 86% yield). $^{1}$H NMR (400 MHz, DMSO-d$_{6}$) δ 12.23 (br, 1H), 10.19 (br, 1H), 8.22 (s, 1H), 6.27 (s, 1H), 1.89 (m, 1H), 0.93 (m, 2H), 0.67 (m, 2H); ESI-MS: calcd for (C$_{10}$H$_{9}$ClFN$_{5}$) 253, found 254 (MH$^{+}$).

Example 7

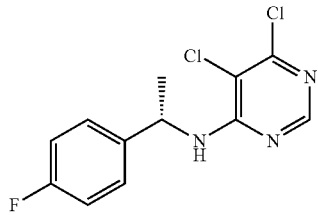

7

A solution of 4,6-dichloropyrimidine (500 mg, 2.73 mmol) and (S)-1-(4-fluorophenyl)ethan-1-amine (379 mg, 2.73 mmol) in isopropanol (10 mL) was added DIPEA (1.42 mL, 8.18 mmol). The solution was stirred for 3 h at 50° C. H$_{2}$O (50 mL) was added to the cooled solution and extracted with 10% IPA/DCM (3×50 mL). The combined organic extracts were dried over anhydrous Na$_{2}$SO$_{4}$ and concentrated in vacuo to afford (S)-5,6-dichloro-N-(1-(4-fluorophenyl)ethyl)pyrimidin-4-amine compound 7 (790 mg, ~100%) as off-white solid. The compound was used for the next step without further purification. MS (ESI): Calcd. for C$_{12}$H$_{10}$Cl$_{2}$FN$_{3}$: 285, found 286 (MH$^{+}$).

Example 8

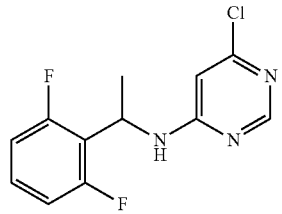

8

A solution of 1-(2,6-difluorophenyl)ethan-1-amine (250 mg, 1.59 mmol) and 4,6-dichloropyrimidine (260.67 mg, 1.75 mmol) in isopropanol (5 mL) was added DIPEA (0.55 mL, 3.18 mmol). The mixture was stirred for 24 h at 50° C. TLC was checked and the reaction was complete. Water (50 mL) was added and the reaction was extracted with 10% IPA/DCM (2×50 mL). The combined organic extracts were dried, and concentrated to obtain compound 8 as yellow solids (385 mg, 90%). The crude product was used for the next step without further purification. MS (ESI): Calcd. for C$_{12}$H$_{10}$ClF$_{2}$N$_{3}$: 269, found 270 (MH$^{+}$).

Example 9

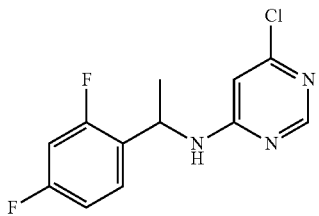

9

A solution of 4,6-dichloropyrimidine (500 mg, 3.36 mmol) and 1-(2,4-difluorophenyl)ethan-1-amine (527.49 mg, 3.36 mmol) in isopropanol (~5 mL) was added DIPEA (1.75 mL, 10.07 mmol). The solution was stirred for 5 h at 50° C. H$_{2}$O (50 mL) was added to the cooled solution and extracted with 10% IPA/DCM (3×50 mL). The combined organic extracts were dried over anhydrous Na$_{2}$SO$_{4}$ and concentrated in vacuo to afford 6-chloro-N-(1-(2,4-difluorophenyl)ethyl)pyrimidin-4-amine compound 9 (828 mg, 91%) as beige solid. The compound was used for the next step without further purification. MS (ESI): Calcd. for C$_{12}$H$_{10}$ClF$_{2}$N$_{3}$: 269, found 270 (MH$^{+}$).

Example 10

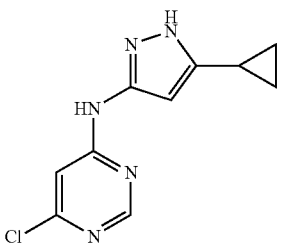

10

A solution of 5-cyclopropyl-1H-pyrazol-3-amine (17.50 g, 142.09 mmol) and 4,6-dichloropyrimidine (23.28 g, 156.30 mmol) in isopropanol (100 mL) was added DIPEA (49.50 mL, 36.73 g, 284.19 mmol). The mixture was stirred for 24 h in a RBF at 85° C. Isopropanol solvent was removed from the reaction mixture under reduced pressure and the residue was dissolved in DCM (200 mL). The solution was washed with H2O (2×150 mL) and the combined aqueous layer was extracted with 10% IPA/DCM. The organic layers were then combined, dried, and concentrated to afford yellow solids. This solid was triturated with DCM and collected by filtration to afford 6-chloro-N-(5-cyclopropyl-1H-pyrazol-3-yl)pyrimidin-4-amine compound 10 (23.27 g, 69.5%) as beige solid. $^{1}$H NMR (400 MHz, DMSO-d): δ 12.13 (bs, 1H), 10.13 (s, 1H), 8.40 (s, 1H), 7.39 (bs, 1H), 5.93 (bs, 1H), 1.85 (m, 1H), 0.90 (m, 2H), 0.66 (m, 2H). MS (ESI): Calcd. for C$_{10}$H$_{10}$ClN$_{5}$: 235, found 236 (MH$^{+}$).

Example 11

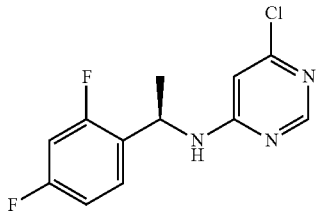

11

A solution of (R)-1-(2,4-difluorophenyl)ethan-1-amine (250 mg, 1.59 mmol) and 4,6-dichloropyrimidine (260.67 mg, 1.75 mmol) in isopropanol (5 mL) was added DIPEA (0.55 mL, 3.18 mmol). The mixture was stirred for 24 h at 50° C. TLC was checked and the reaction was complete. Solvent IPA was removed under reduced pressure to obtain compound 11 as yellow oil (400 mg, 93%). The crude product was used for the next step without further purification. MS (ESI): Calcd. for $C_{12}H_{10}ClF_2N_3$: 269, found 270 (MH$^+$).

Example 12

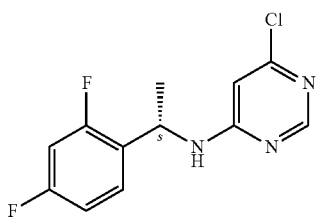

12

To a solution of 4,6-dichloropyrimidine (305 mg, 2.05 mmol) in iPrOH (5 mL) was added (1S)-1-(2,4-difluorophenyl)ethanamine (280 mg, 1.78 mmol) and N,N-diisopropylethylamine (0.78 ml, 4.45 mmol) at room temperature. The reaction was stirred at 50° C. for overnight. TLC was checked and the reaction was completed. Dilute NH$_4$Cl in water (30 ml) was added and the mixture was extracted with EtOAc/Hexanes (90/10, 25 ml×3). The combined organic was washed with brine and dried over sodium sulfate. The solvents were removed under reduced pressure to give compound 12 as yellow oil, which become yellow solids after overnight on vac line. No further purification was performed and the product was used directly for the next step reaction. (480 mg, 100%). $^1$H NMR (400 MHz, DMSO-d$_6$) δ 8.23 (m, 2H), 7.40 (m, 1H), 7.20 (m, 1H), 7.06 (m, 1H), 6.60 (br, 1H), 5.36 (br, 1H), 1.43 (d, J=6.8 Hz, 3H); ESI-MS: calcd for ($C_{12}H_{10}ClF_2N_3$) 269, found 270 (MH$^+$).

Example 13

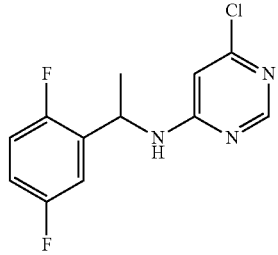

13

A solution of 4,6-dichloropyrimidine (300 mg, 1.91 mmol) and 1-(2,5-difluorophenyl)ethan-1-amine (284.37 mg, 1.91 mmol) in isopropanol (~3 mL) was added DIPEA (1.00 mL, 5.73 mmol). The solution was stirred for 5 h at 50° C. H$_2$O (50 mL) was added to the cooled solution and extracted with 10% IPA/DCM (3×50 mL). The combined organic extracts were dried over anhydrous Na$_2$SO$_4$ and concentrated in vacuo to afford 6-chloro-N-(1-(2,5-difluorophenyl)ethyl)pyrimidin-4-amine compound 13 (455 mg, 88%) as thick yellow liquid. MS (ESI): Calcd. for $C_{12}H_{10}ClF_2N_3$: 269, found 270 (MH$^+$).

Example 14

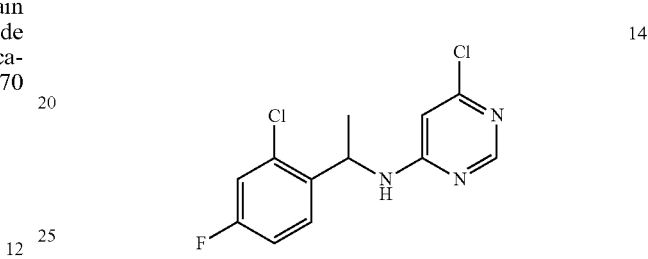

14

To a solution of 4,6-dichloropyrimidine (250 mg, 1.68 mmol) in iPrOH (5 mL) was added (1-(2-chloro-4-fluorophenyl)ethan-1-amine (230 mg, 1.33 mmol) and N,N-diisopropylethylamine (0.64 ml, 3.66 mmol) at room temperature. The reaction was stirred at 50° C. for overnight. TLC was checked and the reaction was completed. Dilute NH$_4$Cl in water (30 ml) was added and the mixture was extracted with EtOAc/Hexanes (90/10, 25 ml×3). The combined organic was washed with brine and dried over sodium sulfate. The solvents were removed under reduced pressure to give compound 14 as yellow solids. No further purification was performed and the product was used directly for the next step reaction. (380 mg, 100%). $^1$H NMR (400 MHz, DMSO-d$_6$) δ 8.31 (br, 1H), 8.22 (s, 1H), 7.44 (m, 2H), 7.21 (m, 1H), 6.61 (br, 1H), 5.40 (br, 1H), 1.42 (d, J=6.8 Hz, 3H); ESI-MS: calcd for ($C_{12}H_{10}Cl_2FN_3$) 285, found 286 (MH$^+$).

Example 15

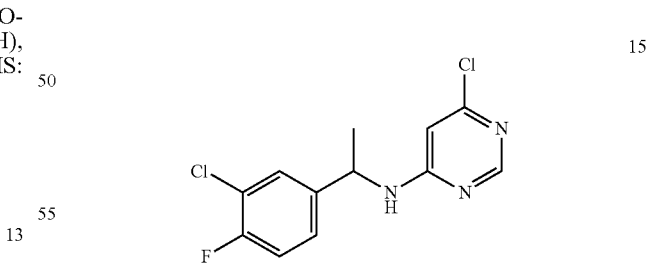

15

A solution of 4,6-dichloropyrimidine (215 mg, 1.44 mmol) and 1-(3-chloro-4-fluorophenyl)ethan-1-amine (250.56 mg, 1.44 mmol) in isopropanol (~3 mL) was added DIPEA (0.75 mL, 4.33 mmol). The solution was stirred for 5 h at 50° C. H$_2$O (50 mL) was added to the cooled solution and extracted with 10% IPA/DCM (3×50 mL). The combined organic extracts were dried over anhydrous Na$_2$SO$_4$ and concentrated in vacuo to afford 6-chloro-N-(1-(3-chloro-4-fluorophenyl)ethyl)pyrimidin-4-amine compound 15 (395 mg, 82%) as thick yellow liquid. The compound was used for the next step without further purification. MS (ESI): Calcd. for $C_{12}H_{10}Cl_2FN_3$: 285, found 286 (MH$^+$).

Example 16

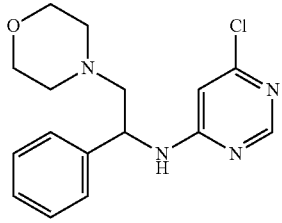

16

A solution of 4,6-dichloropyrimidine (180 mg, 1.21 mmol) and 2-morpholino-1-phenylethan-1-amine (249.25 mg, 1.21 mmol) in isopropanol (~3 mL) was added DIPEA (0.63 mL, 3.62 mmol). The solution was stirred for 5 h at 50° C. H$_2$O (50 mL) was added to the cooled solution and extracted with 10% IPA/DCM (3×50 mL). The combined organic extracts were dried over anhydrous Na$_2$SO$_4$ and concentrated in vacuo to afford 6-chloro-N-(2-morpholino-1-phenylethyl)pyrimidin-4-amine compound 16 (380 mg, 99%) as thick yellow liquid. The compound was used for the next step without further purification. MS (ESI): Calcd. for $C_{16}H_{19}ClN_4O$: 318, found 319 (MH$^+$).

Example 17

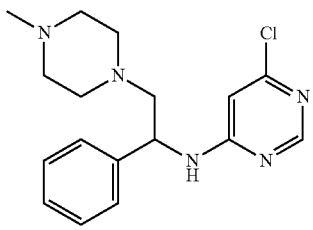

17

A solution of 4,6-dichloropyrimidine (170 mg, 1.14 mmol) and 2-(4-methylpiperazin-1-yl)-1-phenylethan-1-amine (250.29 mg, 1.14 mmol) in isopropanol (~3 mL) was added DIPEA (0.60 mL, 3.42 mmol). The solution was stirred for 5 h at 50° C. H$_2$O (50 mL) was added to the cooled solution and extracted with 10% IPA/DCM (3×50 mL). The combined organic extracts were dried over anhydrous Na$_2$SO$_4$ and concentrated. The residue was then purified by column chromatography using 0-5% MeOH in DCM to afford 6-chloro-N-(2-(4-methylpiperazin-1-yl)-1-phenylethyl)pyrimidin-4-amine compound 17 (81 mg, 21%) as yellowish semi-solid. MS (ESI): Calcd. for $C_{17}H_{22}ClN_5$: 331, found 332 (MH$^+$).

Example 18

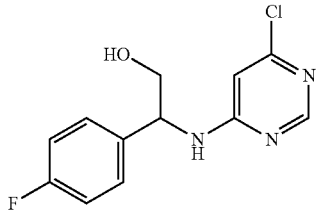

18

A solution of 4,6-dichloropyrimidine (240 mg, 1.61 mmol) and 2-((6-chloropyrimidin-4-yl)amino)-2-(4-fluorophenyl)ethan-1-ol (250.00 mg, 1.61 mmol) in isopropanol (~3 mL) was added DIPEA (0.84 mL, 4.83 mmol). The solution was stirred for 5 h at 50° C. H$_2$O (50 mL) was added to the cooled solution and extracted with 10% IPA/DCM (3×50 mL). The combined organic extracts were dried over anhydrous Na$_2$SO$_4$ and concentrated in vacuo to afford 2-((6-chloropyrimidin-4-yl)amino)-2-(4-fluorophenyl) ethan-1-ol compound 18 (365 mg, 85%) as thick yellow liquid. MS (ESI): Calcd. for $C_{12}H_{11}ClFN_3O$: 267, found 268 (MH$^+$).

Example 19

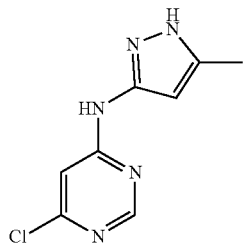

19

A solution of 5-methyl-1H-pyrazol-3-amine (250 mg, 2.57 mmol) and 4,6-dichloropyrimidine (422 mg, 2.83 mmol) in isopropanol (5 mL) was added DIPEA (1.35 mL, 7.72 mmol). The mixture was stirred for 18 h at rt followed by another 5 h at 50° C. After cooling down to rt, precipitation of solids was observed. The solids were filtered, washed with ice-cold isopropanol and dried under vacuum to obtain 205 mg (38%) of compound 19 as beige solids. The product was used to the next step without further purification. $^1$H NMR (400 MHz, DMSO-d): δ 12.10 (bs, 1H), 10.16 (s, 1H), 8.42 (s, 1H), 7.44 (bs, 1H), 6.02 (bs, 1H), 2.21 (s, 3H); MS (ESI): Calcd. for ($C_8H_8ClN_5$): 209, found 210 (MH$^+$).

Example 20

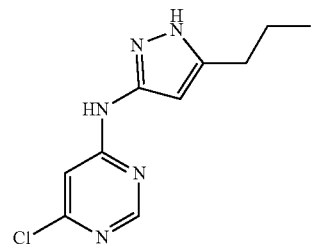

20

A solution of 5-propyl-1H-pyrazol-3-amine (250 mg, 2.00 mmol) and 4,6-dichloropyrimidine (327 mg, 2.20 mmol) in isopropanol (5 mL) was added DIPEA (1.04 mL, 5.99 mmol). The mixture was stirred for 18 h at rt followed by another 18 h at 50° C. The crude reaction mixture was concentrated and the residue was dissolved in DMSO (2 mL). The solution was then added to half-saturated ammonium chloride in water (50 mL) and stirred for 30 min. The solids were collected by filtration, washed by water and dried to obtain compound 20 as beige solids (283 mg, 60% yield). $^1$H NMR (400 MHz, DMSO-d): δ 12.13 (bs, 1H), 10.18 (s, 1H), 8.43 (s, 1H), 7.59 (bs, 1H), 6.07 (bs, 1H), 2.49 (m, 2H), 1.59 (m, 2H), 0.90 (m, 3H); MS (ESI): Calcd. for ($C_{10}H_{10}ClN_5$) 237, found 238 (MH$^+$).

Example 21

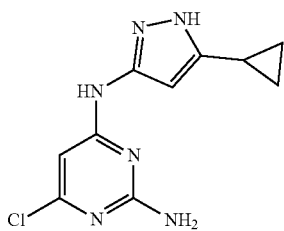

21

The mixture of 2-amino-4,6-dichloropyrimidine (1.50 g, 9.15 mmol), 3-cyclopropyl-1H-pyrazoleamine (1.18 g, 9.60 mmol) and DIPEA (1.76 ml, 10.06 mmol) in IPA/DMSO (15 ml/3 ml) was stirred at 85° C. for 2 days. The reaction mixture was added to half-sat.NH$_4$Cl in water (500 mL) and the mixture was stirred at rt for 30 min. The solids thus formed were collected by filtration and washed by water. The crude product was purified by column chromatography (10-75% EtOH in Hexanes) to give compound 21 as yellow solids (187 mg, 8% yield). $^1$H NMR (400 MHz, DMSO-d$_6$) δ 11.96 (s, 2H), 9.50 (s, 1H), 7.00-5.80 (m, 4H), 1.84 (m, 1H), 0.90 (m, 2H), 0.67 (m, 2H); ESI-MS: calcd for ($C_{10}H_{11}ClN_6$) 250, found 251 (MH$^+$).

Example 22

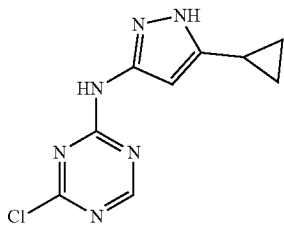

22

To a cold solution of 2,4-dichloro-1,3,5-triazine (2.50 g, 16.67 mmol) in DMF (20 mL) was added a solution of 3-cylopropyl-1-H-pyrazole amine (2.16 g, 17.50 mmol) and N,N-diisopropylethylamine (3.49 ml, 20.00 mmol) in DMF (15 mL) dropwise at 0° C. After addition, the reaction mixture was stirred at 0° C. for 3 hours. TLC was checked and the starting material was consumed. The reaction mixture was added to half-sat. NH$_4$Cl in water (500 ml) and the mixture was stirred at 0° C. for 30 min. The solids were collected by filtration, washed by water and dried by air. The product compound 22 was obtained as yellow solids (3.55 g, 89% yield). No further purification was conducted. $^1$H NMR (400 MHz, DMSO-d$_6$) δ 12.26 (s, 1H), 10.90 (br, 1H), 8.57 (br, 1H), 6.23 (br, 1H), 1.90 (m, 1H), 0.92 (m, 2H), 0.68 (m, 2H); ESI-MS: calcd for ($C_9H_9ClN_6$) 236, found 237 (MH$^+$). SA70_2 (NANT-5117)

Example 23

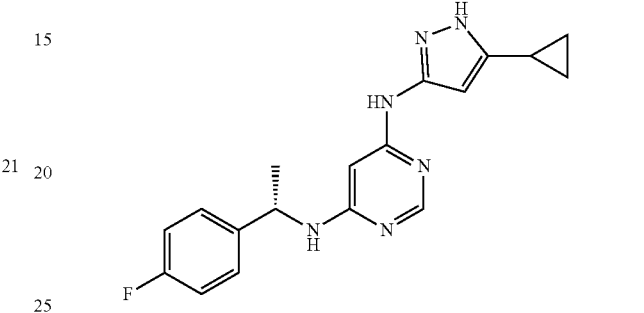

23

A mixture of (S)-6-chloro-N-(1-(4-fluorophenyl)ethyl) pyrimidin-4-amine compound 2 (200 mg, 0.795 mmol), tert-butyl 3-amino-5-cyclopropyl-1H-pyrazole-1-carboxylate compound 1 (221.78 mg, 0.993 mmol), xantphos (4,5-diphenylphosphanyl-9,9'-dimethyl-9-H-xanthene, 114.95 mg, 0.199 mmol), K$_2$CO$_3$ (549.11 mg, 3.97 mmol) and palladium(II) acetate (26.76 mg, 0.119 mmol) in 1,4-dioxane (10 ml) was purged with argon for 1 hour. The mixture was heated in an oil bath for 5 h at 120° C. TLC was checked and the starting material was consumed. After cooling to room temperature, the reaction mixture was passed through a pad of celite using 10% IPA/DCM and was concentrated. The crude product was purified by column chromatography (silica gel, 0-5% MeOH in DCM) to obtain (S)—N4-(5-cyclopropyl-1H-pyrazol-3-yl)-N6-(1-(4-fluorophenyl)ethyl) pyrimidine-4,6-diamine compound 23 as brown solids (50 mg, 19% yield). $^1$H NMR (400 MHz, DMSO-d$_6$) δ 12.00 (br, 1H), 8.92 (s, 1H), 7.96 (s, 1H), 7.36-7.08 (m, 5H), 6.29 (br, 1H), 5.71 (s, 1H), 5.00 (m, 1H), 1.91 (m, 1H), 1.39 (d, J=6.8 Hz, 3H), 0.91 (m, 2H), 0.65 (m, 2H); ESI-MS: calcd for ($C_{18}H_{19}FN_6$) 338, found 339 (MH$^+$).

Example 24

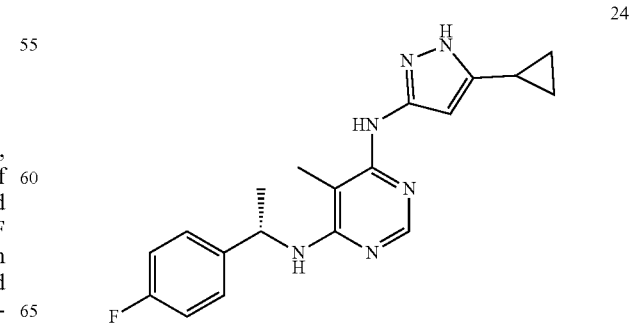

24

A mixture of (S)-6-chloro-N-(1-(4-fluorophenyl)ethyl)-5-methylpyrimidin-4-amine compound 3 (200 mg, 0.753 mmol), tert-butyl 3-amino-5-cyclopropyl-1H-pyrazole-1-carboxylate compound 1 (210.07 mg, 0.941 mmol), xantphos (4,5-diphenylphosphanyl-9,9'-dimehtyl-9-H-xanthene, 108.88 mg, 0.188 mmol), $K_2CO_3$ (520.12 mg, 3.76 mmol) and palladium(II) acetate (25.35 mg, 0.113 mmol) in 1,4-dioxane (11 ml) was purged with argon for 1 hour. The mixture was heated in an oil bath for 5 h at 120° C. TLC was checked and the starting material was consumed. After cooling to room temperature, the reaction mixture was passed through a pad of celite using 10% IPA/DCM and was concentrated. The crude product was purified by column chromatography (silica gel, 0-5% MeOH in DCM) to obtain S)—N4-(5-cyclopropyl-1H-pyrazol-3-yl)-N6-(1-(4-fluorophenyl)ethyl)-5-methylpyrimidine-4,6-diamine compound 24 as light yellow solids (180 mg, 68% yield). $^1$H NMR (400 MHz, DMSO-$d_6$) δ 11.85 (br, 1H), 8.20 (br, 1H), 7.93 (s, 1H), 7.39 (m, 2H), 7.11 (m, 2H), 6.48 (d, J=8.4 Hz, 1H), 6.00 (br, 1H), 5.34 (m, 1H), 2.00 (s, 3H), 1.91 (m, 1H), 1.46 (d, J=6.8 Hz, 3H), 0.86 (m, 2H), 0.62 (m, 2H); ESI-MS: calcd for ($C_{19}H_{21}FN_6$) 352, found 353 (MH$^+$).

Example 25

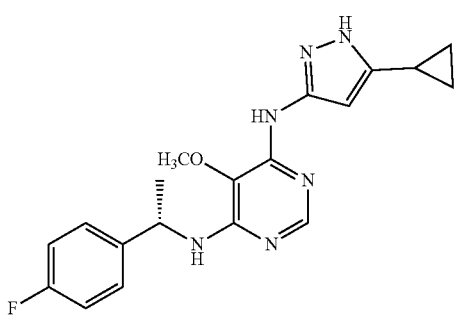

A mixture of (S)-6-chloro-N-(1-(4-fluorophenyl)ethyl)-5-methoxypyrimidin-4-amine compound 4 (200 mg, 0.710 mmol), tert-butyl 3-amino-5-cyclopropyl-1H-pyrazole-1-carboxylate compound 1 (198.14 mg, 0.887 mmol), xantphos (4,5-diphenylphosphanyl-9,9'-dimehtyl-9-H-xanthene, 102.70 mg, 0.177 mmol), $K_2CO_3$ (490.58 mg, 3.55 mmol) and palladium(II) acetate (23.91 mg, 0.107 mmol) in 1,4-dioxane (11 ml) was purged with argon for 1 hour. The mixture was heated in an oil bath for 5 h at 120° C. TLC was checked and the starting material was consumed. After cooling to room temperature, the reaction mixture was passed through a pad of celite using 10% IPA/DCM and was concentrated. The crude product was purified by column chromatography (silica gel, 0-5% MeOH in DCM) to obtain (S)—N4-(5-cyclopropyl-1H-pyrazol-3-yl)-N6-(1-(4-fluorophenyl)ethyl)-5-methoxypyrimidine-4,6-diamine compound 25 as light yellow solids (82 mg, 31% yield). $^1$H NMR (400 MHz, DMSO-$d_6$) δ 11.85 (br, 1H), 8.20 (br, 1H), 7.84 (s, 1H), 7.42 (m, 2H), 7.12 (m, 2H), 6.98 (d, J=8.4 Hz, 1H), 6.009 (br, 1H), 5.28 (m, 1H), 3.63 (s, 3H), 1.83 (m, 1H), 1.48 (d, J=6.8 Hz, 3H), 0.87 (m, 2H), 0.64 (m, 2H); ESI-MS: calcd for ($C_{19}H_{21}FN_6O$) 368, found 369 (MH$^+$).

Example 26

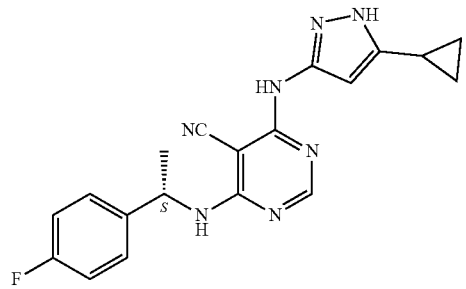

The solution of compound 5 (150 mg, 0.58 mmol), (S)-1-(4-fluorophenyl)ethanamine (80 mg, 0.58 mmol) and DIPEA (0.15 ml, 0.86 mmol) DMSO (3.5 mL) was stirred at 105° C. for 2 hours. TLC was checked and the starting material was consumed. The reaction mixture was added to half-saturated ammonium chloride in water (80 mL) and stirred for 30 min, then cooled with ice bath. The solids were collected by filtration, washed by water. The crude product was triturated with MeOH and the solids were collected by filtration to give the product compound 26 as yellow solids. (87 mg, 41% yield). $^1$H NMR (400 MHz, DMSO-$d_6$) δ 12.12 (br, 1H), 10.90 (s, 1H), 8.44 (s, 1H), 8.23 (s, 1H), 7.42 (m, 2H), 7.16 (m, 2H), 5.69 (s, 1H), 5.45 (m, 1H), 2.00 (m, 1H), 1.52 (d, J=6.8 Hz, 3H), 0.98 (m, 2H), 0.79 (m, 2H); ESI-MS: calcd for ($C_{23}H_{29}N_7O_3$) 363, found 364 (MH$^+$).

Example 27

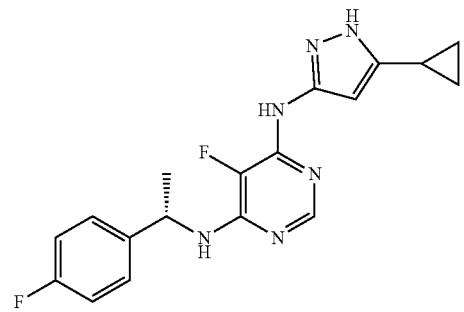

The solution of compound 6 (150 mg, 0.59 mmol), (S)-1-(4-fluorophenyl)ethanamine (99 mg, 0.71 mmol) and KF (103 mg, 1.77 mmol) DMSO (3.5 mL) was heated at 180° C. with Biotage microwave initiator for 30 min. The reaction mixture was added to half-saturated ammonium chloride in water (80 mL) and stirred for 30 min. The solids were collected by filtration, washed by water. The crude product was purified by column chromatography (0-10% MeOH in DCM) to give compound 27 as yellow solids (70 mg, 33% yield). $^1$H NMR (400 MHz, DMSO-$d_6$) δ 11.90 (s, 1H), 9.09 (s, 1H), 7.82 (s, 1H), 7.41 (m, 3H), 7.11 (m, 2H), 6.10 (br, 1H), 5.25 (m, 1H), 1.83 (m, 1H), 1.45 (d, J=7.2 Hz, 3H), 0.87 (m, 2H), 0.65 (m, 2H); ESI-MS: calcd for ($C_{18}H_{18}F_2N_6$) 356, found 357 (MH$^+$).

Example 28

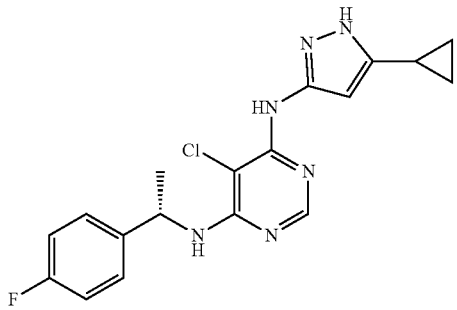

28

A mixture of (S)-5,6-dichloro-N-(1-(4-fluorophenyl)ethyl)pyrimidin-4-amine compound 7 (200 mg, 0.699 mmol), tert-butyl 3-amino-5-cyclopropyl-1H-pyrazole-1-carboxylate compound 1 (195.08 mg, 0.874 mmol), xantphos (4,5-diphenylphosphanyl-9,9'-dimethyl-9-H-xanthene, 101.11 mg, 0.175 mmol), $K_2CO_3$ (483.01 mg, 3.49 mmol) and palladium(II) acetate (23.54 mg, 0.105 mmol) in 1,4-dioxane (10 ml) was purged with argon for 1 hour. The mixture was heated in an oil bath for 5 h at 120° C. TLC was checked and the starting material was consumed. After cooling to room temperature, the reaction mixture was passed through a pad of celite using 10% IPA/DCM and was concentrated. The crude product was purified by column chromatography (silica gel, 0-50% EtOAc in Hexane) to obtain (S)-5-chloro-N4-(5-cyclopropyl-1H-pyrazol-3-yl)-N6-(1-(4-fluorophenyl)ethyl)pyrimidine-4,6-diamine compound 28 as light yellow solids (79 mg, 30% yield). $^1$H NMR (400 MHz, DMSO-d$_6$) δ 12.02 (br, 1H), 8.20 (br, 1H), 7.97 (s, 1H), 7.42-7.08 (m, 5H), 6.20 (br, 1H), 5.35 (m, 1H), 1.85 (m, 1H), 1.51 (d, J=6.8 Hz, 3H), 0.89 (m, 2H), 0.65 (m, 2H); ESI-MS: calcd for ($C_{18}H_{18}ClFN_6$) 372, found 373 (MH$^+$).

Example 29

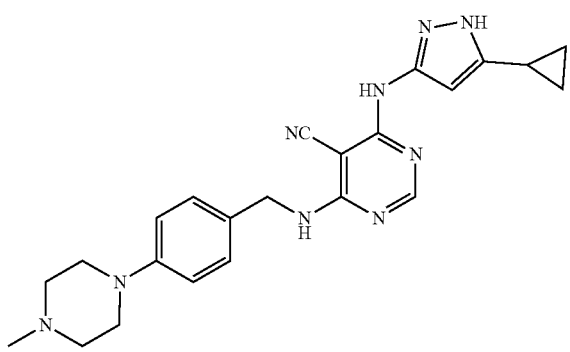

29

The solution of compound 5 (150 mg, 0.58 mmol), 4-(4-Methylpiperazino)benzylamine (118 mg, 0.58 mmol) and DIPEA (0.15 ml, 0.86 mmol) DMSO (3.5 mL) was stirred at 105° C. for 2 hours. TLC was checked and the starting material was consumed. The reaction mixture was added to half-saturated ammonium chloride in water (80 mL) and stirred for 30 min, then cooled with ice bath. The solids were collected by filtration, washed by water. The crude product was purified by column chromatography (0-10% MeOH in DCM) to give the product compound 29 as yellow solids. (98 mg, 39% yield). $^1$H NMR (400 MHz, DMSO-d$_6$) δ 12.10 (br, 1H), 10.67 (s, 1H), 8.34 (s, 1H), 8.28 (s, 1H), 7.20 (d, J=8.8 Hz, 2H), 6.90 (d, J=8.8 Hz, 2H), 5.69 (s, 1H), 4.67 (d, J=5.6 Hz, 2H), 3.10 (m, 4H), 2.43 (m, 4H), 2.21 (s, 3H), 1.98 (m, 1H), 0.98 (m, 2H), 0.79 (m, 2H); ESI-MS: calcd for ($C_{23}H_{27}N_9$) 429, found 452 (MNa$^+$).

Example 30

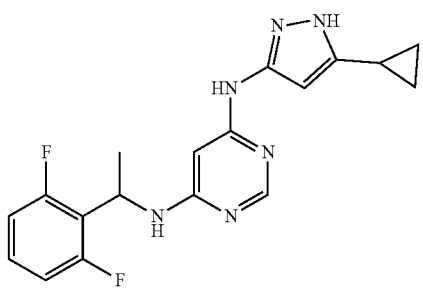

30

A mixture of 6-chloro-N-(1-(2,6-difluorophenyl)ethyl)pyrimidin-4-amine compound 8 (200 mg, 0.742 mmol), tert-butyl 3-amino-5-cyclopropyl-1H-pyrazole-1-carboxylate compound 1 (206.98 mg, 0.927 mmol), xantphos (4,5-diphenylphosphanyl-9,9'-dimethyl-9-H-xanthene, 107.28 mg, 0.185 mmol), $K_2CO_3$ (512.48 mg, 3.71 mmol) and palladium(II) acetate (24.97 mg, 0.111 mmol) in 1,4-dioxane (10 ml) was purged with argon for 1 hour. The mixture was heated in an oil bath for overnight at 100° C. TLC was checked and the starting material was consumed. After cooling to room temperature, the reaction mixture was passed through a pad of celite using 10% IPA/DCM and was concentrated. The crude product was purified by column chromatography (silica gel, 0-5% MeOH in DCM) to obtain two following fractions: fraction 1 of compound 30 was obtained as orange solids (37 mg, 14% yield) (R$_f$=0.2 in 10% MeOH/DCM). $^1$H NMR (400 MHz, DMSO-d$_6$) δ 11.87 (br, 1H), 8.89 (s, 1H), 7.95 (s, 1H), 7.28 (m, 2H), 7.00 (m, 2H), 6.32 (br, 1H), 5.71 (s, 1H), 5.36 (br, 1H), 1.85 (m, 1H), 1.50 (d, J=6.8 Hz, 3H), 0.91 (m, 2H), 0.65 (m, 2H); ESI-MS: calcd for ($C_{18}H_{18}F_2N_6$) 356, found 357 (MH$^+$).

Example 31

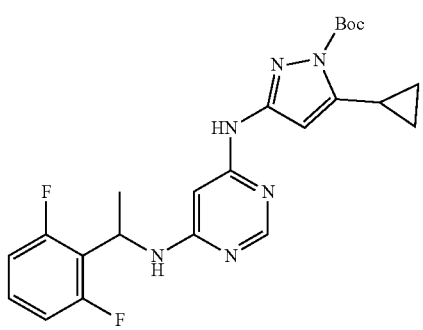

31

From the same reaction, the second fraction of compound 31 was obtained as beige solids (45 mg, 17% yield) ($R_f$=0.5 in 10% MeOH/DCM). $^1$H NMR (400 MHz, DMSO-$d_6$) δ 9.63 (s, 1H), 8.03 (s, 1H), 7.50 (br, 1H), 7.00 (m, 1H), 6.27 (m, 2H), 5.41 (br, 1H), 2.31 (m, 1H), 1.57 (s, 9H), 1.51 (d, J=6.8 Hz, 3H), 0.98 (m, 2H), 0.66 (m, 2H); ESI-MS: calcd for ($C_{23}H_{26}F_2N_6O_2$) 456, found 457 (MH$^+$).

Example 32

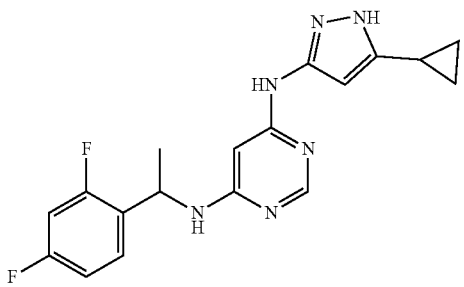

Method 1: A mixture of 6-chloro-N-(1-(2,4-difluorophenyl)ethyl)pyrimidin-4-amine compound 9 (200 mg, 0.742 mmol), tert-butyl 3-amino-5-cyclopropyl-1H-pyrazole-1-carboxylate compound 1 (206.98 mg, 0.927 mmol), xantphos (4,5-diphenylphosphanyl-9,9'-dimethyl-9-H-xanthene, 107.28 mg, 0.185 mmol), $K_2CO_3$ (512.48 mg, 3.71 mmol) and palladium(II) acetate (24.97 mg, 0.111 mmol) in 1,4-dioxane (10 ml) was purged with argon for 1 hour. The mixture was heated in an oil bath for overnight at 120° C. TLC was checked and the starting material was consumed. After cooling to room temperature, the reaction mixture was passed through a pad of celite using 10% IPA/DCM and was concentrated. The crude product was purified by column chromatography (silica gel, 0-10% MeOH in DCM) to obtain compound 32 as orange solids (106 mg, 40% yield). $^1$H NMR (400 MHz, DMSO-$d_6$) δ 11.87 (br, 1H), 8.93 (s, 1H), 7.96 (s, 1H), 7.41 (m, 2H), 7.15 (m, 1H), 7.02 (m, 1H), 6.34 (br, 1H), 5.71 (s, 1H), 5.21 (br, 1H), 1.91 (m, 1H), 1.39 (d, J=6.8 Hz, 3H), 0.91 (m, 2H), 0.63 (m, 2H); ESI-MS: calcd for ($C_{18}H_{18}F_2N_6$) 356, found 357 (MH$^+$).

Method 2: To a solution of compound 10 (150 mg, 0.64 mmol) in n-BuOH (0.5 mL) was added 1-(2,4-difluorophenyl)ethan-1-amine (100 mg, 0.64 mmol), and DIPEA (0.33 mL, 1.91 mmol) at room temperature and the mixture was stirred at 150° C. for 72 h. TLC was taken and the reaction was almost complete. The crude reaction mixture was concentrated and the residue was dissolved in DMSO (1 mL). The solution was then added to half-saturated ammonium chloride in water (80 mL) and stirred for 30 min. The solids were collected by filtration, washed by water. The crude product was purified by column chromatography (0-10% MeOH in DCM) to obtain compound 32 as beige solids (94 mg, 42% yield). $^1$H NMR (400 MHz, DMSO-$d_6$) δ 11.87 (br, 1H), 8.93 (s, 1H), 7.96 (s, 1H), 7.41 (m, 2H), 7.15 (m, 1H), 7.02 (m, 1H), 6.34 (br, 1H), 5.71 (s, 1H), 5.21 (br, 1H), 1.91 (m, 1H), 1.39 (d, J=6.8 Hz, 3H), 0.91 (m, 2H), 0.63 (m, 2H); ESI-MS: calcd for ($C_{18}H_{18}F_2N_6$) 356, found 357 (MH$^+$).

Example 33

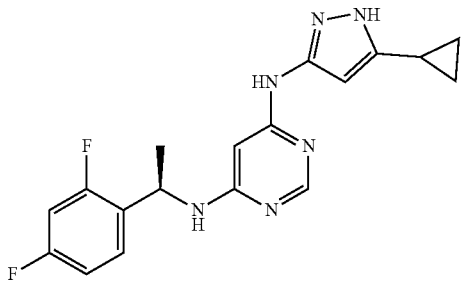

A mixture of (R)-6-chloro-N-(1-(2,4-difluorophenyl)ethyl)pyrimidin-4-amine compound 11 (200 mg, 0.742 mmol), tert-butyl 3-amino-5-cyclopropyl-1H-pyrazole-1-carboxylate compound 1 (206.98 mg, 0.927 mmol), xantphos (4,5-diphenylphosphanyl-9,9'-dimethyl-9-H-xanthene, 107.28 mg, 0.185 mmol), $K_2CO_3$ (512.48 mg, 3.71 mmol) and palladium(II) acetate (24.97 mg, 0.111 mmol) in 1,4-dioxane (10 ml) was purged with argon for 1 hour. The mixture was heated in an oil bath for overnight at 110° C. TLC was checked and the starting material was consumed. After cooling to room temperature, the reaction mixture was passed through a pad of celite using 10% IPA/DCM and was concentrated. The crude product was purified by column chromatography (silica gel, 0-10% MeOH in DCM) to obtain compound 33 as orange solids (15 mg, 6% yield). $^1$H NMR (400 MHz, DMSO-$d_6$) δ 11.84 (br, 1H), 8.94 (s, 1H), 7.95 (s, 1H), 7.40 (m, 2H), 7.15 (m, 1H), 7.02 (m, 1H), 6.35 (br, 1H), 5.72 (s, 1H), 5.22 (br, 1H), 1.84 (m, 1H), 1.39 (d, J=6.8 Hz, 3H), 0.91 (m, 2H), 0.63 (m, 2H); ESI-MS: calcd for ($C_{18}H_{18}F_2N_6$) 356, found 357 (MH$^+$).

Example 34

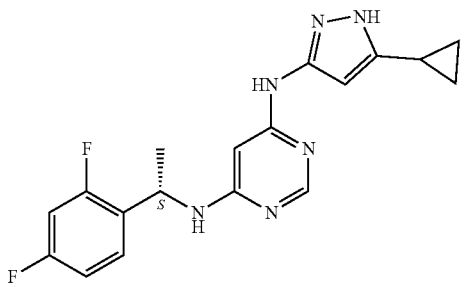

A mixture compound 12 (150 mg, 0.56 mmol), compound 1 (156 mg, 0.70 mmol), Palladium (II) acetate (19 mg, 0.08 mmol), xantphos (4,5-diphenylphosphanyl-9,9'-dimethyl-9-H-xanthene, 81 mg, 0.14 mmol) and $K_2CO_3$ (387 mg, 2.80 mmol) in 1,4-dioxane (15 ml) was purged with argon for 30 min. The mixture was heated with Biotage microwave initiator at 120° C. for 2.5 h. TLC was checked and the starting material was consumed. The reaction mixture was filtered through a pad of celite, washed with DCM/MeOH (10/1) and concentrated. The crude product was purified by column chromatography (silica gel, 0-10% MeOH in DCM) to give the compound 34 as yellow solids (12 mg, 6% yield).

¹H NMR (400 MHz, DMSO-d₆) δ 11.86 (s, 1H), 8.94 (s, 1H), 7.95 (s, 1H), 7.40 (m, 2H), 7.16 (m, 1H), 7.02 (m, 1H), 6.35 (br, 1H), 5.22 (br, 1H), 1.84 (m, 1H), 1.37 (d, J=6.8 Hz, 3H), 0.89 (m, 2H), 0.64 (m, 2H); ESI-MS: calcd for (C₁₈H₁₈F₂N₆) 356, found 357 (MH⁺).

Example 35

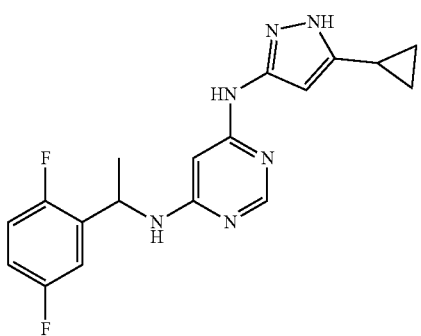

36

A mixture of 6-chloro-N-(1-(2,5-difluorophenyl)ethyl)pyrimidin-4-amine compound 13 (200 mg, 0.742 mmol), tert-butyl 3-amino-5-cyclopropyl-1H-pyrazole-1-carboxylate compound 1 (206.98 mg, 0.927 mmol), xantphos (4,5-diphenylphosphanyl-9,9'-dimethyl-9-H-xanthene, 107.28 mg, 0.185 mmol), K₂CO₃ (512.48 mg, 3.71 mmol) and palladium(II) acetate (24.97 mg, 0.111 mmol) in 1,4-dioxane (10 ml) was purged with argon for 1 hour. The mixture was heated in an oil bath for overnight at 120° C. TLC was checked and the starting material was consumed. After cooling to room temperature, the reaction mixture was passed through a pad of celite using 10% MeOH/DCM and was concentrated. The crude product was purified by column chromatography (silica gel, 0-10% MeOH in DCM) to obtain compound 35 as brown solids (60 mg, 23% yield). ¹H NMR (400 MHz, DMSO-d₆) δ 11.88 (br, 1H), 8.98 (s, 1H), 7.99 (s, 1H), 7.435 (d, J=7.6 Hz, 1H), 7.52 (s, 1H), 7.17 (m, 3H), 6.37 (br, 1H), 5.73 (s, 1H), 5.26 (br, 1H), 1.85 (m, 1H), 1.40 (d, J=6.8 Hz, 3H), 0.91 (m, 2H), 0.64 (m, 2H); ESI-MS: calcd for (C₁₈H₁₈F₂N₆) 356, found 357 (MH⁺).

Example 36

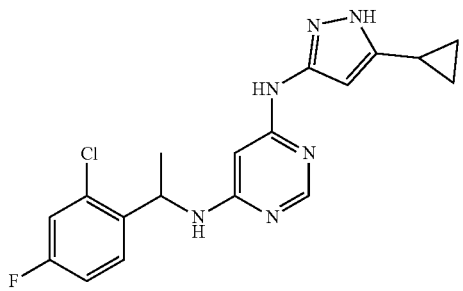

36

A mixture compound 14 (150 mg, 0.52 mmol), compound 1 (156 mg, 0.70 mmol), Palladium (II) acetate (19 mg, 0.08 mmol), xantphos (4,5-diphenylphosphanyl-9,9'-dimethyl-9-H-xanthene, 81 mg, 0.14 mmol) and K₂CO₃ (387 mg, 2.80 mmol) in 1,4-dioxane (15 ml) was purged with argon for 30 min. The mixture was heated with Biotage microwave initiator at 120° C. for 2.5 h. TLC was checked and the starting material was consumed. The reaction mixture was filtered through a pad of celite, washed with DCM/MeOH (10/1) and concentrated. The crude product was purified by column chromatography (silica gel, 0-10% MeOH in DCM) to give the compound 36 as yellow solids (58 mg, 30% yield). ¹H NMR (400 MHz, DMSO-d₆) δ 11.75 (s, 1H), 8.94 (s, 1H), 7.94 (s, 1H), 7.51 (d, J=7.6 Hz, 1H), 7.45 (m, 1H), 7.36 (m, 1H), 7.17 (m, 1H), 5.70 (br, 1H), 5.22 (br, 1H), 1.84 (m, 1H), 1.36 (d, J=6.8 Hz, 3H), 0.89 (m, 2H), 0.64 (m, 2H); ESI-MS: calcd for (C₁₈H₁₈ClFN₆) 372, found 373 (MH⁺).

Example 37

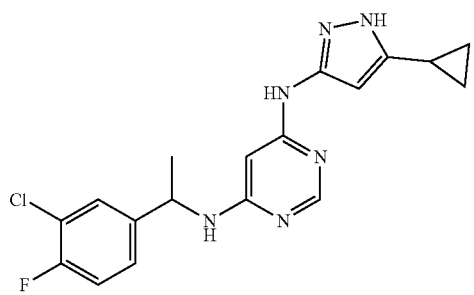

37

A mixture of 6-chloro-N-(1-(3-chloro-4-fluorophenyl)ethyl)pyrimidin-4-amine compound 15 (200 mg, 0.699 mmol), tert-butyl 3-amino-5-cyclopropyl-1H-pyrazole-1-carboxylate compound 1 (171.67 mg, 0.769 mmol), xantphos (4,5-diphenylphosphanyl-9,9'-dimethyl-9-H-xanthene, 101.11 mg, 0.175 mmol), K₂CO₃ (483.01 mg, 3.49 mmol) and palladium(II) acetate (23.54 mg, 0.105 mmol) in 1,4-dioxane (10 ml) was purged with argon for 1 hour. The mixture was heated in an oil bath for overnight at 120° C. TLC was checked and the starting material was consumed. After cooling to room temperature, the reaction mixture was passed through a pad of celite using 10% MeOH/DCM and was concentrated. The crude product was purified by column chromatography (silica gel, 0-10% MeOH in DCM) to obtain compound 37 as yellowish solids (65 mg, 25% yield). ¹H NMR (400 MHz, DMSO-d₆) δ 11.85 (br, 1H), 8.94 (s, 1H), 7.96 (s, 1H), 7.52 (s, 1H), 7.34 (m, 3H), 6.33 (br, 1H), 5.73 (s, 1H), 4.99 (br, 1H), 1.84 (m, 1H), 1.39 (d, J=6.8 Hz, 3H), 0.91 (m, 2H), 0.63 (m, 2H); ESI-MS: calcd for (C₁₈H₁₈ClFN₆) 372, found 373 (MH⁺).

Example 38

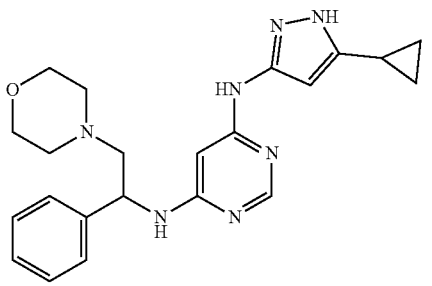

38

A mixture of 6-chloro-N-(2-morpholino-1-phenylethyl) pyrimidin-4-amine compound 16 (200 mg, 0.627 mmol), tert-butyl 3-amino-5-cyclopropyl-1H-pyrazole-1-carboxylate compound 1 (154.08 mg, 0.690 mmol), xantphos (4,5-diphenylphosphanyl-9,9'-dimethyl-9-H-xanthene, 90.75 mg, 0.157 mmol), $K_2CO_3$ (433.51 mg, 3.14 mmol) and palladium(II) acetate (21.13 mg, 0.094 mmol) in 1,4-dioxane (10 ml) was purged with argon for 1 hour. The mixture was heated in an oil bath for overnight at 120° C. TLC was checked and the starting material was consumed. After cooling to room temperature, the reaction mixture was passed through a pad of celite using 10% MeOH/DCM and was concentrated. The crude product was purified by column chromatography (silica gel, 0-10% MeOH in DCM) to obtain compound 38 as brown solids (86 mg, 34% yield). $^1$H NMR (400 MHz, DMSO-$d_6$) δ 11.85 (br, 1H), 8.89 (s, 1H), 7.94 (s, 1H), 7.50-7.10 (m, 6H), 6.33 (br, 1H), 5.68 (s, 1H), 5.03 (br, 1H), 3.54 (m, 4H), 2.70 (m, 1H), 2.44 (m, 5H), 1.84 (m, 1H), 0.91 (m, 2H), 0.64 (m, 2H); ESI-MS: calcd for ($C_{22}H_{27}N_7O$) 405, found 406 (MH$^+$).

Example 39

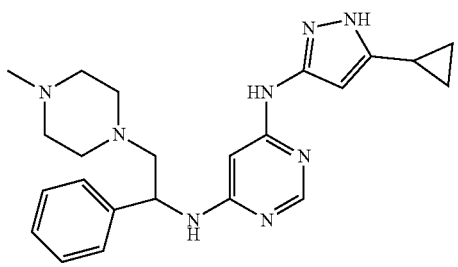

A mixture of 6-chloro-N-(2-(4-methylpiperazin-1-yl)-1-phenylethyl)pyrimidin-4-amine compound 17 (70 mg, 0.211 mmol), tert-butyl 3-amino-5-cyclopropyl-1H-pyrazole-1-carboxylate compound 1 (51.81 mg, 0.232 mmol), xantphos (4,5-diphenylphosphanyl-9,9'-dimethyl-9-H-xanthene, 30.51 mg, 0.053 mmol), $K_2CO_3$ (145.76 mg, 1.05 mmol) and palladium(II) acetate (7.10 mg, 0.032 mmol) in 1,4-dioxane (5 ml) was purged with argon for 1 hour. The mixture was heated in an oil bath for overnight at 120° C. TLC was checked and the starting material was consumed. After cooling to room temperature, the reaction mixture was passed through a pad of celite using 10% MeOH/DCM and was concentrated. The crude product was purified by column chromatography (silica gel, 1:9 1N $NH_3$ in MeOH/DCM) to obtain compound 39 as yellow solids (28 mg, 32% yield). $^1$H NMR (400 MHz, DMSO-$d_6$) δ 11.96 (br, 1H), 8.89 (s, 1H), 7.94 (s, 1H), 7.33 (m, 5H), 7.29 (m, 1H), 6.28 (br, 1H), 5.68 (s, 1H), 5.02 (br, 1H), 2.69 (m, 2H), 2.45 (m, 8H), 2.18 (s, 3H), 1.84 (m, 1H), 0.89 (m, 2H), 0.64 (m, 2H); ESI-MS: calcd for ($C_{23}H_{30}N_8$) 418, found 419 (MH$^+$).

Example 40

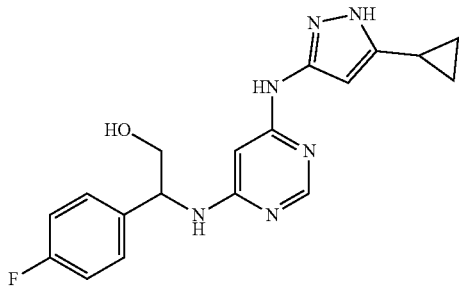

A mixture of 2-((6-chloropyrimidin-4-yl)amino)-2-(4-fluorophenyl)ethan-1-ol compound 18 (200 mg, 0.747 mmol), tert-butyl 3-amino-5-cyclopropyl-1H-pyrazole-1-carboxylate compound 1 (208.52 mg, 0.934 mmol), xantphos (4,5-diphenylphosphanyl-9,9'-dimethyl-9-H-xanthene, 108.08 mg, 0.187 mmol), $K_2CO_3$ (516.29 mg, 3.74 mmol) and palladium(II) acetate (25.15 mg, 0.187 mmol) in 1,4-dioxane (10 ml) was purged with argon for 1 hour. The mixture was heated in an oil bath for overnight at 120° C. TLC was checked and the starting material was consumed. After cooling to room temperature, the reaction mixture was passed through a pad of celite using 10% MeOH/DCM and was concentrated. The crude product was purified by column chromatography (silica gel, 0-10% MeOH in DCM) to obtain compound 40 as beige solids (35 mg, 13% yield). $^1$H NMR (400 MHz, DMSO-$d_6$) δ 11.96 (br, 1H), 9.15 (s, 1H), 8.02 (s, 1H), 7.37 (m, 3H), 7.12 (m, 2H), 6.33 (br, 1H), 5.71 (s, 1H), 4.88 (br, 1H), 3.59 (m, 2H), 1.85 (m, 1H), 0.91 (m, 2H), 0.64 (m, 2H); ESI-MS: calcd for ($C_{18}H_{19}FN_6O$) 354, found 355 (MH$^+$).

Example 41

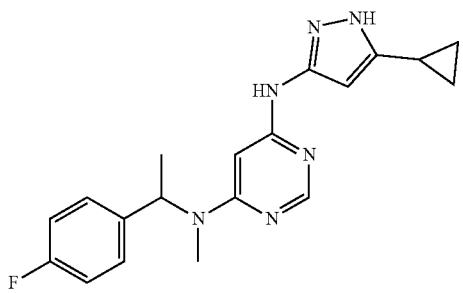

To a solution of compound 10 (150 mg, 0.64 mmol) in iPA (3.0 mL) was added 1-(4-fluorophenyl)-N-methylethan-1-amine (107.26 mg, 0.70 mmol), and DIPEA (0.17 mL, 0.95 mmol) at room temperature and the mixture was stirred at 120° C. for overnight followed by heating at 150° C. for 36 h. TLC was taken and the majority of starting material was consumed. The crude reaction mixture was concentrated and the residue was subjected to flash column chromatography on silica gel using 0-10% MeOH in DCM (v/v) as eluent to obtain compound 41 as yellow solids (30 mg, 13%). $^1$H NMR (400 MHz, DMSO-$d_6$) δ 11.88 (br, 1H), 9.14 (br, 1H), 8.13 (s, 1H), 7.29 (d, J=8.8 Hz, 2H), 7.17 (d, J=8.8 Hz, 2H), 6.57 (br, 1H), 6.10 (br, 1H), 5.81 (s, 1H), 2.62 (s, 3H), 1.83 (m, 1H), 1.49 (d, J=7.2 Hz, 3H), 0.91 (m, 2H), 0.67 (m, 2H); ESI-MS: calcd for ($C_{19}H_{21}FN_6$) 352, found 353 (MH+).

Example 42

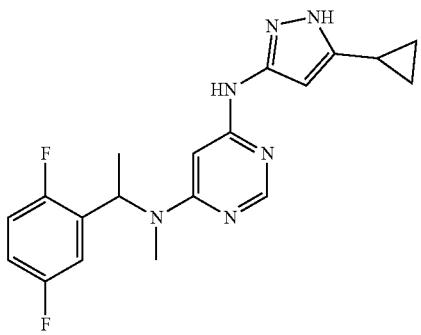

42

To a solution of compound 10 (150 mg, 0.64 mmol) in iPA (3.0 mL) was added 1-(2,5-difluorophenyl)-N-methylethan-1-amine (119.85 mg, 0.70 mmol), and DIPEA (0.17 mL, 0.95 mmol) at room temperature and the mixture was stirred at 120° C. for overnight followed by heating at 150° C. for 36 h. TLC was taken and the majority of starting material was consumed. The crude reaction mixture was concentrated and the residue was subjected to flash column chromatography on silica gel using 0-10% MeOH in DCM (v/v) as eluent to obtain compound 42 as yellow solids (10 mg, 4%). $^1$H NMR (400 MHz, DMSO-$d_6$) δ 11.91 (br, 1H), 9.13 (br, 1H), 8.11 (s, 1H), 7.24 (m, 3H), 6.55 (br, 1H), 6.16 (br, 1H), 5.80 (s, 1H), 2.71 (s, 3H), 1.83 (m, 1H), 1.49 (d, J=7.2 Hz, 3H), 0.90 (m, 2H), 0.65 (m, 2H); ESI-MS: calcd for ($C_{19}H_{20}F_2N_6$) 370, found 371 (MH+).

Example 43

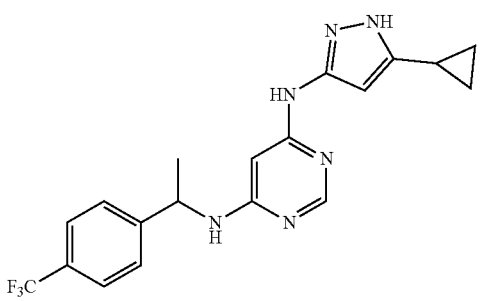

43

A mixture of 6-chloro-N-(5-cyclopropyl-1H-pyrazol-3-yl)pyrimidin-4-amine compound 10 (168 mg, 0.713 mmol), 1-(5-fluoropyridin-2-yl)ethan-1-amine (100 mg, 0.713 mmol), anhydrous DIPEA (0.37 mL, 2.1 mmol; dried over activated 3 Å molecular sieves) and anhydrous n-butanol (0.6 mL; dried over activated 3 Å molecular sieves) was warmed to 145° C. and stirred for 5 days, and then it was cooled to room temperature. The resulting mixture was then diluted with EtOAc (ca. 10 mL) and washed with 1.25 M aq $KH_2PO_4$ (ca. 10 mL). The aqueous layer was separated and washed with additional EtOAc (ca. 10 mL). The combined organic layers were dried over anhydrous $Na_2SO_4$ and concentrated. The resulting residue was purified by flash column chromatography on silica gel using 2-20% MeOH in DCM as eluent to afford the desired product N4-(5-cyclopropyl-1H-pyrazol-3-yl)-N6-(1-(5-fluoropyridin-2-yl)ethyl)pyrimidine-4,6-diamine compound 43 as a glassy yellow solid (146 mg, 60% yield). $^1$H NMR (DMSO-d6, 400 MHz) δ 11.86 (br s, 1H), 8.91 (br s, 1H), 8.48 (d, J=2.8 Hz, 1H), 7.95 (br s, 1H), 7.64 (dt, J=3.2, 8.8 Hz, 1H), 7.41-7.37 (m, 2H), 6.40 (br s, 1H), 5.72 (s, 1H), 5.06 (br s, 1H), 1.84 (sept, J=5.2 Hz, 1H), 1.42 (d, J=7.2 Hz, 3H), 0.91-0.89 (m, 2H), 0.66-0.63 (m, 2H); MS (ESI): calcd for $C_{17}H_{18}FN_7$: 339, found: 340 (MH+).

Example 44

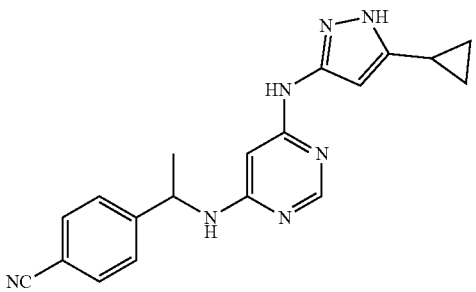

44

A mixture of 6-chloro-N-(5-cyclopropyl-1H-pyrazol-3-yl)pyrimidin-4-amine compound 10 (168 mg, 0.713 mmol), 1-(5-fluoropyridin-2-yl)ethan-1-amine (100 mg, 0.713 mmol), anhydrous DIPEA (0.37 mL, 2.1 mmol; dried over activated 3 Å molecular sieves) and anhydrous n-butanol (0.6 mL; dried over activated 3 Å molecular sieves) was warmed to 145° C. and stirred for 5 days, and then it was cooled to room temperature. The resulting mixture was then diluted with EtOAc (ca. 10 mL) and washed with 1.25 M aq $KH_2PO_4$ (ca. 10 mL). The aqueous layer was separated and washed with additional EtOAc (ca. 10 mL). The combined organic layers were dried over anhydrous $Na_2SO_4$ and concentrated. The resulting residue was purified by flash column chromatography on silica gel using 2-20% MeOH in DCM as eluent to afford the desired product N4-(5-cyclopropyl-1H-pyrazol-3-yl)-N6-(1-(5-fluoropyridin-2-yl)ethyl)pyrimidine-4,6-diamine compound 44 as a glassy yellow solid (146 mg, 60% yield). $^1$H NMR (DMSO-d6, 400 MHz) δ 11.86 (br s, 1H), 8.91 (br s, 1H), 8.48 (d, J=2.8 Hz, 1H), 7.95 (br s, 1H), 7.64 (dt, J=3.2, 8.8 Hz, 1H), 7.41-7.37 (m, 2H), 6.40 (br s, 1H), 5.72 (s, 1H), 5.06 (br s, 1H), 1.84 (sept, J=5.2 Hz, 1H), 1.42 (d, J=7.2 Hz, 3H), 0.91-0.89 (m, 2H), 0.66-0.63 (m, 2H); MS (ESI): calcd for $C_{17}H_{18}FN_7$: 339, found: 340 (MH+).

Example 45

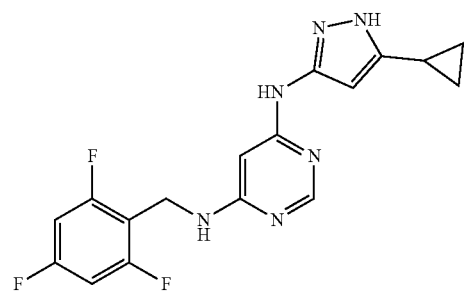

45

A mixture of 6-chloro-N-(5-cyclopropyl-1H-pyrazol-3-yl)pyrimidin-4-amine compound 10 (168 mg, 0.713 mmol), 1-(5-fluoropyridin-2-yl)ethan-1-amine (100 mg, 0.713 mmol), anhydrous DIPEA (0.37 mL, 2.1 mmol; dried over activated 3 Å molecular sieves) and anhydrous n-butanol (0.6 mL; dried over activated 3 Å molecular sieves) was warmed to 145° C. and stirred for 5 days, and then it was cooled to room temperature. The resulting mixture was then diluted with EtOAc (ca. 10 mL) and washed with 1.25 M aq KH$_2$PO$_4$ (ca. 10 mL). The aqueous layer was separated and washed with additional EtOAc (ca. 10 mL). The combined organic layers were dried over anhydrous Na$_2$SO$_4$ and concentrated. The resulting residue was purified by flash column chromatography on silica gel using 2-20% MeOH in DCM as eluent to afford the desired product N4-(5-cyclopropyl-1H-pyrazol-3-yl)-N6-(1-(5-fluoropyridin-2-yl)ethyl)pyrimidine-4,6-diamine compound 45 as a glassy yellow solid (146 mg, 60% yield). $^1$H NMR (DMSO-d6, 400 MHz) δ 11.86 (br s, 1H), 8.91 (br s, 1H), 8.48 (d, J=2.8 Hz, 1H), 7.95 (br s, 1H), 7.64 (dt, J=3.2, 8.8 Hz, 1H), 7.41-7.37 (m, 2H), 6.40 (br s, 1H), 5.72 (s, 1H), 5.06 (br s, 1H), 1.84 (sept, J=5.2 Hz, 1H), 1.42 (d, J=7.2 Hz, 3H), 0.91-0.89 (m, 2H), 0.66-0.63 (m, 2H); MS (ESI): calcd for C$_{17}$H$_{18}$FN$_7$: 339, found: 340 (MH$^+$).

Example 46

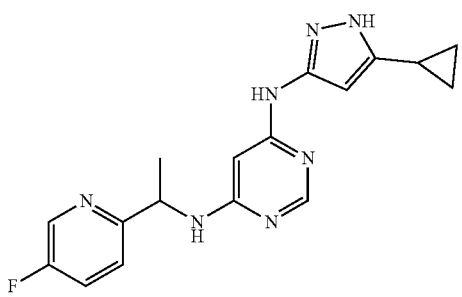

A mixture of 6-chloro-N-(5-cyclopropyl-1H-pyrazol-3-yl)pyrimidin-4-amine compound 10 (168 mg, 0.713 mmol), 1-(5-fluoropyridin-2-yl)ethan-1-amine (100 mg, 0.713 mmol), anhydrous DIPEA (0.37 mL, 2.1 mmol; dried over activated 3 Å molecular sieves) and anhydrous n-butanol (0.6 mL; dried over activated 3 Å molecular sieves) was warmed to 145° C. and stirred for 5 days, and then it was cooled to room temperature. The resulting mixture was then diluted with EtOAc (ca. 10 mL) and washed with 1.25 M aq KH$_2$PO$_4$ (ca. 10 mL). The aqueous layer was separated and washed with additional EtOAc (ca. 10 mL). The combined organic layers were dried over anhydrous Na$_2$SO$_4$ and concentrated. The resulting residue was purified by flash column chromatography on silica gel using 2-20% MeOH in DCM as eluent to afford the desired product N4-(5-cyclopropyl-1H-pyrazol-3-yl)-N6-(1-(5-fluoropyridin-2-yl)ethyl)pyrimidine-4,6-diamine compound 46 as a glassy yellow solid (146 mg, 60% yield). $^1$H NMR (DMSO-d6, 400 MHz) δ 11.86 (br s, 1H), 8.91 (br s, 1H), 8.48 (d, J=2.8 Hz, 1H), 7.95 (br s, 1H), 7.64 (dt, J=3.2, 8.8 Hz, 1H), 7.41-7.37 (m, 2H), 6.40 (br s, 1H), 5.72 (s, 1H), 5.06 (br s, 1H), 1.84 (sept, J=5.2 Hz, 1H), 1.42 (d, J=7.2 Hz, 3H), 0.91-0.89 (m, 2H), 0.66-0.63 (m, 2H); MS (ESI): calcd for C$_{17}$H$_{18}$FN$_7$: 339, found: 340 (MH$^+$).

Example 47

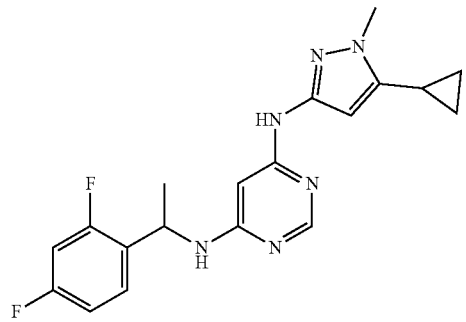

A mixture of N4-(5-cyclopropyl-1H-pyrazol-3-yl)-N6-(1-(2,4-difluorophenyl)ethyl)pyrimidine-4,6-diamine compound 32 (100 mg, 0.281 mmol) and K$_2$CO$_3$ (116.34 mg, 0.842 mmol) in anhydrous DMF (2.5 mL) was chilled to 0° C. in an ice-water bath under Argon atmosphere. Iodomethane (33.85 mg, 0.239 mmol) was then added dropwise and the mixture was stirred at 0° C. for 12 h. Water was added and the solution was extracted with 10% MeOH/DCM. The combined organic extracts was dried and concentrated. The crude product was purified by column chromatography (silica gel, 0-5% MeOH in DCM) to obtain compound 47 as beige solids (16 mg, 15% yield). $^1$H NMR (400 MHz, DMSO-d$_6$) δ 8.96 (s, 1H), 7.95 (s, 1H), 7.41 (m, 2H), 7.17 (m, 1H), 7.03 (m, 1H), 6.37 (br, 1H), 5.64 (s, 1H), 5.16 (br, 1H), 3.73 (s, 3H), 1.83 (m, 1H), 1.40 (d, J=6.8 Hz, 3H), 0.94 (m, 2H), 0.57 (m, 2H); ESI-MS: calcd for (C$_{19}$H$_{20}$F$_2$N$_6$) 370, found 371 (MH$^+$).

Example 48

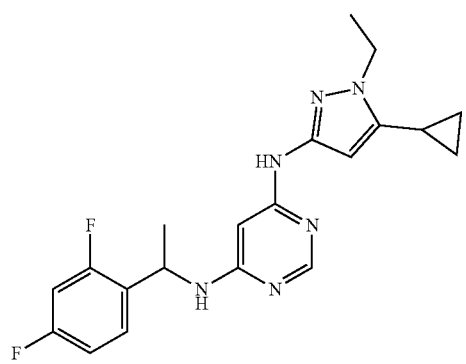

A mixture of 6-chloro-N-(1-(2,4-difluorophenyl)ethyl)pyrimidin-4-amine compound 9 (200 mg, 0.720 mmol), 5-cyclopropyl-1-ethyl-1H-pyrazol-3-amine (140.18 mg, 0.927 mmol), xantphos (4,5-diphenylphosphanyl-9,9'-dimethyl-9-H-xanthene, 107.28 mg, 0.185 mmol), K$_2$CO$_3$ (512.48 mg, 3.71 mmol) and palladium(II) acetate (24.97 mg, 0.111 mmol) in 1,4-dioxane (10 ml) was purged with argon for 1 hour. The mixture was heated in an oil bath for overnight at 90° C. TLC was checked and the starting material was consumed. After cooling to room temperature, the reaction mixture was passed through a pad of celite using 10% MeOH/DCM and was concentrated. The crude product was purified by column chromatography (silica gel, 0-5% MeOH in DCM) to obtain compound 48 as brownish solids (185 mg, 65% yield). $^1$H NMR (400 MHz, DMSO-d$_6$) δ 8.55 (s, 1H), 7.97 (s, 1H), 7.46 (m, 1H), 7.37 (m, 1H), 7.15 (m, 1H), 7.03 (m, 1H), 5.75 (s, 1H), 5.53 (br, 1H), 5.21 (br, 1H), 3.83 (q, J=7.2 Hz, 2H), 1.85 (m, 1H), 1.37 (d, J=6.8 Hz, 3H), 1.19 (t, J=7.2 Hz, 3H), 0.83 (m, 2H), 0.61 (m, 2H); ESI-MS: calcd for (C$_{20}$H$_{22}$F$_2$N$_6$) 384, found 385 (MH$^+$).

Example 49

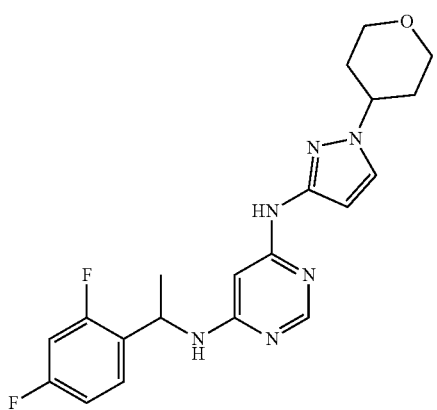

A mixture of 6-chloro-N-(1-(2,4-difluorophenyl)ethyl)pyrimidin-4-amine compound 9 (177.41 mg, 0.658 mmol), 1-(tetrahydro-2H-pyran-4-yl)-1H-pyrazol-3-amine (100.00 mg, 0.598 mmol), xantphos (4,5-diphenylphosphanyl-9,9'-dimethyl-9-H-xanthene, 86.51 mg, 0.150 mmol), K$_2$CO$_3$ (413.26 mg, 2.99 mmol) and palladium(II) acetate (20.14 mg, 0.090 mmol) in 1,4-dioxane (10 ml) was purged with argon for 1 hour. The mixture was heated in an oil bath for overnight at 85° C. TLC was checked and the starting material was consumed. After cooling to room temperature, the reaction mixture was passed through a pad of celite using 10% MeOH/DCM and was concentrated. The crude product was purified by column chromatography (silica gel, 0-5% MeOH in DCM) to obtain compound 49 as white solids (127 mg, 53% yield). $^1$H NMR (400 MHz, DMSO-d$_6$) δ 9.18 (s, 1H), 7.99 (s, 1H), 7.59 (s, 1H), 7.44 (m, 2H), 7.16 (m, 1H), 7.03 (m, 1H), 6.39 (br, 1H), 6.06 (br, 1H), 5.18 (br, 1H), 4.26 (m, 1H), 3.99 (m, 2H), 3.46 (m, 2H), 1.93 (m, 4H), 1.42 (d, J=6.8 Hz, 3H); ESI-MS: calcd for (C$_{20}$H$_{22}$F$_2$N$_6$O) 400, found 401 (MH$^+$).

Example 50

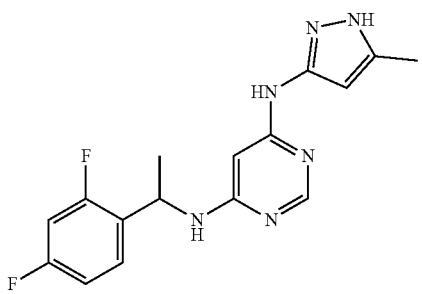

To a solution of 6-chloro-N-(5-methyl-1H-pyrazol-3-yl)pyrimidin-4-amine compound 19 (100 mg, 0.48 mmol) in n-BuOH (0.5 mL) was added 1-(2,4-difluorophenyl)ethan-1-amine (75 mg, 0.48 mmol), and DIPEA (0.27 mL, 1.43 mmol) at room temperature and the mixture was stirred at 150° C. for 72 h. TLC was taken and the reaction was almost complete. The crude reaction mixture was concentrated and the residue was dissolved in DMSO (1 mL). The solution was then added to half-saturated ammonium chloride in water (80 mL) and stirred for 30 min. The solids were collected by filtration, washed by water. The crude product was purified by column chromatography (0-10% MeOH in DCM) to obtain compound 50 as beige solids (59 mg, 37% yield). $^1$H NMR (400 MHz, DMSO-d$_6$) δ 12.25 (br, 1H), 8.98 (s, 1H), 7.96 (s, 1H), 7.41 (m, 2H), 7.15 (m, 1H), 7.02 (m, 1H), 6.41 (br, 1H), 5.82 (s, 1H), 5.24 (br, 1H), 2.18 (s, 3H), 1.39 (d, J=6.8 Hz, 3H); ESI-MS: calcd for (C$_{16}$H$_{16}$F$_2$N$_6$) 330, found 331 (MH$^+$).

Example 51

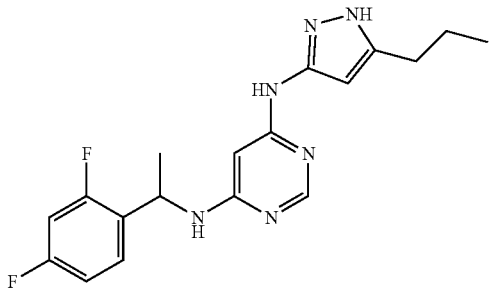

To a solution of 6-chloro-N-(5-propyl-1H-pyrazol-3-yl)pyrimidin-4-amine compound 20 (121 mg, 0.51 mmol) in n-BuOH (0.5 mL) was added 1-(2,4-difluorophenyl)ethan-1-amine (80 mg, 0.51 mmol), and DIPEA (0.27 mL, 1.43 mmol) at room temperature and the mixture was stirred at 150° C. for 72 h. TLC was taken and the reaction was almost complete. The crude reaction mixture was concentrated and the residue was dissolved in DMSO (1 mL). The solution was then added to half-saturated ammonium chloride in water (80 mL) and stirred for 30 min. The solids were collected by filtration, washed by water. The crude product was purified by column chromatography (0-10% MeOH in DCM) to obtain compound 51 as yellow solids (77 mg, 42% yield). $^1$H NMR (400 MHz, DMSO-d$_6$) δ 12.25 (br, 1H), 8.98 (s, 1H), 7.96 (s, 1H), 7.41 (m, 2H), 7.15 (m, 1H), 7.02 (m, 1H), 6.41 (br, 1H), 5.82 (s, 1H), 5.24 (br, 1H), 2.49 (m, 2H), 1.59 (m, 2H), 1.39 (d, J=6.8 Hz, 3H), 0.91 (t, J=7.2 Hz, 3H); ESI-MS: calcd for (C$_{18}$H$_{20}$F$_2$N$_6$) 358, found 359 (MH$^+$).

Example 52

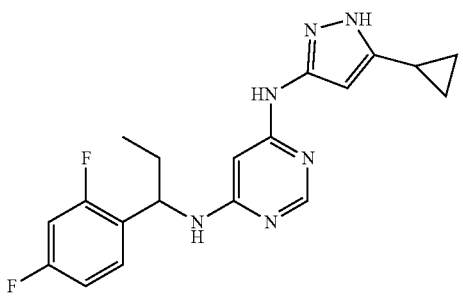

A mixture of 6-chloro-N-(5-cyclopropyl-1H-pyrazol-3-yl)pyrimidin-4-amine compound 10 (168 mg, 0.713 mmol), 1-(5-fluoropyridin-2-yl)ethan-1-amine (100 mg, 0.713 mmol), anhydrous DIPEA (0.37 mL, 2.1 mmol; dried over activated 3 Å molecular sieves) and anhydrous n-butanol (0.6 mL; dried over activated 3 Å molecular sieves) was warmed to 145° C. and stirred for 5 days, and then it was cooled to room temperature. The resulting mixture was then diluted with EtOAc (ca. 10 mL) and washed with 1.25 M aq $KH_2PO_4$ (ca. 10 mL). The aqueous layer was separated and washed with additional EtOAc (ca. 10 mL). The combined organic layers were dried over anhydrous $Na_2SO_4$ and concentrated. The resulting residue was purified by flash column chromatography on silica gel using 2-20% MeOH in DCM as eluent to afford the desired product N4-(5-cyclopropyl-1H-pyrazol-3-yl)-N6-(1-(5-fluoropyridin-2-yl)ethyl)pyrimidine-4,6-diamine compound 52 as a glassy yellow solid (146 mg, 60% yield). $^1$H NMR (DMSO-d6, 400 MHz) δ 11.86 (br s, 1H), 8.91 (br s, 1H), 8.48 (d, J=2.8 Hz, 1H), 7.95 (br s, 1H), 7.64 (dt, J=3.2, 8.8 Hz, 1H), 7.41-7.37 (m, 2H), 6.40 (br s, 1H), 5.72 (s, 1H), 5.06 (br s, 1H), 1.84 (sept, J=5.2 Hz, 1H), 1.42 (d, J=7.2 Hz, 3H), 0.91-0.89 (m, 2H), 0.66-0.63 (m, 2H); MS (ESI): calcd for $C_{17}H_{18}FN_7$: 339, found: 340 (MH$^+$).

Example 53

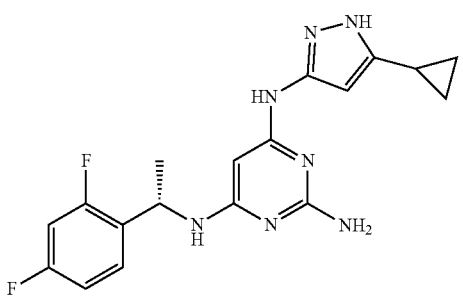 [SMILES: C[C@H](Nc1cc(Nc2cc(C3CC3)[nH]n2)nc(N)n1)c1ccc(F)cc1F]

The suspension of compound 21 (180 mg, 0.72 mmol), (1S)-1-(2,4-difluorophenyl)ethanamine (118 mg, 0.75 mmol) and DIPEA (0.16 ml, 10.90 mmol) in n-BuOH (1 mL) was heated at 150° C. with oil bath for 7 days. The solvent was removed under reduced pressure and the residue was dissolved in DMSO (~2 ml) and was added to half-saturated ammonium chloride in water (50 mL). After stirred at room temperature for 30 min, mixture was cooled with ice bath and the solids were collected by filtration, washed by water. The crude product was purified by column chromatography (0-10% MeOH in DCM) to give the product compound 53 as yellow solids (117 mg, 44% yield). $^1$H NMR (400 MHz, DMSO-d$_6$) δ 11.95 (br, 1H), 9.27 (br, 1H), 7.43 (m, 2H), 7.20 (m, 1H), 7.05 (m, 1H), 6.50-6.20 (br, 2H), 5.70-5.60 (br, 1H), 5.60-5.40 (br, 1H), 5.30-5.10 (br, 1H), 1.83 (m, 1H), 1.38 (d, J=7.2 Hz, 3H), 0.89 (m, 2H), 0.65 (m, 2H); ESI-MS: calcd for ($C_{18}H_{19}F_2N_7$) 371, found 372 (MH$^+$).

Example 54

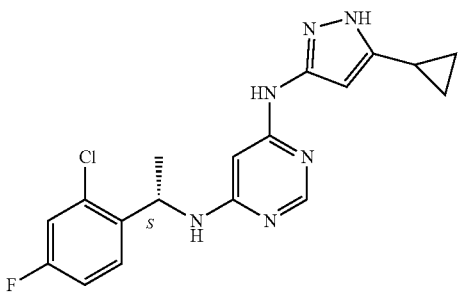

The solution of compound 10 (138 mg, 0.59 mmol), (1S)-1-(2-chloro-4-fluorophenyl)ethan-1-amine hydrochloride [HCl] (135 mg, 0.64 mmol) and DIPEA (0.31 ml, 1.76 mmol) in n-BuOH (1 mL) was heated at 150° C. with oil bath for 4 days. The solvent was removed under reduced pressure and the residue was dissolved in DMSO (~2 ml) and was added to half-saturated ammonium chloride in water (50 mL). After stirred at room temperature for 30 min, mixture was cooled with ice bath and the solids were collected by filtration, washed by water. The crude product was purified by column chromatography (0-10% MeOH in DCM) to give the product compound 54 as yellow solids (107 mg, 49% yield). $^1$H NMR (400 MHz, DMSO-d$_6$) δ 11.85 (s, 1H), 8.92 (s, 1H), 7.51 (d, J=7.2 Hz, 1H), 7.46 (m, 1H), 7.37 (m, 1H), 7.18 (m, 1H), 6.50-6.20 (br, 1H), 5.71 (s, 1H), 5.40-5.10 (br, 1H), 1.85 (m, 1H), 1.36 (d, J=6.8 Hz, 3H), 0.90 (m, 2H), 0.63 (m, 2H); ESI-MS: calcd for ($C_{18}H_{18}ClFN_6$) 372, found 373 (MH$^+$).

Example 55

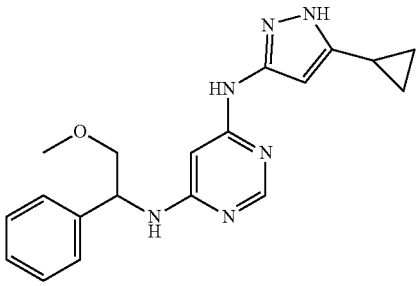

To a solution of 6-chloro-N-(5-cycolpropyl-1H-pyrazol-3-yl)pyrimidin-4-amine compound 10 (155.86 mg, 0.51 mmol) in n-BuOH (0.5 mL) was added 2-methoxy-1-phenylethan-1-amine (100 mg, 0.66 mmol), and DIPEA (0.35 mL, 1.98 mmol) at room temperature and the mixture was stirred at 150° C. for 72 h. TLC was taken and the reaction was almost complete. The crude reaction mixture was concentrated and the residue was dissolved in DMSO (1 mL). The solution was then added to half-saturated ammonium chloride in water (80 mL) and stirred for 30 min. The solids were collected by filtration, washed by water. The crude product was purified by column chromatography (0-10% MeOH in DCM) to obtain compound 55 as beige solids (46 mg, 20% yield). $^1$H NMR (400 MHz, DMSO-d$_6$) δ 11.90 (br, 1H), 8.91 (s, 1H), 7.96 (s, 1H), 7.35 (m, 6H), 6.434 (br, 1H), 5.72 (s, 1H), 5.15 (br, 1H), 3.57 (m, 1H), 3.51 (m, 1H), 3.26 (s, 3H), 1.84 (m, 1H), 0.91 (m, 2H), 0.65 (m, 2H); ESI-MS: calcd for (C$_{19}$H$_{22}$N$_6$O) 350, found 351 (MH$^+$).

Example 56

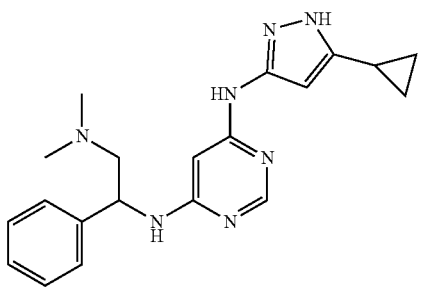

To a solution of 6-chloro-N-(5-cycolpropyl-1H-pyrazol-3-yl)pyrimidin-4-amine compound 10 (143.48 mg, 0.61 mmol) in n-BuOH (0.5 mL) was added N1,N1-dimethyl-2-phenylethane-1,2-diamine (100 mg, 0.61 mmol), and DIPEA (0.32 mL, 1.83 mmol) at room temperature and the mixture was stirred at 150° C. for 72 h. TLC was taken and the reaction was almost complete. The crude reaction mixture was quenched with water (25 mL) and extracted with 10% MeOH/DCM (3×25 mL). The combined organic extracts were dried, and concentrated. The crude product was purified by column chromatography (0-10% MeOH in DCM) to obtain compound 56 as yellow solids (65 mg, 29% yield). $^1$H NMR (400 MHz, DMSO-d$_6$) δ 11.85 (br, 1H), 8.89 (s, 1H), 7.95 (s, 1H), 7.29 (m, 6H), 6.32 (br, 1H), 5.69 (s, 1H), 4.95 (br, 1H), 2.62 (m, 1H), 2.36 (m, 1H), 2.18 (s, 6H), 1.84 (m, 1H), 0.91 (m, 2H), 0.65 (m, 2H); ESI-MS: calcd for (C$_{20}$H$_{25}$N$_7$) 363, found 364 (MH$^+$).

Example 57

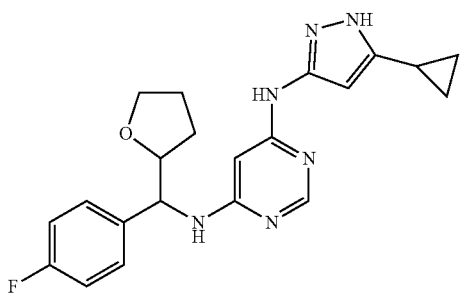

A mixture of 6-chloro-N-(5-cyclopropyl-1H-pyrazol-3-yl)pyrimidin-4-amine compound 10 (168 mg, 0.713 mmol), 1-(5-fluoropyridin-2-yl)ethan-1-amine (100 mg, 0.713 mmol; ca. 3:1 mixture of anti/syn-diastereomers), anhydrous DIPEA (0.37 mL, 2.1 mmol; dried over activated 3 Å molecular sieves) and anhydrous n-butanol (0.6 mL; dried over activated 3 Å molecular sieves) was warmed to 145° C. and stirred for 5 days, and then it was cooled to room temperature. The resulting mixture was then diluted with EtOAc (ca. 10 mL) and washed with 1.25 M aq KH$_2$PO$_4$ (ca. 10 mL). The aqueous layer was separated and washed with additional EtOAc (ca. 10 mL). The combined organic layers were dried over anhydrous Na$_2$SO$_4$ and concentrated. The resulting residue was purified by flash column chromatography on silica gel using 2-20% MeOH in DCM as eluent to afford the desired product N4-(5-cyclopropyl-1H-pyrazol-3-yl)-N6-(1-(5-fluoropyridin-2-yl)ethyl)pyrimidine-4,6-diamine compound 57 as a glassy yellow solid (146 mg, 60% yield). $^1$H NMR (DMSO-d6, 400 MHz): (ca. 3:1 mixture of anti/syn-diastereomers) δ 11.86 (br s, 1H), 8.91 (br s, 1H), 8.48 (d, J=2.8 Hz, 1H), 7.95 (br s, 1H), 7.64 (dt, J=3.2, 8.8 Hz, 1H), 7.41-7.37 (m, 2H), 6.40 (br s, 1H), 5.72 (s, 1H), 5.06 (br s, 1H), 1.84 (sept, J=5.2 Hz, 1H), 1.42 (d, J=7.2 Hz, 3H), 0.91-0.89 (m, 2H), 0.66-0.63 (m, 2H); MS (ESI): calcd for C$_{17}$H$_{18}$FN$_7$: 339, found: 340 (MH$^+$).

Example 58

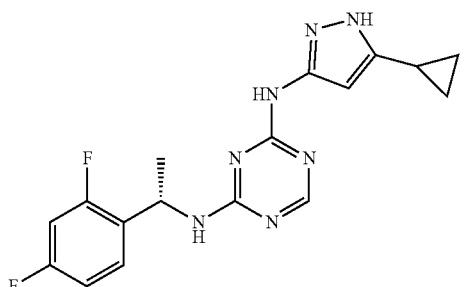

The solution of compound 22 (200 mg, 0.85 mmol), (1S)-1-(2,4-difluorophenyl)ethanamine (139 mg, 0.89 mmol) and DIPEA (0.18 ml, 1.06 mmol) DMSO (2 mL) was stirred at 85° C. for 5 h. The reaction mixture was added to half-saturated ammonium chloride in water (80 mL) and stirred for 30 min. The solids were collected by filtration, washed by water, air-dried to give the product compound 58 as yellow solids (301 mg, 100% yield). (TLC was one spot and no further purification was performed). $^1$H NMR (400 MHz, DMSO-d$_6$) δ 11.94 (br, 1H), 9.64 (br, 1H), 8.19 (br, 1H), 8.08 (br, 1H), 7.45 (m, 1H), 7.20 (m, 1H), 7.05 (m, 1H), 5.60 (br, 1H), 5.35 (m, 1H), 1.84 (m, 1H), 1.41 (d, J=6.8 Hz, 3H), 0.91 (m, 2H), 0.64 (m, 2H); ESI-MS: calcd for (C$_{17}$H$_{17}$F$_2$N$_7$) 357, found 358 (MH$^+$).

Example 59

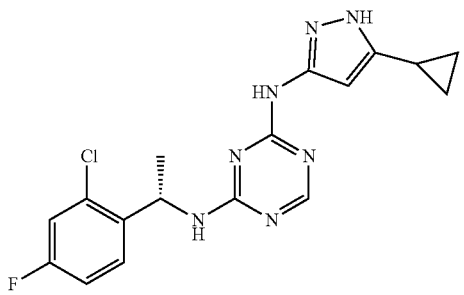

The solution of compound 22 (100 mg, 0.42 mmol), (1S)-1-(2-chloro-4-fluorophenyl)ethan-1-amine hydrochloride [HCl], (89 mg, 0.42 mmol) and DIPEA (0.37 ml, 2.11 mmol) DMSO (2 mL) was stirred at 90° C. for overnight. The reaction mixture was added to half-saturated ammonium chloride in water (75 mL) and stirred for 30 min. The solids were collected by filtration, washed by water and air-dried. The crude product was purified by column chromatography (0-10% MeOH in DCM) to give the product compound 59 as yellow solids (111 mg, 70% yield). $^1$H NMR (400 MHz, DMSO-$d_6$) δ 12.20-11.80 (m, 1H), 9.80-9.60 (m, 1H), 8.20-8.00 (m, 2H), 7.51 (m, 1H), 7.41 (m, 1H), 7.22 (m, 1H), 6.20-6.00 (m, 1H), 5.39 (m, 1H), 1.86 (m, 1H), 1.41 (d, J=6.8 Hz, 3H), 0.91 (m, 2H), 0.65 (m, 2H); ESI-MS: calcd for ($C_{17}H_{17}ClFN_7$) 373, found 374 (MH$^+$).

Example 60

The KinaseProfiler™ Service Assay Protocols (Millipore) were used to test the kinase inhibiting activity of the novel compounds from this invention. To do this, the buffer composition was as follows: 20 mM MOPS, 1 mM EDTA, 0.01% Brij-35, 5% Glycerol, 0.1% β-mercaptoethanol, 1 mg/mL BSA. Test compounds were initially dissolved in DMSO at the desired concentration, then serially diluted into the kinase assay buffer. In a final reaction volume of 25 µL, TrkA(h) (5-10 mU) is incubated with 8 mM MOPS pH 7.0, 0.2 mM EDTA, 200 µM LRRASLG (Kemptide), 10 mM MgAcetate and [γ$^{33}$P-ATP]. The reaction was initiated by the addition of the MgATP mix. After incubation for 40 minutes at room temperature, the reaction was stopped by addition of 5 µL of a 3% phosphoric acid solution. 10 µL of the reaction was then spotted onto a P30 filtermat and washed three times for 5 minutes in 50 mM phosphoric acid and once in methanol prior to drying and scintillation counting. Wells containing substrate but no kinase and wells containing a phosphopeptide control were used to set 0% and 100% phosphorylation value, respectively.

A number of studies were performed to analyze the consequences of TrkA kinase inhibition in cell lines. To do this, KM12 cells (human colorectal adenocarcinoma, 2000 cells/36 µl/well) are seeded into 384-well microplates, which are then placed in a humidified $CO_2$ incubator at 37° C. overnight. The next day, 4 µl/well of 10× concentrated drug is added and the plates are returned to the incubator for 72 hr. After 72 hr incubation, plates are removed and 8 µl/well CellTiterBlue (Promega) viability reagent is added. Plates are returned to the incubator for 3 hr, after which fluorescence measurements are read on the Victor X3 plate reader (Perkin Elmer). Data are analyzed using Excel (Microsoft), and $GI_{50}$ values are determined using Prism (Graphpad).

Table 1 shows representative data for the inhibition of Trk kinases by the compounds of this invention at a concentration of 1 µM. Table 1 also shows representative GI50 data for the inhibition of KM-12 cancer cell lines.

TABLE 1

| Example Number | % Inhibition@ 1 µM (TrkA(h)) | GI50 (nM), Km-12 cell line |
|---|---|---|
| 23 | 99 | 69 |
| 24 | 31 | >500 |
| 25 | 0 | >500 |
| 26 | 49 | >500 |
| 27 | 87 | 183 |
| 28 | 56 | >500 |
| 29 | -5 | >500 |
| 30 | 100 | 75 |
| 31 | 99 | 108 |
| 32 | 104 | 24 |
| 33 | 60 | >500 |
| 34 | 101 | 14 |
| 35 | 99 | 105 |
| 36 | 101 | 39 |
| 37 | 97 | 245 |
| 38 | 71 | >500 |
| 39 | 7 | >500 |
| 40 | 101 | 115 |
| 42 | 95 | 270 |
| 43 | 95 | 164 |
| 44 | 98 | 144 |
| 45 | 100 | 86 |
| 46 | 98 | 45 |
| 47 | 25 | >500 |
| 48 | 10 | >500 |
| 49 | 5 | >500 |
| 50 | 99 | 146 |
| 51 | 100 | 63 |
| 52 | 101 | 48 |
| 53 | 100 | 8 |
| 54 | 100 | 25 |
| 55 | 85 | >500 |
| 56 | 67 | >500 |
| 57 | 95 | 102 |
| 58 | 100 | 7 |
| 59 | 100 | 15 |

What is claimed is:

1. A compound of the formula:

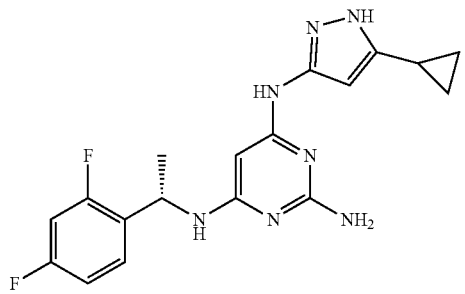

or a pharmaceutically acceptable salt thereof.

2. A pharmaceutical composition comprising a compound of claim 1, or a pharmaceutically acceptable salt thereof, and a pharmaceutically acceptable diluent or carrier.

* * * * *